US008796422B2

(12) United States Patent
Lillard, Jr.

(10) Patent No.: US 8,796,422 B2
(45) Date of Patent: Aug. 5, 2014

(54) CHEMOKINE-IMMUNOGLOBULIN FUSION POLYPEPTIDES, COMPOSITIONS, METHOD OF MAKING AND USE THEREOF

(71) Applicant: Morehouse School of Medicine, Atlanta, GA (US)

(72) Inventor: James W. Lillard, Jr., Smyrna, GA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

(21) Appl. No.: 13/962,110

(22) Filed: Aug. 8, 2013

(65) Prior Publication Data

US 2013/0323245 A1    Dec. 5, 2013

Related U.S. Application Data

(63) Continuation-in-part of application No. 13/480,526, filed on May 25, 2012, now Pat. No. 8,541,564.

(60) Provisional application No. 61/492,260, filed on Jun. 1, 2011.

(51) Int. Cl.
*C07K 1/00*        (2006.01)
*C12P 21/08*       (2006.01)
*C07K 16/28*       (2006.01)
*A61K 38/00*       (2006.01)

(52) U.S. Cl.
CPC .............. *C07K 16/2866* (2013.01); *A61K 38/00* (2013.01); *C07K 2319/30* (2013.01)
USPC ....................................... 530/351; 530/387.3

(58) Field of Classification Search
None
See application file for complete search history.

(56) References Cited

U.S. PATENT DOCUMENTS

| 5,766,897 | A | 6/1998 | Braxton |
| 7,740,833 | B2 * | 6/2010 | Proudfoot et al. ........... 424/85.1 |
| 2005/0053579 | A1 | 3/2005 | Galipeau et al. |
| 2007/0116669 | A1 | 5/2007 | Merzouk et al. |
| 2009/0098101 | A1 | 4/2009 | Raines et al. |
| 2010/0166733 | A1 * | 7/2010 | Levin et al. ................ 424/130.1 |
| 2010/0196406 | A1 | 8/2010 | Karin et al. |

OTHER PUBLICATIONS

The International Search Report and the Written Opinion of the International Searching Authority (Application No. PCT/ US2012/ 039550, International Filing Date: May 25, 2012), mailed Dec. 18, 2012.

Biragyn, A. et al., "Mediators of Innate Immunity That Target Immature, But Not Mature, Dendritic Cells Induce Antitumor Immunity When Genetically Fused with Nonimmunogenic Tumor Antigens", The Journal of Immunology, Dec. 1, 2001, vol. 167, No. 11, pp. 6644-6653.

Fagète, S., et al., "Specificity tuning of antibody fragments to neutralize two human chemokines with a single agent", MAbs, May-Jun. 2009, vol. 1, No. 3, pp. 288-296.

(Continued)

*Primary Examiner* — Shulamith H Shafer
(74) *Attorney, Agent, or Firm* — Ping Wang; Andrews Kurth LLP

(57) ABSTRACT

This application is directed to chemokine-immunoglobulin fusion polypeptides and chemokine-polymer conjugates. The fusion polypeptides and conjugates can be used for treating chemokine receptor-mediated disorders and modulating inflammation, inflammatory cell motility, cancer cell motility, or cancer cell survival.

6 Claims, 70 Drawing Sheets

(56) References Cited

OTHER PUBLICATIONS

Van Heeke, G., et al., "Expression of Human Asparagine Synthetase in *Escherichia coli*," The Journal of Biological Chemistry, vol. 264, No. 10, Apr. 5, 1989, pp. 5503-5509.

Allen, S.J., et al., "Chemokine: Receptor Structure, Interactions, and Antagonism," Annu. Rev. Immunol., 2007. 25: 787-820.

File history of U.S. Appl. No. 13/480,526, filed May 25, 2012.

* cited by examiner

FIG.1A
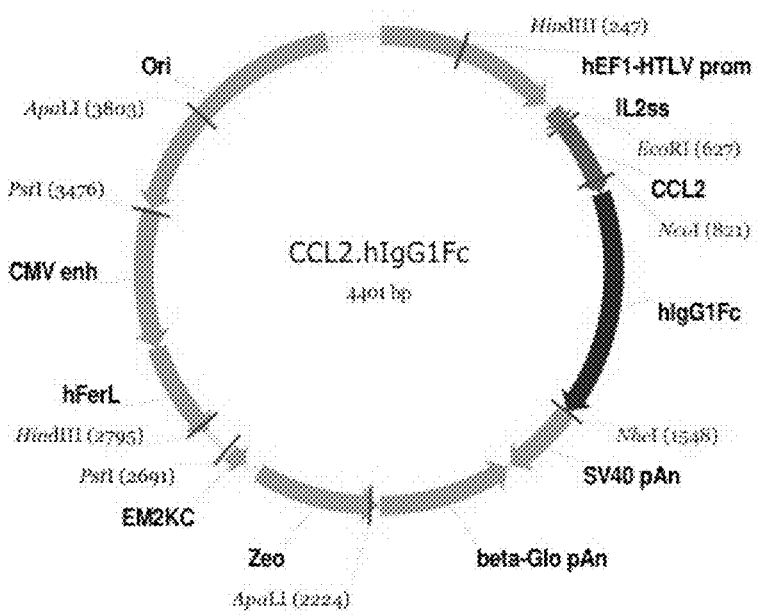
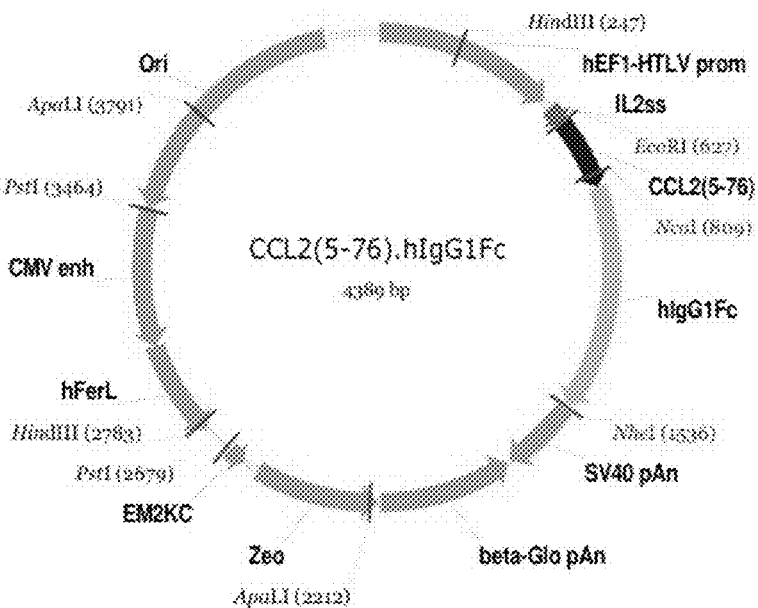
FIG.1B

FIG.1C

IL2ss.CCL2.hIgG1Fc GAGless plasmid sequence

```
   1 GGATCTGCGA TCGCTCCGGT GCCCCTCAGT GGGCAGAGCC CACAGTCCCC ACAGTCCCCG AGAAGTTGGG GGGAGGGGTC GGCAATTGAA CGGGTGCCTA
 101 GAGAAGTGGG CGCGGGGTAA ACTGGGAAAG TGATGTCGTG TACTGGGCTC GCCTTTTCC CGAGGGTGGG GGAGAACCGT ATATAGTGA AGTAGTCGCC
 201 GTGAACGTTC TTTTTCGCAA CGGGTTGCC GCCAGAACGA AGTGAAGCT TGGAGGGGT CGCATCTCTC CCTCACGCGC CCTCCCCCT ACCTGAGGCC
 301 GCCATCCACG CCGGTCAGT CGGGTTCTGC CCCCTCCCGC CGTGGTGCC CTCCTGAACTG CGTCCGCCGT CTAGGTAAGT CTTAAAGCTCA GGTCAGAGCC
 401 GGGCCTTTGT CCGGGCCTCC CCTTGGAGCCT ACCTAGAGTC AGCCGGGTCT CCACGCCTG CCTGGCCCTG CCTGGCTGCA GGGCTCAAC TCTACGTCTT TGTTCGTTT
 501 TCTGTTCTGC GCCGTTACAG ATCCAAGCTG TGACCGGCGC CTAACCTGAGA TCACCGGCGA AGGAGGGCCA CCATGTACAG GATGCAACTC CTGTCTTGCA
                                    EcoRI                    ~~~~ CCL2 (1-76)
                                    KasI
                                    NarI
                                    SfoI
                                    BbeI
                                                                                         IL-2 secretion signal (SEQ ID NO:106)
                                                                                            MetTyrArg MetGlnLeu LeuSerCysIle
     AlaLeuSer LeuAlaLeu ValThrAsnSer GlnProAsp AlaIleAsn AlaProValThr CysCysTyr AsnPheThr AsnArgLysIle SerValGln
 601 TTGCACTAAG TCTTGGACTT GTCACGAATT CGCAGCCAGA TGCAATCAAT GCCCCAGTCA CCTGCTGTTA TAACTTCACC AATAGGAAGA TCTCAGTGCA
     ArgLeuAla SerTyrArgArg IleThrSer SerLysCys ProLysGluAla ValIlePhe LysThrIle ValAlaLysGlu IleCysAla AspProLys
 701 GAGGCTGGCG AGCTATAGAA GAATCACCAG CAGCAAGTGT CCCAAAGAAG CTGTGATCTT CAAGACCATT GTGGCCAAGG AGATTTGTGC TGACCCCAAG
                                                                                              human IgG1 Fc (constant region)
     GlnLysTrpVal GlnAspSer MetAspHis LeuAspLysGln ThrGlnThr ProLysThr AspLysThrHis ThrCysPro ProCysPro AlaProGluLeu
 801 CAGAAGTGGG TTCAGGATTC CATGGACCAC CTGGACAAAC AAACCCAAAC TCCGAAGACT GACAAAACC ACATGCCCA CCGTGCCCA GCACCTGAAC
     LeuGlyGly ProSerVal PheLeuPhePro LysAspThr LeuMetIleSer ArgThrPro GluValThr CysValValVal AspValSer
 901 TCCTGGGGG ACCGTCAGTC TTCCTCTTCC CCCCCAAAAC CCAAGGACACC CTCATGATCT CCCGGACCCC TGAGGTCACA TGCGTGGTGG TGGACGTGAG
     HisGluAsp ProGlyValLys PheAsnTrp TyrValAsp GlyValGluVal HisAsnAla LysThrLys ProArgGluGlu GlnTyrAsn SerThrTyr
1001 CCACGAAGAC CCTGAGGTCA AGTTCAACTG GTACGTGGAC GGCGTGGAGG TGCATAATGC CAAGACAAAG CCGCGGGAGG AGCAGTACAA CAGCACGTAC
     ArgValValSer ValLeuThr ValLeuHis GlnAspTrpLeu AsnGlyLys GluTyrLys CysLysValSer AsnLysAla LeuProAla ProIleGluLys
1101 CGTGTGGTCA GCGTCCTCAC CGTCCTGCAC CAGGACTGGC TGAATGGCAA GGAGTACAAG TGCAAGGTCT CCAACAAAG CCTCCCAGCC CCCATCGAGA
     ThrIleSer LysAlaLys GlyGlnProArg GluProGln ValTyrThr LeuProProSer ArgGluGlu MetThrLys AsnGlnValSer LeuThrCys
1201 AAACCATCTC CAAGGCCAAA GGGCAGCCCC GAGAACCACA GGTGTACACC CTGCCCCCAT CCCGGGAGGA GATGACCAAG AACCAGGTCA GCCTGACCTG
     LeuValLys GlyPheTyrPro SerAspIle AlaValGlu TrpGluSerAsn GlyGlnPro GluAsnAsn TyrLysThrThr ProProVal LeuAspSer
1301 CCTGGTCAA GGCTTCTATC CCAGCGACAT CGCCGTGGAG TGGGAGAGCA ATGGGCAGCC GGAGAACAAC TACAAGACCA CGCCTCCCGT GCTGGACTCC
     AspGlySerPhe PheLeuTyr SerLysLeu ThrValAspLys SerArgTrp GlnGlnGly AsnValPheSer CysSerVal MetHisGlu AlaLeuHisAsn
1401 GACGGCTCCT TCTTCCTCTA CAGCAAGCTC ACCGTGGACA AGAGCAGGTG GCAGCAGGGG AACGTCTTCT CATGCTCCGT GATGCACGAG GCTCTGCACA
                                                                                                    BmtI
                                                                                                    NheI
     HisTyrThr GlnLysSer LeuSerLeuSer ProGlyLys *** (SEQ ID NO: 52)
1501 ACCACTACAC GCAGAAGAGC CTCTCCCTGT CTCCGGGTAA ATGAGTGCTA GCTGCCCAGA CATGATAAGA TACATTGATG AGTTTGGACA AACCACAACT
1601 AGAATGCAGT GAAAAAAATG CTTTATTTGT GAAATTTGTG ATGCTATTGC TTTATTTGTA ACCATTATAA GCTGCAATAA ACAAGTAAC AACAACAATT
                                                                                                    AseI
1701 GCATTCATTT TATGTTTCAG GTTCAGGGGG AGGTGTGGGA GGTTTTTTAA AGCAAGTAAA ACCTCTACAA ATGTGGTATG GAATTAATTC TAAAATACAG
1801 CATAGCAAAA CTTTAACCTC CAAATCAAGG CTCTACTTGA ATCCTTTTCT GAGGGATGAA TAAGGCATAG GCATCAGGGG CTGTTCCCAA TGTGCATTAG
```

```
1901  CTGTTTGCAG  CCTCACCTTC  TTTCATGGAG  TTTAAGATAT  AGTGTATTTT  CCCAAGGTTT  GAACTAGCTC  TTCATTTCTT  TATGTTTTAA  ATGGACTGAC
2001  CTCCCACATT  CCCTTTTTAG  GTTTAGTAGT  TAAAATATTC  AGAAATAATT  ATTGCAATGA  ACCTTTAATA  AATAAAATGT  TTTTTATTAG  GCAGAATCCA  GATGCTCAAG
2101  GCCCTTCATA  ATATCCCCCA  GTTTAGTAGT  TGGACTTAGG  GAACAAAGGA  ACCTTTAATA  GAAATTGGAC  AGCAAGAAAG  CGAGCTTCTA  GCTTATCCTC
2201  AGTCCTGCTC  CTCTGCCACA  AAGTGCACGC  AGTTGCCGGC  CGGGTCGCGC  CCCGCCCCCA  CAGGCGAACT  CGGCTGCTCG  CCGATCTCGG  TCATGGCCGG
2301  CCCGAGGCG   TCCCGGAAGT  TCGTGGACAC  GACCTCCGAC  ACAGCCGTC   CAGGCCGGC   CACCACCCC   AGGCCAGGGT  GTTGTCCGGC
2401  ACCACCTGGT  CCTGGACCGG  GCTGATGAAC  AGGGTCACGT  CGTCCCGGAC  CACACCGGCG  AAGTCGTCCT  CCACGAAGTC  CGGGAGAAC   CCGACCGGT
2501  CGGTCCAGAA  CTCGACCGCT  CCGGCGACGT  CGCGCCGACGT CGCGCCGACGT GAGCACCGGA  ACGGCACTGG  TCAACTTGGC  CATGATGGCT  CCTCCTGTCA  GGAGAGGAAA

AseI
                                                                                                         ~~~~~~~~
2601  GAGAGAGAAGG TTAGTACAAT  TGCTATAGTG  AGTTGTATTA  TACTATGCAG  ATATACTATG  CCAATGATTA  ATTGTCAAAC  TAGGGCTGCA  GGGTTCATAG
2701  TGCCACTTTT  CCTGCACTGC  CCATCTCCT   GCCCACCCTT  TCCCAGGCAT  AGACAGTCAG  TGACTTACCA  AACTCACAGG  AGGGAGAAGG  CAGAAGCTTG
2801  AGACAGACCC  GCCGGACCCC  CCAACTGCGA  GGGCACTTGG  CTAGGCGCGC  TTCTTTTATG  GTCCGCCGGC  CCTCGGAGGC  AGGCGCTCC   GGGAGCCTA
2901  GCGCCAATC   TGCCGTGGCA  GGAGGCGGGG  CCGAAGGCCG  TGCCTGACCA  ATCCGGAGCA  CATAGGAGTC  TCAGCCCCGC  GCCCCAAAGC  AAGGGAAGT
3001  CACCGCCTG   TAGCGCCAGC  TGCTTGTGAA  ATGGGGGCTT  GGGCCCCGTG  GCCCCTGACC  TAGTGTACTG  AAACTCCCAT  TGACGTCAAT  GGGGTGGAGA
3101  CTTGGAAATC  CCCGTGAGTC  AAACCGCTAT  CCACGCCCAT  TGATGTACTG  CCAAAACCGC  ATCATCATGG  TAATAGCGAT  GACTAATACG  TAGATGTACT
3201  GCCAAGTAGG  AAAGTCCCAT  AAGGTCATGT  ATGCCAAGCG  GGCCATTTAC  CGTCATTGAC  GTCAATAGGG  GGCGTACTTG  GCATATGATA
3301  CACTTGATGT  ACTGCCAAGT  GGGCAGTTTA  CCGTAAATAC  TCCACCCATT  GACGTCAATG  GAAAGTCCCT  ATTGGCGTTA  CTATGGGAAC  ATACGTCATT
3401  ATTGACGTCA  ATGGGCGGGG  GTCGTTGGGC  GGTCAGCCAG  GCGGGCCATT  TACCGTAAGT  TATGTAACGC  CTGCAGTTA   ATTAAGAACA  TGTGAGCAAA
3501  AGGCCAGCAA  AAGGCCAGGA  ACCGTAAAAA  GGACTATAA   AGATACCAGG  CGTTTCCCC   TGGAAGCTCC  CTCGTGTTCC  GACCCTGCCG  ACGCTCAAGT
3601  CAGAGGTGGC  GAAACCCGAC  CTTTCTCCCT  TCGGGAAGCG  TGGCGCTTTC  TCATAGCTCA  CGCTGTAGGT  ATCTCAGTTC  GGTGTAGGTC  GTTCGCTCCA  AGCTGGGCTG
3701  ACCTGTCCGC  CTTTCTCCCT  TCGGGAAGCG  TGGCGCTTTC  TCATAGCTCA  CGCTGTAGGT  ATCTCAGTTC  GGTGTAGGTC  GTTCGCTCCA  AGCTGGGCTG
3801  TGTGCACGAA  CCCCCCGTTC  AGCCCGACCG  CTGCGCCTTA  TCCGGTAACT  ATCGTCTTGA  GTCCAACCCG  GTAAGACACG  ACTTATCGCC  ACTGGCAGCA
3901  GCCACTGGTA  ACAGGATTAG  CAGAGCGAGG  TATGTAGGCG  GTGCTACAGA  GTTCTTGAAG  TGGTGGCCTA  ACTACGGCTA  CACTAGAAGA  ACAGTATTTG
4001  GTATCTGCGC  TCTGCTGAAG  CCAGTTACCT  TCGGAAAAAG  AGTTGGTAGC  TCTTGATCCG  GCAAACAAAG  ACCGCGTGT   AGCGGTGGTT  TTTTGTTTG
4101  CAAGCAGCAG  ATTACGCGCA  GAAAAAAAGG  ATCTCAAGAA  GATCCTTTGA  TCTTTTCTAC  GGGGTCTGAC  GCTCAGTGGA  ACGAAAACTC  ACGTTAAGGG
4201  ATTTTGGTCA  TGGCTAGTTA  ATTAACATTT  AAATCAGCGG  CCGCAATAAA  ATATCTTTAT  TTTCATTACA  TCTGTGTGTT  GGTTTTTTGT  GTGAATCGTA
4301  ACTAACATAC  GCTCTCCATC  AAAACAAAAC  GAAACAAAAC  AAACTAGCAA  AATAGGCTGT  CCCCAGTGCA  AGTGCAGGTG  CCAGAACATT  TCTCTATCGA
4401  A (SEQ ID NO: 79)
```

IL2ss.CCL2(5-76).hIgG1Fc GAGless plasmid sequence

```
   1  GGATCTGCGA TGCCTCCGGT GCCCTCAGT GCCCAGAGCG CACATCCCGC ACAGTCCCAG AGAAGTTGGG GGGAGGGCTC GGCAATTCAA CGGGTCCCTA
 101  GAGAAGTGG CCGGGGTAA ACTGGGAAAG TGATGTCGTG GCCCTTTTCC GCCTTTTCC GCAGGGTGGG GGAGAACCGT CTTCACGCGC ATATAAGTGC AGTAGTCGCC
 201  GTGAACGTTC TTTTTCGCAA CGGGTTGCC GCCAGAACAC CGGCTGAAGCT TCGAGGGCCA TCGCTCTC CGCATCGCGC CGGCCGCCCA ACTGAGGCC
 301  GCCATCCACG CGGCTTGAGT CGCCTTCTGC CGCCTCCGGC CGTGTGGTGCG TCCTGAACTG CGTCCGCCGT CTAGGTAAGT TTAAAGCTCA GGTCGAGACC
 401  CGGCCTTTGT CCCGGGCTCC CTTGGAGCCT ACCTAGCTC AGCCGGCTCT CCAGCCTTTG CCTGACCCTG CTGGCTCAAC TCTACGTCT TGTTTCGTT
                             KasI
                             NarI
                             SfoI
                             BbeI
                                                                                       IL-2 secretion signal
                                                                                       MetTyrArg MetGlnLeu LeuSerCysIle
 501  TCTGTCTGC GCCGTTACAA ATCCAAGCTG TGACCGGCGC CTACCCTGAGA TCACCGGGCA AGGAGGGCCA CCATGTACAG GATGCAACTC CTGTCTTGCA
                                         EcoRI
                                                                 ---- CCL2(5-76)
      AlaLeuSer LeuAlaLeu ValThrAsnSer IleAsnAla ProValThr CysCysTyrAsn PheThrAsn ArgLysIle SerValGlnArg LeuAlaSer
 601  TTGCACTAAG TCTTGCACTT GTCACGAATT CGATCAATGC CCCAGTCACC TGCTGTTATA ACTTCACCAA TAGGAAGATC TCAGTGCAGA GGCTCGGAG
      TyrArgArg IleThrSerSer LysCysProLys CysValVal IleCysAlaAsp ProLysGln LysTrpVal
      CTATAGAAGA ATCACCAGCA GCAAGTGTCC CAAAGAAGCT GTGATCTTCA AGACCATGT GGCCAAGCAG ATCTGGTGGCTG ACCCAAGCCA GAAGTGGGTT
                                                                    ---- human IgG1 Fc (constant region)
      GlnAspSerMet AspHisLeu ValThrHis ThrGlnThrPro LysThrAsp LysThrHis ThrCysProPro CysProAla ProGluLeu LeuGlyGlyPro
 801  CAGGATTCCA TGGACCACCT GGAACAAGCA ACCCAAACTC CGAAGACTGA CAAAACTCAC ACATGCCCAC CGTGCCCAGC ACCTGAACTC CTGGGGGGAC
      SerValPhe LeuPhePro ProLysProLys AspThrLeu MetIleSer ArgThrProGlu ValThrCys ValValVal AspValSerHis GluAspPro
 901  CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
      GluValLys PheAsnTrpTyr ValAspGly ValGluVal HisAsnAlaLys ThrLysPro ArgGluGlu GlnTyrAsnSer ThrTyrArg ValValSer
1001  TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
      ValLeuThrVal LeuHisGln AspTrpLeu AsnGlyLysGlu TyrLysCys LysValSer AsnLysAlaLeu ProAlaPro IleGluLys ThrIleSerLys
1101  GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
      AlaLysGly GlnProArg GluProGlnVal TyrThrLeu ProProSer ArgGluGluMet ThrLysAsn GlnValSer LeuThrCysLeu ValLysGly
1201  AAGCCAAAGG GCAGCCCCGA GAACCAGGTG TACACCCCT CCCCATCCC CGGGAGGAGA TGACCAAGAA CCAGGTCAGC CTGACCTGCC TGGTCAAAGG
      PheTyrPro SerAspIleAla ValGluTrp GluSerAsn GlyGlnProGlu AsnAsnTyr LysThrThr ProProValLeu AspSerAsp GlySerPhe
1301  CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
      PheLeuTyrSer LysLeuThr ValAspLys SerArgTrpGln GlnGlyAsn ValPheSer CysSerValMet HisGluAla LeuHisAsn HisTyrThrGln
1401  TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                                 BmtI
                                 NheI
      LysSerLeu SerLeuSer ProGlyLys***(SEQ ID NO: 53)
1501  AGAAGAGCCT CTCCCTGTCT CCGGGTAAAT GAGTGCTAGC TGGCCAGACA TGATAAGATA CATTGATGAG TTTGGACAAA CCAACACTAG AATGCAGTGA
1601  AAAAAATGCT TTATTTGTGA AATTTGTGAT GCTATTGCTT TATTTGTAAC CATTATAAGC TGCAATAAAC AAGTTAACAA CAACAATTGC ATTCATTTTA
                                                                                                   AseI
1701  TGTTTCAGGT TCAGGGGGAG GTGTGGGAGG TTTTTTAAAG CAACTAAAAC CTCTACAAAT GTGGTATGGA ATTAATTCTA AAATACACCA TAGCAAAACT
1801  TTAACCTCCA AATCAAGGGG CTACTTGAAT CCCTTTTCTGA GGGATGAATA AGGCATAGCC GTTGCCAATG ATCAGGGTGA ATCAGGGTGA GTTTGCAGCC
```

```
1901  TCACCTTCTT TCATGGAGTT TAAGATATAG TGTATTTTCC CAAGGTTTGA ACTAGCTCTT CATTTCTTA TGTTTTAAAT GCACTGACCT CCCACATTCC
2001  CTTTTAGTA AAATATTCAG AAATAATTTA GACTTAGGGA ACAAAGGAAC TGCAATGAAA ATAAATGTTT TTTATTAGGC AGAATCCAGA TGCTCAAGGC CCTTCATAAT

2101  ATCCCCCAGT TTAGTAGTTG CTATAGTGAG TTGCACGCAG TGGCACGCAG CCTCCGACCA CTCCGGCTAC AGCTCGTTCA CACCGCGCAC GCCAGGGTGT TGTCCGGCAC CACCTGGTCC
2201  CTGCCACAAA GTGCACGCAG TTGCCGGCCG CCTCCGACCA CTCCGGCTAC AGCTCGTTCA CACCGCGCAC GCCAGGGTGT TGTCCGGCAC CACCTGGTCC
2301  CCGGAAGTTC GTGGACACGA CCTCCGACCA CTCCGGCTAC AGCTCGTTCA CACCGCGCAC GCCAGGGTGT TGTCCGGCAC CACCTGGTCC
2401  TGGACGCGGC TGATGAACAG GGTCACGTCG TCCCGGACCA GTCGTCCTCC ACGAAGTCCC GGGAGAACCC GAGCCGGTCG GTCCAGAACT
2501  CGACCGCTCC GGCGACGTCG CGCACGGTGA GCACCGGAAC GGCACTGGTC AACTTGGCCA TGATTGGCTCC TCCTGTCAGG TCGGAGAACGA GAAGAAGGTT

AseI
2601  AGTACAAATG CTATAGTGAG TTGATTATA CTATGCAGAT ATACTATGCC AATGATTAAT TGTCAAACTA GGGCTGCAAGG GTTCATAGTG CCACTTTTCC
2701  TGGACTGCCC CATCTCCTGC CCACCCTTTC CCAGCCATAG ACAGTCAGTG CTCACAGGAG GGAGAAGGCA GAAGCTTGAG ACAGACCCGC
2801  TGGACCGCCG AACTGCGAGG GGACGTGGCT CTTTTATGGT GCGCCGCCCC TCGGAGGCAG GCGGCTCGGG GAGGCCTAGC GGCCAATCTG
2901  CGGTGGCAGG GAAGGGCCGC CCTGACCAAT AGGAGTCTC AGCCCCGGC ACTCCCATTG AGCTCAATGG GGGAAGTCA CGCGCCTGTA
3001  GCGCCAAGCG GTTGTGAAAT GGGGGCTTGG GCCCTGACTA GTCAAAACAA ACTCCCATTG ACGTCAATGG GTGGAGACT TGGAAATCCC
3101  CGTGAGTCAA ACCGCTATCC ATGTACTGCC AAAACTGCC CATCATGCAT ATAGCGATGA CTAATACGTA GATGTACTGC CAAGTAGGAA
3201  AGTCCCATAA GGTCATGTAC TGGGCATTAAT GCCAGGCGGG TCATTTACCG TCATTGACGT CGTACTTGGC ATATGATACA CTTGATGTAC
3301  TGCCAAGTGG GCAGTTTACC GTAAATACTC CACCCATTGA AAGTCCCTAT CAATTGACGT ATGGGAACAT ACGTCATTAT TGACGTCAAT
3401  GGGCGGGGGT CGTTGGGCGG TCAGCCAGGC GGGCCATTTA CCGTAAGTTA TGTAACGCCT GCAGGTAAT GCAGCATCAC TGAGCAAAAG GCCAGCAAAA
3501  AACCCAGGAAC CGTATAAAGG ATACCAGGCG TTTCCCCCTG GAAGCTCCCT GTGCGCTCT CCTGTTCCGA CCGGCTCCC TACCGGATAC CTGTCCGCCT
3601  TTCTCCCTTC GGGAAGCGTG GCGCTTTCTC ATAGCTCACG CTGTAGGTAT CTCAGTTCGG TGTAGGTCGT TCGCTCCAAG CTGGGCTGTG TGCACGAACC
3701  CCCGTTCAG CCCGACCGCT GCGCCTTATC CGGTAACTAT CGTCTTGAGT CCAACCGGT AAGACACAGAC TTATCGCCAC TGGCAGCAGC CACTGGTAAC
3801  AGGATTAGCA GAGCGAGGTA TGTAGGCGGT GCTACAGAGT TCTTGAAGTG GTGGCCTAAC AACAAACCA CCGCTGGTAG CGGTGGTTT TTTGTTTGCA AGCAGCAGAT
3901  TGCTGAAGCC AGTTACCTTC GGAAAAAGAG CTGAAGATAGAG TTGGTAGCTC TTGATCCGGG AAACAAACCA CCGCTGGTAG CGGTGGTTT TTTGTTTGCA AGCAGCAGAT
4001  TACGCGCAGA AAAAAAGGAT CTCAAGAAGA TCCTTTGATC TTTTCTACGG GGTCTGACGC TCAGTGGAAC GAAAACTCAC GTTAAGGGAT TTTGGTCATG
4101  GCTAGTTAAT TAACATTTAA ATCAGCGGCC GCAATAAAAT ATCTTTATTT TCATTACATC TGTGTGTTGG TTTTTGTGT GAATCGTAAC TAACATACGC
4201  TCTCCAATCAA AACAAAACGA AACAAAACAA ACTAGCAAAA TAGGCTGTCC CCAGTGCAAG TGCAGGTGCC AGAACATTTC TCTATCGAA    (SEQ ID NO: 80)
```

IL2ss.CCL2(5-76).hIgG1Fc sequence [Alanine substitutions for removal of GAG binding sites – Lys & His]

```
   1  GGATCCCCGA TCGCTCCGGT GCCCGTCAGT GGGCAGAGCC CACATCGCCC ACAGTCCCCG AGAAGTTGGG GGGAGGGG

```
1901 TCACCTTCTT TCAATGGAGTT TAAGATATAG TGTATTTTCC CAAGGTTTGA ACTAGCTCTT CATTTCTTTA TGTTTTAAAT GCACTGACCT CCCACATTCC
2001 CTTTTTAGTA AAATATTCAG AATATAATTTA GACTTAGGGA AATACATCAT TGCAATGAAA ATAAATGTTT TTTATTAGGC AGAATCCAGA TGCTCAAGGC CCTTCATAAT
2101 ATCCCCAGT TTAGTAGTTG GACTTAGGGA ACAAAGGAAC CTTTAATAGA AATTGGACAG CAAGAAAGCG AGCTTCTAGC TTATCCTCAG TCCTGCTCCT
2201 CTGCCACAAA GTGCACGCAG TTGCCGGCCG GGCGAACTCC CGCTCGGCAG GCTGCTCGCC GATCTCGGTC ATGGCCCGCC GGGAGGCGTC
2301 CCGGAAGTTC GTGGACACGA CCTCCGACCA CTCGGCGTAC AGCTCGTCCA GGCCGCGCAC CCACACCCAG GCCAGGGCAC TGTCCGGCAC CACCTGGTCC
2401 TGGACCGCGC TGATGAACAG GGTCAGTCG TCCCGGACCA GTCGTCCTCC ACGAAGTCCC GGGAGAACCC GAGCCGTCG GTCCAGAACT
2501 CGACCGCTCC GGCGACGTCG CGCGCGGTGA GCACCGGAAC AACTTGCCA TGATGGCTCC TGGTCTCAGG TCCTGTCAGG AGAGGAAAGA GAAGAAGTT
                                                                    AseI
2601 AGTACAATTG CTATAGTGAG TTGTATTATA CTATGCAGAT AATGATTAAT TGTCAAACTA GGGCTGCAGG GTTCATAGTG CCACTTTCC
2701 TGCACTGCCC CATCTCCTGC CCACCCTTTC CCAGGCATAG ACAGTCAGTG ACTTACCAAA CTCACAGGAG GGAGAAGGCA GAAGCTTGAG ACAGACCCGC
2801 GGGACCGCCG AACTTAGAAGG GGACGTTGCTT AGGGCCGGCG CTTTTATGGT GCCGCGGCC TCGGAGGCAA GGCGCTCGGG GAGGCCTAGG GGCCAATCTG
2901 CGGTGGCAGG AGGCGGGCC GAAGGCCGTG CCTGACCAAT CCGGAGCACA TAGGAGTCTC AGCCCCCGC GGGAAGTCA CGGCCTGTA
3001 GCGCCAGCGT GTTGTGAAAT GGGGCCTTGG GCCCTGACTA GTCAAAACAA ACTCCCCATTG ACGTCAATGG GGTGGAGACT TGGAATCCC
3101 CGTGAGTCAA ACCGCTATCC ACGCCTATTG ATGTACTGCC AAAACCGCAT CATCATGGTA ATAGCGATGA CTAATACGTA GATGTACTGC CAAGTAGGAA
3201 AGTCCCATAA GGTCATGTAC TGGGCATAAT GCCAGGCGGG CCATTTACCG TCAATTGACGT CGTACTTGGC ATATGATACA CTTGATGTAC
3301 TGCCAAGTGG GCAGTTTACC GTAATACTC CACCCATTGA CGTCAATGGA CCGTTAACGT ATGGGAACAT AAGCTCATTAT TGACGTCAAT
3401 GGGCGGGGG CGTTGGGCGG TCAGCCAGGC GGGCGTTTTC CCGGTTTTC CCATAGGCTCC TGTAACGCCT AAAAATCGAC GCTCAAGTCA GAGGTGGCGA
3501 GCCCGGGAAC CGTAAAAAGG GACTATAAAG TTTCCCCCTG GAAGCTCCCT CCTGTTCCGA CCCTGCCCT TACCGGATAC CTGTCCGCCT
3601 AACCCGACAG GACTATAAAG ATACCAGGCG GCGCTTTCTC ATAGCTCACG CTGTAGGTAT CTCAGTTCGG TGTAGGTCGT TCGCTCCAAG CTGGGCTGTG TGCACGAACC
3701 TTCTCCCTTC GGGAAGCGTG GCGCTTTCTC ATAGCTCACG CGGCCTTATC CGGCCTTATC CGGTAACTAT CGTCTTGAGT AAGACACGAC TTATCGCCAC TGGCAGCAG CACTGGTAAC
3801 CCCCGTTCAG CCCGACCGCT GCGCCTTATC CGGTAACTAT CGTCTTGAGT TCTTGAAGTG GTGGCCTAAC TACGGCTACA CTAGAAGAAC AGTATTTGGT ATCTGCGCTC
3901 AGGATTAGCA GAGCGAGGTA TGTAGGCGGT GCTACAGAGT TTGGTAGCTC TTGATCCGGC AAACAAACCA CCGCTGGTAG CGGTGGTTT TTTGTTTGCA AGCAGCAGAT
4001 TGCTGAAGCC AGTTACCTTC GGAAAAAGAG CTCAAGAAGA TCCTTTGATC TTTTCTACGG GGTCTGACGC TCAGTGGAAC GAAAACTCAC GTTAAGGGAT TTTGGTCATG
4101 TACGCGCAGA AAAAAGGAT CTCAAGAAGA TCCTTTGATC TTTTCTACGG GGTCTGACGC TCAGTGGAAC GAAAACTCAC GTTAAGGGAT TTTGGTCATG
4201 GCTAGTTAAT TAACATTTAA ATCAGCGGCC GCAATAAAAT ACTAGCAAAA TCATTACATC TGTGTGTTGG TTTTTTGT GAATCGTAAC TAACATAGC
4301 TCTCCATCAA AACAAAACGA AACAAAACAA ACTAGCAAAA TAGGCTGTCC CCAGTGCAAG TGCAGGTGCC AGAACATTTC TCTATCGAA (SEQ ID NO: 81)
```

H2ss.CCL7.hIgG1Fc sequence

```
   1  GGATCTGCGA TCGCTCCCGT GCCCGTCAGT GGGCAGAGCG CACATGCCCC ACAGTCCCCG AGAAGTTGGG GGGAGGGGTC GGCAATTGAA CGGGTGCCTA
 101  GAGAGGTGG  CGCGGGGTAA ACTGGGAAAG TGATGTCGTG TACTGGCTCC GCCTTTTCC  GGAGCGGCTC TCGAGCCGCG CGAGGGTGGG GGAGAACCGT AGTAGTGCC
 201  GTGAACGTTC TTTTTCGCAA GCCAGAACAC GCCAGAAGCT TCGAAGCT   TCGAACCG   TCGAACTCTC CCCATCCTC CTTCACGCGC CCCCCCCCT ACCTGAGCGC
 301  GCCATCCACG CGGTTGAGT  CGGTTCTGC  CGGTTCTGC  CTGTGGTGCC CTGCCCGCGT TCGCCGCT   CTAGCTAGGT TAAAGCTCA GGTCGAGACC
 401  GGGCCTTTGT CCGGCGCTCC CTTGGAGCCT ACCTAGACTG AGCCGGCTCT AGCCGGCTCT CCACCGCTTTG CCTGACCCTG CTTGCTCAAC TCTACGTCTT TGTTTCGTTT
                              KasI
                              NarI
                              SfoI
                              BbeI
                                                                                                       IL-2 secretion signal
                                                                                              MetTyrArg MetGlnLeu LeuSerCysIle
 501  TCTGTTCTGC GCCGTTACAG ATCCAAGCTG TGACCCGCGC CTACCTGAGA TCACCGGCGA AGGAGGGCCA CATGTACAG  GATGCAACTC CTGTCTTGCA
                              EcoRI
                                          ~~~~~~~ CCL7 (1-76)
       AlaLeuSer LeuAlaLeu ValThrAsnSer CysCysTyr ArgPheIle AsnLysIle ProLysGln ArgLeuGlu SerTyrArg ThrThrSer
 601  TTGCACTAAG TCTTGCACTT GTCACGAATT CGTGCTGCTA CAGATTTATC AATAAGAAAA TCCCTAAGCA GAGGCTGGAG AGCTACAGA GGACCACCAG
       SerHisCys ProArgGluAla ValIlePhe LysThrLys LeuAspLysGlu IleCysAla AspProThr GlnAspPhe MetLysHis
 701  TAGCCACTGT CCCCGGGAAG CTGTAATCTT CAAGACAAA CTGGACAAG  AGATCTGTGC TGACCCCACA CAGAAGTGGG TCCAGGACTT TATGAAGCAC
       LeuAspLysLys ThrGlnThr ProLysThr AspLysHis ThrCysPro ProCysPro AlaProGluLeu LeuGlyGly ProSerVal PheLeuPhePro
 801  CTGGACAAGA AAACCCAAAC TCCAAAGACT GACAAACAC  ACATGTCCA  CCGTGCCCA  GCACCTGAAC TCCTGGGGG  ACCGTCAGTC TTCCTCTTCC
                                                                                       human IgG1 Fc (constant region)
       ProLysPro LysAspThr LeuMetIleSer ArgThrPro GluValThr CysValVal ValAspValSer HisGluAsp ProGluValLys PheAsnTrp
 901  CCCAAAACCC AAGGACACC CTCATGATCT CCCGGACCCC TGAGGTCACA TGCGTGGTGG TGGACGTGAG CCACGAAGAC CCTGAGGTCA AGTTCAACTG
       TyrValAsp GlyValGluVal HisAsnAla LysThrLys ProArgGluGlu GlnTyrAsn SerThrTyr ArgValValSer ValLeuThr ValLeuHis
1001  GTACGTGGAC GGCGTGGAGG TGCATAATGC CAAGACAAAG CCGCGGGAGG AGCAGTACAA CAGCACGTAC CGTGTGGTCA GCGTCCTCAC CGTCCTGCAC
       GlnAspTrpLeu AsnGlyLys GluTyrLys CysLysValSer AsnLysAla LeuProAla ProIleGluLys ThrIleSer LysAlaLys GlyGlnProArg
1101  CAGGACTGGC TGAATGGCAA GGAGTACAAG TGCAAGGTCT CCAACAAAGC CCTCCCAGCC CCCATCGAGA AAACCATCTC CAAGCCAAA  GGGCAGCCCC
       GluProGln ValTyrThr LeuProProSer ArgGluGlu MetThrLys AsnGlnValSer LeuThrCys LeuValLys GlyPheTyrPro SerAspIle
1201  GAGAACCAA GGTGTACACC CTGCCCCCAT CCCGCGAAGA GATGACCAAG AACCAGGTCA GCCTGACCTG CCTGGTCAAA GGCTTCTATC CCAGCGACAT
       AlaValGlu TrpGluSerAsn GlyGlnPro GluAsnAsn TyrLysThrThr ProProVal LeuAspSer AspGlySerPhe PheLeuTyr SerLysLeu
1301  CGCCGTGGAG TGGGAGAGCA ATGGGCAGCC GGAGAACAAC TACAAGACCA CGCCTCCCGT GCTGGACTCC GACGGCTCCT TCTTCCTCTA CAGCAAGCTC
       ThrValAspLys SerArgTrp GlnGlnGly AsnValPheSer CysSerVal MetHisGluAla LeuHisAsn HisTyrThr GlnLysSer LeuSerLeuSer
1401  ACCGTGGACA AGAGCAGGTG GCAGCAGGGG AACGTCTTCT CATGCTCCGT GATGCACGAG GCTCTGCACA ACCACTACAC GCAGAAGAGC CTCTCCCTGT
                 EntI
                 NheI
       ProGlyLys ***(SEQ ID NO: 55)
1501  CTCCCGGTAA ATGAGTGCTA AGCAAGTAAA GCTGGCCAGA CATGATAAGA TACATTGATG AGTTTGGACA AACCACAACT AGAATGCAGT GAAAAAAATG CTTTATTTGT
1601  GAAATTTGTG ATGCTATTGC TTTATTTGTA AGCAAGTAAA ACCATTATAA GCTGCAATAA ACAAGTTAAC AACAACAATT GCATTCATTT TATGTTTCAG GTTCAGGGGG
                                                                                       AseI
1701  AGGTGTGGGA GGTTTTTTAA AGCAAGTAAA ACCTCTACAA GAATAATTC  GAATCGTATG ATGTGGATAA TGTGCAGGGG TAAAATACAG CTTAACCCTC CAAATCAAGC
1801  CTCTACTTGA ATCCTTTTCT GAGGGATGAA TAAGGCATAG GCATCAGGGG CTGTTGCCAA TGTGCATTAA CTGTTTGCAG CATAGCAAAA CCCTCACCTTC TTTCATGGAG
```

```
1901  TTTAAGATAT AGTGTATTTT CCCAAGGTTT GAACTAGCTC TTCATTTCTT TATGTTTTAA ATGCACTGAC CTCCCACATT CCCTTTTTAG TAAAATATTC
2001  AGAAATAATT TAAATACATC ATTGCAATGA AAATAAAATGT TTTTTATTAG GCAAGAAAAG GATGCTCAAG GCCCTTCATA ATATCCCCCA GTTTAGTAGT
2101  TGGACTTAGG GAACAAAGGA ACCTTTAATA GAAATTGGAC AGCAAGAAAG CGAGCTTCTA GCTTATCCTC AGTCCTGCTC CTCTGCCACA AAGTGCACGC
2201  AGTTGCCGGC CGGGTCGCGC AGGGCGAACT CCCCCCCCCA CGGCTCCTCG CCGATCTCGG TCATGGCCGG CCCGGAGGCG TCCCGGAAGT TCGTGGACAC
2301  GACCTCCGAC CACTCGGCGT ACAGCTCGTC CAGGCCCCGC ACCCACACCC AGCCCAGGGT GTTGTCCGGC ACCACCTGGT CCTGGACCCC GCTGATGAAC
2401  AGGGTCACGT CGTCCCGGAC CACACCGGCG AAGTCGTCCT CCACGAAGTC CCGAGCCGGT CGGTCCAGAA CTCGACCGCT CCGGCGACGT
2501  CGCGCGCGGT GAGCACCGGA ACGGCACTGG TCAACTTGGC CATGATGGCT CCTCCTGTCA GAGAAGAAGG TTAGTACAAT TGCTATAGTG

2601  AGTTGTATTA TACTTATGCAG ATATACTATG ATTGTCAAAC ATTGCACTGA GGGTTCATAG TGCCACTTTT CCTGCACTGC CCCATCTCCT
                    AseI
2701  GCCCACCCTT TCCCAGGCAT ATTGCAATGA ACTTCACAGG AACTCACAGG CAGAAGCTTG AGACAGACCC GCGGGACCGC CGAACTGCGA
2801  GGGGACGTGG CTAGGGCGGC TTCTTTTATG GTGCGCCGGC CCTCGGAGGC AGGGCGCTCG GGGAGGCCTA GCGGCCAATC TCCGGTGGCA GGAGGCGGGG
2901  CCGAAGGCCG TGCCTGACCA CATAGGAGTC TCAGGGAGTC GCCCCAAAGG AAGGAAGT CACGCGCCTG TAGGCGCCTG CCCGTGAGTC GTGTTGTGAA
3001  ATGGGGCTT GGGGGGGTTG GGCCCCTGAC TAGTCAAAAA AAACTCCCAT GGGGTGGAGA CTTGGAAATC CCCGTGAGTC AAAGTCCCAT AACCGCTAT
3101  CCACGCCCAT TGATGTACTG CCAAAACCGC ATCATCATGG TAATAGCGAT TAGATGTACT GCCAAGTAGG AAAGTCCCAT AAGGTCATGT
3201  ACTGGGCATA ATGCCAGGCG GGCCATTTAC CGTCATTGAC GTCAATAGGG GGCGTACTTG CACTTGATGT ACTGCCAAGT GGGCAGTTTA
3301  CCGTAAATAC TCCACCCATT GACGTCAATG GAAAGTCCCT ATTGGGCGTTA CTATGGGAAC ATACGTCATT ATTGACGTCA ATGGGCGGGG GTCGTTGGGC
3401  GGTCAGCCAG GCGGGCCATT TACCGTAAGT TATGTAACGC CTGCAGTTA GACGAGCATC ACAAAAATCG TGTGAGCAAA AGGCAGCAA AAGGCCAGGA ACCGTAAAA
3501  GCGCCGTTG CTGGCGTTTT TCCATAGGCT CCGCCCCCCT CTCGTGTTCC GACCCTGCCG CTTACCGGAT ACCTGTCCGC CTTTCTCCCT TCGGGAAGCG
3601  AGATACCAGG CGTTTCCCCC TGGAAGCTCC CTCGTGCGCT CTCCTGTTCC GACCCTGCCG AGCTGGGCTG TGTGCACGAA CCCCCGTTC AGCCGACCG
3701  TGGCGCTTTC TCATAGCTCA CGCTGTAGGT ATCGTCAGTC GGTGTAGGTC GTTCGCTCCA AGCTGGGCTG TGTGCACGAA ACCTGGAAGT TCGGGAAGCG
3801  CTGCGCCTTA TCCGGTAACT ATCGTCTTGA GTCCAACCCG GTAAGACACG ACTTATCGCC ACTGGCAGCA ACAGTATTTG GTATCTGCGC CCAGTTACCT
3901  TATGTAGGCG GTGCTACAGA GTTCTTGAAG TGGTGGCCTA CTACGGCTA CACCGCTGGT AGCGGTGGTT TTTTTGTTG GTATCTGCGC CCAGTTACCT
4001  TCGGAAAAAG AGTTGGTAGC TCTTGATCCG GCAAACAAAC CACCGCTGGT AGCGGTGGTT TTTTTGTTG CAAGCAGCAG ATTACGCGCA GAAAAAAAGG
4101  ATCTCAAGAA GATCCTTTGA TCTTTTCTAC GGGGTCTGAC GCTCAGTGGA ACGAAAACTC ACGTTAAGGG ATTTTGGTCA TGCTAGTTA ATTAACATTT
4201  AAATCAGCGG CCGCAATAAA ATATCTTTAT TTTCATTACA TCTGTGTGTT GGTTTTTTGT GTGAATCGTA ACTAACATAC GCTCTCCATC AAAACAAAAC
4301  GAAACAAAAC AAACTAGCAA AATAGGCTGT CCCCAGTGCA AGTGCAGGTG CCAGAACATT TCTCTATCGA A  (SEQ ID NO: 82)
```

IL2ss.CCL7(5-76).hIgG1Fc sequence

```
   1 GGATCTCGGA TGCCTCCGGT GCCGTCAGT GGGCAGAGCG CACATCGCCC ACAGTCCCGC AGAAGTTGGG GGGAGGGGTC GGCAATTGAA CGGGTGCTA
 101 GAGAAGGTGG CCGGGGGTAA ACTGGGAAAG TGATGTCGTG GCCAGAACAC CGGTTATCAA AGCTGAAGCT TCGAGGGGCT CGCACTCTC CTTCACGCGC CCGCCGCCC AGTAGTGCC
 201 GTGAACGTTC TTTTTCGCAA CGGGTTTGCC GCGGTTCTGC CGCCTCCGC CTGTGGTGCC TCCTGAACTG CGTCGGCGT CTAGGTAAGT CTTAAGCTCA GGTCAGACC
 301 GCCATCCACG CCGGTTGAGT GCGGTTCTGC AGCCGGCTCC CCTAGACCT AGCCGGCTCT AGCCGGCCCTC TCCAAGCCCTG CTTGCTCAAC TCTACGTCTT TGTTTGCTTT
 401 GGGCCTTTGT CCGGCGCTCC

501 TCTGTTCTGC GCCGTTACAG ATCCAAGCTG TGACCGGCGC CTACCTGAGA AGGAGGGCA CCATGTACAG GATGCAACTC CTGTCTTGCA
                                                                         MetTyrArg MetGlnLeu LeuSerCysIle
                          KasI
                          NarI
                          SfoI
                          BbeI                                             IL-2 secretion signal
                          EcoRI          ~~~~~~~~~~ CCL7 (5-76)

601 TTGCACTAAG TCTTGCACTT GTCACGAATT CGTTTATCAA TAAGAAAATC CCTGAACGAA GGCTGGAGAG CTACAGAAGG ACCACCAGTA GCCACTGTCC
     AlaLeuSer LeuAlaLeu ValThrAsnSer PheIleAsn LysLysIle ProLysAsn ArgLeuGluSer TyrArgArg ThrThrSer HisCysPro

701 CGGGAAGCT GTAATCTTCA AGACCAAGTG AGCAAGGAG ATCTGTGCTG ACCCACACA GAAGTGGGTC CAGGACTTTA TGAAGCACCT GGACAAGAAA
     ArgGluAla ValIlePheLys ThrLysVal SerLysGlu IleCysAlaAsp ProThrGln LysTrpVal GlnAspPheMet LysHisLeu AspLysLys
                                                        human IgG1 Fc (constant region)

801 ACCCAAACTC CAAAACCTGA CAAAACTCAC ACATGCCCAC CGTGCCCAGC ACCTGAACTC CTGGGGGGAC CGTCAGTCTT CCTCTTCCCC CCAAAACCCA
     ThrGlnThr LysLeuAsp LysThrHis ThrCysProPro CysProAla ProGluLeu LeuGlyGlyPro SerValPhe LeuPhePro ProLysProLys

901 AGGACACCCT CATGATCTCC CGGACCCCTG AGGTCACATG CGTGGTGGTG GACGTGAGC CACGAAGACC CTGAGGTCAA GTTCAACTGG TACGTGGACGG
     AspThrLeu MetIleSer ArgThrProGlu ValThrCys ValValVal AspValSerHis GluAspPro GluValLys PheAsnTrp TyrValAspGly

1001 CGTGGAGGTG CATAATGCCA AGACAAAGCC GCGGGAGGAG CAGTACAACA GCACGTACCG TGTGGTCAGC GTCCTCACC GTCCTGCACC AGGACTGGCTG
     ValGluVal HisAsnAlaLys ThrLysPro ArgGluGlu GlnTyrAsnSer ThrTyrArg ValValSer ValLeuThrVal LeuHisGln AspTrpLeu

1101 AATGGCAAGG AGTACAAGTG CAAGGTCTCC AACAAAGCCC TCCCAGCCCC CATCGAGAAA ACCATCTCCA AAGCCAAAGG CCAGCCCCGA GAACCACAGG
     AsnGlyLysGlu TyrLysCys LysValSer AsnLysAlaLeu ProAlaPro IleGluLys ThrIleSerLys AlaLysGly GlnProArg GluProGlnVal

1201 TGTACACCCT GCCCCCATCC CGGGAGGAGA TGACCAAGAA CCAGGTCAGC CTGACCTGCC TGGTCAAAGG CTTCTATCCC AGCGACATCG CCGTGGAGTG
     TyrThrLeu ProProSer ArgGluGluMet ThrLysAsn GlnValSer LeuThrCysLeu ValLysGly PheTyrPro SerAspIleAla ValGluTrp

1301 GGAGAGCAAT GGGCAGCCGG AGAACAACTA CAAGACCACG CCTCCCGTGC TGGACTCCGA CGGCTCCTTC TTCCTCTACA GCAAGCTCAC CGTGGACAAG
     GluSerAsn GlyGlnProGlu AsnAsnTyr LysThrThr ProProVal LeuAspSerAsp GlySerPhe PheLeuTyrSer LysLeuThr ValAspLys

1401 AGCAGGTGGC AGCAGGGGAA CGTCTTCTCA TGCTCCGTGA TGCATGAGGC TCTGCACAAC CACTACACGC AGAAGAGCCT CTCCCTGTCT CCGGGTAAAT
     SerArgTrpGln GlnGlyAsn ValPheSer CysSerVal MetHisGluAla LeuHisAsn HisTyrThr GlnLysSerLeu SerLeuSer ProGlyLys***
                                                                                                      (SEQ ID NO: 56)

1501 GAGTGCTAGC TGGCCAGACA TGATAAGATA CATTGATGAG TTTGGACAAA CCACAACTAG AATGCAGTGA AAAAAATGCT TTATTTGTGA AATTTGTGAT
1601 GCTATTGCTT TATTTGTAAC CATTATAAGC TGCAATAACA AAGTTAACAA CAACAATTGC ATTCATTTTA TGTTTCAGGT TCAGGGGGAG GTGTGGGAGG
            EmcI                                   AseI
            NheI
1701 TTTTTTAAAG CAAGTAAAAC CTCTACAAAT GTGGTATGGA ATTAATTCCA AAATACAGCA TAGCAAAACT TTAACCTCCA AATCAAGCCT CTACTTGAAT
```

```
1801  CCTTTTCTGA GGGATGAATA AGGCATAGGC ATCAGCGGCT CTTGCCAATG TGCATTAGCT TCACCTTCTT CTTTGCAGCC TCACCTTCTT TCATCCAGTT TAAGATATAG
1901  TGTATTTTCC CAAGGTTTGA ACTAGCTCTT CATTTCTTTA TGTTTTAAAT GCACTGACCT CCCACATTCC CTTTTTAGTA AAATATTCAG AAATAATTTA
2001  AATACATCAT TGCAATGAAA ATAAATGTTT TTTATTAGGC AGAATCCAGA TGCTCAAGGC TTATCCTCCT CCTGCTCCT CTGCCACAAA GTGCACGCAG TTAGTAGTTG GACTTAGGGA
2101  ACAAAGGAAC CTTTAATAGA AATTGGACAG CAAGAAAGCG AGCTTCTAGC ATGGCCGGCC CGGAAGGGTC CGGAAGTTC GTGGACACGA CCTCCGACCA
2201  GGTCGCGCAG GGCGAACTCC CGCCCCCACG GCTGCTCGCC GATCTCGGTC GCCAAGTGT CACCTGGTCC CACCCGGTGT TGATGAACAG GGTCACGTCG
2301  CTCGGCGTAC AGCTCGTCCA CGCCCGCGCA CCCAACCCAG GCCAAGTCCC ACGAAGTCCC GAGCCGGTCG GTCCAGAACT GGGACGTCG CGGCGGTGA
2401  TCCGGACCA CACCGGCGAA GTCGTCCTCC ACGAAGTCCC GAGCCGGTCG GTCCAGAACT GGGACGTCG CGGCGGTGA
2501  GCACCGGAAC GGCACTGGTC AACTTGGCCA TGATGGCTCC TCCTGCTCAG AGAGAAAGA GAAGAAGGTT AGTACAATTG CTATAGTGAG TTGTATTATA
                              AseI
2601  CTATGCAGAT ATACTATGCC AATGATTAAT TGTCAAACTA GGGCTGCAGG GTTCATAGTG CCACTTTTCC TGCACTGCCC CATCCCTGC CCACCCTTTC
2701  CCAGGCATAG ACAGTCAGTG CTTTTATGGT GCGCCCGGCCC TCGGAGCCAG GGCGCTCGGG GAGGCTAGC CGCCAATCTG AGGCGGCCC GAAGGCCGTG
2801  AGGCGGGCTT CTTTTATGGT GCGCCCGGCCC TCGGAGCCAG GGCGCTCGGG GAGGCTAGC CGCCAATCTG AGGCGGCCC GAAGGCCGTG
2901  CCTGACCAAT CCGGAGCACA TAGGAGTCTC AGCCCCCGC CCCAAAGCAA GGGAAGTCA CGGCCAGCGT GTTGTCAAAT GGGGGCTTGG
3001  GGGGTTGGG GCCCTGACTA GTCAAAACAA ACTCCCATTG ACGTCAATGG GTGGAGACT TGGAAATCGC CGTGAGTCAA ACCCGCTATCC ACGCCCATTG
3101  ATGTACTGCC AAAACCCCAT CATCATGGTA ATAGCGATGA CTAATACGTA GATGTACTGC CAAGTAGGAA AGTGATGTAC CTTGATGTAC TGGGCATAAT
3201  GCCAAGCGGG CCATTTACCG TCATTGACGT CAATAGGGGG CGTACTTTGC AATGATACA ATATGACGTA TGCCAAGTGG GCAGTTTACC GTAAATACTC
3301  CACCATTGA CGTCAATGGA AAGTCCCTAT TGGCGTTACT ATGGAACAT ACGTCAATAT GGACGTCAAT GGGCGGGT CGTGGGGCG TCAGCCAGGC
3401  GGGACTTTA CGGTAGTTA TGTAACGCCT GCAGGTTAAT TAAGAACATG TGAGCAAAAG GCCAGCAAAA GGCCAGGAAC CGTAAAAAGG CCGCGTTGCT
3501  GGCGTTTTTC CATAGGCTCC GCCCCCCTGA CGAGCATCAC CGAAAATCGA AAAAATCGAC GCTCAAGTCA GAGGTGGCGA AACCCGACAG ATACCAGGCG
3601  TTTCCCCCTG GAAGCTCCCT CGTGCGCTCT CCTGTTCCGA CCCTGCCGCT TACCGGATAC CTGTCCGCCT TCTCCCTTC GGGAAGCGTG GCGCTTTCTC
3701  ATAGCTCACG CTGTAGGTAT CTCAGTTCGG TGTAGGTCGT TCGCTCCAAG CTGGGCTGTG TGCACGAACC CCCGACCGCT GCGCCTTATC
3801  CGGTAACTAT CGTCTTGAGT CCAACCCGGT AAGACACGAC TTATCGCCAC TGGCAGCAGC CACTGGTAAC AGGATTAGCA GAGCGAGGTA TGTAGGCGGT
3901  GCTACAGAGT TCTTGAAGTG GTGGCCTAAC TACGGCTACA CTAGAAGAAC AGTATTTGGT ATCTGCGCTC TGCTGAAGCC AGTTACCTTC GGAAAAAGAG
4001  TTGGTAGCTC TTGATCCGGC AAACAAACCA CCGCTGGTAG CGGTGGTTTT TTTGTTTGCA AGCAGCAGAT TACGCGCAGA AAAAAGGAT CTCAAGAAGA
4101  TCCTTTGATC TTTTCTACGG GGTCTGACGC TCAGTGGAAC GAAAACTCAC GTTAAGGGAT TTTGGTCATG AGATTATCAA TAACATTTAA ATCAGCGGCC
4201  GCAATAAAAT ATCTTATTT TCATTACATC TGTGTGTTGG TTTTTTGTGT GAATCGTAAC TAACATACGC TCTCCATCAA AACAAAACAA
4301  ACTAGCAAAA TAGGCGTGTCC CCAGTGCAAG TGCAGGTGCC AGAACATTTC TCTATCGAA  (SEQ ID NO:83)
```

IL2ss.CCL7(5-76).hIgG1Fc sequence
[Alanine substitutions for removal of GAG binding sites – Lys & His]

```
   1 GGACTGCGA TCGCTCCGGT GCCGCAGCC GCACAGAGCG CACATGCCCC ACAGTCCCCG AGAAGTGGG GGGAGGGGTC GGCAATTGAA CGGGTGCCTA
 101 GAGAAGGTGG ACTGGGGTAA CGGGGCTCC TGATGTCGTG T

```
1701  TTTTTTAAAG CAAGTAAAAC CTCTACAAAT GTGGTATGGA ATTAATTCTA AAATACAGCA TAGCCAAAACT TTAACCTCCA AATCAAGCCT CTACTTGAAT
1801  CCTTTTCTGA GGGATGAATA AGGCATAGGC ATCAGGGGCT GTTGCCAATG TGCATTAGCT GTTTGCAGCC TCACCTTCTT TCATGGAGTT TAAGATATAG
1901  TGTATTTTCC CAAGGTTTGA ACTAGCTCTT CATTTCTTTA TGTTTTAAAT GCACTGACCT CCCACATTCC CTTTTTAGTA AAATATTCAG AAATAATTTA
2001  AATACATCAT TGCAATGAAA ATAAATGTTT TTTATTAGGC AGAATCCAGA TGCTCAAGGC CCTTCATAAT ATCCCCCAGT TTAGTAGTTG GACTTAGGGA
2101  ACAAAGGAAC CTTTAATAGA AATTGCACAG CAAGAAAGCC AGCTTCTAGC AGTTCCTCAG CCGGAAGCGT CTGCCACCAG GTGCACGCAG TTGCCGGCCG
2201  GGTCGCGCAG GGCGAACTCC CGCCCCCACG GCTGCTCGCC GATCTCGGTC ATGGCCGGCC CGGAGGCGCC CACCTGGTGC CCGAAGTTC GTGGACACGA CCTCCGACCA
2301  CTCGGCGTAC AGTCGTCCA CACCGGCGAA GGCCCGGCAC GCCAGGGTGT GTCCGGCAC GGGAGAACCC GAGCCGGTCG CACCTGGTCC TGGATGAACAG GGTCACGTCG
2401  TCCCGGACCA CACCGGCGAA GTCGTCCTCC ACGAAGTCCC ACGAAGTCCC GGGAGAACCC GAGCCGGTCG GTCCAGAACT CGACCGCTCC CGACGACGTCC CGCGCGGTGA
2501  GCACCGGAAC GGCACTGGTC AACTTGGCCA TGATGGCTCC TCCTGTCAGG AGAGGAAAGA GAAGAAGTT AGTACAATTG CTATAGTGAG TTGTATTATA
             AseI
2601  CTATGCAGAT ATACTATGCC AATGATTAAT TGTCAAACTA GGGCTGCAGG GTTCATAGTG CCACTTTTTC TGCACTGCCC CATCTCCTGC CCACCCTTTC
2701  CCAGGCATAG ACAGTCAGTG ACTTACCAAA CTTCACAGGAG GAGAAGGCA GAAGCTTGAG ACAGACCCGC GGACGCGCCG AACTGCGAGG GGACGTGGCT
2801  AGGGCGCTT CTTTTATGGT CCGCCGGCCC TCGGAGGCAG GCGCTCGGG GAGGCCTAGC CCAATCTG CGGTGGCAGG CGGTGGCAGG AGGCGGGGCC GAAGGCCGTG
2901  CCTGACCAAT CCGGAGCACTC TAGGAGTCTC AGCCCCCCGC CCCAAAGCAA GGGAAGTCA CGCGCCTGTA GCGCCAGCGT GTTGTGAAAT GGGGGCTTGG
3001  GGGGGTTGGG GCCCCTGACTA GTCAAAACAA ACTCCCATTG ACGTCAATGG GGTGGAGACT TGGAAATCCC CGTGAGTCAA AGTCCCATAA ACCGCTATCC ACGCCCATTG
3101  ATGTACTGCC AAAACCGCAT CATCATGATGA ATAGCGATAA CTAATACGTA GATGTACTGC CAAGTAGGAA CTTGATGTAC TGCCAAGTGG GCAGTTTACC GTAAATACTC
3201  GCCAGGCGGG CCATTTACCG TCATTGACGT ATGGGGGG TGGCGTTACT ATGGGAACAT CGTTCATTAT TGCCAAGTGG GCAGTTGCC CGTTGGGCGG TCAGCCAGGC
3301  CACCCATTGA CGTCAATGAA AGTCCCTAT TGGCGTTACT GCAGTTAAT CGGCCATCAC AAAAATCGAC GCTCAAGTCA CCCGACAACC CCGGATAACG CCGCTTATCC
3401  GGGCCATTTA CCGTAAGCTA TGTAACGCCT GCCCCCCTGA CGGCATCAC AAAAATCGAC GCTCAAGTCA GAGGTGGCGA AACCCGACAG GACTATAAAG ATACCAGGCG
3501  GGCTTTTTC CATAGGCTCC GCCCCCCTGA CGGCATCAC AAAAATCGAC GCTCAAGTCA CTGTCCGCCT TTCTCCCTTC GGGAAGCGTG GCGCTTTCTC
3601  TTTCCCCCTG GAAGCTCCCT CGTGCGCTCT CTGTTCCGA CCCTGCGCT TCGCTCCAAG CTGGGCTGTG TGCACGAACC CCCGGTCAG AGGATTAGCA GCGAGGTA GCGCCTATC
3701  ATAGCTCACG CTGTAGGTAT CTCAGTTCGG TGTAGGTCGT TCGCTCCAAG CTGGGCTGTG TGCACGAACC CCCGGTCAG AGGATTAGCA GAGCGAGGTA TGTAGGCGGT
3801  CGGTAACTAT CGTCTTGAGT CCAACCCGGT AAGACACGAC TTATCGCCAC TGGCAGCAGC CACTGGTAAC AGGATTAGCA AGTTACCTTC GGAAAAAGAG
3901  GCTACAGAGT TCTTGAAGTG GTGGCCTAAC TACGGCTACA CTAGAAGAAC AGTATTTGGT ATCTGCGTC TGCTGAAGCC AGTTACCTTC GGAAAAAGAG
4001  TTGGTAGCTC TTGATCCGGC AAACAAACCA CCGCTGGTAG CGGTGGTTT TTTGTTTGCA AGCAGCAGAT TACGCGCAGA AAAAAGGAT CTCAAGAAGA
4101  TCCTTTGATC TTTTCTACGG GTCTGACGCT CAGTGGAACG AAAACTCAC GTTAAGGGAT TTTGGTCATG AGATTATCAA AAAGGAT CTCAAGAAGA
4201  GCAATAAAAT ACTTTATT ACTTTGTGT TTTTTGTGT AGAACATTTC TCTATCGAA (SEQ ID NO: 84)
4301  ACTAGCAAAA TAGGCTGTCC CCAGTGCAAG TGCAGGTGCC AGAACATTTC TCTATCGAA (SEQ ID NO: 84)
```

IL2ss.CCL8.hIgG1Fc sequence

```
   1  GGATCTGCGA TGCCTCCCGGT GCCCGTCAGT GGGCAGAGCG CACATGCCCC ACAGTCCCCC AGAGTTGGG GGGAGGGGTC GGCAATTGAA CGGGTGCCTA
 101  GAGAAGGTGC CGCGGGGTAA ACTGTCGTG TGATGTCGTG GCCAGAACGC CGGATTCTC GGCATCTCTC CTTCACGCGC CGAGGAACCGT ATATAAGTGC
 201  GTGAACGTTC TTTTTCGCAA CGGGTTTGCC GCCAAACCAC CGGCTGAGCT TCGAGGGGCT TCGATGAACTG CGCATCTCTC CTTCACGCGC ACCTGAGCGC
 301  GCCATCCACG CCGGTTGAGT CGCGCCTCTGC CGCCTCCCGC CGTGGGTGCC TCCTGAACTG CGTCCGCCGT CTAGGTAAGT TAAAGCTCA GGTCGAGACC
 401  GGCGCTTTGT CCGGCGCTCC CTTGGAGGCT ACCTAGAGCTC AGCCGGGTCT CCTGACCCTG CTTGCTCAAC TCTACCTCTT TGTTTCGTT

501  TCTGTTCTGC GCCGTTACAG ATCCAAGCTG TGACCGGCGC CTACCTGAGA TCACCGGCGCA AGGAGGGCCA CCAGTACAG GATGCAACTC CTGTCTTGCA
                                                                                        IL-2 secretion signal
                                                                                        MetTyrArg MetGlnLeu LeuSerCysIle
           EcoRI
           ~~~~~ CCL8 (1-76)
 601  AlaLeuSer LeuAlaLeu ValThrAsnSer GlnProAsp SerValSer IleProIleThr CysCysPhe AsnArgLysIle AsnValIle ProIleGln
      TGCACTAAG TCTTCACTTT GTCACGAATT CGCAGCCAGA TTCAGTTCC ATTCCAATCA CCTGCTGCTT TAACGTGATC AATAGGAAAA TTCCTATCCA
 701  ArgLeuGlu SerTyrThrArg IleThrAsn IleGlnCys ProLysPhe LysValAsp ValIlePhe ArgGlyLysGlu ValCysAla AspProLys
      AGGCTGGAG AGCTACACAA GAATCACCAA CATCCAATGC CCCAAACCT AAAGTTGATC GTGATATTC CGGGGCAAGG AGTCTGTGC TGACCCAAG
                                                                                                 human IgG1 Fc (constant region)
 801  GluArgTrpVal ArgAspSer MetLysHis LeuGlnPro IlePheGlnIle PheGlnAsn LeuGlnPro AspLysThrHis ThrCysPro AlaProGluLeu
      GAGACGTGG TCACGGATTC CATGAAGCAT CTGCAGCCCA TATTTCAAAA TCTGAAGCCA GACAAACTC ACACATGCCC ACCGTCCCA GCACCTGAAC
 901  LeuGlyGly ProSerVal PheLeuPhePro ProLysPro LysAspThr LeuMetIleSer ArgThrPro GluValThr CysValValVal AspValSer
      TCCTGGGGGG ACCGTCAGTC TTCCCTCTTCC CCCCAAACC AAGGACACC CTCATGATCT CCCGGACCCC TGAGGTCACA TGCGTGGTGG TGGACGTGAG
1001  HisGluAsp ProGluValLys PheAsnTrp TyrValAsp GlyValGluVal HisAsnAla LysThrLys ProArgGluGlu GlnTyrAsn SerThrTyr
      CCACGAAGAC CCTGAAGTCA AGTTCAACTG GTACGTGGAC GGCGTGGAGG TGCATAATGC CAAGACAAAG CCGCGGGAGG AGCAGTACAA CAGCACGTAC
1101  ArgValValSer ValLeuThr ValLeuHis GlnAspTrpLeu AsnGlyLys GluTyrLys CysLysValSer AsnLysAla LeuProAla ProIleGluLys
      CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA
1201  ThrIleSer LysAlaLys GlyGlnProArg GluProGln ValTyrThr LeuProProSer ArgGluGlu MetThrLys AsnGlnValSer LeuThrCys
      AAACCATCTC CAAAGCCAAA GGGCAGCCCC GAGAACCACA GGTGTACACC CTGCCCCAT CGCGAGGAA ATGACCAAG AACCAGGTCA GCCTGACCTG
1301  LeuValLys GlyPheTyrPro SerAspIle AlaValGlu TrpGluSerAsn GlyGlnPro GluAsnAsn TyrLysThrThr ProProVal LeuAspSer
      CCTGGTCAAA GGTTCTAC CCACCGACAT CGCCGTGGAG TGGGAGAGCA ATGGGCACCC GGAGAACAAC TACAAGACCA CGCCTCCCGT GCTGGACTCC
1401  AspGlySerPhe PheLeuTyr SerLysLeu ThrValAspLys SerArgTrp GlnGlnGly AsnValPheSer CysSerVal MetHisGlu AlaLeuHisAsn
      GACGGCTCCT TCTTCCTCTA CAGCAAGCTC ACCGTGGACA AGAGCAGGTG GCAGCAGGGG AACGTCTTCT CATGCTCCGT GATGCACGAG GCTCTGCACA
1501  HisTyrThr GlnLysSer LeuSerLeuSer ProGlyLys ***(SEQ ID NO: 58)
      ACCACTACAC GCAGAAGAGC CTCTCCCTGT CTCCGGGTAA ATCAGTGCTA GCTGGCCAGA CATGATAAGA TACATTGATG AGTTTGGACA AACCACAACT
1601  AGAATGCAGT GAAAAAAATG CTTTATTTGT GAAATTTGTA ATGCTATTGC TTTATTTGTA ACCATTATAA GCTGCAATAA ACAAGTTAAC AACAACAATT
                                                                                                 AseI
1701  GCATTCATTT TATGTTTCAG GTTCAGGGGG AGGTGTGGGA GGTTTTTTAA AGCAAGTAAA ACCTCTACAA ATGTGGTATG GAATAAGTAC AAAAATACAG
1801  CATACCAAAA CTTTAACCTC CAAATCAAGC CTCTACTTGA ATCCTTTTCT GAGGGATGAA TAAGGCATAG GCATCAGGGG CTGTTCCCAA TGTGCAATAG
```

```
1901  CTGTTTGCAG CCTCACCTTC TTTCATGGAG AGTGTATTTT CCCAAGGTTT GAACTAGCTC TTCATTTCTT TATGTTTAAA ATGCACTGAC
2001  CTCCCACATT CCCTTTTTAG GTTTAGTAGT TGGACTTAGG TAAATAAATT ATTGCAATGA AAATAAATGT TTTTTATTAG GCAGAATCCA GATGCTCAAG
2101  GCCCTTCATA ATATCCCCA  GTTTAGTAGT TGGACTTAGG GAACAAAGGA ACCTTTAATA AGCAAGAAAG CGAGCTTCTA GCTTATCCTC
2201  AGTCCTGCTC CTCTGCCACA AAGTGCACGC AGTTGCCGGC GGGGTGCGGC CCCGCCCCCA CGGCTGCTCG CCGATCTCGG TCATGGCCGG
2301  CCCGGAGGCG TCCGGAAGT  TCCGGAGACA CACTCGGTCT CAGCGTCGTC CAGGCCCGAC ACCCACACCC AGGCCAGGGT GTTGTCCGGC
2401  ACCACCTGGT CCTGGACCGC GCTGATGAAC AGGGTCACGT CGTCCCGGAC CACACCGGCG AAGTCGTCCT CCACGAAGTC CCGGAGAAC  CCGAGCCGGT
2501  CGGTCCAGGA CTCGACCGCT CCGCGCGACGT CGGCGCACGT CGGCGCACCGGA AGTCACCGGT GAGCACTGG  TCAACTTGGC CATGATGGCT CCTCCTGTCA GGAGAGGAAA

AseI
2601  GAGAAGAAGG TTAGTACAAT TGCTATATGTG AGTTGTATTA TACTATGCAG ATATACTATG CCAATGATTA ATTGTCAAAC TAGGGCTGCA GGGTTCATAG
2701  TGCCACTTTT CCTGCACTGC CCATCTCCT  GCCCACCCTT TCCCAGGCAT AGACAGTCAG TGACTTACCA AACTCACAGG AGGGAGAAGG CAGAAGCTTG
2801  AGACAGACCC GGGGACCGC  CGAACTGCGA GGGGACGTGG CTAGGCCGGC TTCTTTATG  GTGCGCCGGC CCTCGGAGGC AGGGCGCTCG GGGAGGCCTA
2901  GCCCCAATC  TGCCGTGGCA CGAAGGCGG  CCCAAGGCCG GCCTTGACCA CATAGGAGTC TCAGCGCCCC CCCCAAAGC  AGGGGCTTG  GCCCAAAGCC AAGGGAACT
3001  CACGCGCCTG TAGCGCCAGC GTGTTGTGAA GGGGGGCTT  ATGGGGGGCT TGGGGGGTTG CAATAGGAGT AAACTCCCAT TGACGTCAAT GGGGTGGAGA
3101  CTTGGAAATC CCCGTGAGTC AAACGCTAT  CCACGCCCAT TGATGTACTG CCAAAACCGC ATCATCATGG TAATAGCGAT TAGATGTACT
3201  GCCAAGTAGG AAAGTCCCAT AAGGTCATGT ACTGGGCATA ATGCCAGGCG GGCCATTTAC CGTCATTGAC GTCAATAGGG GGCGTACTTG GCATATGATA
3301  CACTTGATGT ACTGGCCAGT TTA         GGGCAGTTTA CCGTAAATAC TCCACCCATT GACGTCAATG GAAAGTCCCT ATTGGCGTTA CTATGGAAAC ATACGTCATT
3401  ATTGACGTCA ATGGGCGGGG GTCGTTGGGC GGTCAGCCAG GCGGGCCATT TACCGTAAGT TATGTAACGC CTGCAGGTTA ATTAAGAACA TGTGAGCAAG
3501  AGGCCAGCAA AAGGCCAGGA ACCGTAAAAA GGCCGCGTTG CTGGCGTTTT TCCATAGGCT CCGCCCCCCT GACGAGCATC ACAAAAATCG ACGCTCAAGT
3601  CAGAGGTGGC GAAACCCGAC AGGACTATAA AGATACCAGG CGTTTCCCCC TGGAAGCTCC CTCGTGCGCT CTCCTGTTCC GACCCTGCCG CTTACCGGAT
3701  ACCTGTCCGC CTTTCTCCCT TCGGGAAGCG TGGCGCTTTC TCATAGCTCA CGCTGTAGGT ATCTCAGTTC GGTGTAGGTC GTTCGCTCCA AGCTGGGCTG
3801  TGTGCACGAA CCCCCGTTC  AGCCCGACCG CTGCGCCTTA TCCGGTAACT ATCGTCTTGA GTCCAACCCG GTAAGACACG ACTTATCGCC ACTGGCAGCA
3901  GCCACTGGTA ACAGGATTAG CAGAGCGAGG TATGTAGGCG GTGCTACAGA GTTCTTGAAG TGGTGGCCTA ACTACGGCTA CACTAGAAGA ACAGTATTTG
4001  GTATCTGCGC TCTGCTGAAG CCAGTTACCT TCGGAAAAAG AGTTGGTAGC TCTTTTCTAC GGGGTCTGAC GCTCAGTGGA ACGAAAACTC ACGTTAAGGG
4101  CAAGCAGCAG ATTACGCGCA GAAAAAAAGG ATCTCAAGAA GATCCTTTGA TCTTTTCTAC GGGGTCTGAC TCTCATTACA TCTGTGTGTT GGTTTTTTGT GTGAATGTA
4201  ATTTTGGTCA TGGCTAGTTA ATTAACATTT AAATCAGCGG CCGCAATAAA ATATCTTTAT TTTCATTACA TCTGTGTGTT GGTTTTTTGT GTGAATGTA
4301  ACTAACATAC GCTCTCCATC AAAACAAAAC GAAACAAAAC AAACTAGCAA AATAGGCTGT CCCCAGTGCA AGTGCAGGTG CCAGAACATT TCTCTATCGA
4401  A (SEQ ID NO: 85)
```

IL2ss.CCL8(5-76).hIgG1Fc sequence

```
   1 GGATCTCGGA TGCTCCGGT GCCCCTCAGT ACTGGGAAAG CGGCAGACG CACATCCCGC AGAAGTTGGG GGCAGGGGTC GGCAATTGAA CGGGTCGCTA
 101 GAGAAGGTGG CGCGGGGTAA ACTGGGAAAG TGATGTCGTG TACTGGCTCC GCCTTTTTCC GGAGGGGTGG GGAGAAACCT CTTCAGCGC ATATAAGTGC AGTAGTCGCA
 201 GTGAACGTTC TTTTTCGCAA CGGGTTTGCC GCCAGAACAC AGTTGAAGCT CTGTGGTGCC TCGAGGGGCT TGCAAACTG CTCCAGGCGC CCGCCGCCCT ACCTGAGGCC
 301 GCATCCACG CCGGTTGAGT CGCGTTCTGC CGCCTCCGC CGCTCCCGC CTGTGGTGCC TCCTGAACTG GTCCCCGT CTAGGTAAGT TTAAGCTCA GGTCGAGACC
 401 GGGCTTTGT CCGGGCTCC CTTGGAGCCT ACCTACACTG AGCGGCGTCT AGCCCGCTCT CCACGCTTTG CCTGACCCTG CTTGCTCAAC TCTACGTCTT TGTTTCGTTT

KasI
                                                                                    NarI
                                                                                    SfoI
                                                                                    BbeI                     IL-2 secretion signal
                                                                                                             MetTyrArg MetGlnLeu LeuSerCysIle
 501 TCTGTCTGC GCCGTTACAG ATCCAAGCTG TGACGGCCGC CTACCTGAGA AGGAGGGCCA CCATTGTACAG GATGCAACTC CTGTCTTGCA
                                    EcoRI
                                                     ~~~~~~ CCL8 (5-76)

AlaLeuAlaLeu ValThrAsnSer ValSerIle ProIleThr CysCysPheAsn ValIleGluAsn ArgLysIle ProIleGlnArg LeuGluSer
 601 TTGCACTAAG TCTTCCACTT GTCACCAATT CCGTTTCCAT CCGATTCCA TCCAATCACC TGCTGCTTTA ACGTGATCAA TAGGAAAATT CCTATCCAGA GGCTCGAGAG
    TyrThrArg IleThrAsnIle GlnCysSerPro LysGluAla ValIlePheLys ThrLysArg GlyLysGlu ValCysAlaAsp ProLysGlu ArgTrpVal
 701 CTACACAGA ATCACCAACA TCCAATGTCC CAAGGAAGCT GTGATCTTCA AGGAAGCGGG GGCAAGGAG GTCTGTGCTG ACCCCAAGGA GAGATGGGTC
                                                                                    human IgG1 Fc (constant region)
    ArgAspSerMet LysHisLeu AspGlnIle PheGlnAsnLeu LysProAsp LysThrHis ThrCysProPro CysProAla ProGluLeu LeuGlyGlyPro
 801 AGGGATTCCA TGAAGCATCT GGACCAATA TTTCAAAATC TGAAGCCAGA CAAAACTCAC ACATGCCCAC CGTGCCCAGC ACCTGAACTC CTGGGGGGAC
    SerValPhe LeuPhePro ProLysProLys AspThrLeu MetIleSer ArgThrProGlu ValThrCys ValValVal AspValSerHis GluAspPro
 901 CGTCAGTCTT CCTCTTCCCC CCAAAACCCA AGGACACCCT CATGATCTCC CGGACCCCTG AGGTCACATG CGTGGTGGTG GACGTAAGCC ACGAAGACCC
    GluValLys PheAsnTrpTyr ValAspGly ValGluVal HisAsnAlaLys ThrLysPro ArgGluGlu GlnTyrAsnSer ThrTyrArg ValValSer
1001 TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
    ValLeuThrVal LeuHisGln AspTrpLeu AsnGlyLysGlu TyrLysCys LysValSer AsnLysAlaLeu ProAlaPro IleGluLys ThrIleSerLys
1101 GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
    AlaLysGly GlnProArg GluProGlnVal TyrThrLeu ProProSer ArgGluGluMet ThrLysAsn GlnValSer LeuThrCys ValLysGly
1201 AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG
    PheTyrPro SerAspIleAla ValGluTrp GluSerAsn GlyGlnProGlu AsnAsnTyr LysThrThr ProProValLeu AspSerAsp GlySerPhe
1301 CTTCTATCC AGCGACATCG CCGTGGAGTG GGAGAGCAAT GGGCAGCCGG AGAACAACTA CAAGACCACG CCTCCCGTGC TGGACTCCGA CGGCTCCTTC
    PheLeuTyrSer LysLeuThr ValAspLys SerArgTrpGln GlnGlyAsn ValPheSer CysSerValMet HisGluAla LeuHisAsn HisTyrThrGln
1401 TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                                    BmoI
                                    NbeI                                                                 AseI
    LysSerLeu SerLeuSer ProGlyLys*** (SEQ ID NO. 59)
1501 AGAAGAGCCT CTCCCTGTCT CCGGGTAAAT GAGTGCTAGC TGGCCAGACA TGATAAGATA CATTGATGAG TTTGGACAAA CCAACAACTAG AATGCAGTGA
1601 AAAAAATGCT TTATTTCTGA AATTTGTCAT GCTATTCCTT TATTTCTAAC CATTATAAGC AACTAATAAAC TGCAATAAAC AACAATTGC ATTCATTTA
1701 TGTTTCAGGT TCAGGGGAG GTGTGGCAGG TTTTTTAAAG CAAGTAAAAC CTCTACAAAT GTGGTATGAA ATTAATTCTA AAATACAGCA TAGCAAAACT
1801 TTAACCTCCA AATCAAGCT CTACTTGTGA CCTTTTCTGA GGCATAAGGC GTTGCCAATG TGCATTAGCT GTTTGCAGCC
```

```
1901  TCACCTTCTT TCATGAGGTT TAAGATATAG TGTATTTTCC CAAGGTTTGA ACTAGCTCTT CATTTCTTTA TGTTTTAAAT GCACTGACCT CCCACATTCC
2001  CTTTTTAGTA AAATATTCAG AAATAATTTA ACAAAGGAAC TCCAATGAAA ATAAATGTTT TTTATTAGGC AGAATCCAGA TGCCTCAAGGC CCTTCATAAT
2101  ATCCCCAGT TTAGTAGTTG GACTTAGGGA ACAAGGACAG CTTTAATAGA AATTGGACAG CAAGAAAGCG AGCTTCTAGC TTATCCTCAG TCCTGCTCCT
2201  CTGCCACAAA GTGCACCCAG TTGCCGGCCG GGTCGGCGCA CCCCCACCG GCTCCTCGGTC CATCTCGGTC AGCTCCGGCC ATGGCCCGTC CGGACGCGTC
2301  CCGAAGTTC GTGGACACGA CCTCCGACCA AGCTCGTCCA AGCTCGTCCA GCCAGGGTGT TGTCCGGCAC CACCTGGTCC
2401  TGGACCCGCC TGATGAACAG GGTCACGTCG TCCCGGCACCA CACCGGCGAA GTCGTCCTCC ACGAAGTCCC CGGAGAACCC GAGCCGGTCG GTCCAGAACT
2501  CGACCGCTCC GGCGAGCGTCG CGCGGGGTGA GCACCGGAAC GGCACTGGTC AACTTGGCCA TGATGGCTCC TCCTGTCAGG AGAGGAAAGA GAAGAAGGTT

AseI
2601  AGTACAATTC CTATATAGTGAG TTGTATTATA CTATGCAGAT ATACTATGCC AATGATTAAT TGTCAAACTA CGGCTCCAGG GTCCATACTG CCACTTTTCC
2701  TGCACTGCCC CATCTCCTGC CCACCCTTTC CCAGGCATAG ACAGTCAGTG ACTTACCAAG CTCACAGGAG GGAGAAGGCA GAAGCTTGAG ACAGACCCGC
2801  GGGACCGCCG AACTGCCGCC CGTGCGGCT GGAAGGCCGT G CCTGACCAC TAGGAGTGTC GCCCGGGGCC CCCAAGCAA GCCCCTCGGG GAGGCCTAGC GCGCCAATCTG
2901  CGGTGGCAGG AGGCGGGCC GAAGCCCGTG CCTGACCAGT CCGGACGCACA AGCCGCTCT ACTCCCATTG GGTGGAAGTCA GGCCCTGA
3001  GCGCCAGCGT GTTGTGAAAT GGGGGTTGG GCCCTGACTA GTCAAAACAA CATCATGGTA ATAGCGATGA CTAATACTA GATGTACTGC TGGAAATCCC
3101  CGTGAGTCAA ACCGCTATCC ATGTACTGC ATGCCCATTG GCCAGCGCGG TCATTGACGT CAATAGGGGG CGTACTTGGC ATATGATGAC CAAGTAGGAA
3201  AGTCCCATAA GGTCATGTAC TGGGCATAAT GCCAAATGGA CGTCAATGA AAGTCCCTAT TGGCGTTACT ATGGGAACAT ACGCATTAT TGACGTCAAT
3301  TGGCCAAGTGG GCAGTTTACC GTAAATACTC CACCATTTA CGTCAATGGG TGTAACGCCT GCAAGGTTAAT AAGAACATG GCTCAAGTCA GCAGCAAAA
3401  GGGCGGGGGT CGTTGGGCGG TCAGCCAGGC GGGCCATTTA CCCCCCTGA CATAGCCTC CCCCCCCGA AAAAATCGAC CCTCAAGTCA GAGGTGGCGA
3501  GGCCAGGAAC CGTAAAAGG GACTATAAAG ATACAGCGCG TTTCCCCTG GAAGCTGCCT CGTGTTCGGA CCTGCGCTT TACCGATAC CTGTCCGCT
3601  AACCGAGGAAC GACTATAAAG ATACAGCGCG ATAGCTCACG CTGTAGGTAT CTCGTCTGAGT TGTAGGTCGT TCGCTCCAAG CTGGCTGTG TGCACGAACC
3701  TTTCCCTTC GGGAAGCGTG GCGCTTCCTC ATAGCTCACG CGGTAACTAT CGTCTTGAGT CCAACCCGGT AAGACACGAC TTATCGCCAC CACTGGTAAC
3801  CCCGGTCAG CCCGACCGCT GCGCCTTATC CGGTAACTAT GCTACAGAGT TCTTGAAGTG GTGGCCTAACA CTAGAAGAAC AGTATTTGGT ATCTGCGCTC
3901  AGGATTAGCA GAGCGAGGTA TGTAGGCGGT TTGGTAGCTC TTGATCCGGC AAACAACCA CGGCTGGTAG CGGGCGGTTTT TTTGTTTGCA AGCAGCAGAT
4001  TGCTGAAGCC AGTTACCTTC GGAAAAAGAG CTCAAGAAGA TCCTTTGATC TTTTCTACGG GGTCTGACGC TCAGTGGAAC GAAAACTCAC GTTAAGGGAT TTTGGTCATG
4101  ACGGCAGA AAAAAAGGAT CTCAAGAAGA TCCTTTGATC TTTTCTACGG GGTCTGACGC TCAGTGGAAC GAAAACTCAC GTTAAGGGAT TTTGGTCATG
4201  GCTAGTTAAT TAACATTTAA ATCAGCGGCC GCAATAAAAT ATCTTTATT TCATTACATC TGTGTGTTGG TTTTTTGTGT GAATCGTAAC TAACATACGC
4301  TCTCCATCAA AACAAAACGA AACAAAACAA ACTAGCAAAA TAGGCTGTCC CCAGTGCAAG TGCAGGTGCC AGAACATTTC TCTATCGAA  (SEQ ID NO: 86)
```

IL2ss.CCL8(5-76).hIgG1Fc sequence
[Alanine substitutions for GAG binding sites – Lys, Arg & His]

```
   1  GGATCTGCGA TGCCTCCGGT GCCCGTCCGT GGGCAGAGCG CACATCGCCC ACAGTCCCCG AGAAGTGGGG GGGAGGGGTG GGCAATTGAA CGGGTGCCTA
 101  GAGAAGGTCG CGCCGGGTAA ACTCGGAAAG TGAT

```
1801  TTAACCTCCA  AATCAAGCCT  CTACTTGAAT  CCTTTTCTGA  GGGATGAATA  AGGCATAGGC  ATCAGGGGCT  GTTGCCAATG  TGCATTAGCT  GTTTGCAGCC
1901  TCACCTTCTT  TCATGGAGTT  TAAGATATAG  TGTATTTTCC  CAAGGTTTGA  ACTAGTCTTT  CATTTCTTTA  TGTTTTAAAT  GCACTGACCT  CCCACATTCC
2001  CTTTTAGTA   AATATTCAG   AATACATCAT  TGCAATGAAA  CTTTAATAGA  ATAAATGTTT  TTTATTAGGC  AGAATCCAGA  TGCTCAAGGC  CCTTCATAAT
2101  ATCCCCAGT   TTAGTAGTTG  GACTTAGGGA  ACAAAGGAAC  CTTTAATAGA  CGCCCCCACG  CAAGAAAGCG  AGCTTCTAGC  TTATCCTCAG  TCCTGCTCCT
2201  CTGCCACAAA  GTGCACGCAG  TTGCCGGCCG  GGTCGCGCAG  GGCGAACTCC  GGCGAACTCC  GCTGCTCGCC  GATCTCGGTC  ATGGCCGGCC  CGGAGGCGTC
2301  CCGGAAGTTC  GTGGACACGA  CCTCCGACCA  CTCGGCGTAC  AGCTCGTCCA  GGCGCGCAC   CCACACCCAG  GCCAGGGTGT  TGTCCGGCAC  CACCTGGTCC
2401  TGGACCGCGC  TGATGAACAG  GGTCACGTCG  TCCCGGACCA  GGTCGTCCCC  CACCGGCGAA  GTCGTCCTCC  ACGAAGTCCC  GGGAGAACCC  GAGCCGGTCG  GTCCAGAACT
2501  CGACCGCTCC  GGCGACGTCG  CGCGGTGA    GCACCGGAAC  GGCACTGGTC  AACTTGGGCA  TGATGGCTCC  TCCTGTCAGG  TCCTGTCAGG  AGAGGAAAGA  GAAGAAGGTT

AseI
2601  AGTACAATTG  CTATAGTGAG  TTGTATTATA  CTATGCAGAT  AATGATTAAT  TGTCAAACTA  TGTCAAACTA  GGGCTGCAGG  GTTCATAGTG  CCACTTTTC
2701  TGCACTGCCC  CATCTCCTGC  CCACCCTTTC  CCAGGCATAG  ACAGTCAGTG  ACTTACCAA   CTCACAGGAG  GGAGAAGGCA  GAAGCTTGAG  ACAGACCCGC
2801  GGGACCGCCG  AACTGCGAGG  GGACGTGGCT  AGGGCGGCTT  CTTTTATGGT  GCGCCGGCCC  TCGGAGGCAG  GGCGCTCGGG  GAGGCCTAGC  GGCCAATCTG
2901  CGGTGGCAGG  AGGGGGGCC   GAAGGCCGTG  CCTGACCATA  CCGGAGCACA  TAGGAGCTCTC  AGCCCCCCGC  CCCAAAGCAA  GGGGAAGTCA  CGCGCCTGTA
3001  GCGCCAGCGT  GTTGTGAAAT  GGGGGCTTGG  GGGGGCTTGG  GCCCTGACTA  GTCAAAACAA  ACTCCCATTG  ACGTCAATGG  GGTGGAGACT  TGGAAATCCC
3101  CGTGAGTCAA  ACCGCTATCC  ACGCCATTG   ATGTACTGCC  AAAACCGCAT  CATCATGGA   ATAGCGATGA  CTAATACGTA  GATGTACTGC  CAAGTAGGAA
3201  AGTCCCATAA  GGTCATGTAC  GGTTACTGG   CCAGGCGGG   CCATTTACCG  TCATTGACGT  CAATAGGGGG  CGTACTTGGC  ATATGATACA  CTTGATGTAC
3301  TGCCAAGTGG  GCAGTTACC   GTAAATACTC  CACCCATTGA  CGTCAATGGA  AAGTCCCTAT  TGGCGTTACT  ATGGGAACAT  ACGTCATTAT  TGACGTCAAT
3401  GGGCGGGGT   CGTTGGGCGG  TCAGCCAGGC  GGGCCATTTA  CCGTAAGTTA  TGTAACGCCT  GCAGGTTAAT  TAAGAACATG  TGAGCAAAAG  GCCAGCAAAG
3501  GCCAGGAAC   CGTAAAAAGG  CCGCGTTGCT  GGCGTTTTTC  CATAGGCTCC  GCCCCCCTGA  CGAGCATCAC  AAAAATCGAC  GCTCAAGTCA  GAGGTGGCGA
3601  AACCCGACAC  GACTATAAAG  ATACCAGGCG  TTTCCCCCTG  GAAGCTCCCT  CGTGCGCTCT  CCTGTTCCGA  CCCTGCCGCT  TACCGGATAC  CTGTCCGCCT
3701  TTCTCCCTTC  GGGAAGCGTG  GCGCTTTCTC  ATAGCTCACG  CTGTAGGTAT  CTCAGTTCGG  TGTAGGTCGT  TCGCTCCAAG  CTGGGCTGTG  TGCACGAACC
3801  CCCCGTTCAG  CCCGACCGCT  GCGCCTTATC  CGGTAACTAT  CGTCTTGAGT  CCAACCCGGT  AAGACACGAC  TTATCGCCAC  TGGCAGCAGC  CACTGGTAAC
3901  AGGATTAGCA  GAGCGAGGTA  TGTAGGCGGT  GCTACAGAGT  TCTTGAAGTG  GTGGCCTAAC  TACGGCTACA  CCGCTGGTAG  AGTATTTGGT  ATCTGCGCTC
4001  TGCTGAAGCC  AGTTACCTTC  GGAAAAAGAG  TTGGTAGCTC  TTGATCCGGC  AAACAAACCA  CCGCTGGTAG  CGGTGGTTTT  TTTGTTTGCA  AGCAGCAGAT
4101  TACGCGCAGA  AAAAAAGGAT  CTCAAGAAGA  TCCTTTGATC  TTTTCTACGG  GGTCTGACGC  TCAGTGGAAC  GAAAACTCAC  GTTAAGGGAT  TTTGGTCATG
4201  GCTAGTTAAT  TAACATTTAA  ATCAGCGGCC  GCAATAAAAT  ATCTTTATTT  TCATTACATC  TGTGTGTTGG  TTTTTTGTGT  GAATCGTAAC  TAACATACGC
4301  TCTCCATCAA  AACAAAACGA  AACAAAACAA  ACTAGCAAAA  TAGGCTGTCC  CCAGTGCAAG  TGCAGGTGCC  AGAACATTTC  TCTATCGAA  (SEQ ID NO:87)
```

IL2ss.CCL13.hIgG1Fc sequence

```
   1 GGATCTGCGA TCGCTCCGGT GCCCGTCCGT GGGCAGAGCG CACATCGCCC ACAGTCCCCG AGAAGTTGGG GGGAGGGGTC GGCAATTGAA CGGGTGCCTA
 101 GAGAAGGTGG CGCGGGGTAA ACTGGGAAAG TGATGTCGTG GCCAGAACGC TACTGGCTCC GCCTTTTTCC CGAGGGTGGG GGAGAACCGT CTTCACGCGC ATATAAGTGC AGTAGTCGCC
 201 GGGAACGTTC TTTTTCGCAA CGGGTTTGCC GCCAGAACGC TCGAGAACGT TCCTGAACTG CGCATCTCTC CGTCCGCGCT CTAGGTAAGT CCGCGCCCT ACCTGAGCC
 301 GCCATCCACG CCGGTTGAGT CGCGTTCTGC CGCCTCCCGC CTGTGGTGCC CTGTGGTGCC AGCGCGGAGA TCTGTGCTGA CCCAAGGAG GGTGAGACC
 401 GGGCCTTTGT CCGGCGCTCC CTTGGAGCCT ACCTAGGCCT AGCCGGCTCT CCACGCTTTG CCTGACCCTG CCTGCTCAAC TCTACGTCTT TGTTTCGTTT
                                                            SfoI
                                                            NarI
                                                            KasI
                                                            BbeI
                                                                                                      IL-2 secretion signal
                                                                                                      MetTyrArg MetGlnLeu LeuSerCysIle
 501 TCTGTTCTGC GCCGTTACAG ATCCAAGCTG TGACCCGGCGC CTACCTGAGA TCACCGGGCGA AGGAGGGCCA CCATGTACAG GATGCAACTC CTGCTTGCA
                            EcoRI
                                  ~~~~~~ CCL13 (1-75)
         AlaLeuSer LeuAlaLeu ValThrAsnSer GlnProAsp AlaLeuAsn ValProSerThr CysCysPhe ThrPheSer SerLysLysIle SerLeuGln
 601 TTGCACTAAG TCTTGCACTT GTCACGAATT CGCAGCCAGA TGCACTCAAC GTCCCATCTA CTTGCTGCTT CACATTAGC AGTAAGAAGA TCTCCTTGCA
         ArgLeuLys SerTyrValIle ThrThrSer ArgCysPro GlnLysPro ValAspPro GlyLysGlu ThrLysLeu GlyAlaAsp CysAlaAsp ProLysGlu
 701 GAGCCTTTGT AGCTATGTGA TCAACTGGTA CAGGTGCCCT CAGAAGCCTG TCATCTTCAG AACCAAACTG GGCAAGGAGA TCTGTGCTGA CCCAAGGAG
         LysTrpValGln AsnTyrMet LysHisLeu GlyArgLysAla HisThrLeu LysThrHisThr CysProPro CysProAla ProGluLeuLeu
 801 AAGTGGGTCC AGAATTATAT GAAACACCTG GGCCGGAAAG CTCACACCCT GAAGACTCAC AAAACTCACA CATGCCCACC GTGCCCAGCA CCTGAACTCC
         GlyGlyPro SerValPhe LeuPhePro LysProLys AspThrLeu MetIleSerArg ThrProGlu ValThrCys ValValVal AspValSerHis
 901 TGGGGGACCG TCAGTCTTC CTCTTCCCCC CAAAACCCAA GGACACCCTC ATGATCTCCC GGACCCCTGA GGTCACATGC GTGGTGGTGG ACGTGAGCCA
         GluAspPro GluValLysPhe AsnTrpTyr ValAspGly ValGluValHis AsnAlaLys ThrLysPro ArgGluGluGln TyrAsnSer ThrTyrArg
1001 CGAAGACCCT GAGGTCAAGT TCAACTGGTA CGTGGACGGC GTGGAGGTGC ATAATGCCAA GACAAAGCCG CGGGAGGAGC AGTACAACAG CACGTACCGT
         ValValSerVal LeuThrVal LeuHisGln AspTrpLeuAsn GlyLysGlu TyrLysCys LysValSerAsn LysAlaLeu ProAlaPro IleGluLysThr
1101 GTGGTCAGCG TCCTCACCGT CCTGCACCAG GACTGGCTGA ATGGCAAGGA GTACAAGTGC AAGGTCTCCA ACAAAGCCCT CCCAGCCCCC ATCGAGAAAA
         IleSerLys AlaLysGly GlnProArgGlu ProGlnVal TyrThrLeu ProProSerArg GluGluMet ThrLysAsn GlnValSerLeu ThrCysLeu
1201 CCATCTCCAA AGCCAAAGGG CAGCCCCGAG AACCACAGGT GTACACCCTG CCCCCATCCC GGGAGGAGAT GACCAAGAAC CAGGTCAGCC TGACCTGCCT
         ValLysGly PheTyrProSer AspIleAla ValGluTrp GluSerAsnGly GlnProGlu AsnAsnTyr LysThrThrPro ProValLeu AspSerAsp
1301 GGTCAAAGGC TTCTATCCCA GCGACATCGC CGTGGAGTGG GAGAGCAATG GGCAGCCGGA GAACAACTAC AAGACCACGC CTCCCGTGCT GGACTCCGAC
         GlySerPhePhe LeuTyrSer LysLeuThr ValAspLysSer ArgTrpGln GlnGlyAsn ValPheSerCys SerValMet HisGluAla LeuHisAsnHis
1401 GGCTCCTTCT TCCTCTACAG CAAGCTCACC GTGGACAAGA GCAGGTGGCA GCAGGGGAAC GTCTTCTCAT GCTCCGTGAT GCATGAGGCT CTGCACAACC
                                                                                              BmtI
                                                                                              NheI
         TyrThrGln LysSerLeu SerLeuSerPro GlyLys***(SEQ ID NO:61)
1501 ACTACACGCA GAAGAGCCTC TCCCTGTCTC CGGGTAAATG AGTGCTAGCT GGCCAGACAT GATAAGATAC ATTGCTTT ATTTGTAAAC GCAATAACA AGTTAACAAC
1601 ATCAGTGAA AAAAATGCTT TATTTGTCAA ATTTGTCATG CTATTGCTTT ATTTGTAAAC AAGTAAAACC TCTACAAATG TGGTATGGAA TTAATTCTAA AATACAGCAT
                                                                                                                   AseI
1701 TTCATTTTAT GTTTCAGGTT CAGGGGAGGT TGTGGGAGGT TTTTAAAAGC CTTTTCTGAG GGTAAGATC TACTTGAATC CTTTTCTGAG TCAGGGCTG TTGCCAATGT GCATTAGCTG
1801 ACCAAAACTT TAACCTCCAA
```

```
1901  TTTGCAGCCT CACCTTCTTT CATGGAGTTT AAGATATAGT GTATTTTCCC AAGGTTGAAA CTAGCTCTTC ATTTCTTTAT GTTTTAAATG CACTGACCTC
2001  CCACATTCCC TTTTTAGTAA AATATTCAGA TAGTAGTTGG ACTTAGGGAA ATACATCATT GCAATGAAAA TAAATGTTTT TTATTAGGCA GAATCCAGAT GCTCAAGCC
2101  CTTCATAATA TCCCCCAGTT TGCCACAAAG TGCACGCAGT CTCCGCCGG GTCGGCGCAGG CAAAGGAACC TTTAATAGAA ATTGGACAGC AAGAAAGCAG GCTTCTAGCT TATCCTCAGT
2201  CCTGCTCCTC TGCCACAAAG TGCACGCAGT CTCCGCCGG GTCGGCGACCAC CCGAACTCCC GCCGCGACCC CTGCTCGCCG ATCTCGGTCA TGGCCGGCCC
2301  GGAGGCGTCC CGGAAGTTCG TGGACACGAC TCGGCGTACA GTCACGTCGT CCCGGACCAC GCTCGTCCAG GCCGCGCACC CACACCCAGG CCAGGGTGTT GTCCGGCACC
2401  ACCTGGTCCT GGACCGCGCT GATGAACAGG GCGACGTCCG CCCGGACCAC GTCACGTCGT CCGGACCACG TGGTCCTCCA CGAAGTCCCG GGAGAACCCG AGCCGGTCGG
2501  TCCAGAACTC GACCGCTCCG GCGACGTGCG GCGGGGTGAG CACCGGAACG GCACTGGTCA ACTTGGCCAT GATGGCTCCT CCTGTCAGGA GAGGAAAGAG
                                                                    AseI
2601  AAGAAGGTTA GTACAATTGC TATAGTGAGT TGTATTATAC ATGATTAATT GTCAAACTAG GGCTGCAGGG TTTCATAGTGC
2701  CACTTTTCCT GCACTGCCCC ATCTCCTGCC CACCCTTCC CAGGCATAGA CTTACCAACA TCACAGGAGG GAGAAGGCAG AAGCTTGAGA
2801  CAGACCCGCG GGACCGCCGA ACTCGCAGGG GACGTTGGCTA TTTTATGGTG CGCCGGCCCT CGGAGGCAGG GCGCTCGGGG AGGCCTAGCG
2901  GCCAATCTGC GGTGGCAGGA GGCGGGGCCG AAGGCCGTGC CTGACCAATC AGGAGTCTCA GCCCCCCGCC CCAAAGCAAG GGGAAGTCAC
3001  GCGCCTGTAG CGGCAGCCTG TTGTGAAATG GGGGCTTCGG GGGCTTCGCC CCCTGACTAG TCAAAACAAA CTCCCATTGA CGTCAATGGG GTGAGACTTT
3101  GGAAATCCCC GTGAGTCAAA CCGCTATCCA CGCCCATTGA TGTACTGCCA AGTGCCCGCT GGGCATAATG CATTTACCGT TAGCGATGAC TAATACGTAG ATGTACTGCC
3201  AAGTAGGAAA GTCCCATAAG GTCATGTACT CGGCCCATTGA GGGCATAATG TAAATACTCC ACCCATTGAC CATTGACGTC AATAGGGGC GTACTTGGCA TATGATACAC
3301  TTGATGTACT GACCCATTAC CAGCCAGGCG CGGTTTTCT GGCCATTTAC GTCAATGGAA AGTCCCTATT GGCGTTACTA TGGAACATA CGTCATTATT
3401  GACGTCAATG GGCGGGGGTC GTTGGGCGGT CAGCCAGGCG TAAATACTCC ATAGGCTCCG CGTAAGTTAT GTAACGCCTG AAGAACATGT GAGCAAAAGG
3501  CCAGCAAAAG GCCAGGAACC GTAAAAAGGC CGCGTTGCTG GCGTTTTTTC CCCCCTGAC AGCTCCCCTG CCCCCCGAC CCTCCCCTT ACCGGATACC
3601  AGGTGGCGAA ACCCCACACG ACTATAAAGA TACCAGGCGT TTCCCCCTGG AAGCTCCCTC GTGCGCTCTC CTGTTCCGAC CCTGCCGCTT ACCGGATACC
3701  TGTCCGCCTT TCTCCCTTCG GGAAGCGTGG CGCTTTCTCA TAGCTCACGC TGTAGGTATC TCAGTTCGGT GTAGGTCGTT CGCTCCAAGC TGGGCTGTGT
3801  GCACGAACCC CCCGTTCAGC CCGACCGCTG CGCCTTATCC GGTAACTATC GTCTTGAGTC CAACCCGGTA AGACACGACT TATCGCCACT GGCAGCAGCC
3901  ACTGGTAACA GGATTAGCAG AGCGAGGTAT GTAGGCGGTG CTACAGAGTT CTTGAAGTGG TGGCCTAACT ACGGCTACAC TAGAAGAACA GTATTTGGTA
4001  TCTGCGCTCT GCTGAAGCCA GTTACCTTCG GAAAAAGAGT TGGTAGCTCT TGATCCGGCA AACAAACCAC CGCTGGTAGC GGTGGTTTTT TTGTTTGCAA
4101  GCAGCAGATT ACGCGCAGAA AAAAAGGATC TCAAGAAGAT CCTTTGATCT TTTCTACGGG GTCTGACGCT CAGTGGAACG AAAACTCACG TTAAGGGATT
4201  TTGGTCATGG CTAGTTAATT AACATTTAAA TCAGCGGCCG CAATAAAATA TCTTTATTT CATTACATCT GTGTGTTGGT TTTTTGTGTG AATCGTAACT
4301  AACATACGCT CTCCATCAAA ACAAAACGAA ACAAAACAAA CTAGCAAAAT AGGCTCTCCC CAGGTGCAAGT GAACATTTCT CTATCGAA
                                                                                                    (SEQ ID NO:88)
```

IL2ss.CCL13(5-75).hIgG1Fc sequence

```
   1 GGATCTGCGA TGGCTCCGGT GCCCGTCAGT GGGCAGAGCG CACATCGCCC ACAGTCCCCG AGAAGTTGGG GGGAGGGGTC GGCAATTGAA CGGGTGCCTA
 101 GAGAAGGTGG CGCCGGGTAA ACTCGGAAAG TCATGCTGTC TACTGCCTCC GCCTTTTTCC CGAGGGTGG CGAGAACCGT CTTCACGCGC AGTAGTCGCC
 201 GTGAACGTTC TTTTTGCAA CGGGTTTGCC TCCAGAACAC AGCTGAAGCT TCGAGGGGCT CGCATCCTC CGCATCCCG CCCGCGCCT ACCTGAGGCC
 301 GCCATCCACG CCGGTTGAGT CGGGTCCCGC CGCGTGTGCG TCCTGAACTG CCTGAACTG CGTCCGCCGT CTAGGTAAGT TTAAAGCTCA GGTCGAGACC
 401 GGGCCTTTGT CCGGCGCTCC CTTGGGAGCT ACCTAGACTC AGCCGGCTCT CCTGACCCCTG CTTGCTCAAC TCTACGTCTT TGTTTCGTTT

IL-2 secretion signal
                                                                        MetTyrArg MetGlnLeu LeuSerCysIle
 501 TCTGTTCTGC GCCGTTACAG ATCCAAGCTG TGACCGGCGC CTACCTGAGA TCACCGGCGA AGGAGGCCA CCATGTACAG GATGCAACTC CTGTCTTGCA
                          EcoRI
                                   ~~~~~~ CCL13 (5-75)
       AlaLeuSer LeuAlaLeu ValThrAsnSer LeuAsnVal ProSerThr CysCysPheThr PheSerLys LysLysIle SerLeuGlnArg LeuLysSer
 601 TTCCACTAAG TCTTGCACTT GTCACGAATT CCCTCAACGT CCCATTCACT TCCTGCTTCA CATTTACCAG TAAGAAGATC TCCTTGCAGA GGCTCAACAG
       TyrValIle ThrThrSerArg CysProGln LysAlaVal IlePheArgThr LysLeuGly LysGluIle CysAlaAspPro LysGluLys TrpValGln
 701 CTATGTGATC ACCACCAGCA GGTGTCCCCA GAAGGCTGTC ATCTTCAGAA CCAAACTGGG CAAGGAGATC TGTGCTGACC CAAAGGAGAA GTGGGTCCAG
                                                            human IgG1 Fc (constant region)
       AsnTyrMetLys HisLeuGly ArgLysAla HisThrLeuLys ThrAspLys CysProProCys ProAlaPro GluLeuLeu GlyGlyProSer
 801 AATTATATGA AACACCTGGG CCGGAAAGCT CACACCCTGA AGACTGACAA AACTCACACA TGCCCACCGT GCCCAGCGCC TGAACTCCTG GGGGGACCGT
       ValPheLeu PheProPro LysProLysAsp ThrLeuMet IleSerArg ThrProGluVal ThrCysVal ValValAsp ValSerHisGlu AspProGlu
 901 CAGTCTTCCT CTTCCCCCCA AAACCCAAGG ACACCCTCAT GATCTCCCGG ACCCCTGAGG TCACATGCGT GGTGGTGGAC GTGAGCCACG AAGACCCTGA
       ValLysPhe AsnTrpTyrVal AspGlyVal GluValHis AsnAlaLysThr LysProArg GluGluGln TyrAsnSerThr TyrArgVal ValSerVal
1001 GGTCAAGTTC AACTGGTACG TGGACGGCGT GGAGGTGCAT AATGCCAAGA CAAAGCCGCG GGAGGAGCAG TACAACAGCA CGTACCGTGT GGTCAGCGTC
       LeuThrValLeu HisGlnAsp TrpLeuAsn GlyLysGluTyr LysCysLys ValSerAsn LysAlaLeuPro AlaProIle GluLysThr IleSerLysAla
1101 CTCACCGTCC TGCACCAGGA CTGGCTGAAT GGCAAGGAGT ACAAGTGCAA GGTCTCCAAC AAAGCCCTCC CAGCCCCCAT CGAGAAAACC ATCTCCAAAG
       LysGlyGln ProArgGlu ProGlnValTyr ThrLeuPro ProSerArg GluGluMetThr LysAsnGln ValSerLeu ThrCysLeuVal LysGlyPhe
1201 CCAAAGGGCA GCCCCGAGAA CCACAGGTGT ACACCCTGCC CCCATCCCGG GAGGAGATGA CCAAGAACCA GGTCAGCCTG ACCTGCCTGG TCAAAGGCTT
       TyrProSer AspIleAlaVal GluTrpGlu SerAsnGly GlnProGluAsn AsnTyrLys ThrThrPro ProValLeuAsp SerAspGly SerPhePhe
1301 CTATCCCAGC GACATCGCCG TGGAGTGGGA GAGCAATGGC CAGCCGGAGA ACAACTACAA GACCACGCCT CCCGTGCTGG ACTCCGACGG CTCCTTCTTC
       LeuTyrSerLys LeuThrVal AspLysSer ArgTrpGlnGln GlyAsnVal PheSerCys SerValMetHis GluAlaLeu HisAsnHis TyrThrGlnLys
1401 CTCTACAGCA AGCTCACCGT GGACAAGAGC AGGTGGCAGC AGGGGAACGT CTTCTCATGC TCCGTGATGC ACGAGGCTCT GCACAACCAC TACACGCAGA
                                     NheI
                                     BmtI                                                                  AseI
       SerLeuSer LeuSerPro GlyLys*** (SEQ ID NO:62)
1501 AGAGCCTCTC CCTGTCTCCG GGTAAATGAG TGCTAGCTGG CGTAACATGA CCAGACATGA TAAGATACAT TGATGAGTTT GGACAAACCA CAACTAGAAT GCAGTGAAAA
1601 AAATGCTTTA TTTGTGAAAT TTGTGATGCT ATTGCTTTAT TTGTAACCAT TATAAGCTGC AATAAACAAG TTAACAACAA CAATTGCATT CATTTTATGT
1701 TTCAGGTTCA GGGGGAGGTG TGGGAGGTTT TTTAAAGCAA GTAAAACCTC TACAAATGTG GTATGGAATT AATTCTAAAA TACAGCATAG CAAAACTTTA
1801 ACCTCCAAAT CAAGCCTCTA CTTGAATCCT TTTCTGAGGG ATGAATAAGG CATGGCCATC AGGGGCTGTT GCCAATGTGT ATTAGCTGTT TGCAGCCCTCA
```

```
1901  CCTTCTTTCA TGGAGTTTAA GATATAGTGT ATTTTCCCAA GGTTTGAACT AGCTCTTCAT TTCTTTATGT TTTAAATGCA CTGACCTCCC ACATTCCCTT
2001  TTTAGTAAAA TATTCAGAAA TAATTTAAAT ACATCATTGC AATGAAAATA ATGTTTTTT ATTAGGCAGA ATCCAGATGC TCAAGGCCCT TCATAATATC
2101  CCCCAGTTTA GTAGTTGGAC TTAGGAACA AAGGAACCTT TAATAGAAAT TGGACAGCAA GAAAGCGAGC TTCTAGCTTA TCCTCAGTCC TGCTCCTCTG
2201  CCACAAAGTG CACGCAGTTG CCGGCCGGT CGGCCAGGGC GAACTCCCGC CCCCACGGCT GCTCGCGCAT CTCGGTCATG GCCGGCCCGG AGGCGTCCCG
2301  GAAGTTCGTG GACACGACCT CCGACCACTC GGGTACAGC TCGTCCAGGC CACCCAGGCC AGGGTGTTGT CGGCACCAC CTGGTCCTGG
2401  ACCGCGCTGA TGAACAGGGT CACGTCGTCC CGGACCACAC CGGCGAAGTC GTCCTGCACG AAGTCCCGGG AGAACCCGAG CCGGTCGGTC CAGAACTCGA
2501  CCGCTCCGGC GACGTCGCGC GCGGTGAGCA CCGGAACGGC ACTGGTCAAC TTGGCCATGA TGGCTCCTCC TGTCAGGAGA GGAAAGAGAA GAAGGTTAGT

AseI
2601  ACAATTGCTA TAGTGAGTTG TATTATACTA TGCAGATATA CTATGCCAAT GATTAATTGT CAAACTAGGG CTGCAGGGTT CATAGTGCCA CTTTTCCTGC
2701  ACTGCCCAT CTCCTGCCCA CCCTTTTCCA GGCATAGACA GTCAGTGACT TACCAAACTC ACAGGAGGGA GAAGGCAGAA GCTTGAGACA GACCCGCGGG
2801  ACCGCCGAAC TGCCAGGGGA CGTGGCTAGG GCGGCTTCTT TTATGGTGCG CCGGCCCTCG GAGTCTCAGC GCTAGCGGC GCCTAGCGGC CAATCTGCGG
2901  TGGCAGGAGG CGGGGCCGAA GGCCGTGCCT GACCACATAG GAGTCACATC AAACAAGGG GCTCGGGGAG AAAGCAAGGG GAAGTCACGC GCCTGTAGCG
3001  CCAGTCGTGTT GTGAAATGGG GGCTTGGGGG CTGACTAGTC AAAACAAACT CCCATTGACG TCAATGGGT GGAGACTTGG AAATCCCGT
3101  GAGTCAAACC GCTATCCACG CCCATTGATG TACTGCCAAG ACCGCATCAT CATGGTAATA GCGATGACTA ATACGTAGAT GTACTGCCAA GTAGGAAAGT
3201  CCCATAAGGT CATGCTACTGG GCATAATGCC AGGCGGGCCA TTGACGTCAA ATGGGGCGT ACTTGGCATA TGATACACTT GATGTACTGC
3301  CAAGTGGGCA GTTTACCGTA AATACTCCAC CCATTGACGT CAATGGGAAAG TCCCTATTGG CGTTACTATG GAACATACG TCATTATTGA CGTCAATGGG
3401  CGGGGGTCGT TGGGCGGTCA GCCAGGCGGG CGTTGCTGGC GTTTAATTAA AACGCCTGCA GGTTAATTAA GAACATGTGA GCAAAAGGC AGCAAAAGGC
3501  CAGGAACCGT AAAAAGGCCG TATAAAGATA CCAGGCGTTT CCCCCTGGAA GCTCCCTCGT GCGCTCTCCT GTTCCGACCC TGCCGCTTAC CGGATACCTG
3601  TCCGCTTCGG AAGCGTGGCG CTTTCTCATA GCTCACGCTG TAGGTATCTC AGTTCGGTGT AGGTCGTTCG CTCCAAGCTG GGCTGTGTGC ACGAACCCCC
3701  CGTTCAGCCC GACCGCTGCG CCTTATCCGG TAACTATCGT CTTGAGTCCA ACCCGGTAAG ACACGACTTA TCGCCACTGG CAGCAGCCAC TGGTAACAGG
3801  ATTAGCAGAG CGAGGTATGT AGGCGGTGCT ACAGAGTTCT TGAAGTGGTG GCCTAACTAC CAAACCACCG CTGGTAGCGG TGGTTTTTT GTTTGCAAGC AGCAGATTAC
3901  TGAAGCCAGT TACCTTCGGA AAAAGAGTTG GTAGCTCTTG ATCGGCAAAC CAAACCACCG CTGGTAGCGG TGGTTTTTT GTTTGCAAGC AGCAGATTAC
4001  GCGCAGAAAA AAAGGATCTC AAGAAGATCC TTTGATCTTT TCTACGGGGT CTGACGCTCA GTGGAACGAA AACTCACGTT AAGGGATTTT GGTCATGGCT
4101  AGTTAATTAA CATTTAAATC AGCGGCCGCA ATAAAATATC TTTATTTTCA TTACATCTGT GTGTTGGTTT TTTGTGTGAA CATAGCGCTCT CATACGCTCT
4201  CCATCAAAAC AAAACGAAAC AAAACAAACT AGCAAAATAG GCTGTCCCA GCTCAAGTGC AGGTGCCAGA ACATTTCTCT ATCGAA (SEQ ID NO:89)
```

IL2ss.CCL13(5-75).hIgG1Fc sequence
[Alanine substitutions for removal of GAG binding sites – Lys & His]

```
   1 GGATCTGCGA TCGCTCCGGT GCCCGTCAGT GGGCAGAGCG CACATGCGCC ACAGTCCCCG AGAAGTGGGG GGACCCCGGT GGCAATTGAA CGGGTGCCTA
 101 GAGAAGTGGG CCCGGGTAA ACTGGGAAAC TGATCTCCT

```
1801  ACCTCCAAAT CAAGCCTCTA CTTGAATCCT TTTCTGAGGG ATGAATAAGG CATAGGCATC AGGGGCGTGT GCCAATGTGC ATTAGCTGTT TGCAGCCTCA
1901  CCTTCTTTCA TGGAGTTTAA GATATAGTGT ATTTTCCCAA GGTTTGAACT AATGAAAATA AGCTCTTCAT TTCTTTATGT TTTAAATGCA CTGACCTCCC ACATTCCCTT
2001  TTTAGTAAAA TATTCAGAAA TAATTTAAAT ACATCATTGC AATGAAACTT TAATAGAAAT TGGACAGCAA CCCACGGCT ATCCAGATGC TCAAGGCCCT TCATAATATC
2101  CCCCAGTTTA GTACTTGGAC TTAGGCAACA AAGGAACCTT CGGGCCAGGG GAACTCCCGC CCCCACGGCT GCTCGCCGAT TTCTAGCTTA TCCTCAGTCC TGCTCCTCTG
2201  CCACAAAGTG CACGCAGTTG CCGACCGGGT CGGGCCAGGC GGCGTACAGC TCGTCCAGGC CGCCACCCA CTCGGTCATG AGGGTGTTGT GCCGCCGG AGGCGTCCGG
2301  GAAGTTCGTG GACACGACCT CCGACCACTC GGCGTACAGC CGGACCACAC TCGTCCAGGC GTCCTCCAGC AGGTGTTGT CCGGCACCAC CTGGTCCTGG
2401  ACCGCGTCGA TGAACAGGGT CACGTCGTCC CGGACCACAC CGGGAAGTC AAGTCCCGGG AGAACCCGGTC CAGAACTCGA
2501  CCGCTCCGGC GACGTCGCGC GCGGTGAGCA CCGGAACGGC ACTGGTCAAC TTGGCTCAAC TGTCAGGAGA GGAAAGAGAA GAAGGTTAGT
                                                           AseI
2601  ACAATTGCTA TAGTGAGTTG TATTATACTA CTATGCCAAT GATTAATTGT CAAACTAGGG CTGCAGGGTT CATAGTGCCA CTTTTCCTGC
2701  ACTGCCCCAT CTCCTGCCCA CCCTTTCCCA GGCATAGACA GTCAGTGACT TACCAAACTC ACAGGAGGGA GCTTGAGACA GACCCGCGGG
2801  ACCGCCGAAC TGCCAGGGGA CGTGGCTAGG GCGGCTTCTT TTATGTGCGG CCGGCCCCTG GAGTCTCAGC CCCCGCCCG GCTCGGGGAG GCCTAGCGGC CAATCTGCGG
2901  TGGCAGGAGG CGGGGCCGAA GGCCGTGCCT GACCAATCCG GAGCACATAG AAAACAAACT AAAGCAAGGG GAAGTCACGC GCCTGTAGCG
3001  CCAGCGTGTT GTGAAATGGG GGCTTGGGGG GGTTGGGGGC CTGACTAGTC CATGGTAATA CCCATTGACG TCAATGGGGT GGAGACTTGG AAATCCCCGT
3101  GAGTCAAACC GCTATCCACG CCCATTGATG TACTGCCAAA ACCGACCATC GCCGGGGCCA TGGGGGCGT ATACGTAGAT GTACTGCCAA GTAGGACTGC
3201  CCCATAAGGT CATGTACTGG GCATAATGCC AGGCGGGCCA TTTACCGTCA TTGACGTCAA TAGGGGCGT ACTTGGCATA TGATACACTT GATGTACTGC
3301  CAAGTGGGCA GTTTACCGTA AATACTCCAC CCATTGACGT CAATGGGAAAG TCCCTATTGG CGTTACTATG GGAACATACG TCATTATTGA CGTCAATGGG
3401  CGGGGGTCGT TGGGCGGTCA GCCAGGCGGG CCATTTACCG TAAGTTATGT AACGCCTGCA GGTTAATTAA GAACATGTGA CCAAAAGGCC AGCAAAAGGC
3501  CAGGAACCGT AAAAGGCCCG CGTTGCTGGC GTTTTTCCAT AGGCTCCGCC CCCCTGACGA GCATCACAAA AATCGACGCT CAAGTCAGAG GTGGCGAAAC
3601  CCGACAGGAC TATAAAGATA CCAGGCGTTT CCCCCTGGAA GCTCCCTCGT GCGCTCTCCT GTTCCGACCC TGCCGCTTAC CGGATACCTG TCCGCCTTTC
3701  TCCCTTCGGG AAGCGTGGCG CTTTCTCATA GCTCACGCTG TAGGTATCTC AGTTCGGTGT AGGTCGTTCG CTCCAAGCTG GGCTGTGTGC ACGAACCCCC
3801  CGTTCAGCCC GACCGCTGCG CCTTATCCGG TAACTATCGT CTTGAGTCCA ACCCGGTAAG ACACGACTTA TCGCCACTGG CAGCAGCCAC TGGTAACAGG
3901  ATTAGCAGAG CGAGGTATGT AGGCGGTGCT ACAGAGTTCT TGAAGTGGTG GCCTAACTAC GGCTACACTA GAAGAACAGT ATTTGGTATC TGCGCTCTGC
4001  TGAAGCCAGT TACCTTCGGA AAAAGAGTTG GTAGCTCTTG ATCCGGCAAA CAAACCACCG CTGGTAGCGG TGGTTTTTTT GTTTGCAAGC AGCAGATTAC
4101  GCGCAGAAAA AAAGGATCTC AAGAAGATCC TTTGATCTTT TCTACGGGGT CTGACGCTCA GTGGAACGAA AACTCACGTT AAGGGATTTT GGTCATGCCT
4201  AGTTAATTAA CATTTAAATC AGCGGCCGCA ATAAAATATC TTTATTTTCA TTACATCTGT TAACATCTGT TTTGTGAAT ACATTTCTCT CATACGCTCT
4301  CCATCAAAAC AAAACGAAAC AAAACAAACT GCTGTCCCCA GTGCAAGTGC AGGTGCCAGA ACATTTCTCT ATCGAA  (SEQ ID NO:90)
```

IL2ss.CCL25.hIgG1Fc sequence

```
   1 GGATCTGCGA TCGCTCCGGT GCCCGTCCAGT GGGCAGAGCG CACATGCCCC ACAGTCCCCG AGAAGTGGGG GGGAGGGGTC GGGAGGGGTC GGCAATTGAA CGGGTGCCTA
 101 GAGAAGTGG CCCGGGGTAA ACTGGGAAAG TGATGTCGTG TACTGGCTCC GCCTTTTCC CGAGGGTGGG GGAGAACCGT CTTCACGCGC ATATAAGTGC AGTAGTCGCC
 201 GTGAACGTTC TTTTTCGCAA CGGGTTTGCC GCCAGAACAC AGTGAAGT TCGAGGGCT CGCATCCTCC CGTCCGCCGT CGTCACGCCC CCGCCGCCC ACCTGAGGCC
 301 GCCATCCACG CCGGTTGAGT CGCGTTCTGC CGCCTCCCGC TCCTGGTGCC CTGTGGTGCG CTGTGAACTG CGTCCGCCGT CTAAGGTAAGT TTAAAGCTCA GGTCGAGACC
 401 GGGCCTTGT CCGGCGCTCC CTTGGAGCCT ACCTAGACTC AGCCGGCTCC CCAGCCTTG CCTGACCCTG CCTGCTCAAC CTTGCTCAAC CTGCTCAAC TCTACGTCTC TGTTTCGTTT
                                                   SfoI
                                                   NarI
                                                   KasI
                                                   BbeI
                                                                                                   IL-2 secretion signal
                                                                                                   MetTyrArg MetGlnLeu LeuSerCysIle
 501 TCTGTTCTGC GCCCGTTACAC ATCCAACCTG TGACCGGCGC CTACCCGGGA TCACCGGCGA AGGAGGGGCA CCATGTACAG GATGCAACTC CTGTCTTCCA
        ~~~~~~ CCL25 (1-127)
        EcoRI
            AlaLeuSer LeuAlaLeu ValThrAsnSer ThrGlnGly ValPheGlu AspCysCysLeu AlaTyrHis TyrProIle GlyTrpAlaVal LeuArgHis
 601 TTGCACTAAG TCTTGCACTT GTCACGGATT CGACCCAAGG TGCCTCTTGA GACTGCTGCC TGGCCTACCA CTACCCCATT GGGTGGCGTG TGCTCCGGCA
            AlaTrpThr TyrArgIleGln GluValSer GlyValSer AsnLeuProAla AlaIlePhe TyrLeuPro LysArgHisArg LysValCys GlyAsnPro
 701 GCCTGGACT TACCGGATCC AGGAGTGAG CGGAGCTGC AATCTGCCTG CTGCGATATT CTACCTGCCC AAGAGACACA GGAAGGTGTG TGGGAACCCC
            LysSerArgGlu ValGlnArg AlaMetLys LeuLeuAsp LeuAspAla ArgAsnLys ValPheAla LysLeuArgHis ThrPheGln GlyProHisAla
 801 AAAAGCAGGG AGTGCAGAG AGCCATGAAG CTCCTGGATG CTCGAAATAA GGTTTTTGCA AAGCTCCGCC ACAACACGCA GACCTTCCAA GGCCCTCATG
                                                                                                               human IgG1 Fc
                                                                                                               (constant region)
            ValLysLys LeuSerSer GlyAsnSerLys LeuSerPhe SerLysLys SerAsnProLeu SerSerSer LysArgAsn ValSerAspLys ThrHisThr
 901 GTGAAAGAA GTTGAGTTCT GGAAACTCCA AGTTATCATC GTCCAAGTTT AGCAATCCCA TCAGCAGCAG CAAAAGGAAT GTCTCCGACA AAACTCACAC
            CysProPro CysProAlaPro GluLeuLeu GlyGlyPro SerValPheLeu PheProPro LysProLys AspThrLeuMet IleSerArg ThrProGlu
1001 ATGCCCACCG TGCCCAGCAC CTGAACCTC GGGGGACCGT CAGTCTTCC TCTTCCCCCC AAAACCCAAG GACACCCTCA TGATCTCCCG GACCCCTGAG
            ValThrCysVal ValValAsp ValSerHis GluAspProGlu ValLysPhe AsnTrpTyr ValAspGlyVal GluValHis AsnAlaLys ThrLysProArg
1101 GTCACATGCG TGGTGGTGGA CGTGAGCCAC GAAGACCCTG AGGTCAAGTT CAACTGGTAC GTGGACGGCG TGGAGGTGCA TAATGCCAAG ACAAAGCCGC
            GluGluGln TyrAsnSer ThrTyrArgVal ValSerVal LeuThrVal LeuHisGlnAsp TrpLeuAsn GlyLysGlu TyrLysCysLys ValSerAsn
1201 GGGAGGAGCA GTACAACAGC ACGTACCGTG TGGTCAGCGT CCTCACCGTC CTGCACCAGG ACTGGCTGAA TGGCAAGGAG TACAAGTGCA AGGTCTCCAA
            LysAlaLeu ProAlaProIle GluLysThr IleSerLys AlaLysGlyGln ProArgGlu ProGlnVal TyrThrLeuPro ProSerArg GluGluMet
1301 CAAAGCCCTC CCAGCCCCA TCGAGAAAAC CATCTCCAAA GCCAAAGGGC AGCCCCGAGA ACCACAGGTG TACACCCTGC CCCCATCCCG GGAGGAGATG
            ThrLysAsnGln ValSerLeu ThrCysLeu ValLysGlyPhe TyrProSer AspIleAla ValGluTrpGlu SerAsnGly GlnProGlu AsnAsnTyrLys
1401 ACCAAGAACC AGGTCAGCCT GACCTGCCTG GTCAAAGGCT TCTATCCCAG CGACATCGCC GTGGAGTGGG AGAGCAATGG GCAGCCGGAG AACAACTACA
            ThrThrPro ProValLeu AspSerAspGly SerPhePhe LeuTyrSer LysLeuThrVal AspLysSer ArgTrpGln GlnGlyAsnVal PheSerCys
1501 AGACCACGCC TCCCGTGCTG GACTCCGACG GCTCCTTCTT CCTCTACAGC AAGCTCACCG TGGACAAGAG CAGGTGGCAG CAGGGGAACG TCTTCTCATG
                                                                                                                     BmtI
                                                                                                                     NheI
            SerValMet HisGluAlaLeu HisAsnHis TyrThrGln LysSerLeuSer LeuSerPro GlyLys*** (SEQ ID NO:64)
1601 CTCCGTGATG CACGAGGCTC TGCACAACCA CTACACGCAG AAGAGCCTCT CCCTGTCTCC GGGTAAATGA GGCTAGCTG GCCAGACATG ATAAGATACA
```

IL2ss.CCL25(4-127).hIgG1Fc sequence

```
   1 GGATCTGCGA TGCGTCCGGT GCCGTCCCGT GCGCGGGTAA ACTGCGTGTG CACAATGCCC ACAGTCCCAG AGAAGTTGGG GGGAGGGGTC GGGCAATTGAA CGGGTGCCTA
 101 GAGAAGGTGG CGCGGGGTAA ACTGCGGGTG TGATGTCGTG GCCAGAACAC CGGGTTTGCC TCGAGGGGCT TGCAGGGGCT CGCATCTCTC CGAGGGTGGG GGAGAACCGT ATATAAGTGC AGTAGTGCCC
 201 GTGAACGTTC TTTTTCGCAA CGGGTTCAGT GCCAGAACAC CGGGTTCTGC TCGAGGGCT TGCAGGGGCT CGCATCTCTC CGCATCCGCC CTTCACCGCC ACGGCTGAGCC
 301 CCCATTCCACG CCGGTTCAGT CCGGTTCTGC GCTGGTGCC CTGTGGTAGT CCTGGAACTG CGTCCGCAGT CGTCCCGCCT CGTCGCAACC CTAGGTAAGT CTTAAAGCTCA GTCGAGACC
 401 GGGCCTTTGT CCGGCCGTCC CTTGGAGCCT ACCTAGACTC ACCCGGCTCT CCACGCTTTG CACCGTTTTG ACCCCCTTG CCTGCTCAAC TCTACGTCTT TGTTTCGTTT

IL-2 secretion signal
                                                                                                         MetTyrArg MetGlnLeu LeuSerCysIle
 501 TCTGTTCTGC GCCGTTACAG ATCCAAGCTG TGACCGGGGC CTACCTGAGA TCACGGGGCA AGGAGGGCCA CCATGTACAG GATGCAACTC CTGTCTTGCA
                                                                                                    ~~~~~~~~~~~~~
                         EcoRI                                         ~~~~~~ CCL25 (4-127)
     AlaLeuSer ValThrAsnSer ValPheGlu AspCysCys LeuAlaTyrHis TyrProIle GlyTrpAla ValLeuArgHis AlaTrpThr
 601 TTGCACTAAG TCTTGCACTT GTCAGAATT CGGTCTTGA CCTGGCCTACC ACTACCCCAT TGGGTGGCGT GTGCTGCGGC ACGGCTGGAC
     TyrArgIle GlnGluValSer AsnLeuPro AlaAlaIlePhe TyrLeuPro LysArgHis ArgLysValCys GlyLysAsnPro LysSerArg
 701 TTACCGGATC CAGGAGGTGA GCGGGAGCTG CAATCTGCCT GCTGCGATAT TCTACCTCCC CAAGAGACAC AGGAAGGTGT GTGGAACCC CAAAAGCAGG
     GluValGlnArg AlaMetLys LeuLeuAsp ValPheAla LysLeuArg HisAsnThrGln ThrPheGln GlyProHis AlaValLysLys
 801 GAGGTGCAGA GAGCCATGAA GCTCCTGGAT GCTTCGAATA AGTTTTTGC AAAGCTCCGC CACAACACGC AGACCTTCCA AGGCCCTCAT GCTGTAAGA
                                                                                                     human IgG1 Fc (constant region)
     LeuSerSer GlyAsnSer LysLeuSerSer PheSerLysPhe SerAsnPro IleSerSerPhe LysArgAsn ValSerArgAsp LysThrHisThr CysProPro
 901 AGTTCAGTTC TGGAAACTCC AAGTTATCAT CGTCCAAGTT TAGCAATCCG ATCAGCAGCA GCAAGAGGAA TGTCTCCGAC AAAACTCACA CATGCCCACC
     CysProAla ProGluLeuLeu GlyGlyPro SerValPhe LeuPheProPro LysProLys AspThrLeu MetIleSerArg ThrProGlu ValThrCys
1001 GTGCCCAGCA CCTGAACTCC TGGGGGACC GTCAGTCTTC CTCTTCCCCC CAAAACCCAA GGACACCCTC ATGATCTCCC GGACCCCTGA GGTCACATGC
     ValValAsp ValSerHis GluAspPro GluValLysPhe AsnTrpTyr ValAspGly ValGluValHis AsnAlaLys ThrLysPro ArgGluGluGln
1101 GTGGTGGTGG ACGTGAGCCA CGAAGACCCT GAGGTCAAGT TCAACTGGTA CGTGGACGGC GTGGAGGTGC ATAATGCCAA GACAAAGCCG CGGGAGGAGC
     TyrAsnSer ThrTyrArg ValValSerVal LeuThrVal LeuHisGln AspTrpLeuAsn GlyLysGlu TyrLysCys LysValSerAsn LysAlaLeu
1201 AGTACAACAG CACGTACCGT GTGGTCAGCG TCCTCACCGT CCTGCACCAG GACTGGCTGA ATGGCAAGGA GTACAAGTGC AAGGTCTCCA ACAAAGCCCT
     ProAlaPro IleGluLysThr IleSerLys AlaLysGly GlnProArgGlu ProThrLeu TyrThrLeu ProProSerArg GluGluMet ThrLysAsn
1301 CCCAGCCCCC ATCGAGAAAA CCATCTCCAA AGCCAAAGGG CAGCCCCGAG AACCACAGGT GTACACCCTG CCCCCATCCC GGGAGGAGAT GACCAAGAAC
     GlnValSerLeu ThrCysLeu ValLysGly PheTyrProSer AspIleAla ValGluTrp GluSerAsnGly GlnProGlu AsnAsnTyr LysThrThrPro
1401 CAGGTCAGCC TGACCTGCCT GGTCAAAGGC TTCTATCCCA GCGACATCGC CGTGGAGTGG GAGAGCAATG GGCAGCCGGA GAACAACTAC AAGACCACGC
     ProValLeu AspSerAsp GlySerPhePhe LeuTyrSer LysLeuThr ValAspLysSer ArgTrpGln GlnGlyAsn ValPheSerCys SerValMet
1501 CTCCCGTGCT GGACTCCGAC GGCTCCTTCT TCCTCTACAG CAAGCTCACC GTGGACAAGA GCAGGTGGCA GCAGGGGAAC GTCTTCTCAT GCTCCGTGAT
                                                                                                      BmtI
                                                                                                      NheI
     HisGluAla LeuHisAsnHis TyrThrGln LysSerLeu SerLeuSerPro GlyLys***   (SEQ ID NO:65)
1601 GCACCAGGCT CTGCACAACC ACTACACGCA GAAGAGCCTC TCCCTGTCTC CGGGTAAATG AGTCCTAGCT GATAAGACAT GATAAGATAC ATTGATGAGT
1701 TTGGACAAAC CACAACTAGA ATGCAGTGAA AAAAATGCTT TATTTGTGAA ATTGTGATG CTATTGCTTT ATTTGTAACC ATTATAAGCT GCAATAAACA
                                                                                                                AseI
```

```
1801  AGTTAACAAC AACAATTGCA TTCATTTTAT GTTTCAGGTT CAGGGGGAGG TGTGGGAGGT TTTTTAAAGC AAGTAAAACC TCTACAAATG TGGTATGGAA
      AseI
1901  TTAATTCTAA AATACAGCAT AGCAAAACTT TAACCTCCAA ATCAAGCCTC TACTCGAATC CTTTTCTGAG GGATGAATAA GGCATAGGCA TCAGGGGCTG
2001  TTGCCAATGT GCATTAGCTG TTTGCAGCCT CACCTTCTTT TTTTAGTAA AATATTCAGA AAGATATAGT CATGGAGTTT GTATTTTCCC AAGGTTTGAA CTAGCTCTTC ATTTCTTTAT
2101  GTTTAAATG CACTGACCTC CCACATTCCC CTTTTAGTAA AATATTCAA ACTTAGGTGG ACTTAGGAA ATACATCATT GCAATGAAAA TAAATGTTTT TTATTAGGCA
2201  GAATCCAGAT GCTCAAGGCC CCTGCTCCTC TCCCCCAGTT TAGTAGTTGG ACTTAGGGAA CAAAGGAACC TTTAATAGAA ATTGGAACGG AAGAAGCGA
2301  GCTTCTAGCT TATCCTCAGT CCTGCTCCTC TGCCACAAAG TGCACGCAGT TGCCGGCCGG GTCGCGCAGG GCGAACTCCC GCCCCCACGG CTGCTCGCCG
2401  ATCTCGGTCA TGGCCGGCCC GGAGGCGTCC CGGAAGTTCG TGGACACGAC CTCCGGACCC TCGGCGTACA GCTCGTCCAG GCCGCGCACC CACACCCAGG
2501  CCAGGGTGTT GTCCGGCACC ACCTGGTCCT GGACGCGCGT GATGAACAGG GTCACGTCGT CCCGGACCAC ACCGGCGAAG TCGTCCTCCA CGAAGTCCCG
2601  GGAGAACCCG AGCCGGTCGG TCCAGAACTC GACCGGCTCC GCGAACGTCG GCCGGTGAG CACCGGAACG GCACTGGTCA ACTTGGCCAT GATGGCTCCT
                                                                                                       AseI
2701  CCTGTCAGGA GAGGAAAGAG AAGAAGGTTA GTACAATTGC TATATGTGAGT ATCTCCTGCC CACCTTTCC TATGCAGATA ATGATTAATT GTCAAACTAG
2801  GGCTGCAGGG TTCATAGTGC CACTTTTCCT GCACTGCCCC CAGGCATAGA CAGTCAGTGA CTTACCAAAC TCACAGGAGG
2901  GAGAAGGCAG AAGCTTGAGA CAGACCCGCG GGACCCCGA ACTGCGAGGG GGGCGGCTTC TTTTATGGTG CGCCGGCCCT CGGAGGCAGG
3001  GCGCTCGGGG AGGCCTAGCG GCCAATCTGC GGTGGCAGGA AAGGCCGTGC CGGAGCACAT AGGAGTCTCA GCCCCCGCC
3101  CCAAGCAAG GGGAAGTCAC GCGCCTGTAG GTGTGAAATG GGGGTTGGGG CCCTGACTAG TCAAAACAAA CTCCCATTGA
3201  CGTCAATGGG GTGGAGACTT GGAAATCCCC CCGCTATCCA TGTACTGCCA AAACCGCATC ATCATGGTAA TAGCGATGAC
3301  TAATACGTAG ATGTACTGCC AAGTAGGAAA GTCCCATAAG GTCTACTACT GGGCATAATG CCAGGCGGGC CATTTACCGT CATTGACGTC AATACGGGC
3401  GTACTTGGCA TATGATACAC TTGATGTACT GCCAAGTGGG CAGTTTACCG TAAATACTCC ACCCATTGAC GTCAATGGAA AGTCCCTATT GGCGTTACTA
3501  TGGGAACATA CGTCATTATT GACGTCAATG GGCGGGGTC GTTGGGCGGT CAGCCAGGCG CGCGTTGCTG CGTAAGTTAT CCCCCCTGAC GAGCATCACA
3601  AAAGAACATG GAGCAAAAGG CCAGCAAAAG CCAGAACCC AGTGGCGAA ACTATAAAGA TACCAGGCGT TTCCCCCTGG AAGCTCCCTC GTGCGCTCTC CTGTTCCGAC
3701  AAAATCGACG CTCAAGTCAG AGGTGGCGAA TGTCCGCCTT TCTCCCTTGC GGAAGCGTGG CGCTTTCTCA TAGCTCACGC TGTAGGTATC TCAGTTCGGT GTAGGTCGTT
3801  CCGGCGTTT ACCGGATACC CCGGCTGTCT GCACGAACCC CCCGTTCAGC CCGACCGCTG CGCCTTATCC GGTAACTATC GTCTTGAGTC CAACCCGGTA AGACACGACT
3901  CCGTCCAAGC TGGCTGTGT GCACGAACCC TCCCGTTCAG CCCGACCGCTG CGCCTTATCC GGTAACTATC GTCTTGAGTC CAACCCGGTA AGACACGACT
4001  TATCGCCACT GGCAGCAGCC ACTGGTAACA GGATTAGCAG AGCGAGGTAT GTAGGCGGTG CTACAGAGTT CTTGAAGTGG TGGCCTAACT ACGGCTACAC
4101  TAGAAGAACA GTATTTGGTA TCTGCTCTGC TGAAGCCA GTTACCTTCG GAAAAGAGT TGGTAGCTCT TGATCCGGCA AACAAACCAC CGCTGGTAGC
4201  GGTGGTTTTT TTGTTTGCAA GCAGCAGATT ACGCGCAGAA AAAAAGGATC TCAAGAAGAT CCTTTGATCT TTTCTACGGG GTCTGACGCT CAGTGGAACG
4301  AAAACTCACG TTAAGGGATT TTGGTCATGG CTAGTTAATT AACATTTAAA TCAGCGGCCG ACAAAAACAA ATAGGGGTT CATTACATCT GTGTGTTGGT
4401  TTTTGTGTG AATCGTAACT AACATACCGT CTCCATCAAA ACAAAACGAA CTAGCAAAAT AGGCCGTCCC CAGTGCAAGT GCAGGTGCCA
4501  GAACATTTCT CTATCGAA
                    (SEQ ID NO:92)
```

IL2ss.CCL25(4-127).hIgG1Fc sequence
[Alanine substitutions for GAG binding sites – Lys, Arg & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                          SfoI
                                          NarI
                                          KasI
                                          BbeI
                                          ~~~~~~~                                         IL-2 secretion signal
                                                                                          MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                EcoRI
                                ~~~~~~~    CCL25 (4-127)
        AlaLeuSer LeuAlaLeu ValThrAsnSer ValPheGlu AspCysCys LeuAlaTyrHis TyrProIle GlyTrpAla ValLeuArgHis AlaTrpThr
 601   TTGCACTAAG TCTTGCACTT GTCACGAATT CGGTCTTTGA GGACTGCTGC CTGGCCTACC ACTACCCCAT TGGGTGGGCT GTGCTCCGGC ACGCCTGGAC
        TyrArgIle GlnGluValSer GlySerCys AsnLeuPro AlaAlaIlePhe TyrLeuPro AlaAlaAla AlaAlaValCys GlyAsnPro AlaSerAla
 701   TTACCGGATC CAGGAGGTGA GCGGGAGCTG CAATCTGCCT GCTGCGATAT TCTACCTCCC Cgctgccgct gccgcgGTGT GTGGGAACCC CgctAGCgcc
       GluValGlnAla AlaMetAla LeuLeuAsp AlaAlaAsnAla ValPheAla AlaLeuAla AlaAsnThrGln ThrPheGln GlyProAla AlaValAlaAla
 801   GAGGTGCAGg ctGCCATGgc gCTCCTGGAT GCTgctAATg ctGTTTTTGC AgcgCTCgct gccAACACGC AGACCTTCCA AGGCCCTgcg GCTGTAgccg
                                                                                       human IgG1 Fc (constant region)
        LeuSerSer GlyAsnSer AlaLeuSerSer SerAlaPhe SerAsnPro IleSerSerSer AlaAlaAsn ValSerAsp LysThrHisThr CysProPro
 901   ctTTGAGTTC TGGAAACTCC gccTTATCAT CGTCCgccTT TAGCAATCCC ATCAGCAGCA GCgctgccAA TGTCTCCGAC AAAACTCACA CATGCCCACC
        CysProAla ProGluLeuLeu GlyGlyPro SerValPhe LeuPheProPro LysProLys AspThrLeu MetIleSerArg ThrProGlu ValThrCys
1001   GTGCCCAGCA CCTGAACTCC TGGGGGGACC GTCAGTCTTC CTCTTCCCCC CAAAACCCAA GGACACCCTC ATGATCTCCC GGACCCCTGA GGTCACATGC
       ValValValAsp ValSerHis GluAspPro GluValLysPhe AsnTrpTyr ValAspGly ValGluValHis AsnAlaLys ThrLysPro ArgGluGluGln
1101   GTGGTGGTGG ACGTGAGCCA CGAAGACCCT GAGGTCAAGT TCAACTGGTA CGTGGACGGC GTGGAGGTGC ATAATGCCAA GACAAAGCCG CGGGAGGAGC
        TyrAsnSer ThrTyrArg ValValSerVal LeuThrVal LeuHisGln AspTrpLeuAsn GlyLysGlu TyrLysCys LysValSerAsn LysAlaLeu·
1201   AGTACAACAG CACGTACCGT GTGGTCAGCG TCCTCACCGT CCTGCACCAG GACTGGCTGA ATGGCAAGGA GTACAAGTGC AAGGTCTCCA ACAAAGCCCT
        ProAlaPro IleGluLysThr IleSerLys AlaLysGly GlnProArgGlu ProGlnVal TyrThrLeu ProProSerArg GluGluMet ThrLysAsn
1301   CCCAGCCCCC ATCGAGAAAA CCATCTCCAA AGCCAAAGGG CAGCCCCGAG AACCACAGGT GTACACCCTG CCCCCATCCC GGGAGGAGAT GACCAAGAAC
       GlnValSerLeu ThrCysLeu ValLysGly PheTyrProSer AspIleAla ValGluTrp GluSerAsnGly GlnProGlu AsnAsnTyr LysThrThrPro
1401   CAGGTCAGCC TGACCTGCCT GGTCAAAGGC TTCTATCCCA GCGACATCGC CGTGGAGTGG GAGAGCAATG GGCAGCCGGA GAACAACTAC AAGACCACGC
        ProValLeu AspSerAsp GlySerPhePhe LeuTyrSer LysLeuThr ValAspLysSer ArgTrpGln GlnGlyAsn ValPheSerCys SerValMet·
1501   CTCCCGTGCT GGACTCCGAC GGCTCCTTCT TCCTCTACAG CAAGCTCACC GTGGACAAGA GCAGGTGGCA GCAGGGGAAC GTCTTCTCAT GCTCCGTGAT
                                                                                BmtI
                                                                                NheI
       HisGluAla LeuHisAsnHis TyrThrGln LysSerLeu SerLeuSerPro GlyLys***(SEQ ID NO:66)
1601   GCACGAGGCT CTGCACAACC ACTACACGCA GAAGAGCCTC TCCCTGTCTC CGGGTAAATG AGTGCTAGCT GGCCAGACAT GATAAGATAC ATTGATGAGT
```

```
                                                                                                                                AseI
1701  TTGGACAAAC CACAACTAGA ATGCAGTGAA AAAAATGCTT TATTTGTGAA ATTTGTGATG CTATTGCTTT ATTTGTAACC ATTATAAGCT GCAATAAACA
1801  AGTTAACAAC AACAATTGCA TTCATTTTAT GTTTCAGGTT TAACCCTCAA ATCAAGCCTC TACTTGAATC CTTTTCTGAG GGATGAATAA TCTACAAATG TGGTATGGAA
      AseI
1901  TTAATTCTAA AATACAGCAT AGCAAAAACTT TTTGCAGCCT CACCTTCTTT TTTTTAGTAA AAGATATAGT GTATTTCCC GCAATGAAAA TAAATGTTTT ATTTCTTTAT
2001  TTGCCAATGT GCATTAGCTG CACTGACCTC CCACATTCCC TTTTTAGTAA AATATTCAGA AATAATTTAA ATACATCATT GCAATGAAAA TAAATGTTTT TTATTAGGCA
2101  GTTTTAAATG CACTGACCTC CCACATTCCC TTTTTAGTAA TCCCCAGTT TAGTAGTTGG ACTTAGGGAA TGCCGGCCGG GTCGCGCAGG GCGAACTCCC GCCGCTCGCCG AAGAAAGCGA
2201  GAATCCAGAT GCTCAAGGCC TATCCTCAGT CCTGCTCCTC TGGACACGAC TGCACGCAGT CCCCAGTT TAGTAGTTGG ACTTAGGGAA TGCCGGCCGG GTCGCGCAGG CTGCTCGCCG
2301  GCTTCTAGCT TATCCTCAGT CCTGCTCCTC TGGACACGAC TGCACGCAGT TGGACACGAC GATGAACAGG GTCACGTCGT CCCGACCAC TGCTCCTCCA GCCGGCGCAC CACACCCAGG
2401  ATCTCGGTCA TGGCCGGCCC GGAGGCGTCC GGAAGTTCG GGACCCGCT GGACACGAC GATGAACAGG GTCACGTCGT CCCGACCAC ACCGGCGAAG CGCGGCGCAC CGAAGTCCCG
2501  CCAGGGTGTT GTCCGGCACC ACCTGGTCCT GTCCGGCACC ACCTGGTCCT TCCAGAACTC GACCGGTCGC GCGACGTCGC ACCGGAACG GCACTGGTCA ACTTGGCCAT GATGGCTCCT
                                                                                                 AseI
2701  CCTGTCAGGA GAGGAAAGAG AAGAAGGTTA GTACAATTGC TATAGTGAGT TGTATTATAC CACCCTTTCC CAGGCATAGA CTTACCAAAC ATGATTAATT GTCAAACTAG
2801  GGCTCCAGGG TCATAGTGC CACTTTTCCT GCACTGCCCC ATCTCCTGCC CAGGCATAGA CAGTCAGTGA CAGGCCGCCC CGCCGGCCCC CGGAGGCAGG
2901  GAGAAGGCAG AAGCTTGAGA CAGACCCGCG GGACCGCCGA ACTGCGAGGG CCCCGGCCTA GGGCGGCTTC TTTTATGTGC CGCCGGCCCC CGGAGGCAGG
3001  GCGCTCGGGG AGGCCTAGCG GCCAATCTGC GGTGGCAGGA GGCGGGGCCG AAGGCCGTGC CTGACCAATC AGGAGTCTCA GCCCCCCGCC
3101  CCAAAGCAAG GGGAAGTCAC GCGCCTGTAG TTGTGAAATG GGGCCTTGGG GGGCCTTGGG GGGTTGGGG TGTACTGCCA ATCATGGTAA CTCCCATTGA
3201  CGTCAATGGG GTGGAGACTT GGAAATCCCC GTGAGTCAAA CCGCTATCCA GTCATGTACT GGGCATAATG CCAGGCGGGC CATTTACCGT TAGCGATGAC
3301  TAATACGTAG ATGTACTGCC AAGTAGGAAA GTCATGTACT GCCAAGTGGG CAGTTTACCG TAAATACTCC ACCCATTGAC AGTCCCTATT AATAGGGGC
3401  GTACTTGGCA TATGATACAC TTGATGTACT GCCAAGTGGG CAGTTTACCG GTTGGGCGGT GTTGGGCGGT CGTAAGTTAT GTAACGCCTG CAGGTTAATT
3501  TGGGAACATA CGTCATTATT GACGTCAATG GCCAAGGCA CCAGCAAAG GCCAGGAACC GTAAAAAGSC GCGTTTTCC ATAGGCTCCG GAGCATCACA
3601  AAGAACATGT CAGCAGAATG CCAGCAAAG CCAGCAAAG ACCCGACAGG ACTATAAAGA TACCAGGCGT TTCCCCCTGG AAGCTCCCTC GTGCGCTCTC CTGTTCCGAC
3701  AAAAATGAGT CTCAAGTGCA AGTGGCGAAA ACCCGACAGG ACTATAAAGA TACCAGGCGT TTCCCCCTGG AAGCTCCCTC GTGCGCTCTC GTAGGTCGTT
3801  CCTGCCGCTT ACCGGATACC TGTCCGGCCT TCTCCCTTCG GGAAGCGTGG CGCTTTCTCA TAGCTCACGC TGTAGGTATC CAACCCGGTA AGACACGACT
3901  CGCTCCAAGC TGGGCTGTGT GCACGAACCC CCGTTCAGC CCGACCGCTG CCGACCGCTG GGTAACTATC CTACAGAGTT GTCTTGAGTC CAACCCGGTA CGGCTGGTAGC
4001  TATCGCCACT GGCAGCAGCC ACTGGTAACA GGATTAGCAG AGCGAGGTAT GTAGGCGGTG CTACAGAGTT GGTAGCTCT TGATCCGGCA AACAAACCAC CGCTGGTAGC
4101  TAGAGAACA GTATTTGGTA TCTGCGCTCT GCTGAAGCCA AAAAGGATC GTTACCTTCG GAAAAGAGT CCTTTGATCT TTTCTACGGG GTCTGACGCT CAGTGGAACG
4201  GGTGGTCTTT TTGTTTGCAA GCAGCAGATT TTAAGGGATT TTGGTCATGAG CTAGTTAATTT AACATTTAAA TCAGGGGCCG CAATAAAATA TCTTTATTT CATTACATCT GTGTGTTGGT
4301  AAAACTCACG TTAAGGGATT AATCGTAACT AACATACGCT CTCCATCGAA GCACTTGATAA ACAAAACGAA TCAGCGGCCG CAATAAAATA CTAGCAAAAT ACGGCTACAC
4401  TTTTTGTGTG AATCGTAACT AACATACGCT CTCCATCGAA GCACTTGATAA ACAAAACGAA CAGCAAAATA CTAGCAAAAT AGGCTGCCCC CAGTGCAAGT GCAGGTGCCA
4501  GAACATTTCT CTATCGAA (SEQ ID NO:93)
```

IL2ss.CXCL11.hIgG1Fc sequence

```
   1 GGATCTGCGA TGGCTCCGGT GCCCGTCAGT GGGCAGAGCG CACATCGCCC ACAGTCCCCG AGAAGTTGGG GGGAGGGGTC GGCAATTGAA CGGGTGCCTA
 101 GAGAAGGTGG GTTTTTGCGA ACTGGGAAAG TGATGCGCTG GCCTTTTTCC GCCTTTTTCC CGAGGGTGGG GGAGAACCGT CTTCACGCGG ATATAAGTGC
 201 GTGAACGTTC TTTTTGCGCA CGGGTTTGCC GCCAGAACAC AGTCGAAGCT TGCAGGGGCT CGCATCTCTC CGCCCGCGCC ACCTGAGCGC
 301 GCCATCCACG CCGGTTCTGC CGCGTTCTCC CGCCTCCCGC CTGTGTGCCT TCCTGAACTG CGTCCGCGCT CTAGGTAAGT CCGCGACCC
 401 GGGCCTTTGT CCGGCGCTCC CTTGGAGCCT AGCCGGCTCT AGCCGGCTCT CCACGCTTTG CCTTGCTCAAC TCTACGTCTT TGTTTCGTTT
                                            KasI
                                            NarI
                                            SfoI
                                            BbeI
                                                                               IL-2 secretion signal
                                                                             MetTyrArg MetGlnLeu LeuSerCysIle
 501 TCTGTTCTGC GCCGTTACAG ATCCAAGCTG TGACCGGCGC CTACCTGAGA TCACCGGGCA AGGAGGGCCA CCATGTACAG GATGCAACTC CTGTCTTGCA
                          ~~~~~ CXCL11 (1-73)
                          EcoRI
     AlaLeuThr LeuAlaAla ValThrAsnSer PheProMet PheLysArg GlyArgCysIleGly CysIleCys Leu ProGlyVal LysAlaValLys ValAlaAsp
 601 TTGCACTAAG TCTTCCACTT GTCACGAATT CGTTCCCCAT CGTTCCCCAT GTTCAAAAGA GGACGCTGTC TTGCATAGG CCCTGGGGTA AAAGCAGTGA AAGTGCAAGA
     IleGluLys AlaSerIleMet TyrProSer AsnAsnCys AspLysIleGlu ThrLeuLys GluAsnLysGly GlnArgCys LeuAsnPro
 701 TATTGAGAAA GCCTCCATAA TCTACCCAAG TAACAACTGT GACAAAATAG AACTGGATG ATGACGATG ATGAAAAAG GAAAATAAAAG GAGACAATCCC CCTAAATCCC
                                                                                                      human IgG1 Fc (constant region)
     LysSerLysGln AlaArgLeu IleIleLys LysValGluArg LysAsnPhe AspLysPhe HisThrCysSer ProCysPro AlaProGlu LeuLeuGlyGly
 801 AAATGAGAAG AAGCAAGGCT TATAATCAAA AAAGTCAAA GAAAGAATTT TGACAAAACT CACACATGCC CACCGTGCCC AGCACCTGAA CTCCTGGGGG
     ProSerVal PheLeuPhe ProProLysPro LysAspThr LeuMetIle SerArgThrPro GluValThr CysValVal ValAspValSer HisGluAsp
 901 GACCGTCAGT CTTCCTCTTC CCCCCAAAC CCAAGGACAC CCTCATGATC TCCCGGACCC CTGAGGTCAC ATGCGTGGTG GTGGACGTGA GCCACGAAGA
     ProGluVal LysPheAsnTrp TyrValAsp GlyValGlu ValHisAsnAla LysThrLys ProArgGlu GluGlnTyrAsn SerThrTyr ArgValVal
1001 CCCTGAGGTC AAGTTCAACT GGTACGTGGA CGGCGTGGAG GTGCATAATG CCAAGACAAA GCCGCGGGAG GAGCAGTACA ACAGCACGTA CCGTGTGGTC
     SerValLeuThr ValLeuHis GlnAspTrp LeuAsnGlyLys GluTyrLys CysLysVal SerAsnLysAla LeuProAla ProIleGlu LysThrIleSer
1101 AGCGTCCTCA CCGTCCTGCA CCAGGACTGG CTGAATGGCA AGGAGTACAA GTGCAAGGTC TCCAACAAAG CCCTCCCAGC CCCCATCGAG AAAACCATCT
     LysAlaLys GlyGlnPro ArgGluProGln ValTyrThr LeuProPro SerArgGluGlu MetThrLys AsnGlnVal SerLeuThrCys LeuValLys
1201 CCAAAGCCAA GGGGCAGCCC CGAGAACCAC AGGTGTACAC CCTGCCCCCA TCCCGGGAGG AGATGACCAA GAACCAGGTC AGCCTGACCT GCCTGGTCAA
     GlyPheTyr ProSerAspIle AlaValGlu TrpGluSer AsnGlyGlnPro GluAsnAsn TyrLysThr ThrProProVal LeuAspSer AspGlySer
1301 AGGCTTCTAT CCCAGCGACA TCGCCGTGGA GTGGGAGAGC AATGGGCAGC CGGAGAACAA CTACAAGACC ACGCCTCCCG TGCTGGACTC CGACGGCTCC
     PhePheLeuTyr SerLysLeu ThrValAsp LysSerArgTrp GlnGlnGly AsnValPhe SerCysSerVal MetHisGlu AlaLeuHis AsnHisTyrThr
1401 TTCTTCCTCT ACAGCAAGCT CACCGTGGAC AAGAGCAGGT GGCAGCAGGG GAACGTCTTC TCATGCTCCG TGATGCACGA GGCTCTGCAC AACCACTACA
                                                       BmtI
                                                       NheI
     GlnLysSer LeuSerLeu SerProGlyLys *** (SEQ ID NO:67)
1501 CGCAGAAGAG CCTCTCCCTG TCTCCGGGTA AATGAGTGCT AGCTGGCCAG ACATGATAAG ATACATTGAT GAGTTTGGAC AAACCACAAC TAGAATGCAG
1601 TGAAAAAAAT GCTTTATTTG TGAAATTTGT GATGCTATTG CTTTATTTGT AACCTGCCAT AACTGCAATA ACCTGCAATA CAACAAGTAA TGCATTCATT
                                                                                                   AseI
1701 TTATGTTTCA GGTTCAGGGG GAGGTGTGGG AGGTTTTTTA AAGCAAGTAA AATGAAGTAA AATGTGGTAT AATGTGGTAT CTAAAATACA GCATACCAAA
1801 ACTTAACCT CCAAATCAAG CCCTCACTTG AATCCCTTTC TGAGGGATGA ATAAGGCATA GGCATCAGGG GCTGTTGCCA ATGTGCATTA GCTGTTTGCA
```

```
1901  GCCTCACCTT CTTTCATGGA GTTTAAGATA TAGTGTATTT TCCCAAGGTT TGAACTAGCT CTTCATTTCT TTATGTTTTA AATGCACTGA CCTCCCACAT
2001  TCCCTTTTA  GTAAATATT  CAGAAATATT TTGGACTTAG GGAACAAAGG AAACCTTTAAT AGAAATAATG GCCAGAATCC AGATGCTCAA GGCCCTTCAT
2101  AATATCCCC  AGTTAGTAG  TTGGACTTAG CCGGGTCGCG CAGGGCGAAC TCCCGCCCCC CAGGCTGCTC GCCGAGCTCT AGCTTATCCT CAGTCCTGCT
2201  CCTCTGCCAC AAAGTGCACG CAGTTGCCGG CGAACCTCGA TACAGCTCGT CAGGCCGCGG TACACCACC CAGGCTGCTC GCCGATCACG GTCATGGCCG GCCCGGAGGC
2301  GTCCCGGAAG TTCGTGGACA CGAACCTCGA TACAGCTCGT CAGGCCGCGG CACCCACACC CAGGCCCAGG TGTTGTCCGG CACCACTGG
2401  TCCTGGACCG CGCTGATGAA CAGGGTCACG TCGTCCCGGA CCACAGCCGG GAAGTCGTCC TCCACGAAGT CCCGAGCCGG TCGGTCCAGA
2501  ACTCGACCGC TCCGGGACGC TCGCGGCCGG TGAGCCACTG GTCAACTTGG CCATGATGGC TCCTCCTGTC AGGAGAGGAA AGAGAGAAG

AseI
2601  GTTAGTACAA TTGCTATAGT GAGTTGTATT ATACTATGCA GATATACTAT GCCAATGATT AATTGTCAAA CTAGGGCTGC AGGGTCATA  GTGCCACTTT
2701  TCCTGACACTG CCCCATCTCC TGCCCACCCG TTCCCACCCT GCTAGGGCGG CTTCTTTTAT AAACTCACAG AAACTCACAG GAGGGAGAAG GCAGAAGCTT GAGACAGACC
2801  CGCGGGACCG AACCGTAAAA CCGAACTGCG AGGGGACGTG GCTAGGGCGG GGTGCGCGG CCCTCGGAGG CAGGGCGCTC GGGGAGGCCT AGCGGCCAAT
2901  CTGCGGTGGC AGGAGGCGGG GCCGAAGCCC GTGCCTGACC ACATAGGAGT CTCAGCGCCC CGCCCAAAG  CAAGGGGAAG TCACGCGCCT
3001  GTAGCGCCAG CGTGTTGTGA AATGGGGGCT TGGGGGGGTT GGGCCCCTGA CTAGTCAAAA CAAACTCCCA TTGACGTCAA TGGGGTGGAG ACTTGGAAAT
3101  CCCCGTGAGT CAAACCCCTA TCCACGCCCA TTGATGTACT GCCAAAACCG CATCATCATG GTAATAGCGA TGACTAATAC GTAGATGTAC TGCCAAGTAG
3201  GAAAGTCCCA TAAGGTCATG TACTGGGCAT AATGCCAGGC GGGCCATTTA CCGTCAATTGA CGTCAATAGG GGGCGTACTT GGCATATGAT ACACTTGATG
3301  TACTGCCAAG TGGGCAGTTT ACCGTAAATA CTCCACCCAT TGACGTCAAT GGAAAGTCCC TATTGGCGTT ACTATGGGAA CATACGTCAT TATTGACGTC
3401  AATGGGCGGG GGTCGTTGGG CGGTCAGCCA GGCGGGCCAT TTACCGTAAG TTATGTAACG CCTGCAGGTT AATTAAGAAC ATGTGAGCAA AAGGCCAGCA
3501  AAAGGCCAGG AACCGTAAAA AGCCGCGTT GCTGGCGTTT TTCCATAGGC TCCGCCCCCC CTGACGAGCAT CACAAAAATC GACGCTCAAG TCAGAGGTGG
3601  CGAAACCCGA CAGGACTATA AAGATACCAG GCGTTTCCCC CTGGAAGCTC CCTCGTGCGC TCTCCTGTTC CGACCCTGCC GCTTACCGGA TACCTGTCCG
3701  CCTTTCTCCC TTCGGAAGC  GTGGCGCTTT CTCATAGCTC ACGCTGTAGG TATCTCAGTT CGGTGTAGGT CGTTCGCTCC AAGCTGGGCT GTGTGCACGA
3801  ACCCCCCGTT CAGCCCGACC GCTGCGCCTT ATCCGGTAAC TATCGTCTTG AGTCCAACCC GGTAAGACAC GACTTATCGC CACTGGCAGC AGCCACTGGT
3901  AACAGGATTA GCAGAGCGAG GTATGTAGGC GGTGCTACAG AGTTCTTGAA GTGGTGGCCT AACTACGGCT ACACTAGAAG AACAGTATTT GGTATCTGCG
4001  CTCTGCTGAA GCCAGTTACC TTCGGAAAAA GAGTTGGTAG CTCTTGATCC GGCAAACAAA CCACCGCTGG TAGCGGTGGT TTTTTTGTTT GCAAGCAGCA
4101  GATTACGCGC AGAAAAAAAG GATCTCAAGA AGATCCTTTG ATCTTTTCTA CGGGGTCTGA CGCTCAGTGG AACGAAAACT CACGTTAAGG GATTTTGGTC
4201  ATGGCTAGTT AATTAACATT TAAATCAGCG GCCAATAA   AATATCTTTA TTTTCATTAC ATCTGTCTGT TGGTTTTTTG TGTGAATCGT AACTAACATA
4301  CGCTCTCCAT CAAAACAAAA CGAAACAAAA CAAACTAGCA AAATAGGCTG TCCCCAGTGC AAGTGCAGGT TCCCAGAACAT TTCTCTATCG AA (SEQ ID NO:94)
```

IL2ss.CXCL11(4-73).hIgG1Fc sequence

(SEQ ID NO:68)

```
1901  TCTTTCATGG AGTTAAGAT ATAGTGTATT TTCCCAAGGT TGGAACTAGC TCTTCATTTC TTTATGTTTT AAATGCACTG ACCTCCCACA TTCCCTTTTT
2001  AGTAAAATAT TCAGAAATAA TTTAAATACA GAACCTTTAA TCATTGCAAT GAAAATAAAT GTTTTTTATT AGGCAGAATC CAGATGCTCA AGGCCCTTCA TAATATCCCC
2101  CAGTTAGTA GTTGGACTTA GGAACAAAAG GCCGGGTCGC CTCCCGCCCC ACAGCAAGAA AGCGAGCTTC CGCCGATCTC TAGCCTTATCC TCAGTCCTGC TCCTCTGCCA
2201  CAAAGTGCAC GCAGTTGCCG GCCGGGTCGC GCAGGGCGAA CTCCCGCCCC CACGGCTGCT CCAGGCCAGG GGTCATGGCC GGCCCGGAGG CGTCCCGGAA
2301  GTTCGTGGAC ACGACCTCCG ACCACTCCGG GTACAGCTCG TCCAGGCCGC GCACCCACAC CCAGGCCAGG GTGTTGTCCG GCACCACCTG GTCCTGGACC
2401  GCGCTGATGA ACAGGGTCAC GTCGTCCCGG ACCACACCGG CGAAGTCGTC CGAAGTCGTC CTCCACGAAG ACCCGAGCCG GTCGGTCCAG AACTCGACCG
2501  CTCCGGCGAC GTCGCGCGCG GTGAGCACCG GAACGGCACT GGTCAACTTG GCCATGATGG CTCCTCCGT CAGGAGAGGA AAGAGAAGAA GGTTAGTACA

AseI
2601  ATTGCTATAG TGAGTTGTAT TATACTATGC AGATATACTA TAATTGTCAA ACTAGGGCTG CAGGGTTCAT AGTGCCACTT TTCCTGCACT
2701  GCCCCATCTC CTGCCAGGC TTTCCAGGGG ATAGACAGTC CAAACTCACA GGAGGGAGAA GGCAGAAGCT TGAGACAGAC CCGCGGGACC
2801  GCCGAACTGC GAGGGCACGT GGCTAGGGCG GCTTCTTTA TGTGCCCGG GCCCTCGGAG GCAAGCGCGT CGGGAGCGCC TAGCGGCCAA TCTGCGGTGG
2901  CAGGAGGCGG GGCCGAAGGC CGTGCCTGAC CAATATAGAG CACATAGGAG TCTCAGCCCC CCGCCCCAAA GCAAGGGGAA GTCACGCGCC TGTAGCGCCA
3001  GCGTGTTGTG AAATGGGGGC TTGGGGGGGT TGGGCCCTG ACAAAACTCC ATTGACGTCA ATGGGGGTGGA GACTTGGAAA TCCCCGTGAG
3101  TCAAACCGCT ATCCACGCCC ATTGATGTAC TGCCAAAACC GCATCATCAT GGTAATAGCG ATGACTAATA CCTAGATGTA CTGCCAAGTA GGAAAGTCCC
3201  ATAAGGTCAT GTACTGGGCA TAATGCCAGG CGGGCCATTT ACCGTCATTG ACGTCAATAG GGGGCGTACT TGGCATATGA TACACTTGAT GTACTGCCAA
3301  GTGGGCAGTT TACCGTAAAT ACTCCACCCA TTGACGTCAA TGGAAAGTCC CTATTGGCGT TACTATGGGA ACATACGTCA TTATTGACGT CAATGGGCGG
3401  GGGTCGTTGG GCGGTCAGCC AGGCGGGCCA TTTACCGTAA GTTATGTAAC GCCTGCAGGT TAATTAAGAA CATGTGAGCA AAAGGCCAGC AAAAGGCCAG
3501  GAACCGTAAA AAGGCCGCGT TGCTGGCGTT TTTCCATAGG CTCCGCCCCC CTGACGAGCA TCACAAAAAT CGACCCCTGC CGCTTACCGG ATACCTGTCC GCCTTTCTCC
3601  ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
3701  CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
3801  TCAGCCCGAC CGCTGCGCCT TATCCGGTAA CTATCGTCTT GAGTCCAACC CGGTAAGACA CGACTTATCG CCACTGGCAG CAGCCACTGG TAACAGGATT
3901  AGCAGAGCGA GGTATGTAGG CGGTGCTACA GAGTTCTTGA AGTGGTGGCC TAACTACGGC TACACTAGAA GAACAGTATT TGCTATCTGC GCTCTGCTGA
4001  AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
4101  CAGAAAAAAA GGATCTCAAG AAGATCCTTT GATCTTTTCT ACGGGGTCTG ACGCTCAGTG GAACGAAAAC TCACGTTAAG GGATTTTGGT CATGCCTAGT
4201  TAATTAACAT GGCCGCAATA ACAAACTAGC AAAATAGGCT GTCCCAGTG CAAGTGCAGG TGGTGAATCG TAACTAACAT ACGCTCTCCA
4301  TCAAAACAAA ACGAAACAAA                                                                           TTTCCTATC GAA (SEQ ID NO:95)
```

IL2ss.CXCL11(4-73).hIgG1Fc sequence [Alanine substitutions for removal of GAG binding sites – Lys & His]

```
   1  GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCT\CC GCCTTTTTCC CGAGGGTGGG GGAGAACCGT ATATAAGTGC AGTAGTCGCC
 201  GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301  GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401  GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                        KasI
                                        NarI
                                        SfoI
                                        BbeI
                                       ~~~~~~~                                     IL-2 secretion signal
                                                                                   MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                             EcoRI
                             ~~~~~~~ CXCL11 (4-73)
       AlaLeuSer LeuAlaLeu ValThrAsnSer PheLysArg GlyArgCys LeuCysIleGly ProGlyVal LysAlaVal LysValAlaAsp IleGluAla
 601  TTGCACTAAG TCTTGCACTT GTCACGAATT CGTTCAAAAG AGGACGCTGT CTTTGCATAG GCCCTGGGGT AAAAGCAGTG AAAGTGGCAG ATATTGAGgc
      AlaSerIle MetTyrProSer AsnAsnCys AspLysIle GluValIleIle ThrLeuAla GluAsnAla GlyGlnAlaCys LeuAsnPro AlaSerAla
 701  gGCCTCCATA ATGTACCCAA GTAACAACTG TGACAAAATA GAAGTGATTA TTACCCTGgc aGAAAATgcc GGACAAgcaT GCCTAAATCC CgccTCGgca
                                                   human IgG1 Fc (constant region)
      GlnAlaAlaLeu IleIleAla AlaValGlu AlaAlaAsnPhe AspLysThr HisThrCys ProProCysPro AlaProGlu LeuLeuGly GlyProSerVal
 801  CAAGCAgccC TTATAATCgc agccGTTGAA gcagccAATT TTGACAAAAC TCACACATGC CCACCGTGCC CAGCACCTGA ACTCCTGGGG GGACCGTCAG
       PheLeuPhe ProProLys ProLysAspThr LeuMetIle SerArgThr ProGluValThr CysValVal ValAspVal SerHisGluAsp ProGluVal
 901  TCTTCCTCTT CCCCCCAAAA CCCAAGGACA CCCTCATGAT CTCCCGGACC CCTGAGGTCA CATGCGTGGT GGTGGACGTG AGCCACGAAG ACCCTGAGGT
      LysPheAsn TrpTyrValAsp GlyValGlu ValHisAsn AlaLysThrLys ProArgGlu GluGlnTyr AsnSerThrTyr ArgValVal SerValLeu
1001  CAAGTTCAAC TGGTACGTGG ACGGCGTGGA GGTGCATAAT GCCAAGACAA AGCCGCGGGA GGAGCAGTAC AACAGCACGT ACCGTGTGGT CAGCGTCCTC
      ThrValLeuHis GlnAspTrp LeuAsnGly LysGluTyrLys CysLysVal SerAsnLys AlaLeuProAla ProIleGlu LysThrIle SerLysAlaLys
1101  ACCGTCCTGC ACCAGGACTG GCTGAATGGC AAGGAGTACA AGTGCAAGGT CTCCAACAAA GCCCTCCCAG CCCCCATCGA GAAAACCATC TCCAAAGCCA
       GlyGlnPro ArgGluPro GlnValTyrThr LeuProPro SerArgGlu GluMetThrLys AsnGlnVal SerLeuThr CysLeuValLys GlyPheTyr
1201  AAGGGCAGCC CCGAGAACCA CAGGTGTACA CCCTGCCCCC ATCCCGGGAG GAGATGACCA AGAACCAGGT CAGCCTGACC TGCCTGGTCA AAGGCTTCTA
      ProSerAsp IleAlaValGlu TrpGluSer AsnGlyGln ProGluAsnAsn TyrLysThr ThrProPro ValLeuAspSer AspGlySer PhePheLeu
1301  TCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC
      TyrSerLysLeu ThrValAsp LysSerArg TrpGlnGlnGly AsnValPhe SerCysSer ValMetHisGlu AlaLeuHis AsnHisTyr ThrGlnLysSer
1401  TACAGCAAGC TCACCGTGGA CAAGAGCAGG TGGCAGCAGG GGAACGTCTT CTCATGCTCC GTGATGCACG AGGCTCTGCA CAACCACTAC ACGCAGAAGA
                                  BmtI
                                  NheI
       LeuSerLeu SerProGly Lys***(SEQ ID NO:69)
1501  GCCTCTCCCT GTCTCCGGGT AAATGAGTGC TAGCTGGCCA GACATGATAA GATACATTGA TGAGTTTGGA CAAACCACAA CTAGAATGCA GTGAAAAAAA
1601  TGCTTTATTT GTGAAATTTG TGATGCTATT GCTTTATTTG TAACCATTAT AAGCTGCAAT AAACAAGTTA ACAACAACAA TTGCATTCAT TTTATGTTTC
                                                                       AseI
1701  AGGTTCAGGG GGAGGTGTGG GACGTTTTTT AAAGCAAGTA AAACCTCTAC AAATGTCGTA TGGAATTAAT TCTAAAATAC AGCATAGCAA AACTTTAACC
1801  TCCAAATCAA GCCTCTACTT GAATCCTTTT CTGAGGGATG AATAAGGCAT AGGCATCAGG GGCTGTTGCC AATGTGCATT AGCTGTTTGC AGCCTCACCT
```

```
1901  TCTTTCATGG AGTTTAAGAT ATAGTGTATT TTCCCAAGGT TTGAACTAGC TCTTCATTTC TTTATGTTTT AAATGCACTG ACCTCCCACA TTCCCTTTTT
2001  AGTAAAATAT TCAGAAATAA TTTAAATACA TCATTGCAAT GAAAATAAAT GTTTTTTATT AGGCAGAAATC CAGATGCTCA AGGCCCTTCA TAATATCCCC
2101  CAGTTTAGTA GTTGGACTTA GGGAACAAAG GAACCTTTAA TAGAAATTGG ACAGCAAGAA AGCGAGCTTC TAGCTTATCC TCAGTCCTGC TCCTCTGCCA
2201  CAAAGTGCAC GCAGTTGCCG GCCGGGTCGC GCAGGGCGAA CTCCCGCCCC CACGGCTGCT CGCCGATCTC GGTCATGGCC GGCCCGGAGG CGTCCCGGAA
2301  GTTCGTGGAC ACGACCTCCG ACCACTCGGC GTACAGCTCG TCCAGGCCGC CCAGGCCAGG GTGTTGTCCG GCCACCACTG GTCCTGGACC
2401  GCGCTGATGA ACAGGGTCAC GTCGTCCCGG ACCACACCGG CGAAGTCGTC CTCCACGAAG TCCCGGGAGA ACCCGAGCCG GTCGGTCCAG AACTCGACCG
2501  CTCCGGCCAC GTCGCGCGCG GTGAGCACCG GAACGGCACT GGTCAACTTG GCCATGATGG CTCCTCCTGT CAGGAGAGGA AGAGAAGAA GGTTAGTACA

AseI
2601  ATTGCTATAG TGAGTTGTAT TATACTATGC AGATATACTA TGCCAATGAT TAATTGTCAA CAAACTCACA ACTAGGGCTG CAGGGTTCAT AGTGCCACTT TTCCTGCACT
2701  GCCCCATCTC CTGCCACCC TTTCCCAGGC ATAGACAGTC AGTGACTTAC CAAACTCACA GGAGGAGAA GGCAGAAGCT TGAGACAGAC CCGCGGGACC
2801  GCCGAACTGC GAGGGGACGT GGCTTCTTTA TGGTGCGCG GCCCTCCGGAG GCCCGGAGCT CGGGAGCGCT CGGGGAGCT TAGCGGCCAA TCTGCGGTGG
2901  CAGGAGGCGG GGCCGAAGGC CGTGCCTGAC CACATAGGAG TCTCAGCCCC CCGCCCCAAA GCAAGGGGAA GTCACGCGCC TGTAGCGCCA
3001  GCGTGTGTG AAATGGGGGC TTGGGGGGT ACTAGTCAAA ACAAACTCCC ATTGACGTCA ATGGGGTGA GACTTGGAAA TCCCCGTGAG
3101  TCAAACCCGCT ATCCACGCCC ATTGATGTAC TGCCAAAACC GCATCATCAT GGTAATAGCG ATGACTAATA CTGCCAAGTA GGAAAGTCCC
3201  ATAAGGTCAT GTACTGGGCA TAATGCCAAG CCGTCGTC ACCGTCATTG ACGTCAATAG GGGGCGTACT TGGCATATGA TACACTTGAT GTACTGCCAA
3301  GTGGGCAGET TACCGTAAAT ACTCCACCCA TTGACGTCAA TGGAAAGTCC CTATTGGCGT ACATACGTCA TTATTGACGT CAATGGGCGG
3401  GAGTCGTTGG GCGGTCAGCC AGGCGGGCCA TTTAACGTAA GCTTCAGTC CTGACGAGCA TCACAAAAAT CGACGCTCAA AAAGGCCAGC
3501  GAACCGTAAA AAGGCCGCGT TGCTGGCGTT TTTCCATAGG CTCCGCCCCC CCTCGTGCG CTCTCCTGTT CCGACCCTGC CGCTTACCGG ATACCTGTCC GCCTTTCTCC
3601  ACAGACTATA AAGATACCA GGCGTTTCCC CCTGGAAGCT CCCTCGTGCG CTCTCCTGTT CCGACCCTGC CGCTTACCGG ATACCTGTCC GCCTTTCTCC
3701  CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCGT
3801  TCAGCCCGAC CGCTGCGCCT TATCCGGTAA GACTTCTCTT GAGTCCAACC CGGTAACACA CGACTTATCG CCACTGGCAG CAGCCACTGG TAACAGGATT
3901  AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGA
4001  AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
4101  CAGAAAAAAA GGATCTCAAG AAGATCCTTT GATCTTTCT ACGGGGTCTG ACGCTCAGTG GAACGAAAAC TCACGTTAAG GGATTTTGGT CATGAGATTA
4201  TAATTAACAT TTAAATCAGC GGCCGCAATA ATTTTCATTA CATCGTGTG TTGGTTTTT GTGTGAATCG TAACTAACAT ACGGCTCTCCA
4301  TCAAAAACAAA ACGAAACAAA ACAAAACTAGC AAAATAGGCT GTCCCCAGTG CAAGTGCAGG TGCCAGAACA TTTCTCTATC GAA  (SEQ ID NO:96)
```

IL2ss.CXCL11.hIgG4Fc sequence

```
   1 GGATCTGCGA TCGCTCCCGT GCCCGTCAGT GGGCAGAGCG CACATCGCCC ACAGTCCCCG AGAAGTTGGG GGGAGGGGTC GGCAATTGAA CGGGTGCCTA
 101 GAGAAGGTGC CGCCGGGTAA ACTGGGAAAG TGATGTCGTG TACTGGCTCC GCCTTTTTCC GCGGGGGGCG CGGAACCGT CCTCGCGCC CTAGTAGTGCC
 201 GTGAACGTTC TTTTTGCAA CGGGTTGCC GCCAGAACAC AGCTGAAGCT TCGAGGGCGT GGCATCCTC CCCCGGCCC CCTGAGACC
 301 GCCATCCACG CCGGTTCTGC CGGGTTCTGC CGCCTCCCGC CTGTGGTGCC TCCTGAACTG CGTCCGCCGT CTAGGTAAGT TTAAAGCTCA GGTCGAGACC
 401 GGGCCTTTGT CCGGGCGTCC CTTGGAGCCT ACCTAGAGCT AGCCGGCTCT CCACGCGTTTG CCTGACCCTG CTTGCTCAAC TCTACGTCTT TGTTTCGTTT
                                 NarI
                                 SfoI
                                 KasI
                                 BbeI
                                                                         IL-2 secretion signal
                                                                         MetTyrArg MetGlnLeu LeuSerCysIle
 501 TCTGTTCTGC GCCGTTACAG ATCCAAGCTG TGACCGGCGC CTACCTGAGA TCACCGGCGA AGGAGGGCCA CAATGTACAG GATGCAACTC CTGTCTTGCA
                          EcoRI                           CXCL11 (1-73)
     AlaLeuSer LeuAlaLeu ValThrAsnSer PheProMet PheLysArg GlyArgCysLeu CysIleGly LysAlaValLys ValAlaAsp
 601 TTGCACTAAG TCTTGCACTT GTCACGAATT CGTTCCCCAT GTTCAAAAGA GGACGCTGTC TTTGCATAGG CCCGGGGTA AAAGCAGTGA AAGTGGCAGA
     IleGluLys AlaSerIleMet TyrProSer AsnAsnCys AspLysSerGlu ValIleIle ThrLeuLys GlnAsnLysGly GlnArgCys LeuAsnPro
 701 TATTGAGAAA GCCTCCATAA TGTACCCAAG TAACAACTGT GACAAATCAG AAGTGATTAT TACCCTGAAA GAAAATAAAG GACAACGATG CCTAAATCCC
                                                                                   human IgG4 Fc (constant region)
     LysSerLysGln AlaArgLeu IleIleLys LysValGluArg LysAsnPhe ProSerCysPro AlaProGlu PheLeuGly GlyProSerVal
 801 AAATCGAAGC AAGCAGGCT TATATCAAGA AAGTTGAGA GAAAGAATTT TCCCCAATGC CCATCAGAGG CAGCACTGA GTTCCTGGGA GGACCATCAG
     PheLeuPhe ProProLys ProLysAspThr LeuMetIle SerArgThr ProGluValThr CysValVal ValAspVal SerGlnGluAsp ProLeuVal
 901 TTCTTCCTGTT CCCCCCAAAA CCCAAGGACA CTCTCATGAT CTCCCGGACC CCTGAGGTCA CGTGCGTGGT GGTGGACGTG AGCCAGGAAG ACCCCGAGGT
     GlnPheAsn TrpTyrValAsp GlyValGlu ValHisAsn AlaLysThrLys ProArgGlu GluGlnPhe AsnSerThrTyr ArgValVal SerValLeu
1001 CCAGTTCAAC TGGTACGTGG ATGGCGTGGA GGTGCATAAT GCCAAGACAA AGCCGCGGGA GGAGCAGTTC AACAGCACGT ACCGTGTGGT CAGCGTCCTC
     ThrValLeuHis GlnAspTrp LeuAsnGly LysGluTyrLys CysLysVal SerAsnLys GlyLeuProSer SerIleGlu LysThrIle SerLysAlaLys
1101 ACCGTCCTGC ACCAGGACTG GCTGAACGGC AAGGAGTACA AGTGCAAGGT CTCCAACAAA GGCCTCCCGT CCTCCATCGA GAAAACCATC TCCAAAGCCA
     GlyGlnPro ArgGluPro GlnValTyrThr LeuProPro SerGlnGlu GluMetThrLys AsnGlnVal SerLeuThr CysLeuValLys GlyPheTyr
1201 AGGGCAGCC CCGAGAGCCA CAGGTGTACA CCCTGCCCCC ATCCCAGGAG GAGATGACCA AGAACCAGGT CAGCCTGACC TGCCTGGTCA AAGGCTTCTA
     ProSerAsp IleAlaValGlu TrpGluSer AsnGlyGln ProGluAsnAsn TyrLysThr ThrProPro ValLeuAspSer AspGlySer PhePheLeu
1301 CCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC
     TyrSerArgLeu ThrValAsp LysSerArg TrpGlnGluGly AsnValPhe SerCysSer ValMetHisGlu AlaLeuHis AsnHisTyr ThrGlnLysSer
1401 TACAGCAGGC TAACCGTGGA CAAGAGCAGG TGGCAGGAGG GGAATGTCTT CTCATGCTCC GTGATGCATG AGGCTCTGCA CAACCACTAC ACACAGAAGA
                                                                                                         AseI
     LeuSerLeu SerProGly Lys***(SEQ ID NO:70)
1501 GCCTCTCCCT GTCTCCGGGT AAATGAGTGC TAGCTGGCCA GACATGATAA GATACATTGA TGAGTTTGGA CAAACCACAA CTAGAATGCA GTGAAAAAAA
1601 TGCTTTATTT GTGAAATTTG TGATGCTATT GCTTTATTTG TAACCATTAT AAGCTGCAAT AAACAAGTTA ACAACAACAA TTGCATTCAT TTTATGTTTC
                                                                                 AseI
1701 AGGTTCAGGG GGAGGTGTGG GAGGTTTTTT AAAGCAAGTA AAACCTCTAC AAATGTGTA TGGAATTAAT TCTAAAATAC AGCATAGCAA AACTTTAACC
1801 TCCAAATCAA GCCCTACTT GAATTCCTTT CCGAGGCATG AATAAGGCAT AGGCATGTGG GGCTGTTGCC AATGCATT AGTGTTTGC AGCCTCACCT
```

```
1901  TCTTTCATGG AGTTTAAGAT ATAGTGTATT TTCCCAAGGT TTGAACTAGC TCTTTCATTTC GTTATGTTTT AAATGCACTG ACCTCCCACA TTCCCTTTTT
2001  AGTAAAATAT TCAGAAATAA TTTAAATACA TCATTGCAAT GAAAATAAAT GTTTTTTATT AGCCAGAAATC CAGATGCTCA AGGCCCTTCA TAAATATCCCC
2101  CAGTTTAGTA GTTGGACTTA GGGAACAAAG GAACCTTTAA TAGAAATTGG ACAGCAAGAA AGCGAGCTTC TAGCTTATCC TCAGTCCTGC TCCTCTGCCA
2201  CAAAGTGCAC GCAGTTGCCG GCCGGGTCGC GCAGGGCGAA CTCCCGCCCC CACGGCTGCT CGCCGATCTC GGTCATGGCC GGCCCGGAGG CGTCCCGGAA
2301  GTTCGTGGAC ACGACCTCCG ACCACTCGGC GTACAGCTCG TCCAGGCCGC GCACCCACAC CCAAGGCCAG GTGTTGTCCG GCACCACCTG GTCCTGGACC
2401  GCGCTGATGA ACAGGGTCAC GTCGTCCCGG ACCACACCGG CGAAGTCGTC CTCCACGAAG TCCCGGGAGA ACCCGAGCCG GTCGGTCCAG AACTCGACCG
2501  CTCCGGCGAC GTCCGCGCGG GTGAGCGACT GAACAGCTTG GCCATGATGC CTCCTCCTGT CAGGAGAGGA CTCCTCCTGT CAGGAGAGGA AGAGAAGAA GGTAGTACA

AseI
2601  ATTGCTATAG TGAGTTGTAT TATACTATGC AGATATACTA TGCCAATGAT TAATTGTCAA ACTAGGGCTG CAGGGTTCAT AGTGCCACTT TTCCTGCACT
2701  GCCCCATCTC CTGCCCACCC TTTCCCAGGC ATAGACAGTC AGTGACTTAC CAAACTCACA GGAGGGAGAA GGCAGAAAGCT TGAGACAGAC CCGGCGGACC
2801  GCCGAACTGC GAGGGGACGT GGCTAGGGCG GCTTCTTTTA TGGTGCCGCG GCCCTCGGAG GCAGGGCGCT CGGGGAGGCC TAGCGGCCAA TCTGCGGTGG
2901  CAGGAGGCGG GGCCGAAGGC CGTGCCTGAC CAATCCGGAG CACATAGGAG TCTCAGCCCC CCGCCCCAAA GCAAGGGGAA GTCACGCGCC TGTAGCGCCA
3001  GCGTGTTGTG AAATGGGGGC TTGGGGGGGT TGGGCCCTG ACAAACTCCC ATTGACGTCA ATGGGGGTGGA GACTTGGAAA TCCCCGTGAG
3101  TCAAACCGCT ATCCACGCCC ATTGATGTAC TGCCAARAACC GCATCATCAT GGTAATAGCG ATGACTAATA CGTAGATGTA CTGCCAAGTA GGAAAGTCCC
3201  ATAAGGTCAT GTACTGGGCA TAATGCCAGG ACTCCACCGA CGGTCCATTG ACCGTCAATG AGTCAATAG GGGGCGTACT TGGCATATGA TACACTTGAT GTACTGCCAA
3301  GTGGCAGTT TACCGTAAAT ACTCCACCCA TTGACGTCAA TGGAAAGTCC CTATTGGCGT TACTATGGGT ACATACGTCA TTATTGACGT CAATGGCGG
3401  GGGTCGTTGG GCGGTCAGCC AGGCGGGCCA TTTACCGTAA GTTATGTAAC GCCTGCAGGT TAATTAAGAA CATGTGAGCA AAAGGCCAGC AAAAGGCCAG
3501  GAACCGTAAA AAGGCCGCGT TGCTGGCGTT TTTCCATAG CCTCGAAAGCT CCCCCCTGCC CTCTCCTGTT CCGACCCTGC CGCTTACCGG ATACCTGTCC GCCTTTCTCC
3601  ACAGGACTAT AAAGATACCA GGCGTTTCCC CCTGGAAGCT CCCTCGTGCG CTCTCCTGTT TCGGTGTAGG TCGTTCGCTC CAAGCTGGGC TGTGTGCACG AACCCCCCGT
3701  CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
3801  TCAGCCCGAC CGCTGCGCCT TATCCGGTAA CTATCGTCTT GAGTCCAACC CGGTAAGACA CGACTTATCG CCACTGGCAG CAGCCACTGG TAACAGGATT
3901  AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGA
4001  AGCCAGTTAC CTTCCAAAA AGAGTTGGTA GCTCTTGATC CGGCAAACAA ACCACCGCTG GTAGCGGTGG TTTTTTTGTT TGCAAGCAGC AGATTACGCG
4101  CAGAAAAAAA GGATCTCAAG AAGATCCTTT GATCTTTTCT ACGGGGTCTG ACGCTCAGTG GAACGAAAAC TCACGTTAAG GGATTTTGGT CATGCTAGT
4201  TAATTAACAT TTAAATCAGC GGCCGCAATA AAATATCTTT ATTTTCATTA ACGGGGTCTG ACGCTCAGTG GAACGAAAAC GTGTGAATCG TAACTAACAT ACGCTCTAGT
4301  TCAAAACAAA ACGAAACAAA ACAAAACTAGC AAAATAGGCC GTCCCCAGTG CAAGTGCAGG TGCAGAGACA TTTCTCTATC GAA (SEQ ID NO:97)
```

IL2ss.CXCL11(4-73).hIgG4Fc sequence

```
   1 GGATCTGCGA TCCCTCCGGT GCCCGTCAGT GGGCAGAGCG CACATCGCCC ACAGTCCCCG AGAAGTTGGG GGGAGGGGTC GGCAATTGAA CGGGTGCCTA
 101 GAGAAGCTGG CCGCGGGTAA ACTGCTGTG TGATGCCTG GCCAGAACGT TACTGCCTCC GCCTTTTCC CGAGGTGCCG CGAGAACCGT CCGCCCCCT AGTAGTCCGC
 201 GTGAACGTTC TTTTCCCAA CGGGTTTGC GCCAGAACCT TCGAGGGCT TCGAGGGGCT TCGAGGCT CGCATCCTC CTTCACGCGC CCGCCGCGC ACCTGAGCC
 301 GCCATCCACG CCGGTTGAGT CGCGTTCTGC CGCCTCCCGC CTGTGGTGCC TCCTGAACTG CGTCGCCGT CAAGGTAAGT TTAAAGCTCA GGTCGAGACC
 401 GGGCCTTTGT CCGGCGCTCC CTTGGAGCCT AGCCGGGCCT ACCTAGACTC AGCCGGGCCT CCACGCTTTG CCTGACCCTG CTTGCTCAAC TCTACGTCTT TGTTTCGTTT
                                                       KasI
                                                       SfoI
                                                       NarI
                                                       BbeI

IL-2 secretion signal
                                                                                                 MetTyrArg MetGlnLeu LeuSerCysIle
 501 TCTGTTCTGC GCCGTTACAG ATCCAAGCTG TGACCGGCGC CTAGCTGAGA TCACCGGCGA AGGAGGGCCA CCATGTACAG GATGCAACTC CTGTCTTGCA
                                         EcoRI
                        ~~~~~~ CXCL11 (4-73)
     AlaLeuSer LeuAlaLeu ValThrAsnSer PheLysArg GlyArgCys LeuCysIleGly ProGlyVal LysAlaVal LysValAlaAsp IleGluLys
 601 TTGCACTAAG TCTTGCACTT GTCACGAATT CGTTCAAAAG AGGACGCTGT CTTTGCATAG GCCCTGGGGT AAAAGCACTG AAAGTGGCAG ATATTGAGAA
     AlaSerIle MetTyrProSer AsnAsnCys AspLysIle ThrLeuIle GluValIleLle ThrProLys GluAsnLys GlyGlnArgCys LeuAsnPro LysSerLys
 701 AGCCTCCATA ATGTACCCAA GTAACAACTG TGACAAAATA GAAGTGATTA TTACCCCTGAA AGAAAATAAA GGACAACGAT GCCTAAATCC CAAATCGAAG
                                                                                        human IgG4 Fc (constant region)
     GlnAlaArgLeu IleIleLys LysValGlu ArgLysAsnPhe ProProCys ProProCys ProAlaProGlu PheLeuGly GlyProSer ValPheLeuPhe
 801 CAAGCAAGGC TTATAATCAA AAAGTTGAA AGAAAGAATT TTCCCCCATG CCCATCATGC CCAGCACCTG AGTTCCTGGG GGGACCATCA GTCTCCTGT
     ProProLys ProLysAsp ThrLeuMetIle SerArgThr ProGluVal ThrCysValVal ValAspVal SerGlnGlu AspProGluVal GlnPheAsn
 901 TCCCCCAAA ACCCAAGGAC ACTCTCATGA TCTCCCGGAC CCCTGAGGTC ACGTGCGTGG TGGTGGACGT GAGCCAGGAA GACCCCGAGG TCCAGTTCAA
     TrpTyrVal AspGlyValGlu ValHisAsn AlaLysThr LysProArgGlu GluGlnPhe AsnSerThr TyrArgValVal SerValLeu ThrValLeu
1001 CTGGTACGTG GATGGCGTGG AGGTGCATAA TGCCAAGACA AAGCCGCGGG AGGAGCAGTT CAACAGCACG TACCGTGTGG TCAGCGTCCT CACCGTCCTG
     HisGlnAspTrp LeuAsnGly LysGluTyr LysCysLysVal SerAsnLys GlyLeuPro SerSerIleGlu LysThrIle SerLysAla LysGlyGlnPro
1101 CACCAGGACT GGCTGAACGG CAAGGAGTAC AAGTGCAAGG TCTCCAACAA AGGCCTCCCG TCCTCCATCG AGAAAACCAT CTCCAAAGCC AAAGGGCAGC
     ArgGluPro GlnValTyr ThrLeuProPro SerGlnGlu GluMetThr LysAsnGlnVal SerLeuThr CysLeuVal LysGlyPheTyr ProSerAsp
1201 CCCGAGAGCC ACAGGTGTAC ACCCTGCCCC CATCCCAGGA GGAGATGACC AAGAACCAGG TCAGCCTGAC CTGCCTGGTC AAAGGTTCT ACCCCAGCGA
     IleAlaVal GluTrpGluSer AsnGlyGln ProGluAsn AsnTyrLysThr ThrProPro ValLeuAsp SerAspGlySer PhePheLeu TyrSerArg
1301 CATCGCCGTG GAGTGGGAGA GCAATGGGCA GCCGGAGAAC AACTACAAGA CCACCCCTCC CGTGCTGGAC TCCGACGGCT CCTTCTTCCT CTACAGCAGG
     LeuThrValAsp LysSerArg TrpGlnGln GlyAsnValPhe SerCysSer ValMetHis GluAlaLeuHis AsnHisTyr ThrGlnLys SerLeuSerLeu
1401 CTAACCGTGG ACAAGAGCAG GTGGCAGGAG GGGAATGTCT TCTCATGCTC CGTGATGCAT GAGGCTCTGC ACAACCACTA CACACAGAAG AGCCTCTCCC
                                        BmtI
                                        NheI
     SerProGly Lys*** (SEQ ID NO:71)
1501 TGTCTCCGGG TAAATGAGTG CTAGCTGCCC AGACATGATA AGATACATTG ACAAACCACA ACTAGAATGC AGTGAAAAAA ATGCTTATT
1601 TGTGAAATTT GTGATGCTAT TGCTTTATTT GTAACCATTA TAAGCTGCAA TAAACAAGTT AACAACAACA ATTGCATTCA TTTTATGTTT CAGTTCAGG
                                                                                          AseI
```

```
1701 GGGAGGTGTG GGAGGTTTTT TAAAGCAAGT AAAACCTCTA CAAATGTGGT ATGGAATTAA TTCTAAAATA CAGCATAGCA AAACTTTAAC CTCCAAATCA
1801 AGCCTCTACT TGAATCCTTT TCTGAGGGAT GAATAAGGCA TTTGAACTAG TAGGCATCAG GGGCTGTTGC CAATGTGCAT TAGCTGTTTG CAGCCTCACC TTCTTTCATG
1901 GAGTTTAAGA TATAGTGTAT TTTCCCAAGG TTTGAACTAG CTCTTCATTT CTTTATGTTT TAAATGCACT GACCTCCCAC ATTCCCTTTT TAGTAAAATA
2001 TTCAGAAATA ATTTAAATAC ATCATTGCAA TGAAAAATAAA TGTTTTTTAT TAGGCAGAAT CCAGATGCTC AAGGCCCTTC ATAATATCCC CCAGTTTAGT
2101 AGTTGGACTT AGGGAACAAA GGAACCTTTA ATAGAAATTG GACAGCAAGA AAGCGAGCTT CTAGCTTATC CTCCTCTGCC ACAAAGTGCA
2201 CGCAGTTGCC GGCCGGGTCG CGCAGGGCGA ACTCCCGCCC CCACACCCAC CCCAGGCTGC CGGTCATGGC CGGACCGGAG GGTCCCGGA AGTTCGTGGA
2301 CACGACCTCC GACCACTCGG CGTACAGCTC GTCCAGGCCG CCGCACCGCG CCCAGGCCAG GGTGTTGTCC CGGCCACCT GGTCCTGGAC GGTCCTGATG
2401 AACAGGGTCA CGTCGTCCCG GACCACACCG GCGAAGTCGT CCTCCACGAA GTCCGGGGAG AACCCGGACC GGTCGGTCCA GAACTCGACC GCTCCGGGA
2501 CGTCGCGCGC GGTGAGCACC GGAACGGCAC TGGTCAACTT GGCCATGATG CTCCTCCTG TCAGGAGAGG AAAGAGAAGA AGGTTAGTAC AATTGCTATA
                                                              AseI
                                                           ~~~~~~~~
2601 GTGAGTTGTA TTATACTATG CAGATATACT ATGCCAATGA TTAATTGTCA AACTAGGGCT GCAGGGTTCA TAGTGCCACT TTTCCTGCAC TGCCCATCT
2701 CCTGCCCACC CTTTCCCAGG CATAGACAGT CAGTGACTTA CCAAAACTCAC AGGAGGGAGA AGCAGAAGC TTGAGACAGA CCCGCGGGAC CGGCCGAACTG
2801 CGAGGGGACG TGGCTAGGGC GGCTTCTTT ATGGTGCGCC GGCCCTCCGGA GGCAGGGCGC TCGGGAGGC CTAGCGGCCA ATCTGCGGTG GCAGGAGGCG
2901 GGGCCGAAGG CCGTGCCTGA CCAATCCGGA GCACATAGGA GTCTCAGCCC CCGCCCCAA AGCAAGGGGA AGTCACGCGC CTGTAGCGCC AGCGTGTTGT
3001 GAAATGGGGG CTTGGGGGGG TTGGGGCCCT GACTAGTCAA AACAAACTCC CATTGACGTC AGACTTGGAA ATCCCCGTGA GTCAAACCGC
3101 TATCCACGCC CATTGATGTA CTGCCAAAAC CGCATCATCA TGGTAATAGC GATGACTAAT ACGTAGATGT ACTGCCAAGT AGGAAAGTCC CATAAGGTCA
3201 TGTACTGGGC ATAATGCCAG GCGCAAAGTC TACCGTCATT GACGTCAATA GGGGGCGTAC TTGGCATATG ATACACTTGA TGTACTGCCA AGTGGGCAGT
3301 TTACCGTAAA TACTCCACCC ATTGACGTCA ATGGAAAGTC CCTATTGGCG TTACTATGGG AACATACGTC ATTATTGACC TCAATGGGCG GGGTCGTTG
3401 GCAGTCCGCG CAGGGCC ATTTACCGTA AGTTATGTAA CGCCTGCAGG CCTGACGAGC TTAATTAAGA ACATGTGAGC AAAAGGCCA GAACCGTAA
3501 AAAGGCCGCG TTGCTGGCGT TTTTCCATAG GCTCCGCCCC CCTGACGAGC ATCACAAAAA TCGACGCTCA AGTCAGAGGT GGCGAAACCC GACAGGACTA
3601 TAAAGATACC AGGCGTTTCC CCCTGGAAGC TCCCTCGTGC GCTCTCCTGT TCCGACCCTG CCGCTTACCG GATACCTGTC CGCCTTTCTC CCTTCGGGAA
3701 GCGTGGCGCT TTCTCATAGC TCACGCTGTA GGTATCTCAG TTCGGTGTAG GTCGTTCGCT CCAAGCTGGG CTGTGTGCAC GAACCCCCCG TTCAGCCCGA
3801 CCGCTGCGCC TTATCCGGTA ACTATCGTCT TGAGTCCAAC CCGGTAAGAC ACGACTTATC GCCACTGGCA GCAGCCACTG GTAACAGGAT TAGCAGAGCG
3901 AGGTATGTAG CGGTGCTACA GAGTTCTTGA AGTGGTGGCC TAACTACGG CTACACTAGA AGAACAGTAT TTGGTATCTG CGCTCTGCTG AAGCCAGTTA
4001 CCTTCGGAAA AAGAGTTGGT AGCTCTTGAT CCGGCAAACA ACCGGGGTCT TACGGGGTCT GTTTTTTTGT TTGCAAGCAG CAGATTACGC GCAGAAAAAA
4101 AGGATCTCAA GAAGATCCTT TGATCTTTTC TACGGGGTCT TATTTTCATT ACCACCGCTG GAACGAAAAA CTCACGTTAA GGGATTTTTGG TCATGGGCTAG TCAAGGCTAG TTAATTAACA
4201 TTTAAATTCAG CGGCCCGGAA ACAAATATCTT TATTTTCATT ACATCTGTGT GTTTGGTTTTT TGTGTGAATC GTAACTAACA TACGCTCTCC ATCAAAACAA
4301 AACGAAACAA CAAAAACTAG TGTCCCCAGT GCAAGTGCAG GTGCCAGAAC ATTTCTCTAT CGAA    (SEQ ID NO:98)
```

IL2ss.CXCL11(4-73).hIgG4Fc sequence [Alanine substitutions for GAG binding sites – Arg, Lys & His]

1 GGATCTGCGA TCCGTCCGGT GCCCGTCAGT GGGCAGAGCG CACATCGCCC ACAGTCCCCG AGAAGTTGGG GGGAGGGGTC GGCAATTGAA CGGGTGCCTA
101 GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
201 GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
301 GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
401 GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
KasI
SfoI
NarI
BbeI
~~~~~~~
IL-2 secretion signal
MetTyrArg MetGlnLeu LeuSerCysIle
501 TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
EcoRI
~~~~~~~ CXCL11 (4-73)
AlaLeuSer LeuAlaLeu ValThrAsnSer PheLysArg GlyArgCys LeuCysIleGly ProGlyVal LysAlaVal LysValAlaAsp IleGluAla
601 TTGCACTAAG TCTTGCACTT GTCACGAATT CGTTCAAAAG AGGACGCTGT CTTTGCATAG GCCCTGGGGT AAAAGCAGTG AAAGTGGCAG ATATTGAGgc
AlaSerIle MetTyrProSer AsnAsnCys AspLysIle GluValIleIle ThrLeuAla GluAsnAla GlyGlnAlaCys LeuAsnPro AlaSerAla
701 cGCCTCCATA ATGTACCCAA GTAACAACTG TGACAAAATA GAAGTGATTA TTACCCTGgc gGAAAATgcc GGACAAgcaT GCCTAAATCC CgccTCGgca
human IgG4 Fc (constant region)
GlnAlaAlaLeu IleIleAla AlaValGlu AlaAlaAsnPhe ProProCys ProSerCys ProAlaProGlu PheLeuGly GlyProSer ValPheLeuPhe
801 CAAGCAgccC TTATAATCgc agccGTTGAA gcagccAATT TTCCCCCATG CCCATCATGC CCAGCACCTG AGTTCCTGGG GGGACCATCA GTCTTCCTGT
ProProLys ProLysAsp ThrLeuMetIle SerArgThr ProGluVal ThrCysValVal ValAspVal SerGlnGlu AspProGluVal GlnPheAsn
901 TCCCCCCAAA ACCCAAGGAC ACTCTCATGA TCTCCCGGAC CCCTGAGGTC ACGTGCGTGG TGGTGGACGT GAGCCAGGAA GACCCCGAGG TCCAGTTCAA
TrpTyrVal AspGlyValGlu ValHisAsn AlaLysThr LysProArgGlu GluGlnPhe AsnSerThr TyrArgValVal SerValLeu ThrValLeu
1001 CTGGTACGTG GATGGCGTGG AGGTGCATAA TGCCAAGACA AAGCCGCGGG AGGAGCAGTT CAACAGCACG TACCGTGTGG TCAGCGTCCT CACCGTCCTG
HisGlnAspTrp LeuAsnGly LysGluTyr LysCysLysVal SerAsnLys GlyLeuPro SerSerIleGlu LysThrIle SerLysAla LysGlyGlnPro
1101 CACCAGGACT GGCTGAACGG CAAGGAGTAC AAGTGCAAGG TCTCCAACAA AGGCCTCCCG TCCTCCATCG AGAAAACCAT CTCCAAAGCC AAAGGGCAGC
ArgGluPro GlnValTyr ThrLeuProPro SerGlnGlu GluMetThr LysAsnGlnVal SerLeuThr CysLeuVal LysGlyPheTyr ProSerAsp
1201 CCCGAGAGCC ACAGGTGTAC ACCCTGCCCC CATCCCAGGA GGAGATGACC AAGAACCAGG TCAGCCTGAC CTGCCTGGTC AAAGGCTTCT ACCCCAGCGA
IleAlaVal GluTrpGluSer AsnGlyGln ProGluAsn AsnTyrLysThr ThrProPro ValLeuAsp SerAspGlySer PhePheLeu TyrSerArg
1301 CATCGCCGTG GAGTGGGAGA GCAATGGGCA GCCGGAGAAC AACTACAAGA CCACGCCTCC CGTGCTGGAC TCCGACGGCT CCTTCTTCCT CTACAGCAGG
LeuThrValAsp LysSerArg TrpGlnGlu GlyAsnValPhe SerCysSer ValMetHis GluAlaLeuHis AsnHisTyr ThrGlnLys SerLeuSerLeu
1401 CTAACCGTGG ACAAGAGCAG GTGGCAGGAG GGGAATGTCT TCTCATGCTC CGTGATGCAT GAGGCTCTGC ACAACCACTA CACACAGAAG AGCCTCTCCC
BmtI
NheI
~~~~~~~
SerProGly Lys***(SEQ ID NO:72)
1501 TGTCTCCGGG TAAATGAGTG CTAGCTGGCC AGACATGATA AGATACATTG ATGAGTTTGG ACAAACCACA ACTAGAATGC AGTGAAAAAA ATGCTTTATT
1601 TGTGAAATTT GTGATGCTAT TGCTTTATTT GTAACCATTA TAAGCTGCAA TAAACAAGTT AACAACAACA ATTGCATTCA TTTTATGTTT CAGGTTCAGG
AseI
~~~~~~~

```
1701  GGGAGGTGTG GGAGGTTTTT TAAAGCAAGT AAAACCTCTA CAAATGTGGT ATGGAATTAA TTCTAAAATA CAGCATAGCA AAACTTTAAC CTCCAAATCA
1801  AGCCTCTACT TGAATCCTTT TCTGAGGGAT GAATAAGGCA TAGGCATCAG GGGCTGTTGC TAGCTGTTTG CAGCCTCACC TTCTTTCATG
1901  GAGTTTAAGA TATAGTGTAT TTTCCAAGG TTTGAACTAG CTCTTCATTT CTTTATGTTT TAAATGCACT GACCTCCCAC ATTCCCTTTT TAGTAAAATA
2001  TTCAGAAATA ATTTAAATAC ATCATTGCAA TGAAAATAAA TGTTTTTTAT TAGGCAGAAT CCAGATGCTC AAGGCCCTTC ATAATATCCC CCAGTTTAGT
2101  AGTTGGACTT AGGGAACAAA GGAACCTTTA ATAGAAATTG GACAGCAAGA AAGCGAGCTT CTAGCTTATC CTCAGTCCTG CTCCTCTGCC ACAAAGTGCA
2201  CGCAGGTGCC GCCGGGGTCG CGCAGGGCGA ACTCCCGGCC CCAAATCTCC TCGCCGATCT CGGTCATGGC CGGCCCGGAG GCGTCCCGGA AGTTCGTGGA
2301  CACGACCTCC GACCACTGGG CGTACAGCTC GTCCAGGCCG CGCACCCACA CCCAGGCCAG GGTGTTGTCC GGCACCACCT GGTCCTGGAC CGCGCTGATG
2401  AACAGGGTCA CGTCGTCCCG GACCACACCG GCGAAGTCGT CCTCCACGAA GTCCCGGGAG AACCCGAGCC GGTCGGTTCA GAACTCGACC GCTCCGGCGA
2501  CGTCGCGCGC GGTGAGCACC GGAACGGCAC TGGTCAACTT GGCCATGATG CTCCCTCCTG TCAGGAGAGG AAAGAGAAGA AGGTTAGTAC AATTGCTATA
                                                                AseI
                                                              ~~~~~~~
2601  GTGAGTTGTA TTATACTATG CAGATATACT TTAATTGTCA ATGCCAATGA AACTAGGGCT GCAGGGTTCA TAGTGCCACT TTTCCTGCAC TGCCCCATCT
2701  CCTGCCACC CTTTCCCAGG CATACACAGT CAGTGACTTA CCAAACTCAC AGGAGGGAGA AGGCAGAAGC TTGAGACAGA CCCGCGGGAC CCGGAACTG
2801  CGAGGGGACG GGCTAGGGC GCTTCTTTT ATGTGCGCG CAGCCCTCGGA GGCAGGGCGC TCGGGGAGGC CTAGCGGCCA ATCTGCCGTG GCAGGAGGCG
2901  GGGCCGAAGG CCGTGCCTGA CCAATCCGGA GCACATAGGA GTCTCAGCGC CCCGCCCAA AGCAAGGGGA AGTCACGCGC CTGTAGCGCC AGCGGTGTTGT
3001  GAAATGGGGG CTTGGGGGGG TTGGGCCCCT GACTAGTCAA AACAAACTCC CATTGACGTC AATGGGGTGG AGACTTGGAA ATCCCCGTGA GTCAAACCGC
3101  TATCCACGCC CATTGATGTA CTGCCAAAAC CGCATCATCA CGGTAATAGC TGTTAATAGT ACTGACTAAT ACGTAGATGT ACTGCCAAGT CATAAGGTCA
3201  TCTACTGGGC ATAATGCCAC CCGCAAATCA TACCGTCATT GACCTCAATA GGGGGCCGTAC TTGCCATATG ATACACTTGA TCTACTGCCA AGTGGGCAGT
3301  TTACCGTAAA TACTCCACCC ATTGACGTCA ATGGAAAGTC CCTATTGGCG TTACTATGGG TTAATTAAGA AACATACGTC ATTATTGACG GGGGTCGTTG
3401  GGCGGTCAGC CAGGCGGGCC ATTTACCGTA AGTTATGTAA CGCCTGCAGG CCTGACGAGC CCTTGACGTC AATGGAGAGG CAAAAGGCCA GGAACCGTAA
3501  AAAGGCCGCG TTGCTGGCGT TTTTCCATAG GCTCCGCCCC CCTGACGAGC ATCACAAAAA TCGACGCTCA AGTCAGAGGT GGCGAAACCC GACAGGACTA
3601  TAAAGATACC AGGCGTTTCC CCCTGGAAGC TCCCTCGTGC GCTCTCCTGT TCCGACCCTG CGCTTACCG GATACCTGTC CGCCTTTCTC CCTTCGGGAA
3701  GCGTGGCGCT TTCTCATAGC TCACGCTGTA GGTATCTCAG TTCGGTGTAG GTCGTTCGCT CCAAGCTGGG CTGTGTGCAC GAACCCCCCG TTCAGCCCGA
3801  CCGCTGCGCC TTATCCGGTA ACTATCGTCT TGAGTCCAAC CCGGTAAGAC ACGACTTATC GCCACTGGCA GCAGCCACTG GTAACAGGAT TAGCAGAGCG
3901  AGGTATGTAG GCGGTGCTAC AGAGTTCTTG AAGTGGTGGC CTAACTACGG CTACACTAGA AGAACAGTAT TTGGTATCTG CGCTCTGCTG AAGCCAGTTA
4001  CCTTCGGAAA AAGAGTTGGT AGCTCTTGAT CCGGCAAACA AACCACCGCT GGTAGCGGTG GTTTTTTTGT TTGCAAGCAG CAGATTACGC GCAGAAAAAA
4101  AGGATCTCAA GAAGATCCTT TGATCTTTTC TACGGGGTCT GACGCTCAGT GGAACGAAAA CTCACGTTAA GGGATTTTGG TCATGCTAG TTAATTAACA
4201  TTTAAATCAG CGGCCGCAAT TATCTTTTCATT ACATCTGTGT GTTGGTTTTT TGTGTGAATC TCACGTTAAG GGATTTTGG TAACTAACA TACGCTCTCC ATCAAAACAA
4301  AACGAAACAA AACAAACTAG TGTCCCCAGT GCAAGTGCAG GTGCCAGAAC ATTTCTCTAT CGAA  (SEQ ID NO:99)
```

FIG.7E (CONT)

*FIG. 8A*
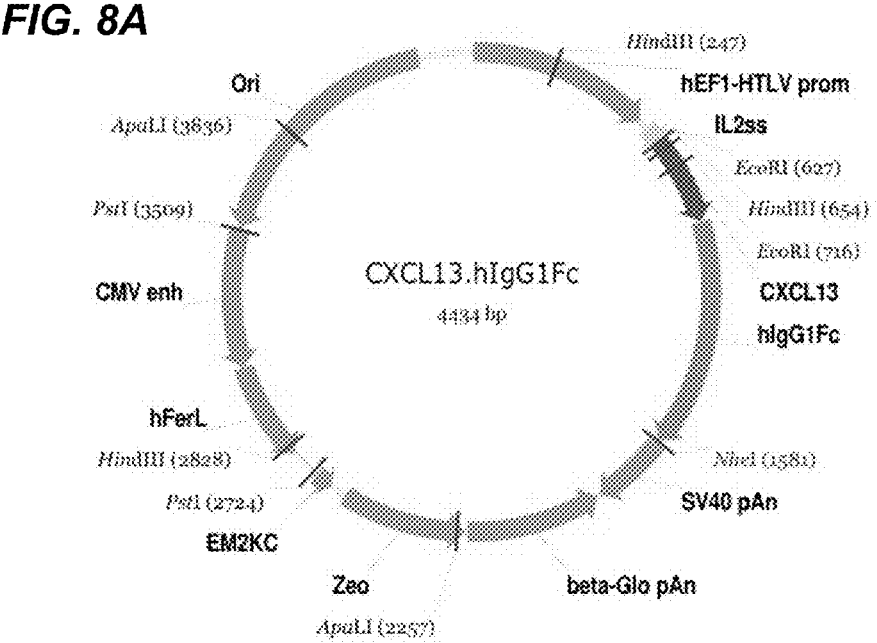
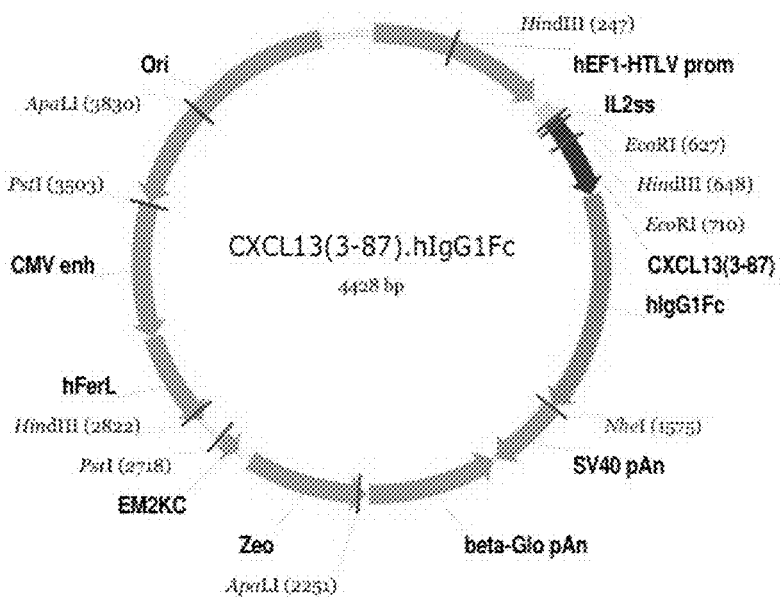
*FIG.8B*

FIG. 8C

IL2ss.CXCL13.hIgG1Fc sequence

```
   1 GGATCTGCGA TGCTCCCGGT GCCCGTCAGT GGGCAGAGCG CACATGCCCC ACAGTCCCCG AGAAGTTGGG GGGAGGGGTC GGCAATTGAA CGGGTGCCTA
 101 GAGAAGGTGG CCGCGGGTAA ACTCGGAAAG TGATGTCGTG GCCAGAACAC AGCTGAAGCT TCGAGGGGCT CGCATCTCTC CGAGGGTGGG GGAGAACCGT ATATAAGTGC AGTAGTCGCC
 201 GTGAACGTTC TTTTTGCAA CGGGTTTGCC GCCTTCTGC CGGTTGAGT CGGTTGCTC CGCCTCTGCC CGTCCGCGT CTAGTAAGT CTTCACGCGC CGCCGCCCT ACCTGAGGC
 301 GCCATCCACG CCGGTTGAGT CCGGTTGCT CCGGTTGAGT CGGTTGAGT CTAGTAAGT CTAGTAAGT CGTCCGACTG CTAGTAAGT TTAAAGCTCA GGTCGAGACC
 401 GGGCCTTTGT CCGGCCTCC CTTGGAGCCT ACCTAGACT AGCCGGCTCT CCGACCCTTG CCGACCCTG CTTGCTCAAC TCTACGTCTT TGTTTCGTTT
                                   KasI
                                   NarI
                                   SfoI
                                   BbeI                                                IL-2 secretion signal
                                                                                       MetTyrArg MetGlnLeu LeuSerCysIle
 501 TCTGTCTGC GCCGTTACAG TGACCGGCGC ATCCAAGCTG TGACCGGCGC CTACCGGAGA TCACCGGCGA AGGAGGCCA CCATGTACAG GATGCAACTC CTGTCTTGCA
                                                                EcoRI
                                                                      CXCL13 (1-87)
                                                                                   human IgG1 Fc
                                   AlaLeuSer LeuAlaLeu ValThrAsnSer ValLeuGlu ValTyrTyr ThrSerLeuArg CysArgCys ValGlnGlu SerSerValPhe IleProArg     (constant region)
 601 TTGCACTAAG TCTTGCACTT GTCACGAATT CGGTTCTGGA GGTCTATTAC ACAAGTTGA TGCACGGAAG TGTCCAAGAG AGTCAGTCT TTATCCCTAG
                                 EcoRI
                                   ArgPheIle AspArgIleGln IleLeuPro ArgGlyAsn GlyCysProArg LysArgSer SerSerThr LeuProValPro ValPheLys ProAspLysThr
 701 ACGGTTCATT GATCGAATTC AAATCTTGCC CGGTGGGAAT GGTGTCCAA GAAAAGAAT CATAGTCGG AAGAAGAACA AGTCAATTGT GTGTGTGGAC
                                   ProGlnAlaGlu TrpIleGln ArgMetMet GluValLeuArg LysArgSer SerSerThr LeuProValPro ValPheLys ProAspLysThr
 801 CCTCAAGCTG AATGGATACA AAGGATGATG GAAGTATTGA GAAAAAGAAG TTCTTCAACT CTACCAGTTC CAGTGTTAA GAGAAAGATT CCCGACAAA
                                   HisThrCys ProProCys AlaProIleGlu LysThrIle SerLysThrIle SerLysAla LysGlyGlnPro ArgGluPro GlnValTyr ThrLeuProPro SerArgGlu
 901 CTCACACATG CCCACCGTGC CCAGCACCTG AACTCCTGG GGGACCGTCA GTCTTCCTCT TCCCCCCAAA ACCCAAGGAC ACCCTCATGA TCTCCCGGAC
                                   ProGluVal ThrCysValVal ValAspVal SerHisGluAsp ProGluVal LysPheAsn TrpTyrVal AspGlyValGlu ValHisAsn AlaLysThr
1001 CCCTGAGGTC ACATGCGTG TGGTGGACGT GAGCCACGAA GACCCCGAGG TCAAGTTCAA CTGGTACGTG GACGGCGTGG AGGTGCATAA TGCCAAGACA
                                   LysProArgGlu GluGlnTyr AsnSerThr TyrArgValVal SerValLeu ThrValLeu HisGlnAspTrp LeuAsnGly LysGluTyr LysCysLysVal
1101 AAGCCGCGGG AGGAGCAGTA CAACAGCACG TACCGTGTGG TCAGCGTCCT CACCGTCCTG CACCAGGACT GGCTGAATGG CAAGGAGTAC AAGTGCAAGG
                                   SerAsnLys AlaProIleGlu AlaProIleGlu LysThrIle SerLysAla LysGlyGlnPro ArgGluPro GlnValTyr ThrLeuProPro SerArgGlu
1201 TCTCCAACAA AGCCCTCCCA GCCCCCATCG AGAAAACCAT CTCCAAAGCC AAAGGGCAGC CCCGAGAACC ACAGGTGTAC ACCCTGCCCC CATCCCGGGA
                                   GluMetThr LysAsnGlnVal SerLeuThr CysLeuVal LysGlyPheTyr ProSerAsp IleAlaVal GluTrpGluSer AsnGlyGln ProGluAsn
1301 GGAGATGACC AAGAACCAGG TCAGCCTGAC CTGCCTGGTC AAAGGCTTCT ATCCCAGCGA CATCGCCGTG GAGTGGGAGA GCAATGGGCA GCCGGAGAAC
                                   AsnTyrLysThr ThrProPro ValLeuAspSer AspPheSerTyrSerLys LeuThrValAsp LysSerArg TrpGlnGln GlyAsnValPhe
1401 AACTACAAGA CCACGCCTCC CGTGCTGGAC TCCGACGGCT CCTTCTTCCT CTACAGCAAG CTCACCGTGG ACAAGAGCAG GTGGCAGCAG GGGAACGTCT
                                   SerCysSer ValMetHis GluAlaLeuHis AsnHisTyr ThrGlnLys SerLeuSerLeu SerProGly Lys***(SEQ ID NO:73)
1501 TCTCATGCTC CGTGATGCAC GAGGCTCTGC ACAACCACTA CACGCAGAAG AGCCTCTCCC TGTCTCCGGG TAAATGAGTG CTAGCTGCCC AGACATGATA
1601 AGATACATTG ATGACTTGG ACAAACCACA ACTAGCAATG ATGAAAAAA ATGCTTTATT TGTGAAATTT GTGATGCTAT TGCTTTATTT GTAACCATTA
1701 TAAGCTGCAA TAAACAAGTT AACAACAACA ATTGCATTCA TTTATGTTT CAGGTTCAGG GGGAGGTGTG GGAGGTTTTT TAAAGCAAGT AAAACCCTCTA
                                                                                                              BmtI
                                                                                                              NheI
```

```
                                    AseI
1801 CAAATGTGGT ATGGAATTAA TTCTAAAATA CAGCATAGCA AAACTTTAAC CTCCAAATCA AGCCTCTACT TGAATCCTTT TCTGAGGGAT GAATAAGGCA
1901 TAGGCATCAG GGGCTGTTGC CAATGTGCAT TAGCTGTTTG GACCCTCACC TTCTTTCATG GAGTTTAAGA TATAGTGTAT TTTCCCAAGG TTTGAACTAG
2001 CTCTTCATTT CTTTATGTTT TAAATGCACT GACCTCCCAC ATTCCCTTTT TAGTAAAATA TTCAGAAATA ATTTAAATAC ATCATTGCAA TGAAAATAAA
2101 TGTTTTTTAT TAGCAGAAT CCAGATGCTC AAGGCCCTTC ATAATATCCC ACAAATTAGT AGTTGGACTT AGGAACAAA GGAACCTTTA ATAGAAATTG
2201 GACAGCAAGA AAGCGAGCTT CTAGCTTATC CTCCTCTGCC CTCCTCCCGA AGTTCGTGGA CGCAGTTGCA CACGACCTCC GCCGGGCTG CGCAGGGCGA ACTCCCGCCC
2301 CCACGGCTGC TCGCCGATCT CGGTCATCGC CGGCCCCGGA GCTCCCCCGA AGTTCGTGGA CACGACCTCC CGTACAGGTC GTCCAGGCCG GCGAAGTCGT
2401 CGCAGCCACA CCCAGGCCAG GGTGTTGTCC GGCACCACCT GGTCCTGGAC CGGCTGATG AACAGGGTCA CGTCGTCCCG GACCACACCG GCGAAGTCGT
2501 CCTCCACGAA GTCCCGGGAG AACCCCAGCC GGTCGGTCCA GAACTCGACC GCTCCGGCGA CGTCGCGCGC GGTGAGCACC GGAACGGCAC TGGTCAACTT
2601 GGCCATGATG GCTCCTCCTG TCAGGAGAGG AAAGAGAAGA AGGTTAGTAC AATTGCTATA GTGAGTTGTA TTATACTATG CAGATATACT ATGCCAATGA
      AseI
2701 TTAATTGTCA AACTAGGGCT GCAGGGTTCA TAGTGCCACT TTTCCTGCAC TGCCCCATCT CCTGCCCACC CTTTCCCAGG CATAGACAGT CAGTGACTTA
2801 CCAAACTCAC AGGAGGGAGA AGGCAGAAGC TTGAGACAGA CCCGGGGAC CGCCGAACTG TGGCTAGGGC GGCTTCTTTT ATGGTGCGCC
2901 GGCCCTCGGA GGCAGGGCGC TCGGGAAGGC CTAGCGGGCA ATCTGCGGTG GCAGGAGGCG GGGCCGAAGG CCGTGCCTGA CCAATCCGGA GCACATAGGA
3001 GTCTCAGCGC CCCGCCCCAA AGCAAGGGGA AGTCACGCGC CTGTAGCGCC AGCGTGTTGT GAAATGGGGG CTTGGGGCCT TTGGGCCCCT GACTAGTCAA
3101 AACAAACTCC CATTGACGTC AATGGGGTGG ATCCCCGTGA GTCAAACCGC TATCCACGCC CATTGATGTA CTGCATCATCA CGCATCATCA
3201 TGGTAATAGC GATGACTAAT ACTGCCAAGT ACTTGCCAAGT CATAAGGTCA TGTACTGGGG ATAATGCCAG TACCCGTCATT
3301 GACGTCAATA GGGGGCGTA TTGGCATATG ATACACTTGA TGTACTGCCA AGTGGGCAGT TTACCGTAAA TACTCCACCC ATTGACGTCA ATGGAAAGTC
3401 CCTATTGGCG TTACTATGGG TTAATTAGCA ATTATTGACG TCAATGGGCA GTGGGCTTG GGGCGGGCC CAGGCGGGCC TTTTCCATAG AGTTATGTAA
3501 CGGCTGCAGG TTAATTAAGA ACATGTGAGC AAAAGGCCAG CAAAAGGCCA GGAACCGTAA AAAGGCCGCG TTGCTGGCGT TTTTCCATAG GCTCCGCCCC
3601 CCTGACGAGC ATCACAAAAA TCGACGCTCA AGTCAGAGGT GGCGAAACCC GACAGGACTA TAAAGATACC AGGCGTTTCC CCCTGGAAGC TCCCTCGTGC
3701 GCTCTCCTGT TCCGACCCTG CCGCTTACCG GATACCTGTC CGCCTTTCTC CCTTCGGGAA GCGTGGCGCT TTCTCATAGC TCACGCTGTA GGTATCTCAG
3801 TTCGGTGTAG GTCGTTCGCT CCAAGCTGGG CTGTGTGCAC GAACCCCCCG TTCAGCCCGA GTAACAGGAT TAGCAGAGCG AGGTATGTAG TGAGTCCAAC
3901 CGGTAAGAC ACGACTTATC GCCACTGGCA GCAGCCACTG GTAACAGGAT TAGCAGAGCG AGGTATGTAG GCGGTGCTAC AGAGTTCTTG AAGTGGTGGC
4001 CTAACTACGG CTACACTAGA AGAACAGTAT TTGGTATCTG CGCTCTGCTG AAGCCAGTTA CCTTCGGAAA AGAGTCTCAA AGCTCTTGAT CCGGCAAACA
4101 AACCACCGCT GGTAGCGGTG GTTTTTTTGT TTGCAAGCAG CAGATTACGC GCAGAAAAAA AGGATCTCAA GAAGATCCTT TGATCTTTTC TACGGGGTCT
4201 GACGCTCAGT GGAACGAAAA CTCACGTTAA GGGATTTTGG TCATGCATAG TTAATAACA TTTAAATCAG ACGAACACAA AAATATCTT TATTTTCATT
4301 ACATCTGTGT GTTGGTTTTT TGTGTGAATC GTAATAACTAA TACGCTCTCC ATCAGAACAA ACGAACAA AACAAACTAG TACGGGGTCT TATTTTCATT
4401 GCAAGTGCAG GTGCCAGAAC ATTTCTCTAT CGAA          (SEQ ID NO:100)
```

IL2ss.CXCL13(3-87).hIgG1Fc sequence

```
   1 GGATCTGCGA TCCTCCGGT GCCCTCAGT GGGCAGAGCG CACATGCCCC ACAGTCCCCG AGAAGTTGGG GGGAGGGGTC GGCAATTGAA CGGGGTCCTA
 101 GAGAAGGTGG CGCGGGGTAA ACTGGGAAAG GATGGAAGTA CGGAGAACAC AGCTGAACTC GCCAGGGCT TCCACGGGCT CGAGGGTGGG GGAGAACCGT CGAGGGCGCG AGTAGTCGCC
 201 GTGAACGTTC TTTTTCGCAA CGGGTTTGCC GCCAGAACAC AGCTGAACTC GCCAGGGCT TCCACGGGCT CCCAATCTCT CTTCAGGGCC CGGCCCGCC ACCTGAGCC
 301 GCCATCCACG CCGGTTGAGT CGCGTTCTGC CGCTCCCGC CGTGTGGTGCG CCCCTGAACTG CGTCGGCGAG TTAAGCTCA GGTCGAGACC
 401 GGGCCTTTGT CCGGCGCTCC CTTGGAGCCT AGCCGGGTCT CCGACCCCTG CTTGCTCAAC CTCTACGTCTT TGTTTCGTTT

IL-2 secretion signal
                                                                 MetTyrArg MetGlnLeu LeuSerCysIle
 501 TCTGTTCTGC GCCGTTACAG ATCCAAGCTG TGACCGGGCG CTACCTGAGA TCACCGGCGA AGGAGGCCA CCATGTACAG GATGCAACTC CTGTCTTGCA
                                                                                                EcoRI
                                                                                              ~~~~~~ CXCL13 (3-87)
     AlaLeuSer LeuAlaLeu ValThrAsnSer GluValTyr TyrThrSer LeuArgCysArg CysValGln GluSerSer ValPhelePro ArgArgPhe
 601 TTGCACTAAG TCTTGCACTT GTCACGAATT CGGAGGTCTA TTACACAAGC TTGAGGTGTA GAGAGCTCA GTCTTATCC CTAGACGTT
     IleAspArg IleGlnIleLeu ProArgGly AsnGlyCys ProArgLysLys IleIleVal TrpLysLys AsnLysSerIle ValCysVal AspProGln
 701 CATTGATCGA ATTCAAATCT TGCCCCCGTTGT GAATGGTGT CCAAGAAAAG AAATCATAGT CTGGAAGAAA AACAAGTCAA TTGTGTGT GGACCCTCAA
                                                                                                          human IgG1 Fc
                                                                                                          (constant region)
     AlaGluTrpIle GlnArgMet LeuArgLysArg SerSerSer ThrLeuPro ValProVal Phe LysArgLys IleProAsp LysThrHisThr
 801 GCTGAATGGA TACAAAGAAT GATGGAAGTA TTGAGAAGTA GAAGTCTTCA AACTCTCCA GTTCCAGTGT TTAAGAGAAA GATTCCCGAT AAAACTCACA
     CysProPro CysProAla ProGluLeuLeu GlyGlyPro SerValPhe LeuPheProPro LysProLys AspThrLeu MetIleSerArg ThrProGlu
 901 TGTCCCCACC GTGCCCAGCA CCTGAACTCC TGGGGGGACC GTCAGTCTTC CTCTTCCCCC CAAAACCCAA GGACACCCTC ATGATCTCCC GGACCCCTGA
     ValThrCys ValValVal AspValSerHis GluAspPro GluValLysPhe AsnTrpTyr ValAspGly ValGluValHis AsnAlaLys ThrLysPro
1001 GGTCACATGC GTGGTGGTG GACGTGAGCCA CGAAGACCCT GAGGTCAAGT TCAACTGGTA CGTGGACGGC GTGGAGGTGC ATAATGCCAA GACAAAGCCG
     ArgGluGluGln TyrAsnSer ThrTyrArg ValValSerVal LeuThrVal LeuHisGln AspTrpLeuAsn GlyLysGlu TyrLysCys LysValSerAsn
1101 CGGGAGGAGCAG AGTACACAAC CGTACCGTT GTGGTCAGCG TCCTCACCGT CCTGCACCAG GACTGGCTGA ATGGCAAGGA GTACAAGTGC AAGGTCTCCA
     LysAlaLeu ProAlaPro IleGluLysThr IleSerLys AlaLysGly GlnProArgGlu ProGlnVal TyrThrLeu ProProSerArg GluGluMet
1201 ACAAAGCCCT CCCAGCCCCC ATCGAGAAAA CCATCTCCAA AGCCAAAGGG CAGCCCCGAG AACCACAGGT GTACACCCTG CCCCCATCCC GGGAGGAGAT
     ThrLysAsn GlnValSerLeu ThrCysLeu ValLysGly PheTyrProSer AspIleAla ValGluTrp GluSerAsnGly GlnProGlu AsnAsnTyr
1301 GACCAAGAAC CAGTCAGCTC TGACCTGCCT GGTCAAAGGC TTCTATCCA GCGACATCGC CGTGGAGTGG GAGAGCAATG GGCAGCCGGA GAACAACTAC
     LysThrThrPro ProValLeu AspSerAspGly SerPhePhe LeuTyrSer LysLeuThr ValAspLysSer ArgTrpGln GlnGlyAsn ValPheSerCys
1401 AAGACCACGC CTCCCGTGCT GGACTCCGAC GGCTCCTTCT TCCTCTACAG CAAGCTCACC GTGGACAAGA GCAGGTGGCA GCAGGGGAAC GTCTTCTCAT SerValMet HisGluAla LeuHisAsnHis TyrThrGln LysSerLeu SerLeuSerPro GlyLys***(SEQ ID NO:74)
1501 GCTCCGTGAT GCACGAGGCT CTGCACAACC ACTACACGCA GAAGAGCCTC TCCCTGTCTC CGGGTAAATG AGTGCTAGCT GGCCAGACAT GATAAGATAC
                                                                                            BmtI
                                                                                            NheI
1601 ATTGATGAGT TTGGACAAAC CACAACTAGA ATGCAGTGAA AAAAATGCTT TATTTGTGAA ATTTGTGATG CTATTGCTTT ATTTGTAACC ATTATAAGCT
1701 GCAATAAACA AGTTAACAAC AACAATTGCA TTCATTTTAT GTTTCAGGTT CAGGGGGAGG TGTGGGAGGT TTTTTAAAGC AAGTAAAACC TCTACAAATG
     AseI
```

```
1801 TGGTATGGAA TTAATTCTAA AATACAGCAT AGCAAAACTT TAACCTCCAA ATCAAGCCTC TACTGAATC  CTTTTCTGAG GGATGAATAA GGCATAGGCA
1901 TCAGGGGCTG TTGCCAATGT GCATTAGCTG TTTGCAGCCT CCACATTCCC TTTTTAGTAA CATGGAGTTT AAGATATAGT AAGGTTTGAA CTAGCTCTTC
2001 ATTTCTTTAT GTTTTAAATG CACTGACCTG CCACATTCAT GCTCAAGGCC CTTCATAATA TCCCCCAGTT AATATTCAGA ACTTAGGGAA CAAAGGAACC GCAATGAAAA TAAATGTTTT
2101 TTATTAGGCA GAATCCAGAT GCTCAAGGCC TATCCTCAGT CCTGCTCCTC TGCCACAAAG TGCACGCAGT TGCCGGCCGG GTCGCGCAGG GCGAACTCCC ATTGACAGC GCCCCGACGG
2201 AAGAAAGCGA GCTTCTAGCT TATCCTCAGT CCTGCTCCTC TGCCACAAAG TGCACGCAGT TGGACACGAC CTCCGACCAC TCGGCGTACA GCTCGTCCAG GCCGCGCACC
2301 CTGCTCGCCG ATCTCGGTCA TGGCCGGCCC GGAGGCGTCC CGAAGTTCCG TGGACACGAC CTCCGACCAC TCGGCGTACA GCTCGTCCAG GCCGCGCACC
2401 CACACCCAGG CCAGGGTGTT GTCCGGCACC ACCTGGTCCT GGACCGCGCT GATGAACAGG GTCACGTCGT CCCGGACCAC ACCGGCGAAG TCGTCCTCCA
2501 CGAAGTCCCG GGAGAACCCG AGCCGGTCGG TCCAGAACTC CCAGAACTC GACCGCTCCG GCGACGTCGC GCGCGGTGAG CACCGGGTCA GCACTGGGTCA ACTTGGCCAT
                                                                                                                                                          AseI
2601 GATGGCTCCT CCTGTCAGGA GAGGAAAGAG GTACAATTGC TATAGTGAGT TGTATTATAC TACTATGCCA ATGATTAATT
2701 GTCAAACTAG GGCTGCAGGG TTCATAGTGC CACTTTTCCT GCACTGCCCC ATCCTCTGCC CACCCTTTCC CAGGCATAGA CAGTCAGTGA CTTACCAAAC
2801 TCACAGGAGG GAGAAGGCAG AAGCTTGAGA CAGACCCGGG ACTGCAGGGG GGACGTGCTA GACGTGGCTA GGGCGGCTTC TTTTTATGTG CGCCGGCCCT
2901 CGGAGGCAGG GCGCTCGGGG AGGCCTAGCG GCCAATCTGC GGTGGCAGGA AAGGCCGGTGC CTGACCAATC CGGAGCACAT AGGAGTCTCA
3001 GCCCCCCGCC CCAAAGCAAG GCGAAGTCAC GCCCACCCTG TTGTCAAATG GGGCCTTGGG CCGCTATCCA AAACCGCATC TCAAAACAAA
3101 CTCCCATTGA CGTCAATGGG GTGGAGACTT GTGAGTCAAA CCGCTATCCA TGTACTGCCA AAACCGCATC ATCATGGTAA
3201 TAGCGATGAC TAATACGTAG ATGTACTCCC AAGTAGGAAA GTCCCATAAG GTCATGTACT CCAGGCGGGC CATTTACCGT CATTGACGTC
3301 AATAGGGGC GTACTTGGCA TATGATACAC TTGATGTACT GCCAAGTGGG TAAATACTCC ACCCATTGAC GTCAATGGAA AGTCCCTATT
3401 GGGCTTACTA TGGGAACATA CGTCATTATT GACGTCAATG GGCGGGGGTC CAGCCAGGCG CGGCCATTAC CGTCAATAAG CGTAACGGCTG
3501 CAGGTTAATT AAGAACATGT GAGCAAAAGG CCAGCAAAG GCCAGGAACC GTAAAAAGGC CGCGTTGCTG GCGTTTTTTC CCCCCTGAC
3601 GAGCATCACA AAAATCGACG CTCAAGTCAG AGGTGGCGAA ACCCGACAGG ACTATAAAGA TACCAGGCGT TTCCCCCTGG AAGCTCCCTC GTGCGCTCTC
3701 CTGTTCCGAC CCTGCCGCTT ACCGGATACC TGTCCGCCTT TCTCCCTTCG GGAAGCGTGG CGCTTTCTCA TAGCTCACGC TGTAGGTATC TCAGTTCGGT
3801 GTAGGTCGTT CGCTCCAAGC TGGGCTGTGT GCACGAACCC CCCGTTCAGC CCGACCGCTG CCGCTTATCC TAGCTATCT GTCTTGAGTC CAACCCGGTA
3901 AGACACGACT TATCGCCACT GGCAGCAGCC ACTGGTAACA GGATTAGCAG AGCGAGGTAT GTACGCGGTG CTACAGAGTT CTTGAAGTGG TGGCCTAACT
4001 ACGGCTACAC TAGAAGAACA GTATTTGGTA TCTGCGCTCT GCTGAAGCCA GTTACCTTCG GAAAAAGAGT TGGTAGCTCT TGATCGGCA AACAACCAC
4101 CGCTGGTAGC GGTGGTTTT TTGTTTGCAA GCAGCAGATT ACGCGCAGAA AAAAAGGATC TCAAGAAGAT CCTTTGATCT TTTCTACGGG GTCTGACGCT
4201 CAGTGGAACG AAAACTCACG TTAAGGGATT TTGGTCATGA GATTATCAAA AAGGATCTTC ACCTAGATCC TTTTAAATTA AAAATGAAGT TTTAAATCAA
4301 GTGTTGTGGT TTTTTGTGTG AATCGTAACT AACATACGCT CTCCATCAA ACAAAACGAA ACAAAACAAA CTAGCAAAAT TCTTTATTT CATTACATCT
4401 GCAGGTGCCA GAACATTTCT CTATCGAA   (SEQ ID NO:101)
```

IL2ss.CXCL13(3-87).hIgG1Fc sequence [Alanine substitutions for removal of GAG binding sites – Lys & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                              KasI
                                              NarI
                                              SfoI
                                              BbeI
                                              ~~~~~~~                                        IL-2 secretion signal
                                                                                             MetTyrArg MetGlnLeu LeuSerCysIle
 501   TCTGTTCTGC GCCGTTACAG ATCCAAGCTG TGACCGGCGC CTACCTCAGA TCACCGGCGA AGGAGGGCCA CCATGTACAG GATGCAACTC CTGTCTTGCA
                                  EcoRI
                                  ~~~~~~~ CXCL13 (3-87)
         AlaLeuSer LeuAlaLeu ValThrAsnSer GluValTyr TyrThrSer LeuArgCysArg CysValGln GluSerSer ValPheIlePro ArgArgPhe
 601   TTGCACTAAG TCTTGCACTT GTCACGAATT CGGAGGTCTA TTACACAAGC TTGAGGTGTA GATGTGTCCA AGAGAGCTCA GTCTTTATCC CTAGACGCTT
            EcoRI
        IleAspAla IleGlnIleLeu ProArgGly AsnGlyCys ProArgLysGlu IleIleVal TrpAlaAla AsnAlaSerIle ValCysVal AspProGln
 701   CATTGATgcc ATTCAAATCT TGCCCCGTGG GAATGGTTGT CCAAGAAAAG AAATCATAGT CTGGgctgcg AACgccTCAA TTGTGTGTGT GGACCCTCAA
                                                                                                   human IgG1 Fc
                                                                                                  (constant region)
       AlaGluTrpIle GlnAlaMet MetGluVal LeuAlaAlaAla SerSerSer ThrLeuPro ValProValPhe AlaAlaAla IleProAsp LysThrHisThr
 801   GCTGAATGGA TACAAgccAT GATGGAAGTA TTGgctgcgg ctAGTTCTTC AACTCTACCA GTTCCAGTGT TTgccgctgc gATTCCCGAC AAAACTCACA
         CysProPro CysProAla ProGluLeuLeu GlyGlyPro SerValPhe LeuPheProPro LysProLys AspThrLeu MetIleSerArg ThrProGlu
 901   CATGCCCACC GTGCCCAGCA CCTGAACTCC TGGGGGGACC GTCAGTCTTC CTCTTCCCCC CAAAACCCAA GGACACCCTC ATGATCTCCC GGACCCCTGA
        ValThrCys ValValValAsp ValSerHis GluAspPro GluValLysPhe AsnTrpTyr ValAspGly ValGluValHis AsnAlaLys ThrLysPro
1001   GGTCACATGC GTGGTGGTGG ACGTGAGCCA CGAAGACCCT GAGGTCAAGT TCAACTGGTA CGTGGACGGC GTGGAGGTGC ATAATGCCAA GACAAAGCCG
       ArgGluGluGln TyrAsnSer ThrTyrArg ValValSerVal LeuThrVal LeuHisGln AspTrpLeuAsn GlyLysGlu TyrLysCys LysValSerAsn
1101   CGGGAGGAGC AGTACAACAG CACGTACCGT GTGGTCAGCG TCCTCACCGT CCTGCACCAG GACTGGCTGA ATGGCAAGGA GTACAAGTGC AAGGTCTCCA
         LysAlaLeu ProAlaPro IleGluLysThr IleSerLys AlaLysGly GlnProArgGlu ProGlnVal TyrThrLeu ProProSerArg GluGluMet
1201   ACAAAGCCCT CCCAGCCCCC ATCGAGAAAA CCATCTCCAA AGCCAAAGGG CAGCCCCGAG AACCACAGGT GTACACCCTG CCCCCATCCC GGGAGGAGAT
        ThrLysAsn GlnValSerLeu ThrCysLeu ValLysGly PheTyrProSer AspIleAla ValGluTrp GluSerAsnGly GlnProGlu AsnAsnTyr
1301   GACCAAGAAC CAGGTCAGCC TGACCTGCCT GGTCAAAGGC TTCTATCCCA GCGACATCGC CGTGGAGTGG GAGAGCAATG GGCAGCCGGA GAACAACTAC
       LysThrThrPro ProValLeu AspSerAsp GlySerPhePhe LeuTyrSer LysLeuThr ValAspLysSer ArgTrpGln GlnGlyAsn ValPheSerCys
1401   AAGACCACGC CTCCCGTGCT GGACTCCGAC GGCTCCTTCT TCCTCTACAG CAAGCTCACC GTGGACAAGA GCAGGTGGCA GCAGGGGAAC GTCTTCTCAT
                                                                                            BmtI
                                                                                            NheI
         SerValMet HisGluAla LeuHisAsnHis TyrThrGln LysSerLeu SerLeuSerPro GlyLys***(SEQ ID NO:75)
1501   GCTCCGTGAT GCACGAGGCT CTGCACAACC ACTACACGCA GAAGAGCCTC TCCCTGTCTC CGGGTAAATG AGTGCTAGCT GGCCAGACAT GATAAGATAC
1601   ATTGATGAGT TTGGACAAAC CACAACTAGA ATGCAGTGAA AAAAATGCTT TATTTGTGAA ATTTGTGATG CTATTGCTTT ATTTGTAACC ATTATAAGCT
1701   GCAATAAACA AGTTAACAAC AACAATTGCA TTCATTTTAT GTTTCAGGTT CAGGGGGAGG TGTGGGAGGT TTTTTAAAGC AAGTAAAACC TCTACAAATG
```

```
         AseI
1801  TGGTATGGAA TTAATTCTAA AATACAGCAT AGCAAAAACTT TAACCTCCAA ATCAAGCCTC TACTTGAATC CTTTTCTGAG GGATGAATAA GGCATAGGCA
1901  TCAGGGGCTG TTGCCAATGT GCATTAGCTG TTTGCAGCCT CACCTTCTTT CTTTTAGTAA CATGGAGTTT CATGGAGTTT AAGGTTTGAA CTAGCTCTTC
2001  ATTTCTTTAT GTTTTAAATG CACTGACCTC CCACATTCCC TTTTTAGTAA AATATTCAGA AATAATTTAA ATACATCATT GCAATGAAAA TAAATGTTTT
2101  TTATTAGGCA GAATCCAGAT GCTCAAGGCC CTTCATAATA TCCCCCAGTT TAGTAGTTGG ACTTAGGGAA CAAAGGAACC ACTTATGGTG ATTGGACAGC
2201  AAGAAAGCGA GCTTCTAGCT TATCCTCCTC TGCCACAAAG TGCACGCAGT TGCCGGCCGG GTCGCGCCAG GCGAACTCCC GCCCCCACGG
2301  CTGCTCGCCG ATCTCGGTCA TGGCCGGCCC GGAGGCGTCC GGAAGTTCG TGGACACGAC CTCCGACCAC TCGGCGTACA GCTCGTCCAG GCCGCGCACC
2401  CACACCAGG CCAGGTGTT GTCCGGCACC ACCTGGTCT GGACCGCGCT GATGAACAGG GTCACGTCGT CCCGACCAC ACCGGCGAAG TCGTCCTCCA
2501  CGAAGTCCCG GGAGAACCCG AGCCGGTCG TCCAGAACTC GACCGCTCCG GACCGCTCG GCGACGTCGC GCGGGTGAG CACCGGAACG GCACTGGTCA ACTTGGCCAT
                                                                                                                  AseI
2601  GATGGCTCCT CCTGTCAGGA GAGGAAAGAG AAGAAGGTTA GTACAATTGC TATAGTGAGT TGTATTATAC TATGCAGATA TACTATGCCA ATGATTAATT
2701  GTCAAACTAG GGCTGCAGGG TTCATAGTGC CACTTTTCCT GCACTGCCCC ATCTCCTGCC CACCCTTTCC CAGGCATAGA CAGTCAGTGA CTTACCAAAC
2801  TCACAGGAGG GAGAAGCCAG AAGCTTGAGA CAGACCGCGG GACCGCGCGA ACTGGCGGCA GACGTGGCTA GGGCGGCTTC TTTTATGGTG CGCGGCCCT
2901  CGGAGGCAGG GCGCTCGGGG AGGCCTAGCG GCCAATCTGC GGTGGCAGGA GCCAGCGTGC AAGGCCGTGC CTGACCAATC CGGAGCACAT AGGAGTCTCA
3001  GCCCCCGC CCAAAGCAAG GGGAAGTCAC GCGGCCTGTA TTGTGAAATG GGGCTTGGG CCCTGACTAG CCCTGACTAG TCAAAACAAA
3101  CTCCCATTGA CGTCAATCGG GTGGAGACTT GGCCTATCCA CCGGTATCAA AAGTAGGAAA GTCCCATTGA CCGCTATCC AAACCCATC ATCATGGTAA
3201  TAGCGATGAC TAATACGTAG ATGTACTGCC AAGTAGGAAA GTCCCATAAG CAGTTTTACCG CCAGGCGGGC CATTTACCGT CATTGACGTC
3301  AATAGGGGGC GTACTTGGCA TATGATACAT TTGATGTACT GCCAAGTGGG CAGTTTTACCG TAAATACTCC ACCCATTGAC GTCAATGGAA AGTCCCTATT
3401  GGGTTACTA TGGAACATA CGTCATTATT GACGTCAATG GGCGGGGGTC GTTGGGCGGT CAGCCAGGCG GCCATTTAC CGTAAGTTAT GTAACGCCTG
3501  CAGGTTAATT AAGAACATGT GAGCAAAAGG CCAGCAAACC GCCAGCAAAG CCAGGAACC ACTATAAAGA TACCAGGCGT TTCCCCCTGG AAGCTCCCTC GTGCGCTCTC
3601  GAGCATCACA AAAATCGACG CTCAAGTCAG AGGTGGCGAA ACCCGACAGG ACTATAAAGA TACCAGGCGT TTCCCCCTGG AAGCTCCCTC GTGCGCTCTC
3701  CTGTTCCGAC CCTGCCGCTT ACCGGATACC TGTCCGCCTT TCTCCCTTCG GAAGCGTGG CGCTTTCTCA TAGCTCACGC TGTAGGTATC TCAGTTCGGT
3801  GTAGTCGTT CGGCTCCAAGC TGGGCTGTGT GCACGAACCC CCGTTCAGC CCGACCGCTG CGCCTTATCC GGCCTAACTAT CGGTAACTAT GTCTTGAGTC CAACCCGGTA
3901  AGACACGACT TATCGCCACT GGCAGCAGCA ACTGGTAACA GGATTAGCAG AGCGAGGTAT GTAGGCGGTG CTACAGAGTT CTTGAAGTGG TGGCCTAACT
4001  ACGGCTACAC TAGAAGAACA GTATTGGTA TCTGCGTCT GCTGAAGCCA GTTACCTTCG GAAAAAGAGT TGGTAGCTCT TGATCCGGCA AACAAACCAC
4101  CGCTGGTAGC GGTGGTTTTT TTGTTTGCAA GCAGCAGATT ACGCGCAGAA AAAAAGGATC TCAAGAAGAT CCTTTGATCT TTTCTACGGG GTCTGACGCT
4201  CAGTGGAACG AAAACTCACG TTAAGGGATT TTGGTCATGA CTAGTTAATT AACATTTAAA TCAGCGGCCG CAATAAAATA TCTTTATTT CATTACATCT
4301  GTGTGTTGGT TTTTTGTGTG AATCGTAACT AACATACGCT CTCCATCAAA ACAAAACGAA CTAGCAAAAT ACAAAACAAA AGGCTGTCCC CAGTGCAAGT
4401  GCAGGTGCCA GAACATTCT CTATCGAA  (SEQ ID NO:102)
```

IL2ss.CXCL13.hIgG4Fc sequence

```
   1 CGATCTCCGA TGCCTCCGGT GCCCGTCAGT GGGCAGAAGC CACATCGCCC ACAGTCCCCG AGAAGTTGGG GGGAGGGGTC GGCAATTGAA CGGGTGCCTA
 101 GAGAAGGTGG CGCGGGGTAA ACTGGGAAAG TGATGTCGTG TACTGGCTCC GCCTTTTTCC CGAGGGTGGG GGAGAACCGT CTTCAGGGGT ATATAAGTGC
 201 GTGAAGCTTC TTTTTCGCAA CGGGTTTGCC CAGGAACTGA AGCTGAAGCT TCGAGGGCGT TGAGGGGCGT CCCATCTCTG CCCGCGCCCT ACTGAGCGC
 301 GCCATCCACG CCGGTTGAGT CCGGTCTCGC CGCTCCCGC CTGTGGTGCC CGGCTGAACTG CGTCCGCCGT CTAGGTAAGT TTAAAGCTCA GGTGAGACC
 401 GGGCCTTTGT CCGGCGCTCC CTTGGAGCCT ACCTAGGCCT AGCCGGGCTC AGCCGGGCTG CCTACCCCTG CTTGCTCAAC TCTACGTCTT TGTTTCGTTT
                                   KasI
                                   NarI
                                   SfoI
                                   BbeI
                                                                                                         IL-2 secretion signal
                                                                                                      MetTyrArg MetGlnLeu LeuSerCysIle
 501 TCTGTTCTGC GCCGTTACAG AGCCAAGCTG TGACCGGCGC CTACCTGAGA TCACCGGCGA AGGAGGGCCA CCATGTACAG GATGCAACTC CTGTCTTGCA
                                    EcoRI
                                               ~~~~~~ CXCL13 (1-87)
       AlaLeuSer LeuAlaLeu ValThrAsnSer ValLeuGlu ValTyrTyr ThrSerLeuArg CysArgCys ValGlnGlu IleProArg
 601 TTGCACTAAG TCTTGCACTT GTCACGAATT CGGTTCTGGA GGTCTATTAC ACAAGTTGAA GGTGTAGATG AGCTCAGTGT TTATCCTGAG
                    EcoRI
       ArgPheIle AspArgIleGln IleLeuPro ArgMetMet GluValLeuArg LysArgSer SerSerThr LeuProValPro ArgLysIle ProProProCys
 701 ACGCTTCATT GATCGAATTC AAATCTTGCC CCGTGGGAAT GGTTGTCAAG AAAAGAAGT CTAGCAGTACA GTTGTGGAC
                                                                                                                  human IgG4 Fc
                                                                                                                  (constant region)
       ProGlnAlaGlu TrpIleGln ArgMetMet GluValLeuArg LysArgSer SerSerThr LeuProValPro ArgLysIle ProProProCys
 801 CCTCAAGCTG AATGATACA AAGAATGATG GAAGTATTGA GAAAAGAAG TTCTTCAACT CTACCAGTTC CAGTGTTTAA GAGAAGATT CCCCCCCAT
       ProSerCys ProAlaPro GluPheLeuGly GlyProSer ValPheLeu PheProPro LysProLysAsp ThrLeuMet IleSerArgThr ProGluVal
 901 CCCATCATG CCCAGACCT GAGTTCCTGG GGGGACCATC AGTCTTCCTG TTCCCCCCAA AACCCAAGGA CACTCTCATG ATCTCCCGGA CCCCTGAGGT
       ThrCysVal ValValAspVal SerGlnGluAsp ProGluVal GlnPheAsn TrpTyrVal AspGlyVal GluValHisAsn AlaLysThr LysProArg
1001 CACGTGCGTG GTGGTGGACG TGAGCCAGGA AGACCCCGAG GTCCAGTTCA ACTGGTACGT GGATGGCGTG GAGGTGCATA ATGCCAAGAC AAAGCCGCGG
       GluGluGlnPhe AsnSerThr TyrArgVal ValSerValLeu ThrValLeu HisGlnAsp TrpLeuAsnGly LysGluTyr LysCysLys ValSerAsnLys
1101 GAGGAGCAGT TCAACAGCAC GTACCGTGTG GTCAGCGTCC TCACCGTCCT GCACCAGGAC TGGCTGAACG GCAAGGAGTA CAAGTGCAAG GTCTCCAACA
       GlyLeuPro SerSerIle GluLysThrIle SerLysAla LysGlyPhe TyrProSerAsp IleAlaVal GluTrpGlu SerAsnGlyGln ProGluAsn AsnTyrLys
1201 AAGGCCTCCC GTCCTCCATC GAGAAAACCA TCTCCAAAGC CAAAGGGCAG CCCCGAGAGC CACAGGTGTA CACCCTGCCC CCATCCCAGG AGGAGATGAC
       LysAsnGln ValSerLeuThr CysLeuVal LysGlyPhe TyrProSerAsp IleAlaVal GluTrpGlu SerAsnGlyGln ProGluAsn AsnTyrLys
1301 CAAGAACCAG GTCAGCCTGA CCTGCCTGGT TAAAGGCTTC TACCCCAGCG ACATCGCCGT GGAGTGGGAG AGCAATGGGC AGCCGGAGAA CAACTACAAG
       ThrThrProPro ValLeuAsp SerAspGly SerPhePheLeu TyrSerArg LeuThrVal AspLysSerArg TrpGlnGluGly AsnValPhe SerCysSer
1401 ACCACGCCTC CCGTGCTGGA CTCCGACGGC TCCTTCTTCC TCTACAGCAG GCTAACCGTG GACAAGAGCA GGTGGCAGGA GGGGAATGTC TTCTCATGCT
                                                                                                           BmtI
                                                                                                           NheI
       ValMetHis GluAlaLeu HisAsnHisTyr ThrGlnLys SerLeuSer LeuSerProGly Lys***(SEQ ID NO:76)
1501 CCGTGATGCA TGAGGCTCTG CACAACCACT ACACACAGAA GAGCCTCTCC CTGTCTCCGG GTAAATGAGT GCTAGCTGGC CAGACATGAT AAGATACATT
1601 GATGAGTTTG GACAAACCAC AACTAGAATG CAGTGAAAAG AATGCTTTAT TTGTGAAATT TGTTGATGCTA TTGCTTTATT TGTAACCATT ATAAGCTGCA
1701 ATAAACAAGT TAACAACAAC AATTGCATTC ATTTATGTT TCAGGTTCAG GGGGAGGTGT GGGAAGGTTTT TTAAAGCAAG TAAAACCTCT ACAAATGTGG
```

```
                AseI
1801  TATGGAATTA ATTCTAAAAT ACAGCATAGC AAAACTTTAA CCTCCAAATC AAGCCTCTAC TTGAATCCTT TTCTGAGGGA TGAATAAGGC ATAGGCATCA
1901  GGGGCTGTTG CCAATGTGCA TTAGCTGTTT GCAGCCCTAC CTTCTTTCAT GGAGTTTAAG ATATCTTCAT GTTTGAACTA GCTCTTCATT
2001  TCTTTATGTT TTAAATGCAC TGACCTCCCA CATTCCCTTT TTAGTAAAAT ATTCAGAAAT CATCATTGCA ATCAAAATAA ATGTTTTTTA
2101  TTAGGCAGAA TCCAGATGCT CAAGGCCCTT CATAATATCC CCCAGTTTAG TAGTNGGACT AGGAACCTTT AATAGAAATT GGACAGCAAG
2201  AAAGCGAGCT TCTAGCTTAT CCTCAGTCCT GCTCCTCTGC CACAAAGTGC ACGCAGTTGC CGGCCGGGTC CGGCAGGGCG AACTCCCGCC CCCACGGCTG
2301  CTCGCCGATC TCGGTCATGG CCGGCCCGGA AAGTTCGTGG ACACGACCTC CGACCACTCG GCGTACAGCT CGTCCAGGCC GCGCACCCAC
2401  ACCCAGGCCA GGGTGTTGTC CGGCACCACC TGGTCCTGGA CCGGCTGAT GAACAGGGTC ACGTCGTCCC GGACCACACC GGCGAAGTCG TCCTCCACGA
2501  AGTCCCGGGA GAACCCGAGC CGTCGGTCC AGAACTCGAC CGTCCCGGCG ACGTCGCGCG CGGTGAGCAC CGGAACGGCA CTGGTCAACT TGGCCATGAT
                                                                                                     AseI
2601  GGCTCCTCCT GTCAGGAGAG GAAAGAGAAG AAGGTTAGTA AGTGAGTTGT ATTATACTAT TATGCCAATG ATTAATTGTC
2701  AAACTAGGGC TGCAGGGTTC ATAGTGCCAC TTTTCCTGCA CTGCCCCATC TCCTGCCCAC GCATAGACAG TCAGTGACTT ACCAAACTCA
2801  CAGGAGGAG AAGCAGAAG CTTGAGACAG ACCCGCGGGA CGCAGAGGAC GGGAGCCGAAG GTGGCTAGGG CGGCTTCTTT TATGGTGCGC CGGCCCTCGG
2901  AGGCAGGGCG CTCGGGGAGG AATCTGCGGT GCCTGCCTG GCCGTGCCTG GTTGGGGCCG ACCAATCCGG AGCACATAGG AGTCTCAGCC
3001  CCCGCCCCA AAGCAAGGGG AAGTCACGCG CCTGTAGGCG CAGGGTGTTG TGAAATGGGG GTTGGGGCCG TGACTAGTCA AAACAAACTC
3101  CCATTGACGT CAATGGGGTG TACGTAGATG TACTGCCAAG AATCCCGGTG AGTCAAACCG CTATCCACGC CATTGATGT ACTGCCAAAA CCGCATCATC ATGGTAATAG
3201  CGATGACTAA CTTGGCATAT GATACACTTG GGGGTCAAG ATGTACTGCC CCATAATGCC CATAATGCCC ATTGACGTC TTACCGTCAT TGACGTCAAT
3301  AGGGGCGTA GAACATACCT CATTATTGAC GTCAATGGGC GGGGTCGTT GGGGCGGTCA CCAGGCGGGC CAAGCGTCC AATGGAAAGT CCCTATTGGC
3401  GTTACTATGG AACATACCGT CATTATGAC CAAAAGGCCA AGGAACCGTA AAAAGGCCGC GTGCTGGCG CATTTCCATA AAGTTATGTA ACGCCTGCAG
3501  GTTAATTAAG AACATGTGAG CAAAAGGCCA AGGAACCGTA AAAAGGCCGC GTGCTGGCG CATTTCCATA GGCTCCGCCC CCTGACGAG
3601  CATCACAAAA ATCGACGCTC AAGTCAGAGG TGGCGAAACC CGACAGGACT ATAAAGATAC CAGGCGTTTC CCCCTGGAAG CTCCCTCGTG CGCTCTCCTG
3701  TTCCGACCCT GCCGCTTACC GGATACCTGT CCGCCTTCT CCCTTCGGGA AGCGTGGCGC TTTCTCATAG CTCACGCTGT AGGTATCTCA GTTCGGTGTA
3801  GGTCGTTCGC TCCAAGCTGG GCTGTGTGCA CGAACCCCC GTTCAGCCCG ACCGCTGCGC CTTATCCGGT AACTATCGTC TTGAGTCCAA CCCGGTAAGA
3901  CACGACTTAT CGCCACTGG TAACAGGGATTA TTAGCAGAGA ACCTTGCT GAAGACAGT ACCTTTCGAA AGAAGATCCT TTGATCTTTT CTACGGGGTG TGCACCTCAG GAACTGGTGG CCTAACTACC
4001  GCTACACTAG AAGAACAGTA TTTGGTATCT GCGCTCTGCT GAAGACAGT ACCTTCGGAA AGAAGATCCT TTGATCTTTT CTACGGGGTCGT GAGCTGATA
4101  TGGTAGCGGT GGTTTTTG TTTGCAAGCA GCAGATTACG CGCAGAAAAA AAGGATCTCA AGAAGATCCT TTGATCTTTT CTACGGGTCTG TGACGCTCAG
4201  TGGAACGAAA ACTCACGTTA AGGGATTTTG GTCATGAGCTA GTTAATTAAC ATTTAAATCA GGGGCCGCAA TAAAATATCT TTATTTTCAT TACATCTGTG
4301  TGTTGGTTT TTGTGTGAAT CGTAACTAAC ATACGCTCTC CATCAAAACA AAACGAAACA GCAAAATAGG CTGTCCCCAG TGCAAGTGCA
4401  GGTGCCAGAA CATTTCTCTA TCGAA     (SEQ ID NO:103)
```

IL2ss.CXCL13(3-87).hIgG4Fc sequence

```
   1  GGATCTGCGA TCGCTCCGGT GCCCGTCAGT GGGCAGAGCG CACATGCGCC GGGCAGTTGAA CGGGTGCCTA
 101  GAGAAGGTGG CGCGGGGTAA ACTGGGAAAG TGATGTCGTG GCCTGGCTCC GCCTTTTTCC CGAGGGTGGG GGAGAACCGT ATATAAGTGC AGTAGTCGCC
 201  GTGAAGGTTC TTTTCGCAA CGGGTTTGCC GCCAGAACAC AGCTGAAGCT TGGAGGGGCT TGCCAGCGCG CCTTCACGCGC CCGCCGCCCT ACCTGAGGCC
 301  GCCATCCACG CCGGTGAGT CCGGTTCTGC CGCTCCCGC CTGTGAACTG TCCTGAACTG CGTCGCCGT CTAGGTAAGT TTAAAGCTCA GTCGAGACC
 401  GGGCCTTTGT CCGGCCGCTC CTTGGCACCCT AGCCGCCTCT ACCTAGACTC AGCCGCCTCT CCTGAACCTG CCTTGCTCAA TCTACGTCTT TGTTCGTTT

IL-2 secretion signal
                                                                                         MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                            EcoRI                          ~~~~~ CXCL13 (3-87)
                            NarI
                            KasI
                            StoI
                            BbeI AlaLeuLeu ValThrAsnSer GluValTyr TyrThrSer LeuArgCysArg CysValGln GluSerSer ValPheIlePro ArgArgPhe
 601  TTGCACTAAG TCTTGCACTT GTCAGAGTA CGGAGTGTCTA TTACACAAGC TTGAGGTGTA GATGTGTCCA AGAGAGCTCA GTCTTTATCC CTAGAGCGTT
                                                                                         EcoRI IleAspArg IleGlnIleLeu ProArgGly AsnGlyCys ProArgLysLys ValProValPhe LysArgIleValProCys ProProSer
 701  CATTGATCGA ATTCAAATCT TGCCCCGTGG GAATGGTTGT CCAAGAAAAG AAATCATAGT CGGAAGCAAG AACAAGTCAA TGTGTGTGT GACCCTCAA
                                                                                         human IgG4 Fc (constant region)

AlaGlyTrpIle GlnArgMet MetGluVal LeuArgGlysArg SerSerSer ThrLeuPro ValProValPhe LysArglys IleProPro ProCysProSer
 801  GCTGGAATGGA TACAAAGAAT GATGGAAGTA TTGAGAAAAA GAAGTCTTC AACTCTACCA GTTCCAGTGT TTAAGAGAAA GATTCCCCCC CCATGCCCAT CysProAla ProGluPhe LeuGlyGlyPro SerValPhe LeuPheProProLys AspThrLeu MetIleSer ArgThrProGlu ValThrCysVal
 901  TGTCCAGCAGC ACCTGAGTTC CTGGGGGGAC CATCAGTCTT CCTGTTCCCC CCAAAACCCA AGGACACTCT CATGATCTCC CGGACCCCTG AGGTCACGTG ValValVal AspValSerGln GluAspPro GluValGln PheAsnTrpTyr ValAspGly ValGluVal HisAsnAlaLys ThrLysPro ArgGluGlu
1001  CGTGGTGGTG GACGTGAGCC AGGAAGACCC CGAGGTCCAG TTCAACTGGT ACGTGGACGG CGTGGAGGTG CATAATGCCA AGACAAAGCC GCGGGAGGAG GlnPheAsnSer ThrTyrArg ValValSer ValLeuThrVal LeuHisGln AspTrpLeu AsnGlyLysGlu TyrLysCys LysValSer AsnLysGlyLeu
1101  CAGTTCAACA GCACGTACCG TGTGGTCAGC GTCCTCACCG TCCTGCACCA GGACTGGCTG AACGGCAAGG AGTACAAGTG CAAGGTCTCC AACAAAGGCC ProSerSer IleGluLys ThrIleSerLys AlaLysGly GlnProArg GluProGlnVal TyrThrLeu ProProSer GlnGluGluMet ThrLysAsn
1201  TCCCGTCCTC CATCGAGAAA ACCATCTCCA AAGCCAAAGG GCAGCCCCGA GAGCCACAGG TGTACACCCT GCCCCCATCC CAGGAGGAGA TGACCAAGAA GlnValSer LeuThrCysLeu ValLysGly PheTyrPro SerAspIleAla ValGluTrp GluSerAsn GlyGlnProGlu AsnAsnTyr LysThrThr
1301  CCAGGTCAGC CTGACCTGC TGGTCAAAGG CTTCTACCCC AGCGACATCG CCGTGGAGTG GGAGAGCAAT GGGCAGCCGG AGAACAACTA CAAGACCACG ProProValleu AspSerAspGly SerPhePhe LeuTyrSer ArgLeuThr ValAspLys SerArgTrpGln GluGlyAsn ValPheSer CysSerValMet
1401  CCTCCCGTGC TGGACTCCGA CGGCTCCTTC TTCCTCTACA GCAGGCTAAC CGTGGACAAG AGCAGGTGGC AGGAGGGGAA TGTCTTCTCA TGCTCCGTGA
                                                                                         BmtI
                                                                                         NheI HisGluAla LeuHisAsn HisTyrThrGln LysSerLeu SerLeuSer ProGlyLys*** (SEQ ID NO:77)
1501  TGCATGAGGC TCTGCACAAC CACTACACAC AGAAGAGCCT CTCCCTGTCT CCGGGTAAAT GAGTGCTAGC TGGCCAGACA TGATAAGATA CATTGATGAG
1601  TTTGGACAAA CCACAACTAG AATGCAGTGA AAAAAATGCT TTATTTGTGA AATTTGTCAT GCTATTGCTT TATTTGTAAC CATTATAAGC TGCAATAAAC
1701  AAGTTAACAA CAACAATTGC ATTCATTTTA TGTTTCAGGT TCAGGGGGAG GTGTGGGAGG TTTTTTAAAG CAAGTAAAAC CTCTACAAAT GTGGTATGGA
      AseI
```

```
1801  ATTAATTCTA AAATACAGCA TAGCAAAACT TTAACCTCCA AATCAAGCCT CTACTTGAAT CCTTTTTCTGA GGGATGAATA AGGCATAGGC ATCAGGGGCT
1901  GTTGCCAATG TGCATTAGCT GTTGCCAGCC CCCACATTCC TCACCTTCTT TCATGGAGTT TAAGATATAG TGTATTTCC CAAGGTTTGA ACTAGCTCTT CATTTCTTTA
2001  TGTTTTAAAT GCACTGACCT CCCACATTCC CTTTTTAGTA AAATATTCAG GACTTAGGGA AAATAATTTA AATACATCAT TGCAATGAAA ATAAATGTTT TTTATTAGGC
2101  AGAATCCAGA TGCTCAAGGC CCTTCATAAT ATCCCCCAGT TTAGTAGTTG GACTTAGGGA ACAAAGAAAC CTTAATAGA AATTGGACAG CAAGAAGCG
2201  AGCTTCTAGC TTATCCTCAG TCCTCCTCCT CTGCCACAAA GTCGCACGAG TTGCCGCCCG GGTCGCGCCA GGCGAACTCC CGCCCCCACG GCTGCTCGCC
2301  GATCTCGGTC ATGGCCGGCC CGGAGGCGTC CGGAAGTTC GTGGACACGA CCTCCGACCA AGCTCGTCCA CTCGGCGTAC GGCCGCGCAC CCACCCCAG
2401  GCCAGGGTGT TGTCCGGCAC CACCTGGTCC TGATGAACAG GGTCACGTCG TCCCGGACCA CACCGGCGAA GTCGTCCTCC ACGAAGTCCC
2501  GGGAGAACCC GAGCCGGTCG GTCCAGAACT CGACCGCTCC GGCGACGTGA CGCACGGTGA GCACTGGTC AACTTGGCCA TGATGGCTCC
                                                                     AseI
2601  TCCTGTCAGG AGAGGAAAGA GAAGAAGGTT AGTACAATTG CTATAGTGAG TTGTATTATA CTATGCAGAT AATGATTAAT TGTCAAACTA
2701  GGGCTGCAGG GTTCATAGTG CCACTCTTTCC TGCCACTGCC CATCTCCCTGC CCACCCTTTC CCAGGCATAG ACAGTCAGTG CTTACCAAA CTCACAGGAG
2801  GGAGAAGGCA GAAGCTTGAG ACAGACCCGC GGGACCGCCG AACTGCGAGG GGCGTTGGCT AGGGCGGCTT CTTTATGGT GCGCCGGCCC TCGGAGGCAG
2901  GCCGCTCCGG GAGGCCTAGC GGCCAATCTG CGGTGGCAGG AGCGCGGGCC CCTGACCAAT CCGGAGCACA TAGGACTCC GCCCCCCGGC
3001  CCCAAAGCAA GGGGAAGTCA CGCGCCCTGTA GCGCCAGCGT GTTGTGAAAT GGGGGCTTGG GCCCTGACTA GTCAAAACAA ACTCCCATTG
3101  ACGTCAATGG GGTGGAGACT TGGAAATCCC CGTGAGTCAA ACCGCTATCC ATGTACTGCC AAAACCGCAT CATCATGGTA ATAGCGATGA
3201  CTAATACGTA GATGTACTGC CAAGTAGGAA AGTCCCATAA GGTCATGTAC TGGGCATAAT GCCAGGCGGG CCATTTACCG TCATTGACGT CAATAGGGGG
3301  CGTACTTGGC ATATGATACA CTTGATGTAC CGCCAAGTGG GCAGTTTACC GTAAATACTC CACCCATTGA CGTCAATGGA AAGTCCCTAT TGGCGTTACT
3401  ATGGAACAT ACGTCATTAT TGACGTCAAT GGGCGGGGT CGTTGGGCGG TCAGCCAGGC GGGCCATTTA CCGTAAGTTA TGTAACGCCT CGAGTTAAT
3501  TAAGAACATG GCTCAAGTCA GAGGTGGCGA GGCCAGAGAG CCGTAAAAGG GACTATAAGG CCGGAGCACG TTTCCCCCTG GAAGCTCCCT CGTGCGCTCT CCTGTTCCGA
3601  AAAAATCGAC GCTCAAGTCA GAGGTGGCGA AACCCGACAG GACTATAAAG ATACCAGGCG TTTCCCCCTG GAAGCTCCCT CGTGCGCTCT CCTGTTCCGA
3701  CCCTGCCGCT TACCGGATAC CTGTCCGCCT TTCTCCCTTC GGGAAGCGTG GCGCTTTCTC ATAGCTCACG CTGTAGGTAT GTCAGTTCGG TGTAGGTCGT
3801  TCGCTCCAAG CTGGGCTGTG TGCACGAACC CCCCGTTCAG CCCGACCGCT GCGCCTTATC CGGTAACTAT CGTCTTGAGT CCAACCCGGT AAGACACGAC
3901  TTATCGCCAC TGGCAGCAGC CACTGGTAAC AGGATTAGCA GAGCGAGGTA TGTAGGCGGT GCTACAGAGT TCTTGAAGTG GTGGCCTAAC TACGGCTACA
4001  CTAGAAGAAC AGTATTTGGT ATCTGCGCTC TGCTGAAGCC AGTTACCTTC GGAAAAAGAG TTGGTAGCTC TTGATCCGGC AAACAAACCA CCGCTGGTAG
4101  CGGTGGTTTT TTTGTTTGCA AGCAGCAGAT TACGCGCAGA AAAAAAGGAT CTCAAGAAGA TCCTTTGATC TTTTCTACGG GGTCTGACGC TCAGTGGAAC
4201  GAAAACTCAC GTTAAGGGAT TTTGCTCATG GCTAGTTAAT TAACATTTAA ATCAGCGGCC GCAATAAAAT TCATTTATTT TGTGTGTTGG
4301  TTTTTTGTGT GAATCGTAAC TAACATACGC TCTCCATCAA AACAAAACAA ACTAGCAAAA TAGGCTGTCC CCAGTGCAAG TGCAGGTGCC
4401  AGAACATTTC TCTATCGAA (SEQ ID NO: 104)
```

IL2ss.CXCL13(3-87).hIgG4Fc sequence [Alanine substitutions for removal of GAG binding sites – Lys & His]

```
   1  GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201  GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301  GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401  GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                       NarI
                                       KasI
                                       SfoI
                                       BbeI
                                       ~~~~~~~                                    IL-2 secretion signal
                                                                                  MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                            EcoRI
                            ~~~~~~~ CXCL13 (3-87)
        AlaLeuSer LeuAlaLeu ValThrAsnSer GluValTyr TyrThrSer LeuArgCysArg CysValGln GluSerSer ValPheIlePro ArgArgPhe
 601  TTGCACTAAG TCTTGCACTT GTCACGAATT CGGAGGTCTA TTACACAAGC TTGAGGTGTA GATGTGTCCA AGAGAGCTCA GTCTTTATCC CTAGACGCTT
           EcoRI
       IleAspAla IleGlnIleLeu ProArgGly AsnGlyCys ProArgLysGlu IleIleVal TrpAlaAla AsnAlaSerIle ValCysVal AspProGln
 701  CATTGATgcc ATTCAAATCT TGCCCCGTGG GAATGGTTGT CCAAGAAAAG AAATCATAGT CTGGgctgcg AACgccTCAA TTGTGTGTGT GGACCCTCAA
                                                                                                human IgG4 Fc
                                                                                              (constant region)
      AlaGluTrpIle GlnAlaMet MetGluVal LeuAlaAlaAla SerSerSer ThrLeuPro ValProValPhe AlaAlaAla IleProPro ProCysProSer
 801  GCTGAATGGA TACAAgccAT GATGGAAGTA TTGgctgcgg ctAGTTCTTC AACTCTACCA GTTCCAGTGT TTGgccgctgc gATTCCCCC CCATGCCCAT
        CysProAla ProGluPhe LeuGlyGlyPro SerValPhe LeuPhePro ProLysProLys AspThrLeu MetIleSer ArgThrProGlu ValThrCys
 901  CATGCCCAGC ACCTGAGTTC CTGGGGGGAC CATCAGTCTT CCTGTTCCCC CCAAAACCCA AGGACACTCT CATGATCTCC CGGACCCCTG AGGTCACGTG
       ValValVal AspValSerGln GluAspPro GluValGln PheAsnTrpTyr ValAspGly ValGluVal HisAsnAlaLys ThrLysPro ArgGluGlu
1001  CGTGGTGGTG GACGTGAGCC AGGAAGACCC CGAGGTCCAG TTCAACTGGT ACGTGGATGG CGTGGAGGTG CATAATGCCA AGACAAAGCC GCGGGAGGAG
      GlnPheAsnSer ThrTyrArg ValValSer ValLeuThrVal LeuHisGln AspTrpLeu AsnGlyLysGlu TyrLysCys LysValSer AsnLysGlyLeu
1101  CAGTTCAACA GCACGTACCG TGTGGTCAGC GTCCTCACCG TCCTGCACCA GGACTGGCTG AACGGCAAGG AGTACAAGTG CAAGGTCTCC AACAAAGGCC
        ProSerSer IleGluLys ThrIleSerLys AlaLysGly GlnProArg GluProGlnVal TyrThrLeu ProProSer GlnGluGluMet ThrLysAsn
1201  TCCCGTCCTC CATCGAGAAA ACCATCTCCA AAGCCAAAGG GCAGCCCCGA GAGCCACAGG TGTACACCCT GCCCCCATCC CAGGAGGAGA TGACCAAGAA
       GlnValSer LeuThrCysLeu ValLysGly PheTyrPro SerAspIleAla ValGluTrp GluSerAsn GlyGlnProGlu AsnAsnTyr LysThrThr
1301  CCAGGTCAGC CTGACCTGCC TGGTCAAAGG CTTCTACCCC AGCGACATCG CCGTGGAGTG GGAGAGCAAT GGGCAGCCGG AGAACAACTA CAAGACCACG
      ProProValLeu AspSerAsp GlySerPhe PheLeuTyrSer ArgLeuThr ValAspLys SerArgTrpGln GluGlyAsn ValPheSer CysSerValMet
1401  CCTCCCGTGC TGGACTCCGA CGGCTCCTTC TTCCTCTACA GCAGGCTAAC CGTGGACAAG AGCAGGTGGC AGGAGGGGAA TGTCTTCTCA TGCTCCGTGA
                                                                                    BmtI
                                                                                    NheI
        HisGluAla LeuHisAsn HisTyrThrGln LysSerLeu SerLeuSer ProGlyLys***(SEQ ID NO:78)
1501  TGCATGAGGC TCTGCACAAC CACTACACAC AGAAGAGCCT CTCCCTGTCT CCGGGTAAAT GAGTGCTAGC TGGCCAGACA TGATAAGATA CATTGATGAG
1601  TTTGGACAAA CCACAACTAG AATGCAGTGA AAAAAATGCT TTATTTGTGA AATTTGTGAT GCTATTGCTT TATTTGTAAC CATTATAAGC TGCAATAAAC
1701  AAGTTAACAA CAACAATTCC ATTCATTTTA TGTTTCAGGT TCAGGGGGAG GTGTGGGAGG TTTTTTAAAG CAAGTAAAAC CTCTACAAAT GTGGTATGGA
```

```
               AseI
1801   ATTAATTCTA AAATACAGCA TAGCAAAAACT TTAACCTCCA AATCAAGCCT CTACTTGAAT CCTTTTCTGA GGGATGAATA AGGCATAGGC ATCAGGGGCT
1901   GTTGCCAATG TGCATTAGCT GTTTGCAGCC TCACCTTCTT CTTTTTAGTA TCATGGAGTT AAATAATTCAG TAAGATATAG TGTATTTTCC CAAGGTTTGA ACTAGCTCTT CATTTCTTTA
2001   TGTTTTAAAT GCACTGACCT CCCACATTCC CTTTTTAGTA ATCCCCCAGT CTGCCACAAA GTGACACCGA TTAGTAGTTG GACTTAGGGA AATAATTCAG ACAAAGGAAC TGCAATGAAA ATAAATGTTT TTTATTAGGC
2101   AGAATCCAGA TGCTCAAGGC CCTTTCATAT ATCCCCCAGT CTGCCACAAA GTGACACCGA TTGCCGGCCG ACAAAGGAAC GGCGAACTCC CGCCCCCACG GCTGCTCGCC
2201   AGCTTCTAGC TTATCCTCAG TCCTGCTCCT CGGAGGCGTC CGGAAGTTC CGGACACGA TTGCCGGCCG CCTCCGACCA CTCGGCGTAC AGCTGTCCA GGCGCGCAC CCACACCAG
2301   GATCTCGGTC ATGGCGGCC CGGAAGGTC CGGACACGA CTCCGCGTC TGGACACGA TGAATGAACAG GGTCACGTCG TCCCGGACCA GTCCTCCTCC ACGAAGTCCC
2401   GCCAGGGTGT TGTCCGGCAC CACCTGGTCC GTCCAGAACT CGACCGGTCG CGGACGTCG GGCGACGTCG GCACCGGAAC GGCACTGGTC AACTTGGCCA TGATGGCTCC
2501   GGGAGAACCC GAGCCGGTCG GTCCAGAACT CGACCGGTCG CGGACGTCG GGCGACGTCG GCACCGGAAC GGCACTGGTC AACTTGGCCA TGATGGCTCC
                                                                                                        AseI
2601   TCCTGTCAGG AGAGGAAAGA GAAGAAGGTT AGTACAATTG CTATAGTGAG TTGTATTATA CTATGCAGAT ATACTATTAAT TGTCAAACTA
2701   GGGCTGCAGG GTTCATAGTG CCACTTTTCC TGCACTGCCC CATCTCCTGC CCACCCTTTC CCAGGCATAG ACAGTCAGTG ACTTACCAAA CTCACAGGAG
2801   GGAGAAGGCA GAAGCTTAGG ACAGACCCGC GGGACCGCCG AACTGCGAGG GACTGGCTT AGGGGCCTT AGGGGCCT GGGGGCTT AGGGGCGCTT GCGCCGGCCC TCGGAGGCAG
2901   GGCGCTCGGG GAGGCTTAGC ACAGACCCGC CGGTGGCAGG GCCCAGCCT CCTGACCAAT CCGGAGCACA TAGGAGTCTC AGCCCCCGC
3001   CCCAAAGCAA GGGGAAGTCA CCGGCCTGTA GCGCCAGCCT GTTCTGAAAT CGGGCTTGG GCCCTGACTA GTCAAAACAA ACTCCCATTG
3101   ACGTCAATGG GGTGGAGACT TGGAAATCCC CGTGAGTCAA ACCGCTATCC ATGTACTGCC AAAACCGCAT CATCATGGTA ATAGCGATGA
3201   CTAATACGTA GATGTACTGC CAAGTAGGAA AGTCCCATAA GGTCATGTAC TGGGCATAAT GCCAGGCGGG CCATTTACCG TCATTGACGT CAATAGGGGG
3301   CGTACTTGGC ATATGATACA CTTGATGTAC TGCCAAGTGG GCAGTTTACC GTAAATACTC CACCCATTGA CGTCAATGGA AAGTCCCTAT TGGCGTTACT
3401   ATGGGAACAT ACGTCATTAT TGACGTCAAT GGGCGGGGGT CGTTGGGCGG TCAGCCAGGC GGGCCATTTA CCGTTTTTC GCCCCCCTGA TGTAACGCCT GCAGTTAAT
3501   TAAGAACATG TGAGCAAAAG GCCAGCAAAA GGCCAGGAAC CGTAAAAAGG GACTATAAAG ATACCAGGCG TTTCCCCCTG GAAGCTCCCT CGTGCGCTCT CGAGCATCAC CCTGTTCCGA
3601   AAAAATCGAC GCTCAAGTCA GAGGTGGCGA AACCCGACAG TTTCTCCCTT CGGGAAGCGT GGCGCTTTCT CATAGCTCACG CTGTAGGTAT CTCAGTTCGG TGTAGGTCGT
3701   CCCTGCCGCT TACCGGATAC CTGTCCGCCT TTCTCCCTTC GGGAAGCGTG CCGACCGCT CCCGACCCGCT CCCGACCGCT ATAGCTCACG GCGCCTTATC CGGTAACTAT CGTCTTGAGT CCAACCCGGT AAGACACGAC
3801   TTATCGCCAC TGGCAGCAGC CACTGGTAAC AGGATTAGCA GAGCGAGGTA TGTAGGCGGT GCTACAGAGT TCTTGAAGTG GTGGCCTAAC TACGGCTACA
3901   CTAGAAGAAC AGTATTTGGT ATCTGCGCTC TGCTGAAGCC AGTTACCTTC GCAAAAAAGAG TTGGTAGCTC TTGATCCGGC AAACAAACCA CCGCTGGTAG
4101   CGGTGGTTTT TTTGTTTGCA AGCAGCAGAT TACGCGCAGA AAAAAAGGAT CTCAAGAAGA TCCTTTGATC TTTTCTACGG GGTCTGACGC TCAGTGGAAC
4201   GAAAACTCAC GTTAAGGGAT TTTGGTCATG AGATTATCAA AAAGGATCTT CACCTAGATC CTTTTAAATT AAAAATGAAG TTTTAAATCA ATCTAAAGTA TATATGAGTA AACTTGGTCT GACAGTTACC
4301   TTTTTTGTGT GAATCGTAAC TAACATACGC TCTCCATCAA AACAAAACGA ACAAAAACAA ACTAGCAAAA ACTACACAAA TCATTACATC CCAGTGCAAG TGCAGTGCC
4401   AGAACATTTC TCTATCGAA (SEQ ID NO:105)
```

*FIG. 9E (CONT)*

↯ indicate potential sites for pegylation of CXCL11.

FIG. 12

CCL1      NP_002972      SEQ ID NO:1
mqiittalvc lllagmwped vdsksmqvpf srccfsfaeq eiplrailcy rntssicsne
glifklkrgk eacaldtvgw vqrhrkmlrh cpskrk

CCL2      NP_002973      SEQ ID NO:2
mkvsaallcl lliaatfipq glaqpdaina pvtccynftn rkisvqrlas yrritsskcp
keavifktiv akeicadpkq kwvqdsmdhl dkqtqtpkt

CCL3      NP_002974      SEQ ID NO:3
mqvstaalav llctmalcnq fsaslaadtp taccfsytsr qipqnfiady fetssqcskp
gvifltkrsr qvcadpseew vqkyvsdlel sa

CCL4      NP_002975      SEQ ID NO:4
mklcvtvlsl lmlvaafcsp alsapmgsdp ptaccfsyta rklprnfvvd yyetsslcsq
pavvfqtkrs kqvcadpses wvqeyvydle ln

CCL4L1      NP_001001435      SEQ ID NO:5
mklcvtvlsl lvlvaafcsl alsapmgsdp ptaccfsyta rklprnfvvd yyetsslcsq
pavvfqtkrg kqvcadpses wvqeyvydle ln

CCL5      NP_002976      SEQ ID NO:6
mkvsaaalav iliatalcap asaspyssdt tpccfayiar plprahikey fytsgkcsnp
avvfvtrknr qvcanpekkw vreyinslem s

CCL7      NP_006264      SEQ ID NO:7
mkasaallcl lltaaafspq glaqpvgint sttccyrfin kkipkqrles yrrttsshcp
reavifktkl dkeicadptq kwvqdfmkhl dkktqtpkl

CCL8      NP_005614      SEQ ID NO:8
mkvsaallcl llmaatfspq glaqpdsvsi pitccfnvin rkipiqrles ytritniqcp
keavifktkr gkevcadpke rwvrdsmkhl dqifqnlkp

CCL11      CAG33702      SEQ ID NO:9
mkvsaallwl lliaaafspq glagpasvpt tccfnlanrk iplqrlesyr ritsgkcpqk
avifktklak dicadpkkkw vqdsmkyldq ksptpkp

CCL13      NP_005399      SEQ ID NO:10
mkvsavllcl llmtaafnpq glaqpdalnv pstccftfss kkislqrlks yvittsrcpq
kavifrtklg keicadpkek wvqnymkhlg rkahtlkt

CCL14-1      NP_116739      SEQ ID NO:11
mkisvaaipf fllitialgt ktesssrgpy hpseccftyt tykiprqrim dyyetnsqcs
kpgivfitkr ghsvctnpsd kwvqdyikdm ken

CCL14-2      NP_116738      SEQ ID NO:12
mkisvaaipf fllitialgt ktesssqtgg kpkvvkiqlk lvggpyhpse ccftyttyki
prqrimdyye tnsqcskpgi vfitkrghsv ctnpsdkwvq dyikdmken

FIG. 12 (CONT)

CCL15  NP_116741  SEQ ID NO:13
mkvsvaalsc lmlvavlgsq aqfindaete lmmsklplen pvvlnsfhfa adcctsyisq
sipcslmksy fetssecskp gvifltkkgr qvcakpsgpg vqdcmkklkp ysi

CCL16  NP_004581  SEQ ID NO:14
mkvseaalsl lvliiliitsa srsqpkvpew vntpstcclk yyekvlprrl vvgyrkalnc
hlpaiifvtk rnrevctnpn ddwvqeyikd pnlpllptrn lstvkiitak ngqpqllnsq

CCL17  NP_002978  SEQ ID NO:15
maplkmlalv tlllgaslqh ihaargtnvg reccleyfkg aiplrklktw yqtsedcsrd
aivfvtvqgr aicsdpnnkr vknavkylqs lers

CCL18  NP_002979  SEQ ID NO:16
mkglaaailv lvctmalcsc aqvgtnkelc clvytswqip qkfivdyset spqcpkpgvi
lltkrgrqic adpnkkwvqk yisdlklna

CCL19  NP_006265  SEQ ID NO:17
mallialsll vlwtspaptl sgtndaedcc lsvtqkpipg yivrnfhyll ikdgcrvpav
vfttlrgrql cappdqpwve riiqrlqrts akmkrrss

CCL20-1  NP_004582  SEQ ID NO:18
mcctkslllla almsvlllhl cgeseaasnf dcclgytdri lhpkfivgft rqlanegcdi
naiifhtkkk lsvcanpkqt wvkyivrlls kkvknm

CCL20-2  NP_001123518  SEQ ID NO:19
mcctkslllla almsvlllhl cgeseasnfd cclgytdril hpkfivgftr qlanegcdin
aiifhtkkkl svcanpkqtw vkyivrllsk kvknm

CCL21  NP_002980  SEQ ID NO:20
maqslalsll ilvlafgipr tqgsdggaqd cclkysqrki pakvvrsyrk qepslgcsip
ailflprkrs qaelcadpke lwvqqlmqhl dktpspqkpa qgcrkdrgas ktgkkgkgsk
gckrtersqt pkgp

CCL22  NP_002981  SEQ ID NO:21
mdrlqtallv vlvllavalq ateagpygan medsvccrdy vryrlplrvv khfywtsdsc
prpgvvlltf rdkeicadpr vpwvkmilnk lsq

CCL23-1  NP_665905  SEQ ID NO:22
mkvsvaalsc lmlvtalgsq arvtkdaete fmmsklplen pvlldrfhat sadccisytp
rsipcslles yfetnsecsk pgvifltkkg rrfcanpsdk qvqvcvrmik ldtriktrkn

CCL23-2  NP_005055  SEQ ID NO:23
mkvsvaalsc lmlvtalgsq arvtkdaete fmmsklplen pvlldmlwrr kigpqmtlsh
aagfhatsad ccisytprsi pcsllesyfe tnsecskpgv ifltkkgrrf canpsdkqvq
vcvrmlkldt riktrkn

CCL24  NP_002982  SEQ ID NO:24
maglmtivts llflgvcahh iiptgsvvip spccmffvsk ripenrvvsy qlssrstclk
agvifttkkg qqfcgdpkqe wvqrymknld akqkkaspra ravavkgpvq rypgnqttc

FIG. 12 (CONT)

CCL25-1    NP_005615          SEQ ID NO:25
mnlwllaclv agflgawapa vhtqgvfedc clayhypigw avlrrawtyr iqevsgscnl
paaifylpkr hrkvcgnpks revqramkll darnkvfakl hhntqtfqag phavkklssg
nsklssskfs npissskrnv sllisansgl

CCL25-2    NP_683686          SEQ ID NO:26
mnlwllaclv agflgawapa vhtqgvfedc clayhypigw avlrrawtyr iqevsgscnl
paairpscck evefwklqvi ivqv

CCL25-3    EAW68951           SEQ ID NO:27
mnlwllaclv agflgawapa vhtqgvfedc clayhypigw avlrrawtyr iqevsgscnl
paairpscck evefwklqvi iiqv

CCL26      NP_006063          SEQ ID NO:28
mmglslasav llasllslhl gtatrgsdis ktccfqyshk plpwtwvrsy eftsnscsqr
avifttkrgk kvcthprkkw vqkyisllkt pkql

CCL27      NP_006655          SEQ ID NO:29
mkgpptfcsl llisillspd ptaafilpps tacctqlyrk plsdkllrkv iqvelqeadg
dchlqafvlh laqrsicihp qnpslsqwfe hqerklhgtl pklnfgmlrk mg

CCL28      NP_683513          SEQ ID NO:30
mqqrqlaiva lavcaalhas eailpiassc ctevshhisr rllervnmcr iqradgdcdl
aavilhvkrr ricvsphnht vkqwmkvqaa kkngkgnvch rkkhhgkrns nrahqgkhet
yghktpy

CXCL1      NP_001502          SEQ ID NO:31
maraalsaap snprilrval lllllvaagr raagasvate lrcqclqtlq gihpkniqsv
nvkspgphca qteviatlkn grkacinpas pivkkiiekm lnsdksn

CXCL2      NP_002080          SEQ ID NO:32
maratlsaap snprilrval lllllvaasr raagaplate lrcqclqtlq gihlkniqsv
kvkspgphca qteviatlkn gqkacinpas pmvkkiiekm lkngksn

CXCL3      NP_002081          SEQ ID NO:33
mahatlsaap snprilrval lllllvaasr raagasvvte lrcqclqtlq gihlkniqsv
nvrspgphca qteviatlkn gkkacinpas pmvqkiieki lnkgstn

CXCL4      NP_002610          SEQ ID NO:34
mssaagfcas rpgllflqll llplvvafas aeaeedgdlq clcvkttsqv rprhitslev
ikagphcpta qliatlkngr kicldiqapl ykkiikklle s

CXCL5      NP_002985          SEQ ID NO:35
msllssraar vpgpssslca llvllillltq pgpiasagpa aavlrelrcv clqttqgvhp
kmisnlqvfa igpqcskvev vaslkngkei cldpeapflk kviqkildgg nken

CXCL6      NP_002984          SEQ ID NO:36
mslpssraar vpgpsgslca llalllilltp pgplasagpv savltelrct clrvtlrvnp
ktigklqvfp agpqcskvev vaslkngkqv cldpeapflk kviqkildsg nkkn

FIG. 12 (CONT)

CXCL7    NP_002695    SEQ ID NO:37
mslrldttps cnsarplhal qvllllslll talasstkgq tkrnlakgke esldsdlyae
lrcmciktts gihpkniqsl evigkgthcn qveviatlkd grkicldpda prikkivqkk
lagdesad

CXCL8    NP_000575    SEQ ID NO:38
mtsklavall aaflisaalc egavlprsak elrcqcikty skpfhpkfik elrviesgph
canteiivkl sdgrelcldp kenwvqrvve kflkraens

CXCL9    NP_002407    SEQ ID NO:39
mkksgvlfll giillvligv qgtpvvrkgr cscistnqgt ihlqslkdlk qfapspscek
ieiiatlkng vqtclnpdsa dvkelikkwe kqvsqkkkqk ngkkhqkkkv lkvrksqrsr
qkktt

CXCL10    NP_001556    SEQ ID NO:40
mnqtailicc lifltlsgiq gvplsrtvrc tcisisnqpv nprsleklei ipasqfcprv
eiiatmkkkg ekrcinpesk aiknllkavs kerskrsp

CXCL11    NP_005400    SEQ ID NO:41
msvkgmaial avilcatvvq gfpmfkrgrc lcigpqvkav kvadiekasi mypsnncdki
eviitlkenk gqrcinpksk qarliikkve rknf

CXCL12    NP_000600    SEQ ID NO:42
mnakvvvvlv lvltalclsd gkpvslsyrc pcrffeshva ranvkhlkil ntpncalqiv
arlknnnrqv cidpklkwiq eylekalnkr fkm

CXCL13    NP_006410    SEQ ID NO:43
mkfistslll mllvsslspv qgvlevyyts lrcrcvqess vfiprrfidr iqilprgngc
prkeiivwkk nksivcvdpq aewiqrmmev lrkrssstlp vpvfkrkip

CXCL16    NP_071342    SEQ ID NO:44
msgsqsevap spqsprspem grdlrpgsrv llllllllv yltqpgngne gsvtgscycg
krissdspps vqfmnrlrkh lrayhrclyy trfqllswsv cggnkdpwvq elmscldlke
cqhaysgiva hqkhllptsp pisqasegas sdihtpaqml lstlqstqrp tlpvgslssd
keltrpnett ihtaghslaa gpeagenqkq peknagptar tsatvplcl lalifiltaa
lsyvlckrrr gqspqsspdl pvhyipvapd snt

XCL1    AAH69817    SEQ ID NO:45
mrllilallg icsltayive gvgsevsdkr tcvslttqrl pvsriktyti tegslravif
itkrglkvca dpqatwvrdv vrsmdrksnt rnnmiqtkpt gtqqstntav tltg

XCL2    NP_003166    SEQ ID NO:46
mrllilallg icsltayive gvgsevshrr tcvslttqrl pvsriktyti tegslravif
itkrglkvca dpqatwvrdv vrsmdrksnt rnnmiqtkpt gtqqstntav tltg

FIG. 12 (CONT)

CX3CL1        NP_002987           SEQ ID NO:47
mapislswll  rlatfchltv  llagqhhgvt  kcnitcskmt  skipvallih  yqqnqascgk
raiiletrqh  rlfcadpkeq  wvkdamqhld  rqaaaltrng  gtfekqigev  kprttpaagg
mdesvvlepe  atgessslep  tpssqeaqra  lgtspelptg  vtgssgtrlp  ptpkaqdggp
vgtelfrvpp  vstaatwqss  aphqpgpslw  aeaktseaps  tqdpstqast  asspapeena
pseggqrvwgq  gqsprpensl  ereemgpvpa  htdafqdwgp  gsmahvsvvp  vssegtpsre
pvasgswtpk  aeepihatmd  pqrlgvlitp  vpdaqaatrr  qavgllaflg  llfclgvamf
tyqslqgcpr  kmagemaegl  ryiprscgsn  syvlvpv

IgG1Fc       CBX54381.1           SEQ ID NO:48
sepkscdkth  tcppcpapel  lggpsvflfp  pkpkdtlmis  rtpevtcvvv  dvshedpevk
fnwyvdgvev  hnaktkpree  qynstyrvvs  vltvlhqdwl  ngkeykckvs  nkalpapiek
tiskakgqpr  epqvytlpps  rdeltknqvs  ltclvkgfyp  sdiavewesn  gqpennyktt
ppvldsdgsf  flyskltvdk  srwqqgnvfs  csvmhealhn  hytqkslsls  pgk

IgG2Fc       CBX54382.1           SEQ ID NO:49
erkccvecpp  cpappvagps  vflfppkpkd  tlmisrtpev  tcvvvdvshe  dpevqfnwyv
dgvevhnakt  kpreeqfnst  frvvsvltvv  hqdwlngkey  kckvsnkglp  apiektiskt
kgqprepqvy  tlppsreemt  knqvsltclv  kgfypsdiav  ewesngqpen  nykttppmld
sdgsfflysk  ltvdksrwqq  gnvfscsvmh  ealhnhytqk  slslspgk

IgG3Fc       CBX54383.1           SEQ ID NO:50
elktplgdtt  htcprcpepk  scdtpppcpr  cpepkscdtp  ppcprcpepk  scdtpppcpr
cpapellggp  svflfppkpk  dtlmisrtpe  vtcvvvdvsh  edpevqfkwy  vdgvevhnak
tkpreeqfns  tfrvvsvltv  lhqdwlngke  ykckvsnkal  papiektisk  tkgqprepqv
ytlppsreem  tknqvsltcl  vkgfypsdia  vewessgqpe  nnynttppml  dsdgsfflys
kltvdksrwq  qgnifscsvm  healhnrftq  kslslspgk

IgG4Fc       CBX54384.1           SEQ ID NO:51
eskygppcps  cpapeflggp  svflfppkpk  dtlmisrtpe  vtcvvvdvsq  edpevqfnwy
vdgvevhnak  tkpreeqfns  tyrvvsvltv  vhqdwlngke  ykckvsnkgl  pssiektisk
akgqprepqv  ytlppsqeem  tknqvsltcl  vkgfypsdia  vewesngqpe  nnykttppvl
dsdgsfflys  rltvdksrwq  egnvfscsvm  healhnhytq  kslslslgk

```
SEQUENCE LISTING

<160> NUMBER OF SEQ ID NOS: 106

<210> SEQ ID NO 1
<211> LENGTH: 96
<212> TYPE: PRT
<213> ORGANISM: Homo sapiens

<400> SEQUENCE: 1

Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
            20                  25                  30

Cys Cys Phe Ser Phe Ala Glu Gln Glu Ile Pro Leu Arg Ala Ile Leu
        35                  40                  45

Cys Tyr Arg Asn Thr Ser Ser Ile Cys Ser Asn Glu Gly Leu Ile Phe
    50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95

<210> SEQ ID NO 2
<211> LENGTH: 99
<212> TYPE: PRT
<213> ORGANISM: Homo sapiens

<400> SEQUENCE: 2

Met Lys Val Ser Ala Ala Leu Leu Cys Leu Leu Leu Ile Ala Ala Thr
```

```
1               5                   10                  15
Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr
```

<210> SEQ ID NO 3
<211> LENGTH: 92
<212> TYPE: PRT
<213> ORGANISM: Homo sapiens

<400> SEQUENCE: 3

```
Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
            35                  40                  45

Asp Tyr Phe Glu Thr Ser Ser Gln Cys Ser Lys Pro Gly Val Ile Phe
        50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90
```

<210> SEQ ID NO 4
<211> LENGTH: 92
<212> TYPE: PRT
<213> ORGANISM: Homo sapiens

<400> SEQUENCE: 4

```
Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
            35                  40                  45

Val Asp Tyr Tyr Glu Thr Ser Ser Leu Cys Ser Gln Pro Ala Val Val
        50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90
```

<210> SEQ ID NO 5
<211> LENGTH: 92
<212> TYPE: PRT
<213> ORGANISM: Homo sapiens

<400> SEQUENCE: 5

-continued

Met Lys Leu Cys Val Thr Val Leu Ser Leu Val Leu Val Ala Ala
1               5                   10                  15

Phe Cys Ser Leu Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
            35                  40                  45

Val Asp Tyr Tyr Glu Thr Ser Ser Leu Cys Ser Gln Pro Ala Val Val
    50                  55                  60

Phe Gln Thr Lys Arg Gly Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO 6
<211> LENGTH: 91
<212> TYPE: PRT
<213> ORGANISM: Homo sapiens

<400> SEQUENCE: 6

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 7
<211> LENGTH: 99
<212> TYPE: PRT
<213> ORGANISM: Homo sapiens

<400> SEQUENCE: 7

Met Lys Ala Ser Ala Ala Leu Leu Cys Leu Leu Leu Thr Ala Ala Ala
1               5                   10                  15

Phe Ser Pro Gln Gly Leu Ala Gln Pro Val Gly Ile Asn Thr Ser Thr
                20                  25                  30

Thr Cys Cys Tyr Arg Phe Ile Asn Lys Lys Ile Pro Lys Gln Arg Leu
            35                  40                  45

Glu Ser Tyr Arg Arg Thr Thr Ser Ser His Cys Pro Arg Glu Ala Val
    50                  55                  60

Ile Phe Lys Thr Lys Leu Asp Lys Glu Ile Cys Ala Asp Pro Thr Gln
65                  70                  75                  80

Lys Trp Val Gln Asp Phe Met Lys His Leu Asp Lys Lys Thr Gln Thr
                85                  90                  95

Pro Lys Leu

<210> SEQ ID NO 8
<211> LENGTH: 99
<212> TYPE: PRT
<213> ORGANISM: Homo sapiens

<400> SEQUENCE: 8

Met Lys Val Ser Ala Leu Leu Cys Leu Leu Met Ala Ala Thr
1               5                   10                  15

Phe Ser Pro Gln Gly Leu Ala Gln Pro Asp Ser Val Ser Ile Pro Ile
                20                  25                  30

Thr Cys Cys Phe Asn Val Ile Asn Arg Lys Ile Pro Ile Gln Arg Leu
            35                  40                  45

Glu Ser Tyr Thr Arg Ile Thr Asn Ile Gln Cys Pro Lys Glu Ala Val
    50                  55                  60

Ile Phe Lys Thr Lys Arg Gly Lys Glu Val Cys Ala Asp Pro Lys Glu
65              70                  75                  80

Arg Trp Val Arg Asp Ser Met Lys His Leu Asp Gln Ile Phe Gln Asn
                85                  90                  95

Leu Lys Pro

<210> SEQ ID NO 9
<211> LENGTH: 97
<212> TYPE: PRT
<213> ORGANISM: Homo sapiens

<400> SEQUENCE: 9

Met Lys Val Ser Ala Ala Leu Leu Trp Leu Leu Ile Ala Ala Ala
1               5                   10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
            35                  40                  45

Tyr Arg Arg Ile Thr Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
65              70                  75                  80

Val Gln Asp Ser Met Lys Tyr Leu Asp Gln Lys Ser Pro Thr Pro Lys
                85                  90                  95

Pro

<210> SEQ ID NO 10
<211> LENGTH: 98
<212> TYPE: PRT
<213> ORGANISM: Homo sapiens

<400> SEQUENCE: 10

Met Lys Val Ser Ala Val Leu Leu Cys Leu Leu Leu Met Thr Ala Ala
1               5                   10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
            35                  40                  45

Lys Ser Tyr Val Ile Thr Thr Ser Arg Cys Pro Gln Lys Ala Val Ile
    50                  55                  60

Phe Arg Thr Lys Leu Gly Lys Glu Ile Cys Ala Asp Pro Lys Glu Lys
65              70                  75                  80

Trp Val Gln Asn Tyr Met Lys His Leu Gly Arg Lys Ala His Thr Leu
                85                  90                  95

Lys Thr

<210> SEQ ID NO 11

<211> LENGTH: 93
<212> TYPE: PRT
<213> ORGANISM: Homo sapiens

<400> SEQUENCE: 11

Met Lys Ile Ser Val Ala Ala Ile Pro Phe Phe Leu Leu Ile Thr Ile
1               5                   10                  15

Ala Leu Gly Thr Lys Thr Glu Ser Ser Arg Gly Pro Tyr His Pro
            20                  25                  30

Ser Glu Cys Cys Phe Thr Tyr Thr Thr Tyr Lys Ile Pro Arg Gln Arg
            35                  40                  45

Ile Met Asp Tyr Tyr Glu Thr Asn Ser Gln Cys Ser Lys Pro Gly Ile
50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
            85                  90

<210> SEQ ID NO 12
<211> LENGTH: 109
<212> TYPE: PRT
<213> ORGANISM: Homo sapiens

<400> SEQUENCE: 12

Met Lys Ile Ser Val Ala Ala Ile Pro Phe Phe Leu Leu Ile Thr Ile
1               5                   10                  15

Ala Leu Gly Thr Lys Thr Glu Ser Ser Gln Thr Gly Gly Lys Pro
            20                  25                  30

Lys Val Val Lys Ile Gln Leu Lys Leu Val Gly Gly Pro Tyr His Pro
        35                  40                  45

Ser Glu Cys Cys Phe Thr Tyr Thr Thr Tyr Lys Ile Pro Arg Gln Arg
50                  55                  60

Ile Met Asp Tyr Tyr Glu Thr Asn Ser Gln Cys Ser Lys Pro Gly Ile
65                  70                  75                  80

Val Phe Ile Thr Lys Arg Gly His Ser Val Cys Thr Asn Pro Ser Asp
                85                  90                  95

Lys Trp Val Gln Asp Tyr Ile Lys Asp Met Lys Glu Asn
            100                 105

<210> SEQ ID NO 13
<211> LENGTH: 113
<212> TYPE: PRT
<213> ORGANISM: Homo sapiens

<400> SEQUENCE: 13

Met Lys Val Ser Val Ala Ala Leu Ser Cys Leu Met Leu Val Ala Val
1               5                   10                  15

Leu Gly Ser Gln Ala Gln Phe Ile Asn Asp Ala Glu Thr Glu Leu Met
            20                  25                  30

Met Ser Lys Leu Pro Leu Glu Asn Pro Val Val Leu Asn Ser Phe His
            35                  40                  45

Phe Ala Ala Asp Cys Cys Thr Ser Tyr Ile Ser Gln Ser Ile Pro Cys
50                  55                  60

Ser Leu Met Lys Ser Tyr Phe Glu Thr Ser Ser Glu Cys Ser Lys Pro
65                  70                  75                  80

Gly Val Ile Phe Leu Thr Lys Lys Gly Arg Gln Val Cys Ala Lys Pro
            85                  90                  95

Ser Gly Pro Gly Val Gln Asp Cys Met Lys Lys Leu Lys Pro Tyr Ser
            100                 105                 110

Ile

<210> SEQ ID NO 14
<211> LENGTH: 120
<212> TYPE: PRT
<213> ORGANISM: Homo sapiens

<400> SEQUENCE: 14

Met Lys Val Ser Glu Ala Ala Leu Ser Leu Leu Val Leu Ile Leu Ile
1               5                   10                  15

Ile Thr Ser Ala Ser Arg Ser Gln Pro Lys Val Pro Glu Trp Val Asn
            20                  25                  30

Thr Pro Ser Thr Cys Cys Leu Lys Tyr Tyr Glu Lys Val Leu Pro Arg
        35                  40                  45

Arg Leu Val Val Gly Tyr Arg Lys Ala Leu Asn Cys His Leu Pro Ala
    50                  55                  60

Ile Ile Phe Val Thr Lys Arg Asn Arg Glu Val Cys Thr Asn Pro Asn
65                  70                  75                  80

Asp Asp Trp Val Gln Glu Tyr Ile Lys Asp Pro Asn Leu Pro Leu Leu
                85                  90                  95

Pro Thr Arg Asn Leu Ser Thr Val Lys Ile Ile Thr Ala Lys Asn Gly
            100                 105                 110

Gln Pro Gln Leu Leu Asn Ser Gln
        115                 120

<210> SEQ ID NO 15
<211> LENGTH: 94
<212> TYPE: PRT
<213> ORGANISM: Homo sapiens

<400> SEQUENCE: 15

Met Ala Pro Leu Lys Met Leu Ala Leu Val Thr Leu Leu Leu Gly Ala
1               5                   10                  15

Ser Leu Gln His Ile His Ala Ala Arg Gly Thr Asn Val Gly Arg Glu
            20                  25                  30

Cys Cys Leu Glu Tyr Phe Lys Gly Ala Ile Pro Leu Arg Lys Leu Lys
        35                  40                  45

Thr Trp Tyr Gln Thr Ser Glu Asp Cys Ser Arg Asp Ala Ile Val Phe
    50                  55                  60

Val Thr Val Gln Gly Arg Ala Ile Cys Ser Asp Pro Asn Asn Lys Arg
65                  70                  75                  80

Val Lys Asn Ala Val Lys Tyr Leu Gln Ser Leu Glu Arg Ser
                85                  90

<210> SEQ ID NO 16
<211> LENGTH: 89
<212> TYPE: PRT
<213> ORGANISM: Homo sapiens

<400> SEQUENCE: 16

Met Lys Gly Leu Ala Ala Ala Leu Leu Val Leu Val Cys Thr Met Ala
1               5                   10                  15

Leu Cys Ser Cys Ala Gln Val Gly Thr Asn Lys Glu Leu Cys Cys Leu
            20                  25                  30

Val Tyr Thr Ser Trp Gln Ile Pro Gln Lys Phe Ile Val Asp Tyr Ser
        35                  40                  45

```
Glu Thr Ser Pro Gln Cys Pro Lys Pro Gly Val Ile Leu Leu Thr Lys
    50                  55                  60

Arg Gly Arg Gln Ile Cys Ala Asp Pro Asn Lys Trp Val Gln Lys
65                  70                  75                  80

Tyr Ile Ser Asp Leu Lys Leu Asn Ala
                85

<210> SEQ ID NO 17
<211> LENGTH: 98
<212> TYPE: PRT
<213> ORGANISM: Homo sapiens

<400> SEQUENCE: 17

Met Ala Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
                20                  25                  30

Val Thr Gln Lys Pro Ile Pro Gly Tyr Ile Val Arg Asn Phe His Tyr
                35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser

<210> SEQ ID NO 18
<211> LENGTH: 96
<212> TYPE: PRT
<213> ORGANISM: Homo sapiens

<400> SEQUENCE: 18

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
                20                  25                  30

Cys Leu Gly Tyr Thr Asp Arg Ile Leu His Pro Lys Phe Ile Val Gly
                35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 19
<211> LENGTH: 95
<212> TYPE: PRT
<213> ORGANISM: Homo sapiens

<400> SEQUENCE: 19

Met Cys Cys Thr Lys Ser Leu Leu Leu Ala Ala Leu Met Ser Val Leu
1               5                   10                  15

Leu Leu His Leu Cys Gly Glu Ser Glu Ala Ser Asn Phe Asp Cys Cys
                20                  25                  30

Leu Gly Tyr Thr Asp Arg Ile Leu His Pro Lys Phe Ile Val Gly Phe
```

```
                    35                  40                  45
Thr Arg Gln Leu Ala Asn Glu Gly Cys Asp Ile Asn Ala Ile Ile Phe
 50                  55                  60

His Thr Lys Lys Lys Leu Ser Val Cys Ala Asn Pro Lys Gln Thr Trp
 65                  70                  75                  80

Val Lys Tyr Ile Val Arg Leu Leu Ser Lys Lys Val Lys Asn Met
                     85                  90                  95
```

<210> SEQ ID NO 20
<211> LENGTH: 134
<212> TYPE: PRT
<213> ORGANISM: Homo sapiens

<400> SEQUENCE: 20

```
Met Ala Gln Ser Leu Ala Leu Ser Leu Leu Ile Leu Val Leu Ala Phe
 1                   5                  10                  15

Gly Ile Pro Arg Thr Gln Gly Ser Asp Gly Gly Ala Gln Asp Cys Cys
                    20                  25                  30

Leu Lys Tyr Ser Gln Arg Lys Ile Pro Ala Lys Val Val Arg Ser Tyr
                35                  40                  45

Arg Lys Gln Glu Pro Ser Leu Gly Cys Ser Ile Pro Ala Ile Leu Phe
 50                  55                  60

Leu Pro Arg Lys Arg Ser Gln Ala Glu Leu Cys Ala Asp Pro Lys Glu
 65                  70                  75                  80

Leu Trp Val Gln Gln Leu Met Gln His Leu Asp Lys Thr Pro Ser Pro
                    85                  90                  95

Gln Lys Pro Ala Gln Gly Cys Arg Lys Asp Arg Gly Ala Ser Lys Thr
                100                 105                 110

Gly Lys Lys Gly Lys Gly Ser Lys Gly Cys Lys Arg Thr Glu Arg Ser
                115                 120                 125

Gln Thr Pro Lys Gly Pro
                130
```

<210> SEQ ID NO 21
<211> LENGTH: 93
<212> TYPE: PRT
<213> ORGANISM: Homo sapiens

<400> SEQUENCE: 21

```
Met Asp Arg Leu Gln Thr Ala Leu Leu Val Val Leu Val Leu Leu Ala
 1                   5                  10                  15

Val Ala Leu Gln Ala Thr Glu Ala Gly Pro Tyr Gly Ala Asn Met Glu
                    20                  25                  30

Asp Ser Val Cys Cys Arg Asp Tyr Val Arg Tyr Arg Leu Pro Leu Arg
                35                  40                  45

Val Val Lys His Phe Tyr Trp Thr Ser Asp Ser Cys Pro Arg Pro Gly
 50                  55                  60

Val Val Leu Leu Thr Phe Arg Asp Lys Glu Ile Cys Ala Asp Pro Arg
 65                  70                  75                  80

Val Pro Trp Val Lys Met Ile Leu Asn Lys Leu Ser Gln
                    85                  90
```

<210> SEQ ID NO 22
<211> LENGTH: 120
<212> TYPE: PRT
<213> ORGANISM: Homo sapiens

<400> SEQUENCE: 22

```
Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
                20                  25                  30

Met Ser Lys Leu Pro Leu Glu Asn Pro Val Leu Leu Asp Arg Phe His
        35                  40                  45

Ala Thr Ser Ala Asp Cys Cys Ile Ser Tyr Thr Pro Arg Ser Ile Pro
    50                  55                  60

Cys Ser Leu Leu Glu Ser Tyr Phe Glu Thr Asn Ser Glu Cys Ser Lys
65                  70                  75                  80

Pro Gly Val Ile Phe Leu Thr Lys Lys Gly Arg Arg Phe Cys Ala Asn
                85                  90                  95

Pro Ser Asp Lys Gln Val Gln Val Cys Val Arg Met Leu Lys Leu Asp
            100                 105                 110

Thr Arg Ile Lys Thr Arg Lys Asn
        115                 120

<210> SEQ ID NO 23
<211> LENGTH: 137
<212> TYPE: PRT
<213> ORGANISM: Homo sapiens

<400> SEQUENCE: 23

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
                20                  25                  30

Met Ser Lys Leu Pro Leu Glu Asn Pro Val Leu Leu Asp Met Leu Trp
        35                  40                  45

Arg Arg Lys Ile Gly Pro Gln Met Thr Leu Ser His Ala Ala Gly Phe
    50                  55                  60

His Ala Thr Ser Ala Asp Cys Cys Ile Ser Tyr Thr Pro Arg Ser Ile
65                  70                  75                  80

Pro Cys Ser Leu Leu Glu Ser Tyr Phe Glu Thr Asn Ser Glu Cys Ser
                85                  90                  95

Lys Pro Gly Val Ile Phe Leu Thr Lys Lys Gly Arg Arg Phe Cys Ala
            100                 105                 110

Asn Pro Ser Asp Lys Gln Val Gln Val Cys Val Arg Met Leu Lys Leu
            115                 120                 125

Asp Thr Arg Ile Lys Thr Arg Lys Asn
        130                 135

<210> SEQ ID NO 24
<211> LENGTH: 119
<212> TYPE: PRT
<213> ORGANISM: Homo sapiens

<400> SEQUENCE: 24

Met Ala Gly Leu Met Thr Ile Val Thr Ser Leu Leu Phe Leu Gly Val
1               5                   10                  15

Cys Ala His His Ile Ile Pro Thr Gly Ser Val Val Ile Pro Ser Pro
                20                  25                  30

Cys Cys Met Phe Phe Val Ser Lys Arg Ile Pro Glu Asn Arg Val Val
        35                  40                  45

Ser Tyr Gln Leu Ser Ser Arg Ser Thr Cys Leu Lys Ala Gly Val Ile
    50                  55                  60
```

```
Phe Thr Thr Lys Lys Gly Gln Gln Phe Cys Gly Asp Pro Lys Gln Glu
 65                  70                  75                  80

Trp Val Gln Arg Tyr Met Lys Asn Leu Asp Ala Lys Gln Lys Lys Ala
                 85                  90                  95

Ser Pro Arg Ala Arg Ala Val Ala Val Lys Gly Pro Val Gln Arg Tyr
                100                 105                 110

Pro Gly Asn Gln Thr Thr Cys
            115

<210> SEQ ID NO 25
<211> LENGTH: 150
<212> TYPE: PRT
<213> ORGANISM: Homo sapiens

<400> SEQUENCE: 25

Met Asn Leu Trp Leu Leu Ala Cys Leu Val Ala Gly Phe Leu Gly Ala
 1               5                  10                  15

Trp Ala Pro Ala Val His Thr Gln Gly Val Phe Glu Asp Cys Cys Leu
                 20                  25                  30

Ala Tyr His Tyr Pro Ile Gly Trp Ala Val Leu Arg Arg Ala Trp Thr
             35                  40                  45

Tyr Arg Ile Gln Glu Val Ser Gly Ser Cys Asn Leu Pro Ala Ala Ile
 50                  55                  60

Phe Tyr Leu Pro Lys Arg His Arg Lys Val Cys Gly Asn Pro Lys Ser
 65                  70                  75                  80

Arg Glu Val Gln Arg Ala Met Lys Leu Leu Asp Ala Arg Asn Lys Val
                 85                  90                  95

Phe Ala Lys Leu His His Asn Thr Gln Thr Phe Gln Ala Gly Pro His
                100                 105                 110

Ala Val Lys Lys Leu Ser Ser Gly Asn Ser Lys Leu Ser Ser Ser Lys
            115                 120                 125

Phe Ser Asn Pro Ile Ser Ser Ser Lys Arg Asn Val Ser Leu Leu Ile
130                 135                 140

Ser Ala Asn Ser Gly Leu
145                 150

<210> SEQ ID NO 26
<211> LENGTH: 84
<212> TYPE: PRT
<213> ORGANISM: Homo sapiens

<400> SEQUENCE: 26

Met Asn Leu Trp Leu Leu Ala Cys Leu Val Ala Gly Phe Leu Gly Ala
 1               5                  10                  15

Trp Ala Pro Ala Val His Thr Gln Gly Val Phe Glu Asp Cys Cys Leu
                 20                  25                  30

Ala Tyr His Tyr Pro Ile Gly Trp Ala Val Leu Arg Arg Ala Trp Thr
             35                  40                  45

Tyr Arg Ile Gln Glu Val Ser Gly Ser Cys Asn Leu Pro Ala Ala Ile
 50                  55                  60

Arg Pro Ser Cys Cys Lys Glu Val Glu Phe Trp Lys Leu Gln Val Ile
 65                  70                  75                  80

Ile Val Gln Val

<210> SEQ ID NO 27
<211> LENGTH: 84
```

```
<212> TYPE: PRT
<213> ORGANISM: Homo sapiens

<400> SEQUENCE: 27
```

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
50                  55                  60

Arg Pro Ser Cys Cys Lys Glu Val Glu Phe Trp Lys Leu Gln Val Ile
65                  70                  75                  80

Ile Ile Gln Val

```
<210> SEQ ID NO 28
<211> LENGTH: 94
<212> TYPE: PRT
<213> ORGANISM: Homo sapiens

<400> SEQUENCE: 28
```

Met Met Gly Leu Ser Leu Ala Ser Ala Val Leu Leu Ala Ser Leu Leu
1               5                   10                  15

Ser Leu His Leu Gly Thr Ala Thr Arg Gly Ser Asp Ile Ser Lys Thr
            20                  25                  30

Cys Cys Phe Gln Tyr Ser His Lys Pro Leu Pro Trp Thr Trp Val Arg
        35                  40                  45

Ser Tyr Glu Phe Thr Ser Asn Ser Cys Ser Gln Arg Ala Val Ile Phe
50                  55                  60

Thr Thr Lys Arg Gly Lys Lys Val Cys Thr His Pro Arg Lys Lys Trp
65                  70                  75                  80

Val Gln Lys Tyr Ile Ser Leu Leu Lys Thr Pro Lys Gln Leu
            85                  90

```
<210> SEQ ID NO 29
<211> LENGTH: 112
<212> TYPE: PRT
<213> ORGANISM: Homo sapiens

<400> SEQUENCE: 29
```

Met Lys Gly Pro Pro Thr Phe Cys Ser Leu Leu Leu Ser Leu Leu
1               5                   10                  15

Leu Ser Pro Asp Pro Thr Ala Ala Phe Leu Leu Pro Pro Ser Thr Ala
            20                  25                  30

Cys Cys Thr Gln Leu Tyr Arg Lys Pro Leu Ser Asp Lys Leu Leu Arg
        35                  40                  45

Lys Val Ile Gln Val Glu Leu Gln Glu Ala Asp Gly Asp Cys His Leu
50                  55                  60

Gln Ala Phe Val Leu His Leu Ala Gln Arg Ser Ile Cys Ile His Pro
65                  70                  75                  80

Gln Asn Pro Ser Leu Ser Gln Trp Phe Glu His Gln Glu Arg Lys Leu
            85                  90                  95

His Gly Thr Leu Pro Lys Leu Asn Phe Gly Met Leu Arg Lys Met Gly
            100                 105                 110

```
<210> SEQ ID NO 30
```

<211> LENGTH: 127
<212> TYPE: PRT
<213> ORGANISM: Homo sapiens

<400> SEQUENCE: 30

Met Gln Gln Arg Gly Leu Ala Ile Val Ala Leu Ala Val Cys Ala Ala
1               5                   10                  15

Leu His Ala Ser Glu Ala Ile Leu Pro Ile Ala Ser Ser Cys Cys Thr
            20                  25                  30

Glu Val Ser His His Ile Ser Arg Arg Leu Leu Glu Arg Val Asn Met
        35                  40                  45

Cys Arg Ile Gln Arg Ala Asp Gly Asp Cys Asp Leu Ala Ala Val Ile
50                  55                  60

Leu His Val Lys Arg Arg Arg Ile Cys Val Ser Pro His Asn His Thr
65                  70                  75                  80

Val Lys Gln Trp Met Lys Val Gln Ala Ala Lys Lys Asn Gly Lys Gly
                85                  90                  95

Asn Val Cys His Arg Lys Lys His Gly Lys Arg Asn Ser Asn Arg
            100                 105                 110

Ala His Gln Gly Lys His Glu Thr Tyr Gly His Lys Thr Pro Tyr
        115                 120                 125

<210> SEQ ID NO 31
<211> LENGTH: 107
<212> TYPE: PRT
<213> ORGANISM: Homo sapiens

<400> SEQUENCE: 31

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
        35                  40                  45

Leu Gln Gly Ile His Pro Lys Asn Ile Gln Ser Val Asn Val Lys Ser
    50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105

<210> SEQ ID NO 32
<211> LENGTH: 107
<212> TYPE: PRT
<213> ORGANISM: Homo sapiens

<400> SEQUENCE: 32

Met Ala Arg Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
            20                  25                  30

Ala Gly Ala Pro Leu Ala Thr Glu Leu Arg Cys Gln Cys Leu Gln Thr
        35                  40                  45

Leu Gln Gly Ile His Leu Lys Asn Ile Gln Ser Val Lys Val Lys Ser
    50                  55                  60

```
Pro Gly Pro His Cys Ala Gln Thr Glu Val Ile Ala Thr Leu Lys Asn
 65                  70                  75                  80

Gly Gln Lys Ala Cys Leu Asn Pro Ala Ser Pro Met Val Lys Lys Ile
                 85                  90                  95

Ile Glu Lys Met Leu Lys Asn Gly Lys Ser Asn
            100                 105
```

<210> SEQ ID NO 33
<211> LENGTH: 107
<212> TYPE: PRT
<213> ORGANISM: Homo sapiens

<400> SEQUENCE: 33

```
Met Ala His Ala Thr Leu Ser Ala Ala Pro Ser Asn Pro Arg Leu Leu
  1               5                  10                  15

Arg Val Ala Leu Leu Leu Leu Leu Val Ala Ala Ser Arg Arg Ala
                 20                  25                  30

Ala Gly Ala Ser Val Val Thr Glu Leu Arg Cys Gln Cys Leu Gln Thr
             35                  40                  45

Leu Gln Gly Ile His Leu Lys Asn Ile Gln Ser Val Asn Val Arg Ser
 50                  55                  60

Pro Gly Pro His Cys Ala Gln Thr Glu Val Ile Ala Thr Leu Lys Asn
 65                  70                  75                  80

Gly Lys Lys Ala Cys Leu Asn Pro Ala Ser Pro Met Val Gln Lys Ile
                 85                  90                  95

Ile Glu Lys Ile Leu Asn Lys Gly Ser Thr Asn
            100                 105
```

<210> SEQ ID NO 34
<211> LENGTH: 101
<212> TYPE: PRT
<213> ORGANISM: Homo sapiens

<400> SEQUENCE: 34

```
Met Ser Ser Ala Ala Gly Phe Cys Ala Ser Arg Pro Gly Leu Leu Phe
  1               5                  10                  15

Leu Gly Leu Leu Leu Leu Pro Leu Val Val Ala Phe Ala Ser Ala Glu
                 20                  25                  30

Ala Glu Glu Asp Gly Asp Leu Gln Cys Leu Cys Val Lys Thr Thr Ser
             35                  40                  45

Gln Val Arg Pro Arg His Ile Thr Ser Leu Glu Val Ile Lys Ala Gly
 50                  55                  60

Pro His Cys Pro Thr Ala Gln Leu Ile Ala Thr Leu Lys Asn Gly Arg
 65                  70                  75                  80

Lys Ile Cys Leu Asp Leu Gln Ala Pro Leu Tyr Lys Lys Ile Ile Lys
                 85                  90                  95

Lys Leu Leu Glu Ser
            100
```

<210> SEQ ID NO 35
<211> LENGTH: 114
<212> TYPE: PRT
<213> ORGANISM: Homo sapiens

<400> SEQUENCE: 35

```
Met Ser Leu Leu Ser Ser Arg Ala Ala Arg Val Pro Gly Pro Ser Ser
  1               5                  10                  15

Ser Leu Cys Ala Leu Leu Val Leu Leu Leu Leu Thr Gln Pro Gly
```

```
                20                  25                  30
Pro Ile Ala Ser Ala Gly Pro Ala Ala Val Leu Arg Glu Leu Arg
            35                  40                  45
Cys Val Cys Leu Gln Thr Thr Gln Gly Val His Pro Lys Met Ile Ser
        50                  55                  60
Asn Leu Gln Val Phe Ala Ile Gly Pro Gln Cys Ser Lys Val Glu Val
65                  70                  75                  80
Val Ala Ser Leu Lys Asn Gly Lys Glu Ile Cys Leu Asp Pro Glu Ala
                85                  90                  95
Pro Phe Leu Lys Lys Val Ile Gln Lys Ile Leu Asp Gly Gly Asn Lys
            100                 105                 110
Glu Asn

<210> SEQ ID NO 36
<211> LENGTH: 114
<212> TYPE: PRT
<213> ORGANISM: Homo sapiens

<400> SEQUENCE: 36

Met Ser Leu Pro Ser Ser Arg Ala Ala Arg Val Pro Gly Pro Ser Gly
1               5                   10                  15
Ser Leu Cys Ala Leu Leu Ala Leu Leu Leu Leu Leu Thr Pro Pro Gly
                20                  25                  30
Pro Leu Ala Ser Ala Gly Pro Val Ser Ala Val Leu Thr Glu Leu Arg
            35                  40                  45
Cys Thr Cys Leu Arg Val Thr Leu Arg Val Asn Pro Lys Thr Ile Gly
        50                  55                  60
Lys Leu Gln Val Phe Pro Ala Gly Pro Gln Cys Ser Lys Val Glu Val
65                  70                  75                  80
Val Ala Ser Leu Lys Asn Gly Lys Gln Val Cys Leu Asp Pro Glu Ala
                85                  90                  95
Pro Phe Leu Lys Lys Val Ile Gln Lys Ile Leu Asp Ser Gly Asn Lys
            100                 105                 110
Lys Asn

<210> SEQ ID NO 37
<211> LENGTH: 128
<212> TYPE: PRT
<213> ORGANISM: Homo sapiens

<400> SEQUENCE: 37

Met Ser Leu Arg Leu Asp Thr Thr Pro Ser Cys Asn Ser Ala Arg Pro
1               5                   10                  15
Leu His Ala Leu Gln Val Leu Leu Leu Ser Leu Leu Leu Thr Ala
                20                  25                  30
Leu Ala Ser Ser Thr Lys Gly Gln Thr Lys Arg Asn Leu Ala Lys Gly
            35                  40                  45
Lys Glu Glu Ser Leu Asp Ser Asp Leu Tyr Ala Glu Leu Arg Cys Met
        50                  55                  60
Cys Ile Lys Thr Thr Ser Gly Ile His Pro Lys Asn Ile Gln Ser Leu
65                  70                  75                  80
Glu Val Ile Gly Lys Gly Thr His Cys Asn Gln Val Glu Val Ile Ala
                85                  90                  95
Thr Leu Lys Asp Gly Arg Lys Ile Cys Leu Asp Pro Asp Ala Pro Arg
            100                 105                 110
```

```
Ile Lys Lys Ile Val Gln Lys Lys Leu Ala Gly Asp Glu Ser Ala Asp
            115                 120                 125
```

<210> SEQ ID NO 38
<211> LENGTH: 99
<212> TYPE: PRT
<213> ORGANISM: Homo sapiens

<400> SEQUENCE: 38

```
Met Thr Ser Lys Leu Ala Val Ala Leu Leu Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 39
<211> LENGTH: 125
<212> TYPE: PRT
<213> ORGANISM: Homo sapiens

<400> SEQUENCE: 39

```
Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
                20                  25                  30

Cys Ile Ser Thr Asn Gln Gly Thr Ile His Leu Gln Ser Leu Lys Asp
            35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
        115                 120                 125
```

<210> SEQ ID NO 40
<211> LENGTH: 98
<212> TYPE: PRT
<213> ORGANISM: Homo sapiens

<400> SEQUENCE: 40

```
Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
                20                  25                  30

Ile Ser Ile Ser Asn Gln Pro Val Asn Pro Arg Ser Leu Glu Lys Leu
            35                  40                  45
```

```
Glu Ile Ile Pro Ala Ser Gln Phe Cys Pro Arg Val Glu Ile Ile Ala
            50                  55                  60

Thr Met Lys Lys Lys Gly Lys Arg Cys Leu Asn Pro Glu Ser Lys
 65                  70                  75                  80

Ala Ile Lys Asn Leu Leu Lys Ala Val Ser Lys Glu Arg Ser Lys Arg
                85                  90                  95

Ser Pro

<210> SEQ ID NO 41
<211> LENGTH: 94
<212> TYPE: PRT
<213> ORGANISM: Homo sapiens

<400> SEQUENCE: 41

Met Ser Val Lys Gly Met Ala Ile Ala Leu Ala Val Ile Leu Cys Ala
 1               5                  10                  15

Thr Val Val Gln Gly Phe Pro Met Phe Lys Arg Gly Arg Cys Leu Cys
                20                  25                  30

Ile Gly Pro Gly Val Lys Ala Val Lys Val Ala Asp Ile Glu Lys Ala
            35                  40                  45

Ser Ile Met Tyr Pro Ser Asn Asn Cys Asp Lys Ile Glu Val Ile Ile
        50                  55                  60

Thr Leu Lys Glu Asn Lys Gly Gln Arg Cys Leu Asn Pro Lys Ser Lys
 65                  70                  75                  80

Gln Ala Arg Leu Ile Ile Lys Lys Val Glu Arg Lys Asn Phe
                85                  90

<210> SEQ ID NO 42
<211> LENGTH: 93
<212> TYPE: PRT
<213> ORGANISM: Homo sapiens

<400> SEQUENCE: 42

Met Asn Ala Lys Val Val Val Val Leu Val Leu Val Leu Thr Ala Leu
 1               5                  10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
 65                  70                  75                  80

Glu Tyr Leu Glu Lys Ala Leu Asn Lys Arg Phe Lys Met
                85                  90

<210> SEQ ID NO 43
<211> LENGTH: 109
<212> TYPE: PRT
<213> ORGANISM: Homo sapiens

<400> SEQUENCE: 43

Met Lys Phe Ile Ser Thr Ser Leu Leu Leu Met Leu Leu Val Ser Ser
 1               5                  10                  15

Leu Ser Pro Val Gln Gly Val Leu Glu Val Tyr Tyr Thr Ser Leu Arg
                20                  25                  30

Cys Arg Cys Val Gln Glu Ser Ser Val Phe Ile Pro Arg Arg Phe Ile
```

```
            35                  40                  45
Asp Arg Ile Gln Ile Leu Pro Arg Gly Asn Gly Cys Pro Arg Lys Glu
 50                  55                  60

Ile Ile Val Trp Lys Lys Asn Lys Ser Ile Val Cys Val Asp Pro Gln
 65                  70                  75                  80

Ala Glu Trp Ile Gln Arg Met Met Glu Val Leu Arg Lys Arg Ser Ser
                 85                  90                  95

Ser Thr Leu Pro Val Pro Val Phe Lys Arg Lys Ile Pro
            100                 105

<210> SEQ ID NO 44
<211> LENGTH: 273
<212> TYPE: PRT
<213> ORGANISM: Homo sapiens

<400> SEQUENCE: 44

Met Ser Gly Ser Gln Ser Glu Val Ala Pro Ser Pro Gln Ser Pro Arg
 1               5                  10                  15

Ser Pro Glu Met Gly Arg Asp Leu Arg Pro Gly Ser Arg Val Leu Leu
                20                  25                  30

Leu Leu Leu Leu Leu Leu Val Tyr Leu Thr Gln Pro Gly Asn Gly
             35                  40                  45

Asn Glu Gly Ser Val Thr Gly Ser Cys Tyr Cys Gly Lys Arg Ile Ser
 50                  55                  60

Ser Asp Ser Pro Pro Ser Val Gln Phe Met Asn Arg Leu Arg Lys His
 65                  70                  75                  80

Leu Arg Ala Tyr His Arg Cys Leu Tyr Tyr Thr Arg Phe Gln Leu Leu
                 85                  90                  95

Ser Trp Ser Val Cys Gly Gly Asn Lys Asp Pro Trp Val Gln Glu Leu
            100                 105                 110

Met Ser Cys Leu Asp Leu Lys Glu Cys Gly His Ala Tyr Ser Gly Ile
            115                 120                 125

Val Ala His Gln Lys His Leu Leu Pro Thr Ser Pro Pro Ile Ser Gln
            130                 135                 140

Ala Ser Glu Gly Ala Ser Ser Asp Ile His Thr Pro Ala Gln Met Leu
145                 150                 155                 160

Leu Ser Thr Leu Gln Ser Thr Gln Arg Pro Thr Leu Pro Val Gly Ser
                165                 170                 175

Leu Ser Ser Asp Lys Glu Leu Thr Arg Pro Asn Glu Thr Thr Ile His
            180                 185                 190

Thr Ala Gly His Ser Leu Ala Ala Gly Pro Glu Ala Gly Glu Asn Gln
            195                 200                 205

Lys Gln Pro Glu Lys Asn Ala Gly Pro Thr Ala Arg Thr Ser Ala Thr
        210                 215                 220

Val Pro Val Leu Cys Leu Leu Ala Ile Ile Phe Ile Leu Thr Ala Ala
225                 230                 235                 240

Leu Ser Tyr Val Leu Cys Lys Arg Arg Arg Gly Gln Ser Pro Gln Ser
                245                 250                 255

Ser Pro Asp Leu Pro Val His Tyr Ile Pro Val Ala Pro Asp Ser Asn
            260                 265                 270

Thr

<210> SEQ ID NO 45
<211> LENGTH: 114
<212> TYPE: PRT
```

```
<213> ORGANISM: Homo sapiens

<400> SEQUENCE: 45

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser Asp Lys Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly

<210> SEQ ID NO 46
<211> LENGTH: 114
<212> TYPE: PRT
<213> ORGANISM: Homo sapiens

<400> SEQUENCE: 46

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser His Arg Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly

<210> SEQ ID NO 47
<211> LENGTH: 397
<212> TYPE: PRT
<213> ORGANISM: Homo sapiens

<400> SEQUENCE: 47

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45

Ile His Tyr Gln Gln Asn Gln Ala Ser Cys Gly Lys Arg Ala Ile Ile
    50                  55                  60

Leu Glu Thr Arg Gln His Arg Leu Phe Cys Ala Asp Pro Lys Glu Gln
```

```
             65                  70                  75                  80
        Trp Val Lys Asp Ala Met Gln His Leu Asp Arg Gln Ala Ala Leu
                         85                  90                  95
        Thr Arg Asn Gly Gly Thr Phe Glu Lys Gln Ile Gly Glu Val Lys Pro
                        100                 105                 110
        Arg Thr Thr Pro Ala Ala Gly Met Asp Glu Ser Val Leu Glu
                        115                 120                 125
        Pro Glu Ala Thr Gly Glu Ser Ser Leu Glu Pro Thr Pro Ser Ser
                        130                 135                 140
        Gln Glu Ala Gln Arg Ala Leu Gly Thr Ser Pro Glu Leu Pro Thr Gly
        145                 150                 155                 160
        Val Thr Gly Ser Ser Gly Thr Arg Leu Pro Pro Thr Pro Lys Ala Gln
                        165                 170                 175
        Asp Gly Gly Pro Val Gly Thr Glu Leu Phe Arg Val Pro Pro Val Ser
                        180                 185                 190
        Thr Ala Ala Thr Trp Gln Ser Ser Ala Pro His Gln Pro Gly Pro Ser
                        195                 200                 205
        Leu Trp Ala Glu Ala Lys Thr Ser Glu Ala Pro Ser Thr Gln Asp Pro
                        210                 215                 220
        Ser Thr Gln Ala Ser Thr Ala Ser Ser Pro Ala Pro Glu Glu Asn Ala
        225                 230                 235                 240
        Pro Ser Glu Gly Gln Arg Val Trp Gly Gln Gly Gln Ser Pro Arg Pro
                        245                 250                 255
        Glu Asn Ser Leu Glu Arg Glu Glu Met Gly Pro Val Pro Ala His Thr
                        260                 265                 270
        Asp Ala Phe Gln Asp Trp Gly Pro Gly Ser Met Ala His Val Ser Val
                        275                 280                 285
        Val Pro Val Ser Ser Glu Gly Thr Pro Ser Arg Glu Pro Val Ala Ser
                        290                 295                 300
        Gly Ser Trp Thr Pro Lys Ala Glu Glu Pro Ile His Ala Thr Met Asp
        305                 310                 315                 320
        Pro Gln Arg Leu Gly Val Leu Ile Thr Pro Val Pro Asp Ala Gln Ala
                        325                 330                 335
        Ala Thr Arg Arg Gln Ala Val Gly Leu Leu Ala Phe Leu Gly Leu Leu
                        340                 345                 350
        Phe Cys Leu Gly Val Ala Met Phe Thr Tyr Gln Ser Leu Gln Gly Cys
                        355                 360                 365
        Pro Arg Lys Met Ala Gly Glu Met Ala Glu Gly Leu Arg Tyr Ile Pro
                        370                 375                 380
        Arg Ser Cys Gly Ser Asn Ser Tyr Val Leu Val Pro Val
        385                 390                 395

<210> SEQ ID NO 48
<211> LENGTH: 233
<212> TYPE: PRT
<213> ORGANISM: Homo sapiens

<400> SEQUENCE: 48

Ser Glu Pro Lys Ser Cys Asp Lys Thr His Thr Cys Pro Pro Cys Pro
        1                   5                   10                  15
        Ala Pro Glu Leu Leu Gly Gly Pro Ser Val Phe Leu Phe Pro Pro Lys
                        20                  25                  30
        Pro Lys Asp Thr Leu Met Ile Ser Arg Thr Pro Glu Val Thr Cys Val
                        35                  40                  45
```

```
Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 49
<211> LENGTH: 228
<212> TYPE: PRT
<213> ORGANISM: Homo sapiens

<400> SEQUENCE: 49

Glu Arg Lys Cys Cys Val Glu Cys Pro Pro Cys Pro Ala Pro Pro Val
  1               5                  10                  15

Ala Gly Pro Ser Val Phe Leu Phe Pro Pro Lys Pro Lys Asp Thr Leu
             20                  25                  30

Met Ile Ser Arg Thr Pro Glu Val Thr Cys Val Val Val Asp Val Ser
         35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190
```

```
Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
        210                 215                 220

Ser Pro Gly Lys
225

<210> SEQ ID NO 50
<211> LENGTH: 279
<212> TYPE: PRT
<213> ORGANISM: Homo sapiens

<400> SEQUENCE: 50

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Phe
        115                 120                 125

Asn Ser Thr Phe Arg Val Val Ser Val Leu Thr Val Leu His Gln Asp
130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 51
<211> LENGTH: 229
<212> TYPE: PRT
<213> ORGANISM: Homo sapiens

<400> SEQUENCE: 51
```

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 52
<211> LENGTH: 303
<212> TYPE: PRT
<213> ORGANISM: Artificial Sequence
<220> FEATURE:
<223> OTHER INFORMATION: CCL2-IgG1Fc

<400> SEQUENCE: 52

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr Asp Lys Thr His
65                  70                  75                  80

Thr Cys Pro Pro Cys Pro Ala Pro Glu Leu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125
```

```
Val Lys Phe Asn Trp Tyr Val Asp Gly Val Glu Val His Asn Ala Lys
        130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
                180                 185                 190

Ser Lys Ala Lys Gly Gln Pro Arg Glu Pro Gln Val Tyr Thr Leu Pro
        195                 200                 205

Pro Ser Arg Glu Glu Met Thr Lys Asn Gln Val Ser Leu Thr Cys Leu
        210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
                260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
        290                 295                 300

<210> SEQ ID NO 53
<211> LENGTH: 309
<212> TYPE: PRT
<213> ORGANISM: Artificial Sequence
<220> FEATURE:
<223> OTHER INFORMATION: CCL2(5-76)-IgG1Fc

<400> SEQUENCE: 53

Ala Leu Ser Leu Ala Leu Val Thr Asn Ser Ile Asn Ala Pro Val Thr
1               5                   10                  15

Cys Cys Tyr Asn Phe Thr Asn Arg Lys Ile Ser Val Gln Arg Leu Ala
                20                  25                  30

Ser Tyr Arg Arg Ile Thr Ser Ser Lys Cys Pro Lys Glu Ala Val Ile
            35                  40                  45

Phe Lys Thr Ile Val Ala Lys Glu Ile Cys Ala Asp Pro Lys Gln Lys
        50                  55                  60

Trp Val Gln Asp Ser Met Asp His Leu Asp Lys Gln Thr Gln Thr Pro
65                  70                  75                  80

Lys Thr Asp Lys Thr His Thr Cys Pro Pro Cys Pro Ala Pro Glu Leu
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190
```

```
Pro Ile Glu Lys Thr Ile Ser Lys Ala Lys Gly Gln Pro Arg Glu Pro
            195                 200                 205

Gln Val Tyr Thr Leu Pro Pro Ser Arg Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
                260                 265                 270

Thr Val Asp Lys Ser Arg Trp Gln Gln Gly Asn Val Phe Ser Cys Ser
            275                 280                 285

Val Met His Glu Ala Leu His Asn His Tyr Thr Gln Lys Ser Leu Ser
        290                 295                 300

Leu Ser Pro Gly Lys
305

<210> SEQ ID NO 54
<211> LENGTH: 299
<212> TYPE: PRT
<213> ORGANISM: Artificial Sequence
<220> FEATURE:
<223> OTHER INFORMATION: CCL2(5-76K/H-A)-IgG1Fc

<400> SEQUENCE: 54

Ile Asn Ala Pro Val Thr Cys Cys Tyr Asn Phe Thr Asn Arg Lys Ile
1               5                   10                  15

Ser Val Gln Arg Leu Ala Ser Tyr Arg Arg Ile Thr Ser Ser Lys Cys
            20                  25                  30

Pro Lys Glu Ala Val Ile Phe Lys Thr Ile Val Ala Ala Glu Ile Cys
        35                  40                  45

Ala Asp Pro Ala Gln Ala Trp Val Gln Asp Ser Met Asp Ala Leu Asp
    50                  55                  60

Ala Gln Thr Gln Thr Pro Ala Thr Asp Lys Thr His Thr Cys Pro Pro
65                  70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
    130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240
```

```
Asn Asn Tyr Lys Thr Thr Pro Pro Val Leu Asp Ser Asp Gly Ser Phe
            245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
            275                 280                 285

Thr Gln Lys Ser Leu Ser Leu Ser Pro Gly Lys
            290                 295
```

<210> SEQ ID NO 55
<211> LENGTH: 289
<212> TYPE: PRT
<213> ORGANISM: Artificial Sequence
<220> FEATURE:
<223> OTHER INFORMATION: CCL7-IgG1Fc

<400> SEQUENCE: 55

```
Phe Ile Asn Lys Lys Ile Pro Lys Gln Arg Leu Glu Ser Tyr Arg Arg
1               5                   10                  15

Thr Thr Ser Ser His Cys Pro Arg Glu Ala Val Ile Phe Lys Thr Lys
            20                  25                  30

Leu Asp Lys Glu Ile Cys Ala Asp Pro Thr Gln Lys Trp Val Gln Asp
        35                  40                  45

Phe Met Lys His Leu Asp Lys Lys Thr Gln Thr Pro Lys Leu Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Glu Glu Met Thr Lys Asn Gln Val Ser Leu Thr
        195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
        275                 280                 285

Lys
```

```
<210> SEQ ID NO 56
<211> LENGTH: 293
<212> TYPE: PRT
<213> ORGANISM: Artificial Sequence
<220> FEATURE:
<223> OTHER INFORMATION: CCL7(5-76)-IgGFc

<400> SEQUENCE: 56

Cys Cys Tyr Arg Phe Ile Asn Lys Lys Ile Pro Lys Gln Arg Leu Glu
1               5                   10                  15

Ser Tyr Arg Arg Thr Thr Ser Ser His Cys Pro Arg Glu Ala Val Ile
            20                  25                  30

Phe Lys Thr Lys Leu Asp Lys Glu Ile Cys Ala Asp Pro Thr Gln Lys
        35                  40                  45

Trp Val Gln Asp Phe Met Lys His Leu Asp Lys Lys Thr Gln Thr Pro
50                  55                  60

Lys Leu Asp Lys Thr His Thr Cys Pro Pro Cys Pro Ala Pro Glu Leu
65                  70                  75                  80

Leu Gly Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Lys Phe Asn Trp Tyr Val Asp Gly Val
        115                 120                 125

Glu Val His Asn Ala Lys Thr Lys Pro Arg Glu Glu Gln Tyr Asn Ser
130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175

Pro Ile Glu Lys Thr Ile Ser Lys Ala Lys Gly Gln Pro Arg Glu Pro
            180                 185                 190

Gln Val Tyr Thr Leu Pro Pro Ser Arg Glu Glu Met Thr Lys Asn Gln
        195                 200                 205

Val Ser Leu Thr Cys Leu Val Lys Gly Phe Tyr Pro Ser Asp Ile Ala
210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly Lys
    290

<210> SEQ ID NO 57
<211> LENGTH: 289
<212> TYPE: PRT
<213> ORGANISM: Artificial Sequence
<220> FEATURE:
<223> OTHER INFORMATION: CCL7(5-76K/H-A)-IgGFc

<400> SEQUENCE: 57

Phe Ile Asn Lys Lys Ile Pro Lys Gln Arg Leu Glu Ser Tyr Arg Arg
1               5                   10                  15
```

-continued

```
Thr Thr Ser Ser His Cys Pro Arg Glu Ala Val Ile Phe Ala Thr Ala
            20                  25                  30

Leu Asp Ala Glu Ile Cys Ala Asp Pro Thr Gln Ala Trp Val Gln Asp
        35                  40                  45

Phe Met Ala Ala Leu Asp Ala Ala Thr Gln Thr Pro Ala Leu Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
                100                 105                 110

Pro Glu Val Lys Phe Asn Trp Tyr Val Asp Gly Val Glu Val His Asn
            115                 120                 125

Ala Lys Thr Lys Pro Arg Glu Glu Gln Tyr Asn Ser Thr Tyr Arg Val
        130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
                180                 185                 190

Leu Pro Pro Ser Arg Glu Glu Met Thr Lys Asn Gln Val Ser Leu Thr
            195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
                260                 265                 270

Ala Leu His Asn His Tyr Thr Gln Lys Ser Leu Ser Leu Ser Pro Gly
            275                 280                 285

Lys

<210> SEQ ID NO 58
<211> LENGTH: 303
<212> TYPE: PRT
<213> ORGANISM: Artificial Sequence
<220> FEATURE:
<223> OTHER INFORMATION: CCL8-IgG1Fc

<400> SEQUENCE: 58

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro Asp Lys Thr His
65                  70                  75                  80
```

```
Thr Cys Pro Pro Cys Pro Ala Pro Glu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
            115                 120                 125

Val Lys Phe Asn Trp Tyr Val Asp Gly Val Glu Val His Asn Ala Lys
130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
                180                 185                 190

Ser Lys Ala Lys Gly Gln Pro Arg Glu Pro Gln Val Tyr Thr Leu Pro
            195                 200                 205

Pro Ser Arg Glu Glu Met Thr Lys Asn Gln Val Ser Leu Thr Cys Leu
            210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
                260                 265                 270

Trp Gln Gln Gly Asn Val Phe Ser Cys Ser Val Met His Glu Ala Leu
            275                 280                 285

His Asn His Tyr Thr Gln Lys Ser Leu Ser Leu Ser Pro Gly Lys
            290                 295                 300

<210> SEQ ID NO 59
<211> LENGTH: 299
<212> TYPE: PRT
<213> ORGANISM: Artificial Sequence
<220> FEATURE:
<223> OTHER INFORMATION: CCL8(5-76)-IgG1Fc

<400> SEQUENCE: 59

Val Ser Ile Pro Ile Thr Cys Cys Phe Asn Val Ile Asn Arg Lys Ile
1               5                   10                  15

Pro Ile Gln Arg Leu Glu Ser Tyr Thr Arg Ile Thr Asn Ile Gln Cys
            20                  25                  30

Pro Lys Glu Ala Val Ile Phe Lys Thr Lys Arg Gly Lys Glu Val Cys
        35                  40                  45

Ala Asp Pro Lys Glu Arg Trp Val Arg Asp Ser Met Lys His Leu Asp
50                  55                  60

Gln Ile Phe Gln Asn Leu Lys Pro Asp Lys Thr His Thr Cys Pro Pro
65                  70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
130                 135                 140
```

```
Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
                260                 265                 270

Asn Val Phe Ser Cys Ser Val Met His Glu Ala Leu His Asn His Tyr
            275                 280                 285

Thr Gln Lys Ser Leu Ser Leu Ser Pro Gly Lys
    290                 295

<210> SEQ ID NO 60
<211> LENGTH: 265
<212> TYPE: PRT
<213> ORGANISM: Artificial Sequence
<220> FEATURE:
<223> OTHER INFORMATION: CCL8(5-76K/H-A)-IgG1Fc

<400> SEQUENCE: 60

Val Ser Ile Pro Ile Thr Cys Cys Phe Asn Val Ile Asn Arg Lys Ile
1               5                   10                  15

Pro Ile Gln Arg Leu Glu Ser Tyr Thr Arg Ile Thr Asn Ile Gln Cys
            20                  25                  30

Pro Lys Glu Ala Val Ile Phe Lys Thr Ala Ala Gly Ala Glu Val Cys
        35                  40                  45

Ala Asp Pro Ala Glu Ala Trp Val Ala Asp Ser Met Ala Ala Leu Asp
    50                  55                  60

Gln Ile Phe Gln Asn Leu Ala Pro Asp Lys Thr His Thr Cys Pro Pro
65                  70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
    130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205
```

```
Glu Met Thr Lys Asn Gln Val Ser Leu Thr Cys Leu Val Lys Gly Phe
            210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Lys Ser Leu Ser Leu Ser Pro Gly Lys
            260                 265
```

<210> SEQ ID NO 61
<211> LENGTH: 302
<212> TYPE: PRT
<213> ORGANISM: Artificial Sequence
<220> FEATURE:
<223> OTHER INFORMATION: CCL13-IgG1Fc

<400> SEQUENCE: 61

```
Gln Pro Asp Ala Leu Asn Val Pro Ser Thr Cys Cys Phe Thr Phe Ser
1               5                   10                  15

Ser Lys Lys Ile Ser Leu Gln Arg Leu Lys Ser Tyr Val Ile Thr Thr
            20                  25                  30

Ser Arg Cys Pro Gln Lys Ala Val Ile Phe Arg Thr Lys Leu Gly Lys
        35                  40                  45

Glu Ile Cys Ala Asp Pro Lys Glu Lys Trp Val Gln Asn Tyr Met Lys
    50                  55                  60

His Leu Gly Arg Lys Ala His Thr Leu Lys Thr Asp Lys Thr His Thr
65                  70                  75                  80

Cys Pro Pro Cys Pro Ala Pro Glu Leu Leu Gly Gly Pro Ser Val Phe
                85                  90                  95

Leu Phe Pro Pro Lys Pro Lys Asp Thr Leu Met Ile Ser Arg Thr Pro
            100                 105                 110

Glu Val Thr Cys Val Val Val Asp Val Ser His Glu Asp Pro Glu Val
        115                 120                 125

Lys Phe Asn Trp Tyr Val Asp Gly Val Glu Val His Asn Ala Lys Thr
    130                 135                 140

Lys Pro Arg Glu Glu Gln Tyr Asn Ser Thr Tyr Arg Val Val Ser Val
145                 150                 155                 160

Leu Thr Val Leu His Gln Asp Trp Leu Asn Gly Lys Glu Tyr Lys Cys
                165                 170                 175

Lys Val Ser Asn Lys Ala Leu Pro Ala Pro Ile Glu Lys Thr Ile Ser
            180                 185                 190

Lys Ala Lys Gly Gln Pro Arg Glu Pro Gln Val Tyr Thr Leu Pro Pro
        195                 200                 205

Ser Arg Glu Glu Met Thr Lys Asn Gln Val Ser Leu Thr Cys Leu Val
    210                 215                 220

Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
                245                 250                 255

Gly Ser Phe Phe Leu Tyr Ser Lys Leu Thr Val Asp Lys Ser Arg Trp
            260                 265                 270

Gln Gln Gly Asn Val Phe Ser Cys Ser Val Met His Glu Ala Leu His
        275                 280                 285

Asn His Tyr Thr Gln Lys Ser Leu Ser Leu Ser Pro Gly Lys
    290                 295                 300
```

```
<210> SEQ ID NO 62
<211> LENGTH: 298
<212> TYPE: PRT
<213> ORGANISM: Artificial Sequence
<220> FEATURE:
<223> OTHER INFORMATION: CCL13(5-75)-IgG1Fc

<400> SEQUENCE: 62

Leu Asn Val Pro Ser Thr Cys Cys Phe Thr Phe Ser Ser Lys Lys Ile
1               5                   10                  15

Ser Leu Gln Arg Leu Lys Ser Tyr Val Ile Thr Thr Ser Arg Cys Pro
            20                  25                  30

Gln Lys Ala Val Ile Phe Arg Thr Lys Leu Gly Lys Glu Ile Cys Ala
        35                  40                  45

Asp Pro Lys Glu Lys Trp Val Gln Asn Tyr Met Lys His Leu Gly Arg
    50                  55                  60

Lys Ala His Thr Leu Lys Thr Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295

<210> SEQ ID NO 63
<211> LENGTH: 298
<212> TYPE: PRT
<213> ORGANISM: Artificial Sequence
<220> FEATURE:
<223> OTHER INFORMATION: CCL13(5-75K/H-A)-IgG1Fc

<400> SEQUENCE: 63

Leu Asn Val Pro Ser Thr Cys Cys Phe Thr Phe Ser Ser Lys Lys Ile
1               5                   10                  15
```

Ser Leu Gln Arg Leu Lys Ser Tyr Val Ile Thr Thr Ser Arg Cys Pro
            20                  25                  30

Gln Lys Ala Val Ile Phe Arg Thr Ala Leu Gly Ala Glu Ile Cys Ala
        35                  40                  45

Asp Pro Ala Glu Ala Trp Val Gln Asn Tyr Met Ala Ala Leu Gly Arg
 50                  55                  60

Lys Ala Ala Thr Leu Ala Thr Asp Lys Thr His Thr Cys Pro Pro Cys
 65                  70                  75                  80

Pro Ala Pro Glu Leu Leu Gly Gly Pro Ser Val Phe Leu Phe Pro Pro
                 85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295

<210> SEQ ID NO 64
<211> LENGTH: 345
<212> TYPE: PRT
<213> ORGANISM: Artificial Sequence
<220> FEATURE:
<223> OTHER INFORMATION: CCL25-IgG1Fc

<400> SEQUENCE: 64

Thr Gln Gly Val Phe Glu Asp Cys Cys Leu Ala Tyr His Tyr Pro Ile
 1               5                  10                  15

Gly Trp Ala Val Leu Arg His Ala Trp Thr Tyr Arg Ile Gln Glu Val
            20                  25                  30

Ser Gly Ser Cys Asn Leu Pro Ala Ala Ile Phe Tyr Leu Pro Lys Arg
        35                  40                  45

His Arg Lys Val Cys Gly Asn Pro Lys Ser Arg Glu Val Gln Arg Ala
 50                  55                  60

Met Lys Leu Leu Asp Ala Arg Asn Lys Val Phe Ala Lys Leu Arg His
 65                  70                  75                  80

```
Asn Thr Gln Thr Phe Gln Gly Pro His Ala Val Lys Lys Leu Ser Ser
                85                  90                  95

Gly Asn Ser Lys Leu Ser Ser Lys Phe Ser Asn Pro Ile Ser Ser
            100                 105                 110

Ser Lys Arg Asn Val Ser Asp Lys Thr His Thr Cys Pro Pro Cys Pro
            115                 120                 125

Ala Pro Glu Leu Leu Gly Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
            195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
            275                 280                 285

Tyr Lys Thr Thr Pro Pro Val Leu Asp Ser Asp Gly Ser Phe Phe Leu
290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 65
<211> LENGTH: 342
<212> TYPE: PRT
<213> ORGANISM: Artificial Sequence
<220> FEATURE:
<223> OTHER INFORMATION: CCL25(4-127)-IgG1Fc

<400> SEQUENCE: 65

Val Phe Glu Asp Cys Cys Leu Ala Tyr His Tyr Pro Ile Gly Trp Ala
1               5                   10                  15

Val Leu Arg His Ala Trp Thr Tyr Arg Ile Gln Glu Val Ser Gly Ser
                20                  25                  30

Cys Asn Leu Pro Ala Ala Ile Phe Tyr Leu Pro Lys Arg His Arg Lys
            35                  40                  45

Val Cys Gly Asn Pro Lys Ser Arg Glu Val Gln Arg Ala Met Lys Leu
        50                  55                  60

Leu Asp Ala Arg Asn Lys Val Phe Ala Lys Leu His Asn Thr Gln
65                  70                  75                  80

Thr Phe Gln Gly Pro His Ala Val Lys Lys Leu Ser Ser Gly Asn Ser
                85                  90                  95
```

Lys Leu Ser Ser Ser Lys Phe Ser Asn Pro Ile Ser Ser Ser Lys Arg
                100                 105                 110

Asn Val Ser Asp Lys Thr His Thr Cys Pro Pro Cys Pro Ala Pro Glu
            115                 120                 125

Leu Leu Gly Gly Pro Ser Val Phe Leu Phe Pro Pro Lys Pro Lys Asp
        130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 66
<211> LENGTH: 342
<212> TYPE: PRT
<213> ORGANISM: Artificial Sequence
<220> FEATURE:
<223> OTHER INFORMATION: CCL25(4-127K/H-A)-IgG1Fc

<400> SEQUENCE: 66

Val Phe Glu Asp Cys Cys Leu Ala Tyr His Tyr Pro Ile Gly Trp Ala
1               5                   10                  15

Val Leu Arg His Ala Trp Thr Tyr Arg Ile Gln Glu Val Ser Gly Ser
            20                  25                  30

Cys Asn Leu Pro Ala Ala Ile Phe Tyr Leu Pro Ala Ala Ala Ala Ala
        35                  40                  45

Val Cys Gly Asn Pro Ala Ser Ala Glu Val Gln Ala Ala Met Ala Leu
    50                  55                  60

Leu Asp Ala Ala Asn Ala Val Phe Ala Leu Ala Ala Asn Thr Gln
65                  70                  75                  80

Thr Phe Gln Gly Pro Ala Ala Val Ala Ala Leu Ser Ser Gly Asn Ser
                85                  90                  95

Ala Leu Ser Ser Ser Ala Phe Ser Asn Pro Ile Ser Ser Ser Ala Ala
            100                 105                 110

Asn Val Ser Asp Lys Thr His Thr Cys Pro Pro Cys Pro Ala Pro Glu
            115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 67
<211> LENGTH: 300
<212> TYPE: PRT
<213> ORGANISM: Artificial Sequence
<220> FEATURE:
<223> OTHER INFORMATION: CXCL11-IgG1Fc

<400> SEQUENCE: 67

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Asp Lys Thr His Thr Cys Pro
65                  70                  75                  80

Pro Cys Pro Ala Pro Glu Leu Leu Gly Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125

```
Asn Trp Tyr Val Asp Gly Val Glu Val His Asn Ala Lys Thr Lys Pro
            130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Val Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly Lys
    290                 295                 300

<210> SEQ ID NO 68
<211> LENGTH: 297
<212> TYPE: PRT
<213> ORGANISM: Artificial Sequence
<220> FEATURE:
<223> OTHER INFORMATION: CXCL11(4-73)-IgG1Fc

<400> SEQUENCE: 68

Phe Lys Arg Gly Arg Cys Leu Cys Ile Gly Pro Gly Val Lys Ala Val
1               5                   10                  15

Lys Val Ala Asp Ile Glu Lys Ala Ser Ile Met Tyr Pro Ser Asn Asn
            20                  25                  30

Cys Asp Lys Ile Glu Val Ile Ile Thr Leu Lys Glu Asn Lys Gly Gln
        35                  40                  45

Arg Cys Leu Asn Pro Lys Ser Lys Gln Ala Arg Leu Ile Ile Lys Lys
    50                  55                  60

Val Glu Arg Lys Asn Phe Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190
```

```
Pro Arg Glu Pro Gln Val Tyr Thr Leu Pro Pro Ser Arg Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
                260                 265                 270

Phe Ser Cys Ser Val Met His Glu Ala Leu His Asn His Tyr Thr Gln
            275                 280                 285

Lys Ser Leu Ser Leu Ser Pro Gly Lys
    290                 295
```

<210> SEQ ID NO 69
<211> LENGTH: 297
<212> TYPE: PRT
<213> ORGANISM: Artificial Sequence
<220> FEATURE:
<223> OTHER INFORMATION: CXCL11(4-73K/H-A)-IgG1Fc

<400> SEQUENCE: 69

```
Phe Lys Arg Gly Arg Cys Leu Cys Ile Gly Pro Gly Val Lys Ala Val
1               5                   10                  15

Lys Val Ala Asp Ile Glu Ala Ala Ser Ile Met Tyr Pro Ser Asn Asn
            20                  25                  30

Cys Asp Lys Ile Glu Val Ile Ile Thr Leu Ala Glu Asn Ala Gly Gln
        35                  40                  45

Ala Cys Leu Asn Pro Ala Ser Ala Gln Ala Ala Leu Ile Ile Ala Ala
    50                  55                  60

Val Glu Ala Ala Asn Phe Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255
```

```
Tyr Ser Lys Leu Thr Val Asp Lys Ser Arg Trp Gln Gln Gly Asn Val
        260                 265                 270

Phe Ser Cys Ser Val Met His Glu Ala Leu His Asn His Tyr Thr Gln
        275                 280                 285

Lys Ser Leu Ser Leu Ser Pro Gly Lys
        290                 295

<210> SEQ ID NO 70
<211> LENGTH: 297
<212> TYPE: PRT
<213> ORGANISM: Artificial Sequence
<220> FEATURE:
<223> OTHER INFORMATION: CXCL11-IgG4Fc

<400> SEQUENCE: 70

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Pro Pro Cys Pro Ser Cys Pro
65                  70                  75                  80

Ala Pro Glu Phe Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser Gln Glu Asp Pro Glu Val Gln Phe Asn Trp Tyr
        115                 120                 125

Val Asp Gly Val Glu Val His Asn Ala Lys Thr Lys Pro Arg Glu Glu
    130                 135                 140

Gln Phe Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Gly Leu Pro Ser Ser Ile Glu Lys Thr Ile Ser Lys Ala Lys Gly Gln
            180                 185                 190

Pro Arg Glu Pro Gln Val Tyr Thr Leu Pro Pro Ser Gln Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Arg Leu Thr Val Asp Lys Ser Arg Trp Gln Glu Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
        290                 295

<210> SEQ ID NO 71
```

<211> LENGTH: 294
<212> TYPE: PRT
<213> ORGANISM: Artificial Sequence
<220> FEATURE:
<223> OTHER INFORMATION: CXCL11(4-73)-IgG4Fc

<400> SEQUENCE: 71

Phe Lys Arg Gly Arg Cys Leu Cys Ile Gly Pro Gly Val Lys Ala Val
1               5                   10                  15

Lys Val Ala Asp Ile Glu Lys Ala Ser Ile Met Tyr Pro Ser Asn Asn
            20                  25                  30

Cys Asp Lys Ile Glu Val Ile Ile Thr Leu Lys Glu Asn Lys Gly Gln
        35                  40                  45

Arg Cys Leu Asn Pro Lys Ser Lys Gln Ala Arg Leu Ile Ile Lys Lys
    50                  55                  60

Val Glu Arg Lys Asn Phe Pro Pro Cys Pro Ser Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser Gln Glu Asp Pro Glu Val Gln Phe Asn Trp Tyr Val Asp Gly
        115                 120                 125

Val Glu Val His Asn Ala Lys Thr Lys Pro Arg Glu Glu Gln Phe Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Gly Leu Pro
                165                 170                 175

Ser Ser Ile Glu Lys Thr Ile Ser Lys Ala Lys Gly Gln Pro Arg Glu
            180                 185                 190

Pro Gln Val Tyr Thr Leu Pro Pro Ser Gln Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Arg
                245                 250                 255

Leu Thr Val Asp Lys Ser Arg Trp Gln Glu Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290

<210> SEQ ID NO 72
<211> LENGTH: 294
<212> TYPE: PRT
<213> ORGANISM: Artificial Sequence
<220> FEATURE:
<223> OTHER INFORMATION: CXCL11(4-73K/H-A)-IgG4Fc

<400> SEQUENCE: 72

Phe Lys Arg Gly Arg Cys Leu Cys Ile Gly Pro Gly Val Lys Ala Val
1               5                   10                  15

Lys Val Ala Asp Ile Glu Ala Ala Ser Ile Met Tyr Pro Ser Asn Asn

```
            20                  25                  30
Cys Asp Lys Ile Glu Val Ile Ile Thr Leu Ala Glu Asn Ala Gly Gln
            35                  40                  45

Ala Cys Leu Asn Pro Ala Ser Ala Gln Ala Leu Ile Ile Ala Ala
    50                  55                  60

Val Glu Ala Ala Asn Phe Pro Pro Cys Pro Ser Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
                100                 105                 110

Val Ser Gln Glu Asp Pro Glu Val Gln Phe Asn Trp Tyr Val Asp Gly
            115                 120                 125

Val Glu Val His Asn Ala Lys Thr Lys Pro Arg Glu Glu Gln Phe Asn
        130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Gly Leu Pro
                165                 170                 175

Ser Ser Ile Glu Lys Thr Ile Ser Lys Ala Lys Gly Gln Pro Arg Glu
                180                 185                 190

Pro Gln Val Tyr Thr Leu Pro Pro Ser Gln Glu Glu Met Thr Lys Asn
            195                 200                 205

Gln Val Ser Leu Thr Cys Leu Val Lys Gly Phe Tyr Pro Ser Asp Ile
        210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Arg
                245                 250                 255

Leu Thr Val Asp Lys Ser Arg Trp Gln Glu Gly Asn Val Phe Ser Cys
                260                 265                 270

Ser Val Met His Glu Ala Leu His Asn His Tyr Thr Gln Lys Ser Leu
            275                 280                 285

Ser Leu Ser Pro Gly Lys
            290

<210> SEQ ID NO 73
<211> LENGTH: 314
<212> TYPE: PRT
<213> ORGANISM: Artificial Sequence
<220> FEATURE:
<223> OTHER INFORMATION: CXCL13-IgG1Fc

<400> SEQUENCE: 73

Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
            20                  25                  30

Pro Arg Gly Asn Gly Cys Pro Arg Lys Glu Ile Ile Val Trp Lys Lys
            35                  40                  45

Asn Lys Ser Ile Val Cys Val Asp Pro Gln Ala Glu Trp Ile Gln Arg
        50                  55                  60

Met Met Glu Val Leu Arg Lys Arg Ser Ser Thr Leu Pro Val Pro
65                  70                  75                  80

Val Phe Lys Arg Lys Ile Pro Asp Lys Thr His Thr Cys Pro Pro Cys
```

```
                   85                  90                  95
Pro Ala Pro Glu Leu Leu Gly Gly Pro Ser Val Phe Leu Phe Pro Pro
                100                 105                 110

Lys Pro Lys Asp Thr Leu Met Ile Ser Arg Thr Pro Glu Val Thr Cys
            115                 120                 125

Val Val Val Asp Val Ser His Glu Asp Pro Glu Val Lys Phe Asn Trp
        130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                165                 170                 175

His Gln Asp Trp Leu Asn Gly Lys Glu Tyr Lys Cys Lys Val Ser Asn
            180                 185                 190

Lys Ala Leu Pro Ala Pro Ile Glu Lys Thr Ile Ser Lys Ala Lys Gly
        195                 200                 205

Gln Pro Arg Glu Pro Gln Val Tyr Thr Leu Pro Pro Ser Arg Glu Glu
    210                 215                 220

Met Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
                245                 250                 255

Asn Tyr Lys Thr Thr Pro Pro Val Leu Asp Ser Asp Gly Ser Phe Phe
            260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
    290                 295                 300

Gln Lys Ser Leu Ser Leu Ser Pro Gly Lys
305                 310

<210> SEQ ID NO 74
<211> LENGTH: 312
<212> TYPE: PRT
<213> ORGANISM: Artificial Sequence
<220> FEATURE:
<223> OTHER INFORMATION: CXCL13(3-87)-IgG1Fc

<400> SEQUENCE: 74

Glu Val Tyr Tyr Thr Ser Leu Arg Cys Arg Cys Val Gln Glu Ser Ser
1               5                   10                  15

Val Phe Ile Pro Arg Arg Phe Ile Asp Arg Ile Gln Ile Leu Pro Arg
            20                  25                  30

Gly Asn Gly Cys Pro Arg Lys Glu Ile Ile Val Trp Lys Lys Asn Lys
        35                  40                  45

Ser Ile Val Cys Val Asp Pro Gln Ala Glu Trp Ile Gln Arg Met Met
50                  55                  60

Glu Val Leu Arg Lys Arg Ser Ser Thr Leu Pro Val Pro Val Phe
65                  70                  75                  80

Lys Arg Lys Ile Pro Asp Lys Thr His Thr Cys Pro Pro Cys Pro Ala
            85                  90                  95

Pro Glu Leu Leu Gly Gly Pro Ser Val Phe Leu Phe Pro Pro Lys Pro
        100                 105                 110

Lys Asp Thr Leu Met Ile Ser Arg Thr Pro Glu Val Thr Cys Val Val
    115                 120                 125

Val Asp Val Ser His Glu Asp Pro Glu Val Lys Phe Asn Trp Tyr Val
```

```
                     130                 135                 140
Asp Gly Val Glu Val His Asn Ala Lys Thr Lys Pro Arg Glu Glu Gln
145                 150                 155                 160

Tyr Asn Ser Thr Tyr Arg Val Val Ser Val Leu Thr Val Leu His Gln
                165                 170                 175

Asp Trp Leu Asn Gly Lys Glu Tyr Lys Cys Lys Val Ser Asn Lys Ala
            180                 185                 190

Leu Pro Ala Pro Ile Glu Lys Thr Ile Ser Lys Ala Lys Gly Gln Pro
        195                 200                 205

Arg Glu Pro Gln Val Tyr Thr Leu Pro Pro Ser Arg Glu Glu Met Thr
    210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
            260                 265                 270

Ser Lys Leu Thr Val Asp Lys Ser Arg Trp Gln Gln Gly Asn Val Phe
        275                 280                 285

Ser Cys Ser Val Met His Glu Ala Leu His Asn His Tyr Thr Gln Lys
    290                 295                 300

Ser Leu Ser Leu Ser Pro Gly Lys
305                 310

<210> SEQ ID NO 75
<211> LENGTH: 312
<212> TYPE: PRT
<213> ORGANISM: Artificial Sequence
<220> FEATURE:
<223> OTHER INFORMATION: CXCL13(3-87K/H-A)-IgG1Fc

<400> SEQUENCE: 75

Glu Val Tyr Tyr Thr Ser Leu Arg Cys Arg Cys Val Gln Glu Ser Ser
1               5                   10                  15

Val Phe Ile Pro Arg Arg Phe Ile Asp Ala Ile Gln Ile Leu Pro Arg
            20                  25                  30

Gly Asn Gly Cys Pro Arg Lys Glu Ile Ile Val Trp Ala Ala Asn Ala
        35                  40                  45

Ser Ile Val Cys Val Asp Pro Gln Ala Glu Trp Ile Gln Ala Met Met
    50                  55                  60

Glu Val Leu Ala Ala Ser Ser Ser Thr Leu Pro Val Pro Val Phe
65                  70                  75                  80

Ala Ala Ala Ile Pro Asp Lys Thr His Thr Cys Pro Pro Cys Pro Ala
                85                  90                  95

Pro Glu Leu Leu Gly Gly Pro Ser Val Phe Leu Phe Pro Pro Lys Pro
            100                 105                 110

Lys Asp Thr Leu Met Ile Ser Arg Thr Pro Glu Val Thr Cys Val Val
        115                 120                 125

Val Asp Val Ser His Glu Asp Pro Glu Val Lys Phe Asn Trp Tyr Val
    130                 135                 140

Asp Gly Val Glu Val His Asn Ala Lys Thr Lys Pro Arg Glu Glu Gln
145                 150                 155                 160

Tyr Asn Ser Thr Tyr Arg Val Val Ser Val Leu Thr Val Leu His Gln
                165                 170                 175

Asp Trp Leu Asn Gly Lys Glu Tyr Lys Cys Lys Val Ser Asn Lys Ala
```

```
            180                 185                 190
Leu Pro Ala Pro Ile Glu Lys Thr Ile Ser Lys Ala Lys Gly Gln Pro
            195                 200                 205

Arg Glu Pro Gln Val Tyr Thr Leu Pro Pro Ser Arg Glu Glu Met Thr
        210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
            260                 265                 270

Ser Lys Leu Thr Val Asp Lys Ser Arg Trp Gln Gln Gly Asn Val Phe
        275                 280                 285

Ser Cys Ser Val Met His Glu Ala Leu His Asn His Tyr Thr Gln Lys
    290                 295                 300

Ser Leu Ser Leu Ser Pro Gly Lys
305                 310

<210> SEQ ID NO 76
<211> LENGTH: 311
<212> TYPE: PRT
<213> ORGANISM: Artificial Sequence
<220> FEATURE:
<223> OTHER INFORMATION: CXCL13-IgG4Fc

<400> SEQUENCE: 76

Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
            20                  25                  30

Pro Arg Gly Asn Gly Cys Pro Arg Lys Glu Ile Ile Val Trp Lys Lys
        35                  40                  45

Asn Lys Ser Ile Val Cys Val Asp Pro Gln Ala Glu Trp Ile Gln Arg
    50                  55                  60

Met Met Glu Val Leu Arg Lys Arg Ser Ser Ser Thr Leu Pro Val Pro
65                  70                  75                  80

Val Phe Lys Arg Lys Ile Pro Pro Cys Pro Ser Cys Pro Ala Pro
                85                  90                  95

Glu Phe Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
        115                 120                 125

Asp Val Ser Gln Glu Asp Pro Glu Val Gln Phe Asn Trp Tyr Val Asp
    130                 135                 140

Gly Val Glu Val His Asn Ala Lys Thr Lys Pro Arg Glu Glu Gln Phe
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Gly Leu
            180                 185                 190

Pro Ser Ser Ile Glu Lys Thr Ile Ser Lys Ala Lys Gly Gln Pro Arg
        195                 200                 205

Glu Pro Gln Val Tyr Thr Leu Pro Pro Ser Gln Glu Glu Met Thr Lys
    210                 215                 220

Asn Gln Val Ser Leu Thr Cys Leu Val Lys Gly Phe Tyr Pro Ser Asp
```

```
                225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
                260                 265                 270

Arg Leu Thr Val Asp Lys Ser Arg Trp Gln Glu Gly Asn Val Phe Ser
                275                 280                 285

Cys Ser Val Met His Glu Ala Leu His Asn His Tyr Thr Gln Lys Ser
                290                 295                 300

Leu Ser Leu Ser Pro Gly Lys
305                 310

<210> SEQ ID NO 77
<211> LENGTH: 309
<212> TYPE: PRT
<213> ORGANISM: Artificial Sequence
<220> FEATURE:
<223> OTHER INFORMATION: CXCL13(3-87)-IgG4Fc

<400> SEQUENCE: 77

Glu Val Tyr Tyr Thr Ser Leu Arg Cys Arg Cys Val Gln Glu Ser Ser
1               5                   10                  15

Val Phe Ile Pro Arg Arg Phe Ile Asp Arg Ile Gln Ile Leu Pro Arg
                20                  25                  30

Gly Asn Gly Cys Pro Arg Lys Glu Ile Ile Val Trp Lys Lys Asn Lys
            35                  40                  45

Ser Ile Val Cys Val Asp Pro Gln Ala Glu Trp Ile Gln Arg Met Met
50                  55                  60

Glu Val Leu Arg Lys Arg Ser Ser Ser Thr Leu Pro Val Pro Val Phe
65                  70                  75                  80

Lys Arg Lys Ile Pro Pro Pro Cys Pro Ser Cys Pro Ala Pro Glu Phe
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser Gln Glu Asp Pro Glu Val Gln Phe Asn Trp Tyr Val Asp Gly Val
    130                 135                 140

Glu Val His Asn Ala Lys Thr Lys Pro Arg Glu Gln Phe Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Gly Leu Pro Ser
            180                 185                 190

Ser Ile Glu Lys Thr Ile Ser Lys Ala Lys Gly Gln Pro Arg Glu Pro
        195                 200                 205

Gln Val Tyr Thr Leu Pro Pro Ser Gln Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Arg Leu
                260                 265                 270

Thr Val Asp Lys Ser Arg Trp Gln Glu Gly Asn Val Phe Ser Cys Ser
```

```
              275                 280                 285
Val Met His Glu Ala Leu His Asn His Tyr Thr Gln Lys Ser Leu Ser
290                 295                 300

Leu Ser Pro Gly Lys
305

<210> SEQ ID NO 78
<211> LENGTH: 309
<212> TYPE: PRT
<213> ORGANISM: Artificial Sequence
<220> FEATURE:
<223> OTHER INFORMATION: CXCL13(3-87K/H-A)-IgG4Fc

<400> SEQUENCE: 78

Glu Val Tyr Tyr Thr Ser Leu Arg Cys Arg Cys Val Gln Glu Ser Ser
1               5                   10                  15

Val Phe Ile Pro Arg Arg Phe Ile Asp Ala Ile Gln Ile Leu Pro Arg
            20                  25                  30

Gly Asn Gly Cys Pro Arg Lys Glu Ile Ile Val Trp Ala Ala Asn Ala
        35                  40                  45

Ser Ile Val Cys Val Asp Pro Gln Ala Glu Trp Ile Gln Ala Met Met
    50                  55                  60

Glu Val Leu Ala Ala Ser Ser Ser Thr Leu Pro Val Pro Val Phe
65                  70                  75                  80

Ala Ala Ala Ile Pro Pro Cys Pro Ser Cys Pro Ala Pro Glu Phe
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser Gln Glu Asp Pro Glu Val Gln Phe Asn Trp Tyr Val Asp Gly Val
    130                 135                 140

Glu Val His Asn Ala Lys Thr Lys Pro Arg Glu Gln Phe Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Gly Leu Pro Ser
            180                 185                 190

Ser Ile Glu Lys Thr Ile Ser Lys Ala Lys Gly Gln Pro Arg Glu Pro
        195                 200                 205

Gln Val Tyr Thr Leu Pro Pro Ser Gln Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Arg Leu
            260                 265                 270

Thr Val Asp Lys Ser Arg Trp Gln Glu Gly Asn Val Phe Ser Cys Ser
        275                 280                 285

Val Met His Glu Ala Leu His Asn His Tyr Thr Gln Lys Ser Leu Ser
290                 295                 300

Leu Ser Pro Gly Lys
305
```

<210> SEQ ID NO 79
<211> LENGTH: 4401
<212> TYPE: DNA
<213> ORGANISM: Artificial Sequence
<220> FEATURE:
<223> OTHER INFORMATION: pCCL2-IgG1Fc

<400> SEQUENCE: 79

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gcctttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | cgagggggct | cgcatctctc | cttcacgcgc | ccgccgccct | acctgaggcc | 300 |
| gccatccacg | ccgttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cgcagccaga | tgcaatcaat | gccccagtca | 660 |
| cctgctgtta | taacttcacc | aataggaaga | tctcagtgca | gaggctcgcg | agctatagaa | 720 |
| gaatcaccag | cagcaagtgt | cccaaagaag | ctgtgatctt | caagaccatt | gtggccaagg | 780 |
| agatctgtgc | tgaccccaag | cagaagtggg | ttcaggattc | catggaccac | ctggacaagc | 840 |
| aaacccaaac | tccgaagact | gacaaaactc | acacatgccc | accgtgccca | gcacctgaac | 900 |
| tcctgggggg | accgtcagtc | ttcctcttcc | cccaaaaccc | aaggacaccc | tcatgatctc | 960 |
| cccggacccc | tgaggtcaca | tgcgtggtgg | tggacgtgag | ccacgaagac | cctgaggtca | 1020 |
| agttcaactg | gtacgtggac | ggcgtggagg | tgcataatgc | caagacaaag | ccgcgggagg | 1080 |
| agcagtacaa | cagcacgtac | cgtgtggtca | gcgtcctcac | cgtcctgcac | caggactggc | 1140 |
| tgaatggcaa | ggagtacaag | tgcaaggtct | ccaacaaagc | cctcccagcc | cccatcgaga | 1200 |
| aaaccatctc | caaagccaaa | gggcagcccc | gagaaccaca | ggtgtacacc | ctgcccccat | 1260 |
| cccgggagga | gatgaccaag | aaccaggtca | gcctgacctg | cctggtcaaa | ggcttctatc | 1320 |
| ccagcgacat | cgccgtggag | tgggagagca | atgggcagcc | ggagaacaac | tacaagacca | 1380 |
| cgcctcccgt | gctggactcc | gacggctcct | tcttcctcta | cagcaagctc | accgtggaca | 1440 |
| agagcaggtg | gcagcagggg | aacgtcttct | catgctccgt | gatgcacgag | gctctgcaca | 1500 |
| accactacac | gcagaagagc | ctctccctgt | ctccgggtaa | atgagtgcta | gctggccaga | 1560 |
| catgataaga | tacattgatg | agtttggaca | aaccacaact | agaatgcagt | gaaaaaaatg | 1620 |
| ctttatttgt | gaaatttgtg | atgctattgc | tttatttgta | accattataa | gctgcaataa | 1680 |
| acaagttaac | aacaacaatt | gcattcattt | tatgtttcag | gttcagggggg | aggtgtggga | 1740 |
| ggttttttaa | agcaagtaaa | acctctacaa | atgtggtatg | gaattaattc | taaaatacag | 1800 |
| catagcaaaa | ctttaacctc | caaatcaagc | ctctacttga | atccttttct | gagggatgaa | 1860 |
| taaggcatag | gcatcagggg | ctgttgccaa | tgtgcattag | ctgtttgcag | cctcaccttc | 1920 |
| tttcatggag | tttaagatat | agtgtatttt | cccaaggttt | gaactagctc | ttcatttctt | 1980 |
| tatgttttaa | atgcactgac | ctcccacatt | ccctttttag | taaatattc | agaaataatt | 2040 |
| taaatacatc | attgcaatga | aaataaatgt | ttttattag | gcagaatcca | gatgctcaag | 2100 |

```
gcccttcata atatccccca gtttagtagt tggacttagg gaacaaagga acctttaata    2160
gaaattggac agcaagaaag cgagcttcta gcttatcctc agtcctgctc ctctgccaca    2220
aagtgcacgc agttgccggc cgggtcgcgc agggcgaact cccgccccca cggctgctcg    2280
ccgatctcgg tcatggccgg cccggaggcg tcccggaagt tcgtggacac gacctccgac    2340
cactcggcgt acagctcgtc caggccgcgc acccacaccc aggccagggt gttgtccggc    2400
accacctggt cctggaccgc gctgatgaac agggtcacgt cgtcccggac cacaccggcg    2460
aagtcgtcct ccacgaagtc ccgggagaac ccgagccggt cggtccagaa ctcgaccgct    2520
ccggcgacgt cgcgcgcggt gagcaccgga acggcactgg tcaacttggc catgatggct    2580
cctcctgtca ggagaggaaa gagaagaagg ttagtacaat tgctatagtg agttgtatta    2640
tactatgcag atatactatg ccaatgatta attgtcaaac tagggctgca gggttcatag    2700
tgccactttt cctgcactgc ccatctcct gcccacccctt tcccaggcat agacagtcag    2760
tgacttacca aactcacagg agggagaagg cagaagcttg agacagaccc gcggaccgc    2820
cgaactgcga ggggacgtgg ctagggcggc ttcttttatg gtgcgccggc cctcggaggc    2880
agggcgctcg gggaggccta gcggccaatc tgcggtggca ggaggcgggg ccgaaggccg    2940
tgcctgacca atccggagca cataggagtc tcagcccccc gccccaaagc aaggggaagt    3000
cacgcgcctg tagcgccagc gtgttgtgaa atgggggctt ggggggggttg gggccctgac    3060
tagtcaaaac aaactcccat tgacgtcaat ggggtggaga cttggaaatc cccgtgagtc    3120
aaaccgctat ccacgcccat tgatgtactg ccaaaaccgc atcatcatgg taatagcgat    3180
gactaatacg tagatgtact gccaagtagg aaagtcccat aaggtcatgt actgggcata    3240
atgccaggcg ggccatttac cgtcattgac gtcaataggg ggcgtacttg gcatatgata    3300
cacttgatgt actgccaagt gggcagttta ccgtaaatac tccacccatt gacgtcaatg    3360
gaaagtccct attggcgtta ctatgggaac atacgtcatt attgacgtca atgggcgggg    3420
gtcgttgggc ggtcagccag gcgggccatt taccgtaagt tatgtaacgc ctgcaggtta    3480
attaagaaca tgtgagcaaa aggccagcaa aaggccagga accgtaaaaa ggccgcgttg    3540
ctggcgtttt tccataggct ccgcccccct gacgagcatc acaaaaatcg acgctcaagt    3600
cagaggtggc gaaacccgac aggactataa agataccagg cgtttccccc tggaagctcc    3660
ctcgtgcgct ctcctgttcc gaccctgccg cttaccggat acctgtccgc ctttctccct    3720
tcgggaagcg tggcgctttc tcatagctca cgctgtaggt atctcagttc ggtgtaggtc    3780
gttcgctcca agctgggctg tgtgcacgaa ccccccgttc agcccgaccg ctgcgcctta    3840
tccggtaact atcgtcttga gtccaacccg gtaagacacg acttatcgcc actggcagca    3900
gccactggta acaggattag cagagcgagg tatgtaggcg gtgctacaga gttcttgaag    3960
tggtggccta actacggcta cactagaaga acagtatttg gtatctgcgc tctgctgaag    4020
ccagttacct tcggaaaaag agttggtagc tcttgatccg gcaaacaaac caccgctggt    4080
agcggtggtt tttttgtttg caagcagcag attacgcgca gaaaaaaagg atctcaagaa    4140
gatcctttga tcttttctac ggggtctgac gctcagtgga acgaaaactc acgttaaggg    4200
attttggtca tggctagtta attaacattt aaatcagcgg ccgcaataaa atatctttat    4260
tttcattaca tctgtgtgtt ggttttttgt gtgaatcgta actaacatac gctctccatc    4320
aaaacaaaac gaaacaaaac aaactagcaa ataggctgtc cccagtgca agtgcaggtg    4380
ccagaacatt tctctatcga a                                             4401
```

<210> SEQ ID NO 80
<211> LENGTH: 4389
<212> TYPE: DNA
<213> ORGANISM: Artificial Sequence
<220> FEATURE:
<223> OTHER INFORMATION: pCCL2(5-76)-IgG1Fc

<400> SEQUENCE: 80

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | cgagggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cgatcaatgc | cccagtcacc | tgctgttata | 660 |
| acttcaccaa | taggaagatc | tcagtgcaga | ggctcgcgag | ctatagaaga | atcaccagca | 720 |
| gcaagtgtcc | caaagaagct | gtgatcttca | agaccattgt | ggccaaggag | atctgtgctg | 780 |
| accccaagca | agagtgggtt | caggattcca | tggaccacct | ggacaagcaa | acccaaactc | 840 |
| cgaagactga | caaaactcac | acatgcccac | cgtgcccagc | acctgaactc | ctgggggggac | 900 |
| cgtcagtctt | cctcttcccc | ccaaaaccca | aggacaccct | catgatctcc | cggacccctg | 960 |
| aggtcacatg | cgtggtggtg | gacgtgagcc | acgaagaccc | tgaggtcaag | ttcaactggt | 1020 |
| acgtggacgg | cgtggaggtg | cataatgcca | agacaaagcc | gcgggaggag | cagtacaaca | 1080 |
| gcacgtaccg | tgtggtcagc | gtcctcaccg | tcctgcacca | ggactggctg | aatggcaagg | 1140 |
| agtacaagtg | caaggtctcc | aacaaagccc | tcccagcccc | catcgagaaa | accatctcca | 1200 |
| aagccaaagg | gcagccccga | gaaccacagg | tgtacaccct | gcccccatcc | cgggaggaga | 1260 |
| tgaccaagaa | ccaggtcagc | ctgacctgcc | tggtcaaagg | cttctatccc | agcgacatcg | 1320 |
| ccgtggagtg | ggagagcaat | gggcagccgg | agaacaacta | caagaccacg | cctcccgtgc | 1380 |
| tggactccga | cggctccttc | ttcctctaca | gcaagctcac | cgtggacaag | agcaggtggc | 1440 |
| agcagggaa | cgtcttctca | tgctccgtga | tgcacgaggc | tctgcacaac | cactacacgc | 1500 |
| agaagagcct | ctccctgtct | ccgggtaaat | gagtgctagc | tggccagaca | tgataagata | 1560 |
| cattgatgag | tttggacaaa | ccacaactag | aatgcagtga | aaaaaatgct | ttatttgtga | 1620 |
| aatttgtgat | gctattgctt | tatttgtaac | cattataagc | tgcaataaac | aagttaacaa | 1680 |
| caacaattgc | attcatttta | tgtttcaggt | tcaggggag | gtgtgggagg | ttttttaaag | 1740 |
| caagtaaaac | ctctacaaat | gtggtatgga | attaattcta | aaatacagca | tagcaaaact | 1800 |
| ttaacctcca | aatcaagcct | ctacttgaat | ccttttctga | gggatgaata | aggcataggc | 1860 |
| atcagggct | gttgccaatg | tgcattagct | gtttgcagcc | tcaccttctt | tcatggagtt | 1920 |
| taagatatag | tgtattttcc | caaggtttga | actagctctt | catttcttta | tgttttaaat | 1980 |
| gcactgacct | cccacattcc | cttttagta | aatattcag | aataattta | aatacatcat | 2040 |
| tgcaatgaaa | ataaatgttt | tttattaggc | agaatccaga | tgctcaaggc | ccttcataat | 2100 |

```
atcccccagt ttagtagttg gacttaggga acaaaggaac ctttaatcga aattggacag    2160
caagaaagcg agcttctagc ttatcctcag tcctgctcct ctgccacaaa gtgcacgcag    2220
ttgccggccg ggtcgcgcag ggcgaactcc cgccccacg gctgctcgcc gatctcggtc     2280
atggccggcc cggaggcgtc ccggaagttc gtggacacga cctccgacca ctcggcgtac    2340
agctcgtcca ggccgcgcac ccacacccag gccagggtgt tgtccggcac cacctggtcc    2400
tggaccgcgc tgatgaacag ggtcacgtcg tcccggacca caccggcgaa gtcgtcctcc    2460
acgaagtccc gggagaaccc gagccggtcg gtccagaact cgaccgctcc ggcgacgtcg    2520
cgcgcggtga gcaccggaac ggcactggtc aacttggcca tgatggctcc tcctgtcagg    2580
agaggaaaga gaagaaggtt agtacaattg ctatagtgag ttgtattata ctatgcagat    2640
atactatgcc aatgattaat tgtcaaacta gggctgcagg gttcatagtg ccactttttcc   2700 tgcactgccc catctcctgc ccacccttte ccaggcatag acagtcagtg acttaccaaa    2760
ctcacaggag ggagaaggca gaagcttgag acagacccgc gggaccgccg aactgcgagg    2820
ggacgtggct agggcggctt cttttatggt gcgccggccc tcggaggcag ggcgctcggg    2880
gaggcctagc ggccaatctg cggtggcagg aggcggggcc gaaggccgtg cctgaccaat    2940
ccggagcaca taggagtctc agccccccgc cccaaagcaa ggggaagtca cgcgcctgta    3000
gcgccagcgt gttgtgaaat gggggcttgg ggggttggg gccctgacta gtcaaaacaa     3060
actcccattg acgtcaatgg ggtggagact tggaaatccc cgtgagtcaa accgctatcc    3120
acgcccattg atgtactgcc aaaaccgcat catcatggta atagcgatga ctaatacgta    3180
gatgtactgc caagtaggaa agtcccataa ggtcatgtac tgggcataat gccaggcggg    3240
ccatttaccg tcattgacgt caatagggg cgtacttggc atatgataca cttgatgtac     3300
tgccaagtgg gcagtttacc gtaaatactc cacccattga cgtcaatgga aagtccctat    3360
tggcgttact atgggaacat acgtcattat tgacgtcaat gggcggggt cgttgggcgg     3420 tcagccaggc gggccattta ccgtaagtta tgtaacgcct gcaggttaat taagaacatg    3480
tgagcaaaag gccagcaaaa ggccaggaac cgtaaaaagg ccgcgttgct ggcgtttttc    3540
cataggctcc gccccctga cgagcatcac aaaaatcgac gctcaagtca gaggtggcga     3600
aacccgacag gactataaag ataccaggcg tttccccctg gaagctccct cgtgcgctct    3660
cctgttccga ccctgccgct taccggatac ctgtccgcct ttctcccttc gggaagcgtg    3720
gcgctttctc atagctcacg ctgtaggtat ctcagttcgg tgtaggtcgt tcgctccaag    3780
ctgggctgtg tgcacgaacc ccccgttcag cccgaccgct cgccttatc cggtaactat     3840 cgtcttgagt ccaacccggt aagacacgac ttatcgccac tggcagcagc cactggtaac    3900
aggattagca gagcgaggta tgtaggcggt gctacagagt tcttgaagtg gtggcctaac    3960
tacggctaca ctagaagaac agtatttggt atctgcgctc tgctgaagcc agttaccttc    4020
ggaaaaagag ttggtagctc ttgatccggc aaacaaacca ccgctggtag cggtggtttt    4080
tttgtttgca agcagcagat tacgcgcaga aaaaaggat ctcaagaaga tcctttgatc     4140
ttttctacgg ggtctgacgc tcagtggaac gaaaactcac gttaagggat tttggtcatg    4200
gctagttaat taacatttaa atcagcggcc gcaataaaat atctttattt tcattacatc    4260
tgtgtgttgg ttttttgtgt gaatcgtaac taacatacgc tctccatcaa acaaaacga    4320 aacaaaacaa actagcaaaa taggctgtcc ccagtgcaag tgcaggtgcc agaacatttc    4380
tctatcgaa                                                            4389
```

```
<210> SEQ ID NO 81
<211> LENGTH: 4389
<212> TYPE: DNA
<213> ORGANISM: Artificial Sequence
<220> FEATURE:
<223> OTHER INFORMATION: pCCL2(5-76K/H-A)-IgG1Fc

<400> SEQUENCE: 81
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc ttttcgcaa cgggtttgcc gccagaacac      240
agctgaagct tcgaggggct cgcatctctc cttcacgcgc ccgccgccct acctgaggcc     300
gccatccacg ccggttgagt cgcgttctgc cgcctcccgc tgtggtgcc tcctgaactg      360
cgtccgccgt ctaggtaagt ttaaagctca ggtcgagacc gggcctttgt ccggcgctcc     420
cttggagcct acctgactc agccggctct ccacgctttg cctgaccctg cttgctcaac      480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgatcaatgc cccagtcacc tgctgttata     660
acttcaccaa taggaagatc tcagtgcaga ggctcgcgag ctatagaaga atcaccagca     720
gcaagtgtcc caaagaagct gtgatcttca agaccattgt ggccgcggag atctgtgctg     780
acccccgctca ggcctgggtt caggattcca tggacgctct ggacgcccaa acccaaactc     840
cggcgactga caaaactcac acatgcccac cgtgcccagc acctgaactc ctgggggga c    900
cgtcagtctt cctcttcccc ccaaaaccca aggacaccct catgatctcc cggacccctg    960
aggtcacatg cgtggtggtg gacgtgagcc acgaagaccc tgaggtcaag ttcaactggt   1020
acgtggacgg cgtggaggtg cataatgcca agacaaagcc gcgggaggag cagtacaaca   1080
gcacgtaccg tgtggtcagc gtcctcaccg tcctgcacca ggactggctg aatggcaagg   1140
agtacaagtg caaggtctcc aacaaagccc tcccagcccc catcgagaaa accatctcca   1200
aagccaaagg gcagccccga gaaccacagg tgtacaccct gcccccatcc cgggaggaga   1260
tgaccaagaa ccaggtcagc ctgacctgcc tggtcaaagg cttctatccc agcgacatcg   1320
ccgtggagtg ggagagcaat gggcagccgg agaacaacta caagaccacg cctcccgtgc   1380
tggactccga cggctccttc ttcctctaca gcaagctcac cgtggacaag agcaggtggc   1440
agcagggaa cgtcttctca tgctccgtga tgcacgagg tctgcacaac cactacacgc    1500
agaagagcct ctccctgtct ccgggtaaat gagtgctagc tggccagaca tgataagata   1560
cattgatgag tttggacaaa ccacaactag aatgcagtga aaaaaatgct ttatttgtga   1620
aatttgtgat gctattgctt tatttgtaac cattataagc tgcaataaac aagttaacaa   1680
caacaattgc attcatttta tgtttcaggt tcaggggag gtgtgggagg ttttttaaag   1740
caagtaaaac ctctacaaat gtggtatgga attaattcta aaatacagca tagcaaaact   1800
ttaacctcca atcaagcct ctacttgaat cctttctga gggatgaata aggcataggc      1860
atcaggggct gttgccaatg tgcattagct gtttgcagcc tcaccttctt tcatggagtt   1920
taagatatag tgtattttcc caaggtttga actagctctt catttcttta tgttttaaat   1980
gcactgacct cccacattcc ctttttagta aatattcag aaataattta atacatcat    2040
tgcaatgaaa ataaatgttt tttattaggc agaatccaga tgctcaaggc ccttcataat   2100
```

```
atcccccagt ttagtagttg gacttaggga acaaaggaac ctttaatgaa aattggacag    2160
caagaaagcg agcttctagc ttatcctcag tcctgctcct ctgccacaaa gtgcacgcag    2220
ttgccggccg ggtcgcgcag ggcgaactcc cgcccccacg gctgctcgcc gatctcggtc    2280
atggccggcc cggaggcgtc ccggaagttc gtggacacga cctccgacca ctcggcgtac    2340
agctcgtcca ggccgcgcac ccacacccag gccagggtgt tgtccggcac cacctggtcc    2400
tggaccgcgc tgatgaacag ggtcacgtcg tcccggacca caccggcgaa gtcgtcctcc    2460
acgaagtccc gggagaaccc gagccggtcg gtccagaact cgaccgctcc ggcgacgtcg    2520
cgcgcggtga gcaccggaac ggcactggtc aacttggcca tgatggctcc tcctgtcagg    2580
agaggaaaga gaagaaggtt agtacaattg ctatagtgag ttgtattata ctatgcagat    2640
atactatgcc aatgattaat tgtcaaacta gggctgcagg gttcatagtg ccacttttcc    2700
tgcactgccc catctcctgc ccaccctttc ccaggcatag acagtcagtg acttaccaaa    2760
ctcacaggag ggagaaggca gaagcttgag acagacccgc gggaccgccg aactgcgagg    2820
ggacgtggct agggcggctt cttttatggt gcgccggccc tcggaggcag ggcgctcggg    2880
gaggcctagc ggccaatctg cggtggcagg aggcggggcc gaaggccgtg cctgaccaat    2940
ccggagcaca taggagtctc agccccccgc cccaaagcaa ggggaagtca cgcgcctgta    3000
gcgccagcgt gttgtgaaat gggggcttgg ggggttggg gccctgacta gtcaaaacaa     3060
actcccattg acgtcaatgg ggtggagact tggaaatccc cgtgagtcaa accgctatcc    3120
acgcccattg atgtactgcc aaaaccgcat catcatggta atagcgatga ctaatacgta    3180
gatgtactgc caagtaggaa agtcccataa ggtcatgtac tgggcataat gccaggcggg    3240
ccatttaccg tcattgacgt caataggggg cgtacttggc atatgataca cttgatgtac    3300
tgccaagtgg gcagtttacc gtaaatactc cacccattga cgtcaatgga aagtccctat    3360
tggcgttact atgggaacat acgtcattat tgacgtcaat gggcgggggt cgttgggcgg    3420
tcagccaggc gggccattta ccgtaagtta tgtaacgcct gcaggttaat taagaacatg    3480
tgagcaaaag gccagcaaaa ggccaggaac cgtaaaaagg ccgcgttgct ggcgtttttc    3540
cataggctcc gccccctga cgagcatcac aaaaatcgac gctcaagtca gaggtggcga     3600
aacccgacag gactataaag ataccaggcg tttccccctg gaagctccct cgtgcgctct    3660
cctgttccga ccctgccgct taccggatac ctgtccgcct ttctcccttc gggaagcgtg    3720
gcgctttctc atagctcacg ctgtaggtat ctcagttcgg tgtaggtcgt tcgctccaag    3780
ctgggctgtg tgcacgaacc ccccgttcag cccgaccgct cgccttatc cggtaactat     3840 cgtcttgagt ccaacccggt aagacacgac ttatcgccac tggcagcagc cactggtaac    3900
aggattagca gagcgaggta tgtaggcggt gctacagagt tcttgaagtg gtggcctaac    3960
tacggctaca ctagaagaac agtatttggt atctgcgctc tgctgaagcc agttaccttc    4020
ggaaaaagag ttggtagctc ttgatccggc aaacaaacca ccgctggtag cggtggtttt    4080
tttgtttgca agcagcagat tacgcgcaga aaaaaggat ctcaagaaga tcctttgatc     4140
ttttctacgg ggtctgacgc tcagtggaac gaaaactcac gttaagggat tttggtcatg    4200
gctagttaat taacatttaa atcagcggcc gcaataaaat atctttattt tcattacatc    4260
tgtgtgttgg ttttttgtgt gaatcgtaac taacatacgc tctccatcaa acaaaacga     4320 aacaaaacaa actagcaaaa taggctgtcc ccagtgcaag tgcaggtgcc agaacatttc    4380
tctatcgaa                                                           4389
```

<210> SEQ ID NO 82
<211> LENGTH: 4371
<212> TYPE: DNA
<213> ORGANISM: Artificial Sequence
<220> FEATURE:
<223> OTHER INFORMATION: pCCL7-IgG1Fc

<400> SEQUENCE: 82

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttcc | cgagggtggg | ggagaaccgt | 180 |
| atataagtgc | agtagtcgcc | gtgaacgttc | ttttcgcaa | cgggtttgcc | gccagaacac | 240 |
| agctgaagct | cgagggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cgtgctgcta | cagatttatc | aataagaaaa | 660 |
| tccctaagca | gaggctggag | agctacagaa | ggaccaccag | tagccactgt | ccccgggaag | 720 |
| ctgtaatctt | caagaccaaa | ctggacaagg | agatctgtgc | tgaccccaca | cagaagtggg | 780 |
| tccaggactt | tatgaagcac | ctggacaaga | aacccaaac | tccaaagctt | gacaaaactc | 840 |
| acacatgccc | accgtgccca | gcacctgaac | tcctgggggg | accgtcagtc | ttcctcttcc | 900 |
| ccccaaaacc | caaggacacc | ctcatgatct | cccggacccc | tgaggtcaca | tgcgtggtgg | 960 |
| tggacgtgag | ccacgaagac | cctgaggtca | agttcaactg | gtacgtggac | ggcgtggagg | 1020 |
| tgcataatgc | caagacaaag | ccgcgggagg | agcagtacaa | cagcacgtac | cgtgtggtca | 1080 |
| gcgtcctcac | cgtcctgcac | caggactggc | tgaatggcaa | ggagtacaag | tgcaaggtct | 1140 |
| ccaacaaagc | cctcccagcc | cccatcgaga | aaaccatctc | caaagccaaa | gggcagcccc | 1200 |
| gagaaccaca | ggtgtacacc | ctgcccccat | cccgggagga | gatgaccaag | aaccaggtca | 1260 |
| gcctgacctg | cctggtcaaa | ggcttctatc | ccagcgacat | cgccgtggag | tgggagagca | 1320 |
| atgggcagcc | ggagaacaac | tacaagacca | cgcctcccgt | gctggactcc | gacggctcct | 1380 |
| tcttcctcta | cagcaagctc | accgtggaca | agagcaggtg | gcagcagggg | aacgtcttct | 1440 |
| catgctccgt | gatgcacgag | gctctgcaca | accactacac | gcagaagagc | ctctccctgt | 1500 |
| ctccgggtaa | atgagtgcta | gctggccaga | catgataaga | tacattgatg | agtttggaca | 1560 |
| aaccacaact | agaatgcagt | gaaaaaaatg | ctttatttgt | gaaatttgtg | atgctattgc | 1620 |
| tttatttgta | accattataa | gctgcaataa | acaagttaac | aacaacaatt | gcattcattt | 1680 |
| tatgtttcag | gttcagggg | aggtgtggga | ggttttttaa | agcaagtaaa | acctctacaa | 1740 |
| atgtggtatg | gaattaattc | taaaatacag | catagcaaaa | ctttaacctc | caaatcaagc | 1800 |
| ctctacttga | atccttttct | gagggatgaa | taaggcatag | gcatcagggg | ctgttgccaa | 1860 |
| tgtgcattag | ctgtttgcag | cctcaccttc | tttcatggag | tttaagatat | agtgtatttt | 1920 |
| cccaaggttt | gaactagctc | ttcatttctt | tatgttttaa | atgcactgac | ctcccacatt | 1980 |
| ccctttttag | taaatattc | agaataatt | taaatacatc | attgcaatga | aaataaatgt | 2040 |
| tttttattag | gcagaatcca | gatgctcaag | gcccttcata | atatcccca | gtttagtagt | 2100 |

```
tggacttagg gaacaaagga acctttaata gaaattggac agcaagaaag cgagcttcta    2160
gcttatcctc agtcctgctc ctctgccaca aagtgcacgc agttgccggc cgggtcgcgc    2220
agggcgaact cccgcccca cggctgctcg ccgatctcgg tcatggccgg cccggaggcg     2280
tcccggaagt tcgtggacac gacctccgac cactcggcgt acagctcgtc caggccgcgc    2340
acccacaccc aggccagggt gttgtccggc accacctggt cctggaccgc gctgatgaac    2400
agggtcacgt cgtcccggac cacaccggcg aagtcgtcct ccacgaagtc ccgggagaac    2460
ccgagccggt cggtccagaa ctcgaccgct ccggcgacgt cgcgcgcggt gagcaccgga    2520
acggcactgg tcaacttggc catgatggct cctcctgtca ggagaggaaa gagaagaagg    2580
ttagtacaat tgctatagtg agttgtatta tactatgcag atatactatg ccaatgatta    2640
attgtcaaac tagggctgca gggttcatag tgccacttt cctgcactgc cccatctcct     2700
gcccacccctt tcccaggcat agacagtcag tgacttacca aactcacagg agggagaagg   2760
cagaagcttg agacagaccc gcgggaccgc cgaactgcga ggggacgtgg ctagggcggc    2820
ttcttttatg gtgcgccggc cctcggaggc agggcgctcg gggaggccta gcggccaatc    2880
tgcggtggca ggaggcgggg ccgaaggccg tgcctgacca atccggagca cataggagtc    2940
tcagccccccc gccccaaagc aagggggaagt cacgcgcctg tagcgccagc gtgttgtgaa   3000
atggggcctt ggggggttg gggccctgac tagtcaaaac aaactcccat tgacgtcaat     3060
ggggtggaga cttggaaatc cccgtgagtc aaaccgctat ccacgcccat tgatgtactg    3120
ccaaaaccgc atcatcatgg taatagcgat gactaatacg tagatgtact gccaagtagg    3180
aaagtcccat aaggtcatgt actgggcata atgccaggcg ggccatttac cgtcattgac    3240
gtcaataggg ggcgtacttg gcatatgata cacttgatgt actgccaagt gggcagttta    3300
ccgtaaatac tccaccccatt gacgtcaatg gaaagtccct attggcgtta ctatgggaac   3360
atacgtcatt attgacgtca atgggcgggg gtcgttgggc ggtcagccag gcgggccatt    3420
taccgtaagt tatgtaacgc ctgcaggtta attaagaaca tgtgagcaaa aggccagcaa    3480
aaggccagga accgtaaaaa ggccgcgttg ctggcgtttt tccataggct ccgcccccct    3540
gacgagcatc acaaaaatcg acgctcaagt cagaggtggc gaaacccgac aggactataa    3600
agataccagg cgtttccccc tggaagctcc ctcgtgcgct ctcctgttcc gaccctgccg    3660
cttaccggat acctgtccgc cttttctccct tcgggaagcg tggcgctttc tcatagctca   3720
cgctgtaggt atctcagttc ggtgtaggtc gttcgctcca agctgggctg tgtgcacgaa    3780
ccccccgttc agcccgaccg ctgcgcctta tccggtaact atcgtcttga gtccaacccg    3840
gtaagacacg acttatcgcc actggcagca gccactggta acaggattag cagagcgagg    3900
tatgtaggcg gtgctacaga gttcttgaag tggtggccta actacggcta cactagaaga    3960
acagtatttg gtatctgcgc tctgctgaag ccagttacct tcggaaaaag agttggtagc    4020
tcttgatccg gcaaacaaac caccgctggt agcggtggtt ttttttgtttg caagcagcag    4080
attacgcgca gaaaaaaagg atctcaagaa gatcctttga tcttttctac ggggtctgac    4140
gctcagtgga acgaaaactc acgttaaggg attttggtca tggctagtta attaacattt    4200
aaatcagcgg ccgcaataaa atatctttat tttcattaca tctgtgtgtt ggttttttgt    4260
gtgaatcgta actaacatac gctctccatc aaaacaaaac gaaacaaaac aaactagcaa    4320
aataggctgt ccccagtgca agtgcaggtg ccagaacatt tctctatcga a             4371
```

<210> SEQ ID NO 83
<211> LENGTH: 4359

<212> TYPE: DNA
<213> ORGANISM: Artificial Sequence
<220> FEATURE:
<223> OTHER INFORMATION: pCCL7(5-76)-IgG1Fc

<400> SEQUENCE: 83

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttcc cgagggtggg ggagaaccgt      180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggccttgt ccggcgctcc      420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgtttatcaa taagaaaatc cctaagcaga     660
ggctggagag ctacagaagg accaccagta gccactgtcc ccgggaagct gtaatcttca     720
agaccaaact ggacaaggag atctgtgctg accccacaca gaagtgggtc caggacttta     780
tgaagcacct ggacaagaaa acccaaactc aaagcttga caaaactcac acatgcccac      840
cgtgcccagc acctgaactc ctggggggac cgtcagtctt cctcttcccc ccaaaaccca     900
aggacaccct catgatctcc cggacccctg aggtcacatg cgtggtggtg gacgtgagcc     960
acgaagaccc tgaggtcaag ttcaactggt acgtggacgg cgtggaggtg cataatgcca    1020
agacaaagcc gcgggaggag cagtacaaca gcacgtaccg tgtggtcagc gtcctcaccg    1080
tcctgcacca ggactggctg aatggcaagg agtacaagtg caaggtctcc aacaaagccc    1140
tcccagcccc catcgagaaa accatctcca agccaaagg gcagcccga gaaccacagg      1200
tgtacaccct gcccccatcc cgggaggaga tgaccaagaa ccaggtcagc ctgacctgcc    1260
tggtcaaagg cttctatccc agcgacatcg ccgtggagtg ggagagcaat gggcagccgg    1320
agaacaacta caagaccacg cctcccgtgc tggactccga cggctccttc ttcctctaca    1380
gcaagctcac cgtggacaag agcaggtggc agcaggggga cgtcttctca tgctccgtga    1440
tgcacgaggc tctgcacaac cactacacgc agaagagcct ctccctgtct ccgggtaaat    1500
gagtgctagc tggccagaca tgataagata cattgatgag tttggacaaa ccacaactag    1560
aatgcagtga aaaaaatgct ttatttgtga aatttgtgat gctattgctt tatttgtaac    1620
cattataagc tgcaataaac aagttaacaa caacaattgc attcatttta tgtttcaggt    1680
tcaggggag gtgtgggagg ttttttaaag caagtaaaac ctctacaaat gtggtatgga    1740
attaattcta aaatacagca tagcaaaact ttaacctcca aatcaagcct ctacttgaat    1800
ccttttctga gggatgaata aggcataggc atcagggct gttgccaatg tgcattagct    1860
gtttgcagcc tcaccttctt tcatggagtt taagatatag tgtattttcc caaggtttga    1920
actagctctt catttcttta tgttttaaat gcactgacct cccacattcc cttttagta    1980
aaatattcag aaataattta aatacatcat tgcaatgaaa ataaatgttt tttattaggc    2040
agaatccaga tgctcaaggc ccttcataat atccccagt ttagtagttg gacttaggga    2100
acaaaggaac ctttaataga aattggacag caagaaagcg agcttctagc ttatcctcag    2160
```

```
tcctgctcct ctgccacaaa gtgcacgcag ttgccggccg ggtcgcgcag ggcgaactcc    2220
cgcccccacg gctgctcgcc gatctcggtc atggccggcc cggaggcgtc ccggaagttc    2280
gtggacacga cctccgacca ctcggcgtac agctcgtcca ggccgcgcac ccacacccag    2340
gccagggtgt tgtccggcac cacctggtcc tggaccgcgc tgatgaacag ggtcacgtcg    2400
tcccggacca caccggcgaa gtcgtcctcc acgaagtccc gggagaaccc gagccggtcg    2460
gtccagaact cgaccgctcc ggcgacgtcg cgcgcggtga gcaccggaac ggcactggtc    2520
aacttggcca tgatggctcc tcctgtcagg agaggaaaga aagaaggtt agtacaattg     2580 ctatagtgag ttgtattata ctatgcagat atactatgcc aatgattaat tgtcaaacta    2640
gggctgcagg gttcatagtg ccacttttcc tgcactgccc catctcctgc ccacccttc     2700 ccaggcatag acagtcagtg acttaccaaa ctcacaggag ggagaaggca gaagcttgag    2760
acagacccgc gggaccgccg aactgcgagg ggacgtggct agggcggctt cttttatggt    2820
gcgccggccc tcggaggcag ggcgctcggg gaggcctagc ggccaatctg cggtggcagg    2880
aggcggggcc gaaggccgtg cctgaccaat ccggagcaca taggagtctc agcccccgc     2940 cccaaagcaa ggggaagtca cgcgcctgta gcgccagcgt gttgtgaaat ggggcttgg     3000 gggggttggg gccctgacta gtcaaaacaa actcccattg acgtcaatgg ggtggagact    3060
tggaaatccc cgtgagtcaa accgctatcc acgcccattg atgtactgcc aaaaccgcat    3120
catcatggta atagcgatga ctaatacgta gatgtactgc caagtaggaa agtcccataa    3180
ggtcatgtac tgggcataat gccaggcggg ccatttaccg tcattgacgt caataggggg    3240
cgtacttggc atatgataca cttgatgtac tgccaagtgg gcagtttacc gtaaatactc    3300
cacccattga cgtcaatgga aagtccctat tggcgttact atgggaacat acgtcattat    3360
tgacgtcaat gggcgggggt cgttgggcgg tcagccaggc gggccattta ccgtaagtta    3420
tgtaacgcct gcaggttaat taagaacatg tgagcaaaag gccagcaaaa ggccaggaac    3480
cgtaaaaagg ccgcgttgct ggcgtttttc cataggctcc gcccccctga cgagcatcac    3540
aaaaatcgac gctcaagtca gaggtggcga aacccgacag gactataaag ataccaggcg    3600
tttccccctg gaagctccct cgtgcgctct cctgttccga ccctgccgct taccggatac    3660
ctgtccgcct ttctcccttc gggaagcgtg gcgctttctc atagctcacg ctgtaggtat    3720
ctcagttcgg tgtaggtcgt tcgctccaag ctgggctgtg tgcacgaacc ccccgttcag    3780
cccgaccgct gcgccttatc cggtaactat cgtcttgagt ccaacccggt aagacacgac    3840
ttatcgccac tggcagcagc cactggtaac aggattagca gagcgaggta tgtaggcggt    3900
gctacagagt tcttgaagtg gtggcctaac tacggctaca ctagaagaac agtatttggt    3960
atctgcgctc tgctgaagcc agttaccttc ggaaaaagag ttggtagctc ttgatccggc    4020
aaacaaacca ccgctggtag cggtggtttt tttgtttgca agcagcagat tacgcgcaga    4080
aaaaaaggat ctcaagaaga tcctttgatc ttttctacgg ggtctgacgc tcagtggaac    4140
gaaaactcac gttaagggat tttggtcatg ctagttaat taacatttaa atcagcggcc     4200
gcaataaaat atctttattt tcattacatc tgtgtgttgg ttttttgtgt gaatcgtaac    4260
taacatacgc tctccatcaa aacaaaacga aacaaaacaa actagcaaaa taggctgtcc    4320
ccagtgcaag tgcaggtgcc agaacatttc tctatcgaa                          4359

<210> SEQ ID NO 84
<211> LENGTH: 4359
<212> TYPE: DNA
<213> ORGANISM: Artificial Sequence
```

<220> FEATURE:
<223> OTHER INFORMATION: pCCL7(5-76K/H-A)-IgG1Fc

<400> SEQUENCE: 84

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | tcgaggggct | cgcatctctc | cttcacgcgc | ccgccgccct | acctgaggcc | 300 |
| gccatccacg | ccgttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cgtttatcaa | taagaaaatc | cctaagcaga | 660 |
| ggctggagag | ctacagaagg | accaccagta | gccactgtcc | ccgggaagct | gtaatcttcg | 720 |
| ccaccgcgct | ggacgctgag | atctgtgctg | accccacaca | ggcctgggtc | caggacttta | 780 |
| tggctgccct | ggacgcggct | acccaaactc | agcccttga | caaaactcac | acatgcccac | 840 |
| cgtgcccagc | acctgaactc | ctggggggac | cgtcagtctt | cctcttcccc | ccaaaaccca | 900 |
| aggacaccct | catgatctcc | cggacccctg | aggtcacatg | cgtggtggtg | gacgtgagcc | 960 |
| acgaagaccc | tgaggtcaag | ttcaactggt | acgtggacgg | cgtggaggtg | cataatgcca | 1020 |
| agacaaagcc | gcgggaggag | cagtacaaca | gcacgtaccg | tgtggtcagc | gtcctcaccg | 1080 |
| tcctgcacca | ggactggctg | aatggcaagg | agtacaagtg | caaggtctcc | aacaaagccc | 1140 |
| tcccagcccc | catcgagaaa | accatctcca | aagccaaagg | gcagcccga | gaaccacagg | 1200 |
| tgtacaccct | gcccccatcc | cgggaggaga | tgaccaagaa | ccaggtcagc | ctgacctgcc | 1260 |
| tggtcaaagg | cttctatccc | agcgacatcg | ccgtggagtg | ggagagcaat | gggcagccgg | 1320 |
| agaacaacta | caagaccacg | cctcccgtgc | tggactccga | cggctccttc | ttcctctaca | 1380 |
| gcaagctcac | cgtggacaag | agcaggtggc | agcaggggaa | cgtcttctca | tgctccgtga | 1440 |
| tgcacgaggc | tctgcacaac | cactacacgc | agaagagcct | ctccctgtct | ccgggtaaat | 1500 |
| gagtgctagc | tggccagaca | tgataagata | cattgatgag | tttggacaaa | ccacaactag | 1560 |
| aatgcagtga | aaaaaatgct | ttatttgtga | aatttgtgat | gctattgctt | tatttgtaac | 1620 |
| cattataagc | tgcaataaac | aagttaacaa | caacaattgc | attcatttta | tgtttcaggt | 1680 |
| tcaggggag | gtgtgggagg | ttttttaaag | caagtaaaac | tctacaaat | gtggtatgga | 1740 |
| attaattcta | aaatacagca | tagcaaaact | ttaacctcca | aatcaagcct | ctacttgaat | 1800 |
| ccttttctga | gggatgaata | aggcataggc | atcagggct | gttgccaatg | tgcattagct | 1860 |
| gtttgcagcc | tcaccttctt | tcatggagtt | taagatatag | tgtattttcc | caaggtttga | 1920 |
| actagctctt | catttcttta | tgttttaaat | gcactgacct | cccacattcc | cttttagta | 1980 |
| aaatattcag | aaataattta | aatacatcat | tgcaatgaaa | ataaatgttt | tttattaggc | 2040 |
| agaatccaga | tgctcaaggc | ccttcataat | atccccagt | ttagtagttg | gacttaggga | 2100 |
| acaaaggaac | ctttaataga | aattggacag | caagaaagcg | agcttctagc | ttatcctcag | 2160 |
| tcctgctcct | ctgccacaaa | gtgcacgcag | ttgccggccg | ggtcgcgcag | ggcgaactcc | 2220 |

| | |
|---|---|
| cgcccccacg gctgctcgcc gatctcggtc atggccggcc cggaggcgtc ccggaagttc | 2280 |
| gtggacacga cctccgacca ctcggcgtac agctcgtcca ggccgcgcac ccacacccag | 2340 |
| gccagggtgt tgtccggcac cacctggtcc tggaccgcgc tgatgaacag ggtcacgtcg | 2400 |
| tcccggacca caccggcgaa gtcgtcctcc acgaagtccc gggagaaccc gagccggtcg | 2460 |
| gtccagaact cgaccgctcc ggcgacgtcg cgcgcggtga gcaccggaac ggcactggtc | 2520 |
| aacttggcca tgatggctcc tcctgtcagg agaggaaaga gaagaaggtt agtacaattg | 2580 |
| ctatagtgag ttgtattata ctatgcagat atactatgcc aatgattaat tgtcaaacta | 2640 |
| gggctgcagg gttcatagtg ccactttttcc tgcactgccc catctcctgc ccacccttttc | 2700 |
| ccaggcatag acagtcagtg acttaccaaa ctcacaggag ggagaaggca gaagcttgag | 2760 |
| acagacccgc gggaccgccg aactgcgagg ggacgtggct agggcggctt ctttttatggt | 2820 |
| gcgccggccc tcggaggcag ggcgctcggg gaggcctagc ggccaatctg cggtggcagg | 2880 |
| aggcggggcc gaaggccgtg cctgaccaat ccggagcaca taggagtctc agccccccgc | 2940 |
| cccaaagcaa ggggaagtca cgcgcctgta gcgccagcgt gttgtgaaat gggggcttgg | 3000 |
| gggggttggg gccctgacta gtcaaaacaa actcccattg acgtcaatgg ggtggagact | 3060 |
| tggaaatccc cgtgagtcaa accgctatcc acgcccattg atgtactgcc aaaaccgcat | 3120 |
| catcatggta atagcgatga ctaatacgta gatgtactgc caagtaggaa agtcccataa | 3180 |
| ggtcatgtac tgggcataat gccaggcggg ccatttaccg tcattgacgt caatagggg | 3240 |
| cgtacttggc atatgataca cttgatgtac tgccaagtgg gcagtttacc gtaaatactc | 3300 |
| cacccattga cgtcaatgga aagtccctat tggcgttact atgggaacat acgtcattat | 3360 |
| tgacgtcaat gggcgggggt cgttgggcgg tcagccaggc gggccattta ccgtaagtta | 3420 |
| tgtaacgcct gcaggttaat taagaacatg tgagcaaaag gccagcaaaa ggccaggaac | 3480 |
| cgtaaaaagg ccgcgttgct ggcgtttttc cataggctcc gccccctga cgagcatcac | 3540 |
| aaaaatcgac gctcaagtca gaggtggcga aacccgacag gactataaag ataccaggcg | 3600 |
| tttccccctg gaagctccct cgtgcgctct cctgttccga ccctgccgct taccggatac | 3660 |
| ctgtccgcct ttctcccttc gggaagcgtg gcgctttctc atagctcacg ctgtaggtat | 3720 |
| ctcagttcgg tgtaggtcgt tcgctccaag ctgggctgtg tgcacgaacc ccccgttcag | 3780 |
| cccgaccgct gcgccttatc cggtaactat cgtcttgagt ccaacccggt aagacacgac | 3840 |
| ttatcgccac tggcagcagc cactggtaac aggattagca gagcgaggta tgtaggcggt | 3900 |
| gctacagagt tcttgaagtg gtggcctaac tacggctaca ctagaagaac agtatttggt | 3960 |
| atctgcgctc tgctgaagcc agttaccttc ggaaaaagag ttggtagctc ttgatccggc | 4020 |
| aaacaaacca ccgctggtag cggtggtttt tttgtttgca agcagcagat tacgcgcaga | 4080 |
| aaaaaaggat ctcaagaaga tcctttgatc ttttctacgg ggtctgacgc tcagtggaac | 4140 |
| gaaaactcac gttaagggat tttggtcatg ctagttaat taacatttaa atcagcggcc | 4200 |
| gcaataaaat atctttattt tcattacatc tgtgtgttgg ttttttgtgt gaatcgtaac | 4260 |
| taacatacgc tctccatcaa aacaaaacga aacaaaacaa actagcaaaa taggctgtcc | 4320 |
| ccagtgcaag tgcaggtgcc agaacatttc tctatcgaa | 4359 |

```
<210> SEQ ID NO 85
<211> LENGTH: 4401
<212> TYPE: DNA
<213> ORGANISM: Artificial Sequence
<220> FEATURE:
<223> OTHER INFORMATION: pCCL8-IgG1Fc
```

<400> SEQUENCE: 85

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc ttttttcgcaa cgggtttgcc gccagaacac    240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgcagccaga ttcagtttcc attccaatca     660
cctgctgctt taacgtgatc aataggaaaa ttcctatcca gaggctggag agctacacaa     720
gaatcaccaa catccaatgt cccaaggaag ctgtgatctt caagaccaaa cggggcaagg     780
aggtctgtgc tgaccccaag gagagatggg tcagggattc catgaagcat ctggaccaaa     840
tatttcaaaa tctgaagcca gacaaaactc acacatgccc accgtgccca gcacctgaac     900
tcctgggggg accgtcagtc ttcctcttcc ccccaaaacc caaggacacc ctcatgatct     960
cccggacccc tgaggtcaca tgcgtggtgg tggacgtgag ccacgaagac cctgaggtca    1020
agttcaactg gtacgtggac ggcgtggagg tgcataatgc caagacaaag ccgcgggagg    1080
agcagtacaa cagcacgtac cgtgtggtca gcgtcctcac cgtcctgcac caggactggc    1140
tgaatggcaa ggagtacaag tgcaaggtct ccaacaaagc cctcccagcc cccatcgaga    1200
aaaccatctc caaagccaaa gggcagcccc gagaaccaca ggtgtacacc ctgcccccat    1260
cccgggagga tgaccaagaa ccaggtcagc ctgacctgcc tggtcaaagg cttctatc     1320
ccagcgacat cgccgtggag tgggagagca atgggcagcc ggagaacaac tacaagacca    1380
cgcctcccgt gctggactcc gacggctcct tcttcctcta cagcaagctc accgtggaca    1440
agagcaggtg gcagcagggg aacgtcttct catgctccgt gatgcacgag gctctgcaca    1500
accactacac gcagaagagc ctctccctgt ctccgggtaa atgagtgcta gctggccaga    1560
catgataaga tacattgatg agtttggaca aaccacaact agaatgcagt gaaaaaaatg    1620
ctttatttgt gaaatttgtg atgctattgc tttatttgta accattataa gctgcaataa    1680
acaagttaac aacaacaatt gcattcattt tatgtttcag gttcaggggg aggtgtggga    1740
ggttttttaa agcaagtaaa acctctacaa atgtggtatg gaattaattc taaaatacag    1800
catagcaaaa ctttaaccct caaatcaagc ctctacttga atcctttttct gagggatgaa    1860
taaggcatag gcatcagggg ctgttgccaa tgtgcattag ctgtttgcag cctcaccttc    1920
tttcatggag tttaagatat agtgtatttt cccaaggttt gaactagctc ttcatttctt    1980
tatgttttaa atgcactgac ctcccacatt cccttttttag taaatattc agaaataatt     2040
taaatacatc attgcaatga aaataaatgt tttttattag gcagaatcca gatgctcaag    2100
gcccttcata atatccccca gtttagtagt tggacttagg gaacaaagga acctttaata    2160
gaaattggac agcaagaaag cgagcttcta gcttatcctc agtcctgctc ctctgccaca    2220
aagtgcacgc agttgccggc cgggtcgcgc agggcgaact cccgccccca cggctgctcg    2280
```

```
ccgatctcgg tcatggccgg cccggaggcg tcccggaagt tcgtggacac gacctccgac    2340
cactcggcgt acagctcgtc caggccgcgc acccacaccc aggccagggt gttgtccggc    2400
accacctggt cctggaccgc gctgatgaac agggtcacgt cgtcccggac cacaccggcg    2460
aagtcgtcct ccacgaagtc ccgggagaac ccgagccggt cggtccagaa ctcgaccgct    2520
ccggcgacgt cgcgcgcggt gagcaccgga acggcactgg tcaacttggc catgatggct    2580
cctcctgtca ggagaggaaa gagaagaagg ttagtacaat tgctatagtg agttgtatta    2640
tactatgcag atatactatg ccaatgatta attgtcaaac tagggctgca gggttcatag    2700
tgccactttt cctgcactgc ccatctcct gcccacccttt cccaggcat agacagtcag     2760 tgacttacca aactcacagg agggagaagg cagaagcttg agacagaccc gcgggaccgc    2820
cgaactgcga gggacgtgg ctaggcggc ttctttatg gtgcgccggc cctcggaggc       2880
agggcgctcg gggaggccta gcggccaatc tgcggtggca ggaggcgggg ccgaaggccg    2940
tgcctgacca atccggagca cataggagtc tcagcccccc gccccaaagc aaggggaagt    3000
cacgcgcctg tagcgccagc gtgttgtgaa atggggggctt gggggggttg gggccctgac   3060
tagtcaaaac aaactcccat tgacgtcaat ggggtggaga cttggaaatc cccgtgagtc    3120
aaaccgctat ccacgcccat tgatgtactg ccaaaaccgc atcatcatgg taatagcgat    3180
gactaatacg tagatgtact gccaagtagg aaagtcccat aaggtcatgt actgggcata   3240
atgccaggcg ggccatttac cgtcattgac gtcaataggg ggcgtacttg gcatatgata   3300
cacttgatgt actgccaagt gggcagttta ccgtaaatac tccacccatt gacgtcaatg   3360
gaaagtccct attggcgtta ctatgggaac atacgtcatt attgacgtca atgggcgggg   3420
gtcgttgggc ggtcagccag gcgggccatt taccgtaagt tatgtaacgc ctgcaggtta   3480
attaagaaca tgtgagcaaa aggccagcaa aaggccagga accgtaaaaa ggccgcgttg   3540
ctggcgtttt tccataggct ccgcccccct gacgagcatc acaaaaatcg acgctcaagt   3600
cagaggtggc gaaacccgac aggactataa agataccagg cgtttccccc tggaagctcc   3660
ctcgtgcgct ctcctgttcc gaccctgccg cttaccggat acctgtccgc ctttctccct   3720
tcgggaagcg tggcgctttc tcatagctca cgctgtaggt atctcagttc ggtgtaggtc   3780
gttcgctcca agctgggctg tgtgcacgaa ccccccgttc agcccgaccg ctgcgcctta   3840
tccggtaact atcgtcttga gtccaacccg gtaagcacg acttatcgcc actggcagca    3900
gccactggta acaggattag cagagcgagg tatgtaggcg gtgctacaga gttcttgaag   3960
tggtggccta actacggcta cactagaaga acagtatttg gtatctgcgc tctgctgaag   4020
ccagttacct tcggaaaaag agttggtagc tcttgatccg gcaaacaaac caccgctggt   4080
agcggtggtt ttttgtttg caagcagcag attacgcgca gaaaaaaagg atctcaagaa    4140
gatcctttga tcttttctac ggggtctgac gctcagtgga cgaaaactc acgttaaggg    4200 attttggtca tggctagtta attaacattt aaatcagcgg ccgcaataaa atatctttat   4260
tttcattaca tctgtgtgtt ggttttttgt gtgaatcgta actaacatac gctctccatc   4320
aaaacaaaac gaaacaaaac aaactagcaa ataggctgt ccccagtgca agtgcaggtg    4380
ccagaacatt tctctatcga a                                             4401

<210> SEQ ID NO 86
<211> LENGTH: 4389
<212> TYPE: DNA
<213> ORGANISM: Artificial Sequence
<220> FEATURE:
<223> OTHER INFORMATION: pCCL8(5-76)-IgG1Fc
```

<400> SEQUENCE: 86

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc ttttttcgcaa cgggtttgcc gccagaacac   240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggccctttgt ccggcgctcc   420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggtttccat tccaatcacc tgctgcttta    660
acgtgatcaa taggaaaatt cctatccaga ggctggagag ctacacaaga atcaccaaca    720
tccaatgtcc caaggaagct gtgatcttca agaccaaacg gggcaaggag gtctgtgctg    780
accccaagga gagatgggtc agggattcca tgaagcatct ggaccaaata tttcaaaatc    840
tgaagccaga caaaactcac acatgcccac cgtgcccagc acctgaactc ctggggggac    900
cgtcagtctt cctcttcccc ccaaaaccca aggacaccct catgatctcc cggacccctg    960
aggtcacatg cgtggtggtg gacgtgagcc acgaagaccc tgaggtcaag ttcaactggt   1020
acgtggacgg cgtggaggtg cataatgcca agacaaagcc gcgggaggag cagtacaaca   1080
gcacgtaccg tgtggtcagc gtcctcaccg tcctgcacca ggactggctg aatggcaagg   1140
agtacaagtg caaggtctcc aacaaagccc tcccagcccc catcgagaaa accatctcca   1200
aagccaaagg gcagccccga gaaccacagg tgtacaccct gcccccatcc cgggaggaga   1260
tgaccaagaa ccaggtcagc ctgacctgcc tggtcaaagg cttctatccc agcgacatcg   1320
ccgtggagtg ggagagcaat gggcagccgg agaacaacta caagaccacg cctcccgtgc   1380
tggactccga cggctccttc ttcctctaca gcaagctcac cgtggacaag agcaggtggc   1440
agcaggggaa cgtcttctca tgctccgtga tgcacgaggc tctgcacaac cactacacgc   1500
agaagagcct ctccctgtct ccgggtaaat gagtgctagc tggccagaca tgataagata   1560
cattgatgag tttggacaaa ccacaactag aatgcagtga aaaaaatgct ttatttgtga   1620
aatttgtgat gctattgctt tatttgtaac cattataagc tgcaataaac aagttaacaa   1680
caacaattgc attcatttta tgtttcaggt tcaggggagg gtgtgggagg ttttttaaag   1740
caagtaaaac ctctacaaat gtggtatgga attaattcta aaatacagca tagcaaaact   1800
ttaacctcca aatcaagcct tacttgaat ccttttctga gggatgaata aggcataggc   1860
atcaggggct gttgccaatg tgcattagct gtttgcagcc tcaccttctt tcatggagtt   1920
taagatatag tgtattttcc caaggtttga actagctctt catttcttta tgttttaaat   1980
gcactgacct cccacattcc cttttttagta aatattcag aaataattta aatacatcat   2040
tgcaatgaaa ataaatgttt tttattaggc agaatccaga tgctcaaggc ccttcataat   2100
atcccccagt ttagtagttg gacttaggga acaaaggaac ctttaataga aattggacag   2160
caagaaagcg agcttctagc ttatcctcag tcctgctcct ctgccacaaa gtgcacgcag   2220
ttgccggccg ggtcgcgcag ggcgaactcc cgccccacg gctgctcgcc gatctcggtc   2280
```

| | |
|---|---|
| atggccggcc cggaggcgtc ccggaagttc gtggacacga cctccgacca ctcggcgtac | 2340 |
| agctcgtcca ggccgcgcac ccacacccag gccagggtgt tgtccggcac cacctggtcc | 2400 |
| tggaccgcgc tgatgaacag ggtcacgtcg tcccggacca caccggcgaa gtcgtcctcc | 2460 |
| acgaagtccc gggagaaccc gagccggtcg gtccagaact cgaccgctcc ggcgacgtcg | 2520 |
| cgcgcggtga gcaccggaac ggcactggtc aacttggcca tgatggctcc tcctgtcagg | 2580 |
| agaggaaaga gaagaaggtt agtacaattg ctatagtgag ttgtattata ctatgcagat | 2640 |
| atactatgcc aatgattaat tgtcaaacta gggctgcagg gttcatagtg ccacttttcc | 2700 |
| tgcactgccc catctcctgc ccacccttc ccaggcatag acagtcagtg acttaccaaa | 2760 |
| ctcacaggag ggagaaggca gaagcttgag acagacccgc gggaccgccg aactgcgagg | 2820 |
| ggacgtggct agggcggctt ctttatggt gcgccggccc tcggaggcag ggcgctcggg | 2880 |
| gaggcctagc ggccaatctg cggtggcagg aggcggggcc gaaggccgtg cctgaccaat | 2940 |
| ccggagcaca taggagtctc agcccccgc cccaaagcaa ggggaagtca cgcgcctgta | 3000 |
| gcgccagcgt gttgtgaaat gggggcttgg ggggttggg gccctgacta gtcaaaacaa | 3060 |
| actcccattg acgtcaatgg ggtggagact tggaaatccc cgtgagtcaa accgctatcc | 3120 |
| acgcccattg atgtactgcc aaaaccgcat catcatggta atagcgatga ctaatacgta | 3180 |
| gatgtactgc caagtaggaa agtcccataa ggtcatgtac tgggcataat gccaggcggg | 3240 |
| ccatttaccg tcattgacgt caatagggg cgtacttggc atatgataca cttgatgtac | 3300 |
| tgccaagtgg gcagtttacc gtaaatactc cacccattga cgtcaatgga aagtccctat | 3360 |
| tggcgttact atgggaacat acgtcattat tgacgtcaat gggcggggt cgttgggcgg | 3420 |
| tcagccaggc gggccattta ccgtaagtta tgtaacgcct gcaggttaat taagaacatg | 3480 |
| tgagcaaaag gccagcaaaa ggccaggaac cgtaaaaagg ccgcgttgct ggcgtttttc | 3540 |
| cataggctcc gccccctga cgagcatcac aaaaatcgac gctcaagtca gaggtggcga | 3600 |
| aacccgacag gactataaag ataccaggcg ttccccctg gaagctccct cgtgcgctct | 3660 |
| cctgttccga ccctgccgct taccggatac ctgtccgcct ttctcccttc gggaagcgtg | 3720 |
| gcgctttctc atagctcacg ctgtaggtat ctcagttcgg tgtaggtcgt tcgctccaag | 3780 |
| ctgggctgtg tgcacgaacc ccccgttcag cccgaccgct gcgccttatc cggtaactat | 3840 |
| cgtcttgagt ccaacccggt aagacacgac ttatcgccac tggcagcagc cactggtaac | 3900 |
| aggattagca gagcgaggta tgtaggcggt gctacagagt tcttgaagtg gtggcctaac | 3960 |
| tacggctaca ctagaagaac agtatttggt atctgcgctc tgctgaagcc agttaccttc | 4020 |
| ggaaaaagag ttggtagctc ttgatccggc aaacaaacca ccgctggtag cggtggtttt | 4080 |
| tttgtttgca agcagcagat tacgcgcaga aaaaaaggat ctcaagaaga tcctttgatc | 4140 |
| ttttctacgg ggtctgacgc tcagtggaac gaaaactcac gttaagggat tttggtcatg | 4200 |
| gctagttaat taacatttaa atcagcggcc gcaataaaat atctttattt tcattacatc | 4260 |
| tgtgtgttgg ttttttgtgt gaatcgtaac taacatacgc tctccatcaa acaaaacga | 4320 |
| aacaaaacaa actagcaaaa taggctgtcc ccagtgcaag tgcaggtgcc agaacatttc | 4380 |
| tctatcgaa | 4389 |

<210> SEQ ID NO 87
<211> LENGTH: 4389
<212> TYPE: DNA
<213> ORGANISM: Artificial Sequence
<220> FEATURE:
<223> OTHER INFORMATION: pCCL8(5-76K/H-A)-IgG1Fc

<400> SEQUENCE: 87

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttcc cgagggtggg ggagaaccgt      180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggtttccat tccaatcacc tgctgcttta     660
acgtgatcaa taggaaaatt cctatccaga ggctggagag ctacacaaga atcaccaaca     720
tccaatgtcc caaggaagct gtgatcttca agaccgccgc gggcgctgag gtctgtgctg     780
accccgccga ggcgtgggtc gctgattcca tggccgcgct ggaccaaata tttcaaaatc     840
tggctccaga caaaactcac acatgcccac cgtgcccagc acctgaactc ctggggggac     900
cgtcagtctt cctcttcccc ccaaaaccca aggacaccct catgatctcc cggacccctg     960
aggtcacatg cgtggtggtg gacgtgagcc acgaagaccc tgaggtcaag ttcaactggt    1020
acgtggacgg cgtggaggtg cataatgcca agacaaagcc gcgggaggag cagtacaaca    1080
gcacgtaccg tgtggtcagc gtcctcaccg tcctgcacca ggactggctg aatggcaagg    1140
agtacaagtg caaggtctcc aacaaagccc tcccagcccc catcgagaaa accatctcca    1200
aagccaaagg gcagccccga gaaccacagg tgtacaccct gcccccatcc cgggaggaga    1260
tgaccaagaa ccaggtcagc ctgacctgcc tggtcaaagg cttctatccc agcgacatcg    1320
ccgtggagtg ggagagcaat gggcagccgg agaacaacta caagaccacg cctcccgtgc    1380
tggactccga cggctccttc ttcctctaca gcaagctcac cgtggacaag agcaggtggc    1440
agcaggggaa cgtcttctca tgctccgtga tgcacgaggc tctgcacaac cactacacgc    1500
agaagagcct ctccctgtct ccgggtaaat gagtgctagc tggccagaca tgataagata    1560
cattgatgag tttggacaaa ccacaactag aatgcagtga aaaaaatgct ttatttgtga    1620
aatttgtgat gctattgctt tatttgtaac cattataagc tgcaataaac aagttaacaa    1680
caacaattgc attcatttta tgtttcaggt tcaggggagg tgtgggagg tttttaaag     1740
caagtaaaac ctctacaaat gtggtatgga attaattcta aaatacagca tagcaaaact    1800
ttaacctcca aatcaagcct ctacttgaat ccttttctga gggatgaata aggcataggc    1860
atcaggggct gttgccaatg tgcattagct gtttgcagcc tcaccttctt tcatggagtt    1920
taagatatag tgtattttcc caaggtttga actagctctt catttcttta tgttttaaat    1980
gcactgacct cccacattcc ctttttagta aatattcag aaataattta aatacatcat    2040
tgcaatgaaa ataaatgttt tttattaggc agaatccaga tgctcaaggc ccttcataat    2100
atccccagt ttagtagttg gacttaggga acaaaggaac ctttaataga aattggacag    2160
caagaaagcg agcttctagc ttatcctcag tcctgctcct ctgccacaaa gtgcacgcag    2220
ttgccggccg ggtcgcgcag ggcgaactcc cgcccccacg gctgctcgcc gatctcggtc    2280
```

```
atggccggcc cggaggcgtc ccggaagttc gtggacacga cctccgacca ctcggcgtac    2340
agctcgtcca ggccgcgcac ccacacccag gccagggtgt tgtccggcac cacctggtcc    2400
tggaccgcgc tgatgaacag ggtcacgtcg tcccggacca caccggcgaa gtcgtcctcc    2460
acgaagtccc gggagaaccc gagccggtcg gtccagaact cgaccgctcc ggcgacgtcg    2520
cgcgcggtga gcaccggaac ggcactggtc aacttggcca tgatggctcc tcctgtcagg    2580
agaggaaaga gaagaaggtt agtacaattg ctatagtgag ttgtattata ctatgcagat    2640
atactatgcc aatgattaat tgtcaaacta gggctgcagg gttcatagtg ccacttttcc    2700
tgcactgccc catctcctgc ccacccttc ccaggcatag acagtcagtg acttaccaaa    2760
ctcacaggag ggagaaggca gaagcttgag acagacccgc gggaccgccg aactgcgagg    2820
ggacgtggct agggcggctt ctttatggt gcgccggccc tcggaggcag ggcgctcggg    2880
gaggcctagc ggccaatctg cggtggcagg aggcggggcc gaaggccgtg cctgaccaat    2940
ccggagcaca taggagtctc agccccccgc cccaaagcaa ggggaagtca cgcgcctgta    3000
gcgccagcgt gttgtgaaat gggggcttgg ggggttggg gccctgacta gtcaaaacaa    3060
actcccattg acgtcaatgg ggtggagact tggaaatccc cgtgagtcaa accgctatcc    3120
acgcccattg atgtactgcc aaaaccgcat catcatggta atagcgatga ctaatacgta    3180
gatgtactgc caagtaggaa agtcccataa ggtcatgtac tgggcataat gccaggcggg    3240
ccatttaccg tcattgacgt caatagggg cgtacttggc atatgataca cttgatgtac    3300
tgccaagtgg gcagtttacc gtaaatactc cacccattga cgtcaatgga aagtccctat    3360
tggcgttact atgggaacat acgtcattat tgacgtcaat gggcggggt cgttgggcgg    3420
tcagccaggc gggccatttta ccgtaagtta tgtaacgcct gcaggttaat taagaacatg    3480
tgagcaaaag gccagcaaaa ggccaggaac cgtaaaaagg ccgcgttgct ggcgttttc    3540
cataggctcc gccccctga cgagcatcac aaaaatcgac gctcaagtca gaggtggcga    3600
aacccgacag gactataaag ataccaggcg tttcccctg gaagctccct cgtgcgctct    3660
cctgttccga ccctgccgct taccggatac ctgtccgcct ttctccttc gggaagcgtg    3720
gcgctttctc atagctcacg ctgtaggtat ctcagttcgg tgtaggtcgt tcgctccaag    3780
ctgggctgtg tgcacgaacc ccccgttcag cccgaccgct gcgccttatc cggtaactat    3840
cgtcttgagt ccaacccggt aagacacgac ttatcgccac tggcagcagc cactggtaac    3900
aggattagca gagcgaggta tgtaggcggt gctacagagt tcttgaagtg gtggcctaac    3960
tacggctaca ctagaagaac agtatttggt atctgcgctc tgctgaagcc agttaccttc    4020
ggaaaaagag ttggtagctc ttgatccggc aaacaaacca ccgctggtag cggtggtttt    4080
tttgtttgca agcagcagat tacgcgcaga aaaaaaggat ctcaagaaga tcctttgatc    4140
ttttctacgg ggtctgacgc tcagtggaac gaaaactcac gttaagggat tttggtcatg    4200
gctagttaat taacatttaa atcagcggcc gcaataaaat atctttattt tcattacatc    4260
tgtgtgttgg ttttttgtgt gaatcgtaac taacatacgc tctccatcaa acaaaacga    4320
aacaaaacaa actagcaaaa taggctgtcc ccagtgcaag tgcaggtgcc agaacatttc    4380
tctatcgaa                                                           4389
```

<210> SEQ ID NO 88
<211> LENGTH: 4398
<212> TYPE: DNA
<213> ORGANISM: Artificial Sequence
<220> FEATURE:
<223> OTHER INFORMATION: pCCL13-IgG1Fc

<400> SEQUENCE: 88

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg taccggcgc      540
ctacctgaga tcaccggcga aggagggcca ccatgtacag gatgcaactc ctgtcttgca     600
ttgcactaag tcttgcactt gtcacgaatt cgcagccaga tgcactcaac gtcccatcta     660
cttgctgctt cacatttagc agtaagaaga tctccttgca gaggctgaag agctatgtga     720
tcaccaccag caggtgtccc cagaaggctg tcatcttcag aaccaaactg ggcaaggaga     780
tctgtgctga cccaaaggag aagtgggtcc agaattatat gaaacacctg gccggaaag     840
ctcacaccct gaagactgac aaaactcaca catgcccacc gtgcccagca cctgaactcc     900
tgggggggacc gtcagtcttc ctcttccccc caaaacccaa ggacaccctc atgatctccc     960
ggacccctga ggtcacatgc gtggtggtgg acgtgagcca cgaagaccct gaggtcaagt    1020
tcaactggta cgtggacggc gtggaggtgc ataatgccaa gacaaagccg cgggaggagc    1080
agtacaacag cacgtaccgt gtggtcagcg tcctcaccgt cctgcaccag gactggctga    1140
atggcaagga gtacaagtgc aaggtctcca acaaagccct cccagccccc atcgagaaaa    1200
ccatctccaa agccaagggg cagccccgag aaccacaggt gtacaccctg cccccatccc    1260
gggaggagat gaccaagaac caggtcagcc tgacctgcct ggtcaaaggc ttctatccca    1320
gcgacatcgc cgtggagtgg gagagcaatg ggcagccgga gaacaactac aagaccacgc    1380
ctcccgtgct ggactccgac ggctccttct tcctctacag caagctcacc gtggacaaga    1440
gcaggtggca gcaggggaac gtcttctcat gctccgtgat gcacgaggct ctgcacaacc    1500
actacacgca gaagagcctc tccctgtctc cgggtaaatg agtgctagct ggccagacat    1560
gataagatac attgatgagt ttggacaaac cacaactaga atgcagtgaa aaaaatgctt    1620
tatttgtgaa atttgtgatg ctattgcttt atttgtaacc attataagct gcaataaaca    1680
agttaacaac aacaattgca ttcattttat gtttcaggtt caggggagg tgtgggaggt    1740
ttttttaaagc aagtaaaacc tctacaaatg tggtatggaa ttaattctaa aatacagcat    1800
agcaaaactt taacctccaa atcaagcctc tacttgaatc cttttctgag ggatgaataa    1860
ggcataggca tcaggggctg ttgccaatgt gcattagctg tttgcagcct caccttcttt    1920
catggagttt aagatatagt gtattttccc aaggtttgaa ctagctcttc atttctttat    1980
gttttaaatg cactgacctc ccacattccc ttttagtaa aatattcaga ataatttaa      2040
atacatcatt gcaatgaaaa taatgttttt ttattaggca gaatccagat gctcaaggcc    2100
cttcataata tcccccagtt tagtagttgg acttagggaa caaggaacc tttaatagaa    2160
attgacagc aagaaagcga gcttctagct tatcctcagt cctgctcctc tgccacaaag    2220
tgcacgcagt tgccggccgg gtcgcgcagg gcgaactccc gcccccacgg ctgctcgccg    2280
```

```
atctcggtca tggccggccc ggaggcgtcc cggaagttcg tggacacgac ctccgaccac   2340
tcggcgtaca gctcgtccag gccgcgcacc cacacccagg ccagggtgtt gtccggcacc   2400
acctggtcct ggaccgcgct gatgaacagg gtcacgtcgt cccggaccac accggcgaag   2460
tcgtcctcca cgaagtcccg ggagaacccg agccggtcgg tccagaactc gaccgctccg   2520
gcgacgtcgc gcgcggtgag caccggaacg gcactggtca acttggccat gatggctcct   2580
cctgtcagga gaggaaagag aagaaggtta gtacaattgc tatagtgagt tgtattatac   2640
tatgcagata tactatgcca atgattaatt gtcaaactag ggctgcaggg ttcatagtgc   2700
cacttttcct gcactgcccc atctcctgcc cacccttttcc caggcataga cagtcagtga   2760
cttaccaaac tcacaggagg gagaaggcag aagcttgaga cagacccgcg ggaccgccga   2820
actgcgaggg gacgtggcta gggcggcttc ttttatggtg cgccggccct cggaggcagg   2880
gcgctcgggg aggcctagcg gccaatctgc ggtggcagga ggcggggccg aaggccgtgc   2940
ctgaccaatc cggagcacat aggagtctca gccccccgcc ccaaagcaag gggaagtcac   3000
gcgcctgtag cgccagcgtg ttgtgaaatg ggggcttggg ggggttgggg ccctgactag   3060
tcaaaacaaa ctcccattga cgtcaatggg gtggagactt ggaaatcccc gtgagtcaaa   3120
ccgctatcca cgcccattga tgtactgcca aaaccgcatc atcatggtaa tagcgatgac   3180
taatacgtag atgtactgcc aagtaggaaa gtcccataag gtcatgtact gggcataatg   3240
ccaggcgggc catttaccgt cattgacgtc aatagggggc gtacttggca tatgatacac   3300
ttgatgtact gccaagtggg cagtttaccg taaatactcc acccattgac gtcaatggaa   3360
agtccctatt ggcgttacta tgggaacata cgtcattatt gacgtcaatg ggcgggggtc   3420
gttgggcggt cagccaggcg ggccatttac cgtaagttat gtaacgcctg caggttaatt   3480
aagaacatgt gagcaaaagg ccagcaaaag gccaggaacc gtaaaaaggc cgcgttgctg   3540
gcgttttttcc ataggctccg ccccccctgac gagcatcaca aaaatcgacg ctcaagtcag   3600
aggtggcgaa acccgacagg actataaaga taccaggcgt ttccccctgg aagctccctc   3660
gtgcgctctc ctgttccgac cctgccgctt accggatacc tgtccgcctt tctcccttcg   3720
ggaagcgtgg cgctttctca gctcacgc tgtaggtatc tcagttcggt gtaggtcgtt   3780
cgctccaagc tgggctgtgt gcacgaaccc cccgttcagc ccgaccgctg cgccttatcc   3840
ggtaactatc gtcttgagtc aacccggta agacacgact tatcgccact ggcagcagcc   3900
actggtaaca ggattagcag agcgaggtat gtaggcggtg ctacagagtt cttgaagtgg   3960
tggcctaact acggctacac tagaagaaca gtatttggta tctgcgctct gctgaagcca   4020
gttaccttcg gaaaaagagt tggtagctct tgatccggca aacaaaccac cgctggtagc   4080
ggtggttttt ttgtttgcaa gcagcagatt acgcgcagaa aaaaaggatc tcaagaagat   4140
cctttgatct tttctacggg gtctgacgct cagtggaacg aaaactcacg ttaagggatt   4200
ttggtcatgg ctagttaatt aacatttaaa tcagcggccg caataaaata tcttttatttt   4260
cattacatct gtgtgttggt ttttttgtgtg aatcgtaact aacatacgct ctccatcaaa   4320
acaaaacgaa acaaaacaaa ctagcaaaat aggctgtccc cagtgcaagt gcaggtgcca   4380
gaacatttct ctatcgaa                                                  4398
```

<210> SEQ ID NO 89
<211> LENGTH: 4386
<212> TYPE: DNA
<213> ORGANISM: Artificial Sequence
<220> FEATURE:
<223> OTHER INFORMATION: pCCL13(5-75)-IgG1Fc

<400> SEQUENCE: 89

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgctcaacgt cccatctact tgctgcttca    660
catttagcag taagaagatc tccttgcaga ggctgaagag ctatgtgatc accaccagca    720
ggtgtcccca gaaggctgtc atcttcagaa ccaaactggg caaggagatc tgtgctgacc    780
caaaggagaa gtgggtccag aattatatga acacctggg ccggaaagct cacaccctga    840
agactgacaa aactcacaca tgcccaccgt gcccagcacc tgaactcctg ggggaccgt    900
cagtcttcct cttcccccca aaacccaagg acaccctcat gatctcccgg acccctgagg    960
tcacatgcgt ggtggtggac gtgagccacg aagaccctga ggtcaagttc aactggtacg   1020
tggacggcgt ggaggtgcat aatgccaaga caaagccgcg ggaggagcag tacaacagca   1080
cgtaccgtgt ggtcagcgtc ctcaccgtcc tgcaccagga ctggctgaat ggcaaggagt   1140
acaagtgcaa ggtctccaac aaagccctcc cagcccccat cgagaaaacc atctccaaag   1200
ccaaagggca gccccgagaa ccacaggtgt acaccctgcc cccatcccgg gaggagatga   1260
ccaagaacca ggtcagcctg acctgcctgg tcaaaggctt ctatcccagc gacatcgccg   1320
tggagtggga gagcaatggg cagccggaga acaactacaa gaccacgcct cccgtgctgg   1380
actccgacgg ctccttcttc ctctacagca agctcaccgt ggacaagagc aggtggcagc   1440
aggggaacgt cttctcatgc tccgtgatgc acgaggctct gcacaaccac tacacgcaga   1500
agagcctctc cctgtctccg ggtaaatgag tgctagctgg ccagacatga taagatacat   1560
tgatgagttt ggacaaacca caactagaat gcagtgaaaa aaatgcttta tttgtgaaat   1620
ttgtgatgct attgctttat ttgtaaccat tataagctgc aataaacaag ttaacaacaa   1680
caattgcatt catttttatgt ttcaggttca gggggaggtg tgggaggttt tttaaagcaa   1740
gtaaaacctc tacaaatgtg gtatggaatt aattctaaaa tacagcatag caaaacttta   1800
acctccaaat caagcctcta cttgaatcct tttctgaggg atgaataagg cataggcatc   1860
aggggctgtt gccaatgtgc attagctgtt tgcagcctca ccttctttca tggagtttaa   1920
gatatagtgt atttttcccaa ggtttgaact agctcttcat ttctttatgt tttaaatgca   1980
ctgacctccc acattccctt tttagtaaaa tattcagaaa taatttaaat acatcattgc   2040
aatgaaaata aatgttttt attaggcaga atccagatgc tcaaggccct tcataatatc   2100
ccccagttta gtagttggac ttagggaaca aaggaacctt aatagaaat tggacagcaa   2160
gaaagcgagc ttctagctta tcctcagtcc tgctcctctg ccacaaagtg cacgcagttg   2220
ccggccgggt cgcgcagggc gaactcccgc ccccacggct gctcgccgat ctcggtcatg   2280
```

```
gccggcccgg aggcgtcccg gaagttcgtg gacacgacct ccgaccactc ggcgtacagc      2340
tcgtccaggc cgcgcaccca cacccaggcc agggtgttgt ccggcaccac ctggtcctgg      2400
accgcgctga tgaacagggt cacgtcgtcc cggaccacac cggcgaagtc gtcctccacg      2460
aagtcccggg agaacccgag ccggtcggtc agaactcga ccgctccggc gacgtcgcgc       2520
gcggtgagca ccggaacggc actggtcaac ttggccatga tggctcctcc tgtcaggaga      2580
ggaaagagaa gaaggttagt acaattgcta tagtgagttg tattatacta tgcagatata     2640
ctatgccaat gattaattgt caaactaggg ctgcagggtt catagtgcca cttttcctgc     2700
actgccccat ctcctgccca cccttttccca ggcatagaca gtcagtgact taccaaactc    2760
acaggaggga gaaggcagaa gcttgagaca gacccgcggg accgccgaac tgcgagggga    2820
cgtggctagg gcggcttctt ttatggtgcg ccggccctcg gaggcagggc gctcggggag    2880
gcctagcggc caatctgcgg tggcaggagg cggggccgaa ggccgtgcct gaccaatccg   2940
gagcacatag gagtctcagc cccccgcccc aaagcaaggg gaagtcacgc gcctgtagcg    3000
ccagcgtgtt gtgaaatggg ggcttggggg ggttggggcc ctgactagtc aaaacaaact    3060
cccattgacg tcaatggggt ggagacttgg aaatccccgt gagtcaaacc gctatccacg    3120
cccattgatg tactgccaaa accgcatcat catggtaata gcgatgacta atacgtagat    3180
gtactgccaa gtaggaaagt cccataaggt catgtactgg gcataatgcc aggcgggcca    3240
tttaccgtca ttgacgtcaa tagggggcgt acttggcata tgatacactt gatgtactgc    3300
caagtgggca gtttaccgta atactccac ccattgacgt caatggaaag tccctattgg     3360
cgttactatg ggaacatacg tcattattga cgtcaatggg cggggtcgt tgggcggtca    3420 gccaggcggg ccatttaccg taagttatgt aacgcctgca ggttaattaa gaacatgtga   3480
gcaaaaggcc agcaaaaggc caggaaccgt aaaaaggccg cgttgctggc gtttttccat    3540
aggctccgcc cccctgacga gcatcacaaa aatcgacgct caagtcagag gtggcgaaac   3600
ccgacaggac tataaagata ccaggcgttt cccctggaa gctccctcgt gcgctctcct    3660
gttccgaccc tgccgcttac cggatacctg tccgccttc tcccttcggg aagcgtggcg     3720
ctttctcata gctcacgctg taggtatctc agttcggtgt aggtcgttcg ctccaagctg    3780
ggctgtgtgc acgaaccccc cgttcagccc gaccgctgcg ccttatccgg taactatcgt    3840
cttgagtcca acccggtaag acacgactta tcgccactgg cagcagccac tggtaacagg    3900
attagcagag cgaggtatgt aggcggtgct acagagttct tgaagtggtg cctaactac     3960 ggctacacta gaagaacagt atttggtatc tgcgctctgc tgaagccagt taccttcgga    4020
aaaagagttg gtagctcttg atccggcaaa caaaccaccg ctggtagcgg tggttttttt    4080
gtttgcaagc agcagattac gcgcagaaaa aaaggatctc aagaagatcc tttgatcttt    4140
tctacggggt ctgacgctca gtggaacgaa aactcacgtt aagggatttt ggtcatggct    4200
agttaattaa catttaaatc agcggccgca ataaatatc tttatttca ttacatctgt      4260 gtgttggttt tttgtgtgaa tcgtaactaa catacgctcc ccatcaaaac aaaacgaaac   4320
aaaacaaact agcaaaatag gctgtcccca gtgcaagtgc aggtgccaga acatttctct    4380
atcgaa                                                                4386
```

<210> SEQ ID NO 90
<211> LENGTH: 4386
<212> TYPE: DNA
<213> ORGANISM: Artificial Sequence
<220> FEATURE:
<223> OTHER INFORMATION: pCCL13(5-75K/H-A)-IgG1Fc

<400> SEQUENCE: 90

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc ttttttcgcaa cgggtttgcc gccagaacac    240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgctcaacgt cccatctact tgctgcttca     660
catttagcag taagaagatc tccttgcaga ggctgaagag ctatgtgatc accaccagca     720
ggtgtcccca gaaggctgtc atcttcagaa ccgccctggg cgcggagatc tgtgctgacc     780
cagccgaggc ctgggtccag aattatatgg cggctctggg ccggaaagct gccaccctgg     840
ctactgacaa aactcacaca tgcccaccgt gcccagcacc tgaactcctg ggggaccgt     900
cagtcttcct cttcccccca aaacccaagg acaccctcat gatctcccgg acccctgagg     960
tcacatgcgt ggtggtggac gtgagccacg aagaccctga ggtcaagttc aactggtacg    1020
tggacggcgt ggaggtgcat aatgccaaga caaagccgcg ggaggagcag tacaacagca    1080
cgtaccgtgt ggtcagcgtc ctcaccgtcc tgcaccagga ctggctgaat ggcaaggagt    1140
acaagtgcaa ggtctccaac aaagccctcc cagcccccat cgagaaaacc atctccaaag    1200
ccaaagggca gccccgagaa ccacaggtgt acaccctgcc cccatcccgg gaggagatga    1260
ccaagaacca ggtcagcctg acctgcctgg tcaaaggctt ctatcccagc gacatcgccg    1320
tggagtggga gagcaatggg cagccggaga acaactacaa gaccacgcct cccgtgctgg    1380
actccgacgg ctccttcttc ctctacagca agctcaccgt ggacaagagc aggtggcagc    1440
aggggaacgt cttctcatgc tccgtgatgc acgaggctct gcacaaccac tacacgcaga    1500
agagcctctc cctgtctccg ggtaaatgag tgctagctgg ccagacatga taagatacat    1560
tgatgagttt ggacaaacca caactagaat gcagtgaaaa aaatgcttta tttgtgaaat    1620
ttgtgatgct attgctttat ttgtaaccat tataagctgc aataaacaag ttaacaacaa    1680
caattgcatt cattttatgt ttcaggttca gggggaggtg tgggaggttt tttaaagcaa    1740
gtaaacctc tacaaatgtg gtatggaatt aattctaaaa tacagcatag caaactttta    1800
acctccaaat caagcctcta cttgaatcct tttctgaggg atgaataagg cataggcatc    1860
aggggctgtt gccaatgtgc attagctgtt tgcagcctca ccttctttca tggagtttaa    1920
gatatagtgt attttcccaa ggtttgaact agctcttcat ttctttatgt tttaaatgca    1980
ctgacctccc acattccctt tttagtaaaa tattcagaaa taatttaaat acatcattgc    2040
aatgaaaata aatgttttt attaggcaga atccagatgc tcaaggccct tcataatatc    2100
ccccagttta gtagttggac ttagggaaca aaggaacctt aatagaaat tggacagcaa    2160
gaaagcgagc ttctagctta tcctcagtcc tgctcctctg ccacaaagtg cacgcagttg    2220
ccggccgggt cgcgcagggc gaactcccgc ccccacggct gctcgccgat ctcggtcatg    2280
```

```
gccggcccgg aggcgtcccg gaagttcgtg gacacgacct ccgaccactc ggcgtacagc    2340
tcgtccaggc cgcgcaccca cacccaggcc agggtgttgt ccggcaccac ctggtcctgg    2400
accgcgctga tgaacagggt cacgtcgtcc cggaccacac cggcgaagtc gtcctccacg    2460
aagtcccggg agaacccgag ccggtcggtc cagaactcga ccgctccggc gacgtcgcgc    2520
gcggtgagca ccggaacggc actggtcaac ttggccatga tggctcctcc tgtcaggaga    2580
ggaaagagaa gaaggttagt acaattgcta tagtgagttg tattatacta tgcagatata    2640
ctatgccaat gattaattgt caaactaggg ctgcagggtt catagtgcca cttttcctgc    2700
actgccccat ctcctgccca ccctttccca ggcatagaca gtcagtgact taccaaactc    2760
acaggaggga gaaggcagaa gcttgagaca gacccgcggg accgccgaac tgcgagggga    2820
cgtggctagg gcggcttctt ttatggtgcg ccggccctcg gaggcagggc gctcggggag    2880
gcctagcggc caatctgcgg tggcaggagg cggggccgaa ggccgtgcct gaccaatccg    2940
gagcacatag gagtctcagc cccccgcccc aaagcaaggg gaagtcacgc gcctgtagcg    3000
ccagcgtgtt gtgaaatggg ggcttggggg ggttggggcc ctgactagtc aaaacaaact    3060
cccattgacg tcaatggggt ggagacttgg aaatccccgt gagtcaaacc gctatccacg    3120
cccattgatg tactgccaaa accgcatcat catggtaata gcgatgacta atacgtagat    3180
gtactgccaa gtaggaaagt cccataaggt catgtactgg gcataatgcc aggcgggcca    3240
tttaccgtca ttgacgtcaa tagggggcgt acttggcata tgatacactt gatgtactgc    3300
caagtgggca gtttaccgta atactccacc cattgacgt caatggaaag tccctattgg    3360
cgttactatg ggaacatacg tcattattga cgtcaatggg cggggtcgt tgggcggtca    3420 gccaggcggg ccatttaccg taagttatgt aacgcctgca ggttaattaa gaacatgtga    3480
gcaaaaggcc agcaaaaggc caggaaccgt aaaaaggccg cgttgctggc gtttttccat    3540
aggctccgcc cccctgacga gcatcacaaa aatcgacgct caagtcagag gtggcgaaac    3600
ccgacaggac tataaagata ccaggcgttt ccccctggaa gctccctcgt gcgctctcct    3660
gttccgaccc tgccgcttac cggatacctg tccgcctttc tcccttcggg aagcgtggcg    3720
ctttctcata gctcacgctg taggtatctc agttcggtgt aggtcgttcg ctccaagctg    3780
ggctgtgtgc acgaaccccc cgttcagccc gaccgctgcg ccttatccgg taactatcgt    3840
cttgagtcca acccggtaag acacgactta tcgccactgg cagcagccac tggtaacagg    3900
attagcagag cgaggtatgt aggcggtgct acagagttct tgaagtggtg gcctaactac    3960
ggctacacta gaagaacagt atttggtatc tgcgctctgc tgaagccagt taccttcgga    4020
aaaagagttg gtagctcttg atccggcaaa caaaccaccg ctggtagcgg tggtttttt    4080 gtttgcaagc agcagattac gcgcagaaaa aaaggatctc aagaagatcc tttgatcttt    4140
tctacggggt ctgacgctca gtggaacgaa aactcacgtt aagggatttt ggtcatggct    4200
agttaattaa catttaaatc agcggccgca ataaatatc tttattttca ttacatctgt    4260
gtgttggttt tttgtgtgaa tcgtaactaa catacgctct ccatcaaaac aaaacgaaac    4320
aaaacaaact agcaaaatag gctgtcccca gtgcaagtgc aggtgccaga catttctct    4380 atcgaa                                                              4386
```

<210> SEQ ID NO 91
<211> LENGTH: 4527
<212> TYPE: DNA
<213> ORGANISM: Artificial Sequence
<220> FEATURE:
<223> OTHER INFORMATION: pCCL25-IgG1Fc

<400> SEQUENCE: 91

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc ttttttcgcaa cgggtttgcc gccagaacac    240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgacccaagg tgtctttgag gactgctgcc     660
tggcctacca ctaccccatt gggtgggctg tgctccggca cgcctggact taccggatcc     720
aggaggtgag cgggagctgc aatctgcctg ctgcgatatt ctacctcccc aagagacaca     780
ggaaggtgtg tgggaacccc aaaagcaggg aggtgcagag agccatgaag ctcctggatg     840
ctcgaaataa ggttttttgca aagctccgcc acaacacgca gaccttccaa ggccctcatg     900
ctgtaaagaa gttgagttct ggaaactcca agttatcatc gtccaagttt agcaatccca     960
tcagcagcag caagaggaat gtctccgaca aaactcacac atgcccaccg tgcccagcac    1020
ctgaactcct gggggggaccg tcagtcttcc tcttcccccc aaaacccaag gacaccctca    1080
tgatctcccg gacccctgag gtcacatgcg tggtggtgga cgtgagccac gaagaccctg    1140
aggtcaagtt caactggtac gtggacggcg tggaggtgca taatgccaag acaaagccgc    1200
gggaggagca gtacaacagc acgtaccgtg tggtcagcgt cctcaccgtc ctgcaccagg    1260
actggctgaa tggcaaggag tacaagtgca aggtctccaa caaagccctc ccagccccca    1320
tcgagaaaac catctccaaa gccaaagggc agccccgaga accacaggtg tacaccctgc    1380
ccccatcccg ggaggagatg accaagaacc aggtcagcct gacctgcctg gtcaaaggct    1440
tctatcccag cgacatcgcc gtggagtggg agagcaatgg gcagccggag aacaactaca    1500
agaccacgcc tcccgtgctg gactccgacg gctccttctt cctctacagc aagctcaccg    1560
tggacaagag caggtggcag caggggaacg tcttctcatg ctccgtgatg cacgaggctc    1620
tgcacaacca ctacacgcag aagagcctct ccctgtctcc gggtaaatga gtgctagctg    1680
gccagacatg ataagataca ttgatgagtt tggacaaacc acaactagaa tgcagtgaaa    1740
aaaatgcttt atttgtgaaa tttgtgatgc tattgcttta tttgtaacca ttataagctg    1800
caataaacaa gttaacaaca caattgcat tcattttatg tttcaggttc aggggaggt     1860
gtgggaggtt ttttaaagca agtaaaacct ctacaaatgt ggtatggaat taattctaaa    1920
atacagcata gcaaaacttt aacctccaaa tcaagcctct acttgaatcc ttttctgagg    1980
gatgaataag gcataggcat caggggctgt tgccaatgtg cattagctgt ttgcagcctc    2040
accttctttc atggagttta agatatagtg tattttccca aggtttgaac tagctcttca    2100
tttcttatg ttttaaatgc actgacctcc cacattccct ttttagtaaa atattcagaa    2160
ataatttaaa tacatcattg caatgaaaat aaatgttttt tattaggcag aatccagatg    2220
ctcaaggccc ttcataatat cccccagttt agtagttgga cttagggaac aaaggaacct    2280
```

```
ttaatagaaa ttggacagca agaaagcgag cttctagctt atcctcagtc ctgctcctct    2340
gccacaaagt gcacgcagtt gccggccggg tcgcgcaggg cgaactcccg ccccacggc    2400 tgctcgccga tctcggtcat ggccggcccg gaggcgtccc ggaagttcgt ggacacgacc    2460
tccgaccact cggcgtacag ctcgtccagg ccgcgcaccc acaccaggc cagggtgttg    2520 tccggcacca cctggtcctg gaccgcgctg atgaacaggg tcacgtcgtc ccggaccaca    2580
ccggcgaagt cgtcctccac gaagtccggg agaacccga gccggtcggt ccagaactcg    2640
accgctccgg cgacgtcgcg cgcggtgagc accggaacgg cactggtcaa cttggccatg    2700
atggctcctc ctgtcaggag aggaaagaga agaaggttag tacaattgct atagtgagtt    2760
gtattatact atgcagatat actatgccaa tgattaattg tcaaactagg gctgcagggt    2820
tcatagtgcc acttttcctg cactgcccca tctcctgccc acccttccc aggcatagac    2880 agtcagtgac ttaccaaact cacaggaggg agaaggcaga agcttgagac agacccgcgg    2940
gaccgccgaa ctgcgagggg acgtggctag ggcggcttct tttatggtgc gccggccctc    3000
ggaggcaggg cgctcgggga ggcctagcgg ccaatctgcg gtggcaggag gcggggccga    3060
aggccgtgcc tgaccaatcc ggagcacata ggagtctcag cccccgccc caaagcaagg    3120 ggaagtcacg cgcctgtagc gccagcgtgt tgtgaaatgg gggcttgggg gggttggggc    3180
cctgactagt caaaacaaac tcccattgac gtcaatgggg tggagacttg gaaatccccg    3240
tgagtcaaac cgctatccac gcccattgat gtactgccaa aaccgcatca tcatggtaat    3300
agcgatgact aatacgtaga tgtactgcca agtaggaaag tcccataagg tcatgtactg    3360
ggcataatgc caggcgggcc atttaccgtc attgacgtca ataggggcg tacttggcat    3420 atgatacact tgatgtactg ccaagtgggc agtttaccgt aaatactcca cccattgacg    3480
tcaatggaaa gtccctattg gcgttactat gggaacatac gtcattattg acgtcaatgg    3540
gcgggggtcg ttgggcggtc agccaggcgg gccatttacc gtaagttatg taacgcctgc    3600
aggttaatta agaacatgtg agcaaaaggc cagcaaaagg ccaggaaccg taaaaaggcc    3660
gcgttgctgg cgttttttcca taggctccgc cccctgacg agcatcacaa aaatcgacgc    3720
tcaagtcaga ggtggcgaaa cccgacagga ctataaagat accaggcgtt ccccctggaa    3780
agctccctcg tgcgctctcc tgttccgacc ctgccgctta ccggatacct gtccgccttt    3840
ctcccttcgg gaagcgtggc gctttctcat agctcacgct gtaggtatct cagttcggtg    3900
taggtcgttc gctccaagct gggctgtgtg cacgaacccc ccgttcagcc cgaccgctgc    3960
gccttatccg gtaactatcg tcttgagtcc aacccggtaa gacacgactt atcgccactg    4020
gcagcagcca ctggtaacag gattagcaga gcgaggtatg taggcggtgc tacagagttc    4080
ttgaagtggt ggcctaacta cggctacact agaagaacag tatttggtat ctgcgctctg    4140
ctgaagccag ttaccttcgg aaaaagagtt ggtagctctt gatccggcaa acaaaccacc    4200
gctggtagcg gtggtttttt tgtttgcaag cagcagatta cgcgcagaaa aaaggatct    4260 caagaagatc ctttgatctt ttctacgggg tctgacgctc agtggaacga aaactcacgt    4320
taagggattt tggtcatggc tagttaatta acatttaaat cagcggccgc aataaaatat    4380
ctttattttc attacatctg tgtgttggtt ttttgtgtga atcgtaacta acatacgctc    4440
tccatcaaaa caaaacgaaa caaaacaaac tagcaaaata ggctgtcccc agtgcaagtg    4500
caggtgccag aacatttctc tatcgaa                                        4527
```

<210> SEQ ID NO 92
<211> LENGTH: 4518

<212> TYPE: DNA
<213> ORGANISM: Artificial Sequence
<220> FEATURE:
<223> OTHER INFORMATION: pCCL25(4-127)-IgG1Fc

<400> SEQUENCE: 92

| | | | | |
|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttcc | cgagggtggg | ggagaaccgt | 180 |
| atataagtgc | agtagtcgcc | gtgaacgttc | ttttcgcaa | cgggtttgcc | gccagaacac | 240 |
| agctgaagct | tcgaggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cggtctttga | ggactgctgc | ctggcctacc | 660 |
| actacccat | tgggtgggct | gtgctccggc | acgcctggac | ttaccggatc | caggaggtga | 720 |
| gcgggagctg | caatctgcct | gctgcgatat | tctacctccc | caagagacac | aggaaggtgt | 780 |
| gtgggaaccc | caaaagcagg | gaggtgcaga | gagccatgaa | gctcctggat | gctcgaaata | 840 |
| aggttttgc | aaagctccgc | cacaacacg | agaccttcca | aggccctcat | gctgtaaaga | 900 |
| agttgagttc | tggaaactcc | aagttatcat | cgtccaagtt | tagcaatccc | atcagcagca | 960 |
| gcaagaggaa | tgtctccgac | aaaactcaca | catgcccacc | gtgcccagca | cctgaactcc | 1020 |
| tgggggacc | gtcagtcttc | ctcttccccc | caaaacccaa | ggacaccctc | atgatctccc | 1080 |
| ggacccctga | ggtcacatgc | gtggtggtgg | acgtgagcca | cgaagaccct | gaggtcaagt | 1140 |
| tcaactggta | cgtggacggc | gtggaggtgc | ataatgccaa | gacaaagccg | cgggaggagc | 1200 |
| agtacaacag | cacgtaccgt | gtggtcagcg | tcctcaccgt | cctgcaccag | gactggctga | 1260 |
| atggcaagga | gtacaagtgc | aaggtctcca | acaaagcccc | ccagccccc | atcgagaaaa | 1320 |
| ccatctccaa | agccaaaggg | cagccccgag | aaccacaggt | gtacaccctg | cccccatccc | 1380 |
| gggaggagat | gaccaagaac | caggtcagcc | tgacctgcct | ggtcaaaggc | ttctatccca | 1440 |
| gcgacatcgc | cgtggagtgg | gagagcaatg | ggcagccgga | gaacaactac | aagaccacgc | 1500 |
| ctcccgtgct | ggactccgac | ggctccttct | tcctctacag | caagctcacc | gtggacaaga | 1560 |
| gcaggtggca | gcaggggaac | gtcttctcat | gctccgtgat | gcacgaggct | ctgcacaacc | 1620 |
| actacacgca | gaagagcctc | tccctgtctc | cgggtaaatg | agtgctagct | ggccagacat | 1680 |
| gataagatac | attgatgagt | ttggacaaac | cacaactaga | atgcagtgaa | aaaatgctt | 1740 |
| tatttgtgaa | atttgtgatg | ctattgcttt | atttgtaacc | attataagct | gcaataaaca | 1800 |
| agttaacaac | aacaattgca | ttcatttat | gtttcaggtt | caggggagg | tgtgggaggt | 1860 |
| ttttaaagc | aagtaaaacc | tctacaaatg | tggtatggaa | ttaattctaa | aatacagcat | 1920 |
| agcaaaactt | taacctccaa | atcaagcctc | tacttgaatc | cttttctgag | ggatgaataa | 1980 |
| ggcataggca | tcaggggctg | ttgccaatgt | gcattagctg | tttgcagcct | caccttcttt | 2040 |
| catggagttt | aagatatagt | gtattttccc | aaggtttgaa | ctagctcttc | atttctttat | 2100 |
| gttttaaatg | cactgacctc | ccacattccc | tttttagtaa | aatattcaga | aataatttaa | 2160 |

```
atacatcatt gcaatgaaaa taaatgtttt ttattaggca gaatccagat gctcaaggcc    2220
cttcataata tcccccagtt tagtagttgg acttagggaa caaaggaacc tttaatagaa    2280
attggacagc aagaaagcga gcttctagct tatcctcagt cctgctcctc tgccacaaag    2340
tgcacgcagt tgccggccgg gtcgcgcagg gcgaactccc gccccacgg ctgctcgccg     2400
atctcggtca tggccggccc ggaggcgtcc cggaagttcg tggacacgac ctccgaccac    2460
tcggcgtaca gctcgtccag gccgcgcacc cacacccagg ccagggtgtt gtccggcacc    2520
acctggtcct ggaccgcgct gatgaacagg gtcacgtcgt cccggaccac accggcgaag    2580
tcgtcctcca cgaagtcccg ggagaacccg agccggtcgg tccagaactc gaccgctccg    2640
gcgacgtcgc gcgcggtgag caccggaacg gcactggtca acttggccat gatggctcct    2700
cctgtcagga gaggaaagag aagaaggtta gtacaattgc tatagtgagt tgtattatac    2760
tatgcagata tactatgcca atgattaatt gtcaaactag ggctgcaggg ttcatagtgc    2820
cacttttcct gcactgcccc atctcctgcc caccctttcc caggcataga cagtcagtga    2880
cttaccaaac tcacaggagg gagaaggcag aagcttgaga cagacccgcg ggaccgccga    2940
actgcgaggg gacgtggcta gggcggcttc ttttatggtg cgccggccct cggaggcagg    3000
gcgctcgggg aggcctagcg gccaatctgc ggtggcagga ggcggggccg aaggccgtgc    3060
ctgaccaatc cggagcacat aggagtctca gccccccgcc ccaaagcaag gggaagtcac    3120
gcgcctgtag cgccagcgtg ttgtgaaatg ggggcttggg ggggttgggg ccctgactag    3180
tcaaaacaaa ctcccattga cgtcaatggg gtggagactt ggaaatcccc gtgagtcaaa    3240
ccgctatcca cgcccattga tgtactgcca aaaccgcatc atcatggtaa tagcgatgac    3300
taatacgtag atgtactgcc aagtaggaaa gtcccataag gtcatgtact gggcataatg    3360
ccaggcgggc catttaccgt cattgacgtc aataggggggc gtacttggca tatgatacac    3420
ttgatgtact gccaagtggg cagtttaccg taaatactcc acccattgac gtcaatggaa    3480
agtccctatt ggcgttacta tgggaacata cgtcattatt gacgtcaatg ggcgggggtc    3540
gttgggcggt cagccaggcg ggccatttac cgtaagttat gtaacgcctg caggttaatt    3600
aagaacatgt gagcaaaagg ccagcaaaag gccaggaacc gtaaaaaggc cgcgttgctg    3660
gcgttttttcc ataggctccg ccccccctgac gagcatcaca aaaatcgacg ctcaagtcag   3720
aggtggcgaa acccgacagg actataaaga taccaggcgt ttccccctgg aagctccctc    3780
gtgcgctctc ctgttccgac cctgccgctt accggatacc tgtccgcctt tctcccttcg    3840
ggaagcgtgg cgctttctca tagctcacgc tgtaggtatc tcagttcggt gtaggtcgtt    3900
cgctccaagc tgggctgtgt gcacgaaccc cccgttcagc ccgaccgctg cgccttatcc    3960
ggtaactatc gtcttgagtc aacccggta agacacgact tatcgccact ggcagcagcc    4020
actggtaaca ggattagcag agcgaggtat gtaggcggtg ctacagagtt cttgaagtgg    4080
tggcctaact acggctacac tagaagaaca gtatttggta tctgcgctct gctgaagcca    4140
gttaccttcg gaaaaagagt tggtagctct tgatccggca acaaaccac cgctggtagc     4200
ggtggttttt ttgtttgcaa gcagcagatt acgcgcagaa aaaaaggatc tcaagaagat    4260
cctttgatct tttctacggg gtctgacgct cagtggaacg aaaactcacg ttaagggatt    4320
ttggtcatgg ctagttaatt aacatttaaa tcagcggccg caataaaata tctttatttt    4380
cattacatct gtgtgttggt tttttgtgtg aatcgtaact aacatacgct ctccatcaaa    4440
acaaaacgaa acaaaacaaa ctagcaaaat aggctgtccc cagtgcaagt gcaggtgcca    4500
gaacatttct ctatcgaa                                                  4518
```

<210> SEQ ID NO 93
<211> LENGTH: 4518
<212> TYPE: DNA
<213> ORGANISM: Artificial Sequence
<220> FEATURE:
<223> OTHER INFORMATION: pCCL25(4-127K/H-A)-IgG1Fc

<400> SEQUENCE: 93

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc ttttcgcaa cgggtttgcc gccagaacac      240
agctgaagct tcgaggggct cgcatctctc cttcacgcgc ccgccgccct acctgaggcc     300
gccatccacg ccggttgagt cgcgttctgc cgcctcccgc tgtggtgcc tcctgaactg      360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggtctttga ggactgctgc tggcctacc      660
actacccat gggtgggct gtgctccggc acgcctggac ttaccggatc caggaggtga      720
gcgggagctg caatctgcct gctgcgatat tctacctccc cgctgccgct gccgcggtgt     780
gtgggaaccc cgctagcgcc gaggtgcagg ctgccatggc cctcctggat gctgctaatg     840
ccgtttttgc agcgctcgct gccaacacg agaccttcca aggccctgcg gctgtagccg      900
ctttgagttc tggaaactcc gccttatcat cgtccgcgtt tagcaatccc atcagcagca     960
gcgctgccaa tgtctccgac aaaactcaca catgcccacc gtgcccagca cctgaactcc    1020
tgggggggacc gtcagtcttc ctcttccccc caaaacccaa ggacaccctc atgatctccc    1080
ggacccctga ggtcacatgc gtggtggtgg acgtgagcca cgaagaccct gaggtcaagt    1140
tcaactggta cgtggacggc gtggaggtgc ataatgccaa gacaaagccg cgggaggagc    1200
agtacaacag cacgtaccgt gtggtcagcg tcctcaccgt cctgcaccag gactggctga    1260
atggcaagga gtacaagtgc aaggtctcca acaaagccct cccagccccc atcgagaaaa    1320
ccatctccaa agccaagggg cagccccgag aaccacaggt gtacaccctg cccccatccc    1380
gggaggagat gaccaagaac caggtcagcc tgacctgcct ggtcaaaggc ttctatccca    1440
gcgacatcgc cgtggagtgg gagagcaatg ggcagccgga gaacaactac aagaccacgc    1500
ctcccgtgct ggactccgac ggctccttct cctctacag caagctcacc gtggacaaga    1560
gcaggtggca gcaggggaac gtcttctcat gctccgtgat gcacgaggct ctgcacaacc    1620
actacacgca gaagagcctc tccctgtctc cgggtaaatg agtgctagct ggccagacat    1680
gataagatac attgatgagt ttggacaaac cacaactaga atgcagtgaa aaaaatgctt    1740
tatttgtgaa atttgtgatg ctattgcttt atttgtaacc attataagct gcaataaaca    1800
agttaacaac aacaattgca ttcattttat gtttcaggtt caggggggagg tgtgggaggt    1860
tttttaaagc aagtaaaacc tctacaaatg tggtatggaa ttaattctaa aatacagcat    1920
agcaaaactt taacctccaa atcaagcctc tacttgaatc cttttctgag ggatgaataa    1980
ggcataggca tcaggggctg ttgccaatgt gcattagctg tttgcagcct caccttcttt    2040
```

```
catggagttt aagatatagt gtattttccc aaggtttgaa ctagctcttc atttctttat    2100
gttttaaatg cactgacctc ccacattccc tttttagtaa aatattcaga ataaatttaa    2160
atacatcatt gcaatgaaaa taaatgtttt ttattaggca gaatccagat gctcaaggcc    2220
cttcataata tcccccagtt tagtagttgg acttagggaa caaaggaacc tttaatagaa    2280
attggacagc aagaaagcga gcttctagct tatcctcagt cctgctcctc tgccacaaag    2340
tgcacgcagt tgccggccgg gtcgcgcagg gcgaactccc gccccacgg ctgctcgccg     2400
atctcggtca tggccggccc ggaggcgtcc cggaagttcg tggacacgac ctccgaccac    2460
tcggcgtaca gctcgtccag gccgcgcacc cacacccagg ccagggtgtt gtccggcacc    2520
acctggtcct ggaccgcgct gatgaacagg gtcacgtcgt cccggaccac accggcgaag   2580
tcgtcctcca cgaagtcccg ggagaacccg agccggtcgg tccagaactc gaccgctccg    2640
gcgacgtcgc gcgcggtgag caccggaacg gcactggtca acttggccat gatggctcct   2700
cctgtcagga gaggaaagag aagaaggtta gtacaattgc tatagtgagt tgtattatac   2760
tatgcagata tactatgcca atgattaatt gtcaaactag gctgcaggg ttcatagtgc    2820
cacttttcct gcactgcccc atctcctgcc caccctttcc caggcataga cagtcagtga   2880
cttaccaaac tcacaggagg gagaaggcag aagcttgaga cagacccgcg ggaccgccga   2940
actgcgaggg gacgtggcta gggcggcttc ttttatggtg cgccggccct cggaggcagg   3000
gcgctcgggg aggcctagcg gccaatctgc ggtggcagga ggcggggccg aaggccgtgc   3060
ctgaccaatc cggagcacat aggagtctca gccccccgcc ccaaagcaag gggaagtcac   3120
gcgcctgtag cgccagcgtg ttgtgaaatg ggggcttggg ggggttgggg ccctgactag   3180
tcaaaacaaa ctcccattga cgtcaatggg gtggagactt ggaaatcccc gtgagtcaaa   3240
ccgctatcca cgcccattga tgtactgcca aaaccgcatc atcatggtaa tagcgatgac   3300
taatacgtag atgtactgcc aagtaggaaa gtcccataag gtcatgtact gggcataatg   3360
ccaggcgggc catttaccgt cattgacgtc aataggggc gtacttggca tatgatacac    3420
ttgatgtact gccaagtggg cagtttaccg taaatactcc acccattgac gtcaatggaa   3480
agtccctatt ggcgttacta tgggaacata cgtcattatt gacgtcaatg ggcggggggtc  3540
gttgggcggt cagccaggcg ggccatttac cgtaagttat gtaacgcctg caggttaatt   3600
aagaacatgt gagcaaaagg ccagcaaaag gccaggaacc gtaaaaaggc cgcgttgctg   3660
gcgttttttcc ataggctccg ccccctgac gagcatcaca aaaatcgacg ctcaagtcag   3720
aggtggcgaa acccgacagg actataaaga taccaggcgt ttccccctgg aagctccctc   3780
gtgcgctctc ctgttccgac cctgccgctt accggatacc tgtccgcctt tctcccttcg   3840
ggaagcgtgg cgctttctca tagctcacgc tgtaggtatc tcagttcggt gtaggtcgtt   3900
cgctccaagc tgggctgtgt gcacgaaccc cccgttcagc ccgaccgctg cgccttatcc   3960
ggtaactatc gtcttgagtc aacccggta agacacgact tatcgccact ggcagcagcc    4020
actggtaaca ggattagcag agcgaggtat gtaggcggtg ctacagagtt cttgaagtgg   4080
tggcctaact acggctacac tagaagaaca gtatttggta tctgcgctct gctgaagcca   4140
gttaccttcg gaaaaagagt tggtagctct tgatccggca acaaaccac cgctggtagc    4200
ggtggttttt ttgtttgcaa gcagcagatt acgcgcagaa aaaaggatc tcaagaagat   4260
cctttgatct tttctacggg gtctgacgct cagtggaacg aaaactcacg ttaagggatt   4320
ttggtcatgc ctagttaatt aacatttaaa tcagcggccg caataaaata tctttatttt   4380
cattacatct gtgtgttggt ttttttgtgtg aatcgtaact aacatacgct ctccatcaaa  4440
```

```
acaaaacgaa acaaaacaaa ctagcaaaat aggctgtccc cagtgcaagt gcaggtgcca    4500
gaacatttct ctatcgaa                                                  4518

<210> SEQ ID NO 94
<211> LENGTH: 4392
<212> TYPE: DNA
<213> ORGANISM: Artificial Sequence
<220> FEATURE:
<223> OTHER INFORMATION: pCXCL11-IgG1Fc

<400> SEQUENCE: 94
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgttccccat gttcaaaaga ggacgctgtc     660
tttgcatagg ccctggggta aaagcagtga agtggcaga tattgagaaa gcctccataa     720
tgtacccaag taacaactgt gacaaaatag aagtgattat taccctgaaa gaaaataaag     780
gacaacgatg cctaaatccc aaatcgaagc aagcaaggct tataatcaaa aagttgaaa     840 gaaagaattt tgacaaaact cacacatgcc caccgtgccc agcacctgaa ctcctggggg     900
gaccgtcagt cttcctcttc cccccaaaac ccaaggacac cctcatgatc tcccggaccc     960
ctgaggtcac atgcgtggtg gtggacgtga gccacgaaga ccctgaggtc aagttcaact    1020
ggtacgtgga cggcgtggag gtgcataatg ccaagacaaa gccgcgggag gagcagtaca    1080
acagcacgta ccgtgtggtc agcgtcctca ccgtcctgca ccaggactgg ctgaatggca    1140
aggagtacaa gtgcaaggtc tccaacaaag ccctcccagc ccccatcgag aaaaccatct    1200
ccaaagccaa agggcagccc cgagaaccac aggtgtacac cctgccccca tcccgggagg    1260
agatgaccaa gaaccaggtc agcctgacct gcctggtcaa aggcttctat cccagcgaca    1320
tcgccgtgga gtgggagagc aatgggcagc cggagaacaa ctacaagacc acgcctcccg    1380
tgctggactc cgacggctcc ttcttcctct acagcaagct caccgtggac aagagcaggt    1440
ggcagcaggg gaacgtcttc tcatgctccg tgatgcacga ggctctgcac aaccactaca    1500
cgcagaagag cctctccctg tctccgggta aatgagtgct agctggccag acatgataag    1560
atacattgat gagtttggac aaaccacaac tagaatgcag tgaaaaaaat gctttatttg    1620
tgaaatttgt gatgctattg ctttatttgt aaccattata agctgcaata acaagttaa    1680 caacaacaat tgcattcatt ttatgtttca ggttcagggg gaggtgtggg aggttttta     1740 aagcaagtaa aacctctaca aatgtggtat ggaattaatt ctaaaataca gcatagcaaa    1800
actttaacct ccaaatcaag cctctacttg aatccttttc tgagggatga ataaggcata    1860
ggcatcaggg gctgttgcca atgtgcatta gctgtttgca gcctcacctt ctttcatgga    1920
```

```
gtttaagata tagtgtatttt tcccaaggtt tgaactagct cttcatttct ttatgtttta   1980
aatgcactga cctcccacat tccctttta gtaaaatatt cagaaataat ttaaatacat    2040
cattgcaatg aaaataaatg ttttttatta ggcagaatcc agatgctcaa ggcccttcat   2100
aatatccccc agtttagtag ttggacttag ggaacaaagg aacctttaat agaaattgga   2160
cagcaagaaa gcgagcttct agcttatcct cagtcctgct cctctgccac aaagtgcacg   2220
cagttgccgg ccgggtcgcg cagggcgaac tcccgccccc acggctgctc gccgatctcg   2280
gtcatggccg gcccggaggc gtcccggaag ttcgtggaca cgacctccga ccactcggcg   2340
tacagctcgt ccaggccgcg cacccacacc caggccaggg tgttgtccgg caccacctgg   2400
tcctggaccg cgctgatgaa cagggtcacg tcgtcccgga ccacaccggc gaagtcgtcc   2460
tccacgaagt cccgggagaa cccgagccgg tcggtccaga actcgaccgc tccggcgacg   2520
tcgcgcgcgg tgagcaccgg aacggcactg gtcaacttgg ccatgatggc tcctcctgtc   2580
aggagaggaa agagaagaag gttagtacaa ttgctatagt gagttgtatt atactatgca   2640
gatatactat gccaatgatt aattgtcaaa ctagggctgc agggttcata gtgccacttt   2700
tcctgcactg ccccatctcc tgcccaccct ttcccaggca tagacagtca gtgacttacc   2760
aaactcacag gagggagaag gcagaagctt gagacagacc cgcgggaccg ccgaactgcg   2820
aggggacgtg gctagggcgg cttctttat ggtgcgccgg ccctcggagg cagggcgctc   2880
ggggaggcct agcggccaat ctgcggtggc aggaggcggg gccgaaggcc gtgcctgacc   2940
aatccggagc acataggagt ctcagcccc cgccccaaag caaggggaag tcacgcgcct   3000
gtagcgccag cgtgttgtga atgggggct ggggggggtt ggggccctga ctagtcaaaa   3060
caaactccca ttgacgtcaa tggggtggag acttggaaat cccgtgagt caaaccgcta   3120 tccacgccca ttgatgtact gccaaaaccg catcatcatg gtaatagcga tgactaatac   3180
gtagatgtac tgccaagtag gaaagtccca taaggtcatg tactgggcat aatgccaggc   3240
gggccattta ccgtcattga cgtcaatagg gggcgtactt ggcatatgat acacttgatg   3300
tactgccaag tgggcagttt accgtaaata ctccacccat tgacgtcaat ggaaagtccc   3360
tattggcgtt actatgggaa catacgtcat tattgacgtc aatgggcggg ggtcgttggg   3420
cggtcagcca ggcgggccat ttaccgtaag ttatgtaacg cctgcaggtt aattaagaac   3480
atgtgagcaa aaggccagca aaaggccagg aaccgtaaaa aggccgcgtt gctggcgttt   3540
ttccataggc tccgcccccc tgacgagcat cacaaaaatc gacgctcaag tcagaggtgg   3600
cgaaacccga caggactata agataccag gcgtttcccc ctggaagctc cctcgtgcgc   3660
tctcctgttc cgaccctgcc gcttaccgga tacctgtccg cctttctccc ttcgggaagc   3720
gtggcgcttt ctcatagctc acgctgtagg tatctcagtt cggtgtaggt cgttcgctcc   3780
aagctgggct gtgtgcacga accccccgtt cagcccgacc gctgcgcctt atccggtaac   3840
tatcgtcttg agtccaaccc ggtaagacac gacttatcgc cactggcagc agccactggt   3900
aacaggatta gcagagcgag gtatgtaggc ggtgctacag agttcttgaa gtggtggcct   3960
aactacggct acactagaag aacagtattt ggtatctgcg ctctgctgaa gccagttacc   4020
ttcggaaaaa gagttggtag ctcttgatcc ggcaaacaaa ccaccgctgg tagcggtggt   4080
ttttttgttt gcaagcagca gattacgcgc agaaaaaaag gatctcaaga agatcctttg   4140
atcttttcta cggggtctga cgctcagtgg aacgaaaact cacgttaagg gattttggtc   4200
atgagattat caaaaaggat cttcacctag atccttttaa attaaaaatg aagttttaaa   4260
atcaatctaa agtatatatg agtaaacttg gtctgacagt taccaatgct taatcagtga   4320
```

```
cgaaacaaaa caaactagca aaataggctg tccccagtgc aagtgcaggt gccagaacat   4380
ttctctatcg aa                                                       4392

<210> SEQ ID NO 95
<211> LENGTH: 4383
<212> TYPE: DNA
<213> ORGANISM: Artificial Sequence
<220> FEATURE:
<223> OTHER INFORMATION: pCXCL11(4-73)-IgG1Fc

<400> SEQUENCE: 95
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct cgagggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgttcaaaag aggacgctgt ctttgcatag    660
gccctggggt aaaagcagtg aaagtggcag atattgagaa agcctccata atgtacccaa    720
gtaacaactg tgacaaaata gaagtgatta ttaccctgaa agaaaataaa ggacaacgat    780
gcctaaatcc caaatcgaag caagcaaggc ttataatcaa aaaagttgaa agaaagaatt    840
ttgacaaaac tcacacatgc ccaccgtgcc cagcacctga actcctgggg ggaccgtcag    900
tcttcctctt ccccccaaaa cccaaggaca cctcatgat ctcccggacc cctgaggtca    960
catgcgtggt ggtggacgtg agccacgaag accctgaggt caagttcaac tggtacgtgg   1020
acggcgtgga ggtgcataat gccaagacaa agccgcggga ggagcagtac aacagcacgt   1080
accgtgtggt cagcgtcctc accgtcctgc accaggactg gctgaatggc aaggagtaca   1140
agtgcaaggt ctccaacaaa gccctcccag cccccatcga gaaaaccatc tccaaagcca   1200
aagggcagcc ccgagaacca caggtgtaca ccctgccccc atcccgggag gagatgacca   1260
agaaccaggt cagcctgacc tgcctggtca aaggcttcta tcccagcgac atcgccgtgg   1320
agtgggagag caatgggcag ccggagaaca actacaagac cacgcctccc gtgctggact   1380
ccgacggctc cttcttcctc tacagcaagc tcaccgtgga cagagcagg tggcagcagg   1440 ggaacgtctt ctcatgctcc gtgatgcacg aggctctgca caaccactac acgcagaaga   1500
gcctctccct gtctccgggt aaatgagtgc tagctggcca gacatgataa gatacattga   1560
tgagtttgga caaccacaa ctagaatgca gtgaaaaaa tgctttattt gtgaaatttg   1620
tgatgctatt gctttatttg taaccattat aagctgcaat aaacaagtta acaacaacaa   1680
ttgcattcat tttatgtttc aggttcaggg ggaggtgtgg gaggtttttt aaagcaagta   1740
aaacctctac aaatgtggta tggaattaat tctaaaatac agcatagcaa aactttaacc   1800
tccaaatcaa gcctctactt gaatccttt ctgagggatg aataaggcat aggcatcagg   1860
ggctgttgcc aatgtgcatt agctgtttgc agcctcacct tctttcatgg agtttaagat   1920
```

```
atagtgtatt ttcccaaggt ttgaactagc tcttcatttc tttatgtttt aaatgcactg   1980
acctcccaca ttcccttttt agtaaaatat tcagaaataa tttaaataca tcattgcaat   2040
gaaaataaat gttttttatt aggcagaatc cagatgctca aggcccttca taatatcccc   2100
cagtttagta gttggactta gggaacaaag gaacctttaa tagaaattgg acagcaagaa   2160
agcgagcttc tagcttatcc tcagtcctgc tcctctgcca caaagtgcac gcagttgccg   2220
gccgggtcgc gcagggcgaa ctcccgcccc cacggctgct cgccgatctc ggtcatggcc   2280
ggcccggagg cgtcccggaa gttcgtggac acgacctccg accactcggc gtacagctcg   2340
tccaggccgc gcacccacac ccaggccagg gtgttgtccg gcaccacctg gtcctggacc   2400
gcgctgatga acagggtcac gtcgtcccgg accacaccgg cgaagtcgtc ctccacgaag   2460
tcccgggaga cccgagccg gtcggtccag aactcgaccg ctccggcgac gtcgcgcgcg   2520
gtgagcaccg gaacggcact ggtcaacttg gccatgatgg ctcctcctgt caggagagga   2580
aagagaagaa ggttagtaca attgctatag tgagttgtat tatactatgc agatatacta   2640
tgccaatgat taattgtcaa actagggctg cagggttcat agtgccactt ttcctgcact   2700
gccccatctc ctgcccaccc tttcccaggc atagacagtc agtgacttac caaactcaca   2760
ggagggagaa ggcagaagct tgagacagac ccgcgggacc gccgaactgc gagggacgt   2820 ggctagggcg gcttctttta tggtgcgccg gccctcggag gcagggcgct cggggaggcc   2880
tagcggccaa tctgcggtgg caggaggcgg ggccgaaggc cgtgcctgac caatccggag   2940
cacataggag tctcagcccc ccgccccaaa gcaaggggaa gtcacgcgcc tgtagcgcca   3000
gcgtgttgtg aaatggggc ttggggggt tggggccctg actagtcaaa acaaactccc   3060
attgacgtca atggggtgga gacttggaaa tccccgtgag tcaaaccgct atccacgccc   3120
attgatgtac tgccaaaacc gcatcatcat ggtaatagcg atgactaata cgtagatgta   3180
ctgccaagta ggaaagtccc ataaggtcat gtactgggca taatgccagg cgggccattt   3240
accgtcattg acgtcaatag ggggcgtact tggcatatga tacacttgat gtactgccaa   3300
gtgggcagtt taccgtaaat actccaccca ttgacgtcaa tggaaagtcc ctattggcgt   3360
tactatggga acatacgtca ttattgacgt caatgggcgg gggtcgttgg gcggtcagcc   3420
aggcgggcca tttaccgtaa gttatgtaac gcctgcaggt taattaagaa catgtgagca   3480
aaaggccagc aaaaggccag gaaccgtaaa aaggccgcgt tgctggcgtt tttccatagg   3540
ctccgccccc ctgacgagca tcacaaaaat cgacgctcaa gtcagaggtg gcgaaacccg   3600
acaggactat aaagatacca ggcgtttccc cctggaagct ccctcgtgcg ctctcctgtt   3660
ccgaccctgc cgcttaccgg atacctgtcc gcctttctcc cttcgggaag cgtggcgctt   3720
tctcatagct cacgctgtag gtatctcagt tcggtgtagg tcgttcgctc caagctgggc   3780
tgtgtgcacg aaccccccgt tcagcccgac cgctgcgcct tatccggtaa ctatcgtctt   3840
gagtccaacc cggtaagaca cgacttatcg ccactggcag cagccactgg taacaggatt   3900
agcagagcga ggtatgtagg cggtgctaca gagttcttga agtggtggcc taactacggc   3960
tacactagaa gaacagtatt tggtatctgc gctctgctga agccagttac cttcggaaaa   4020
agagttggta gctcttgatc cggcaaacaa accaccgctg gtagcggtgg ttttttttgtt   4080 tgcaagcagc agattacgcg cagaaaaaaa ggatctcaag aagatccttt gatcttttct   4140
acggggtctg acgctcagtg gaacgaaaac tcacgttaag ggattttggt catggctagt   4200
taattaacat ttaaatcagc ggccgcaata aaatatcttt attttcatta catctgtgtg   4260 ttggttttttt gtgtgaatcg taactaacat acgctctcca tcaaaacaaa acgaaacaaa   4320
```

```
acaaactagc aaaataggct gtccccagtg caagtgcagg tgccagaaca tttctctatc    4380
gaa                                                                   4383

<210> SEQ ID NO 96
<211> LENGTH: 4383
<212> TYPE: DNA
<213> ORGANISM: Artificial Sequence
<220> FEATURE:
<223> OTHER INFORMATION: pCXCL11(4-73K/H-A)-IgG1Fc

<400> SEQUENCE: 96
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgttcaaaag aggacgctgt ctttgcatag     660
gccctggggt aaaagcagtg aaagtggcag atattgaggc cgcctccata atgtacccaa     720
gtaacaactg tgacaaaata gaagtgatta ttaccctggc agaaaatgcc ggacaagcat     780
gcctaaatcc cgcctcggca caagcagccc ttataatcgc agccgttgaa gcagccaatt     840
ttgacaaaac tcacacatgc ccaccgtgcc cagcacctga actcctgggg ggaccgtcag     900
tcttcctctt ccccccaaaa cccaaggaca cctcatgat ctcccggacc cctgaggtca     960
catgcgtggt ggtggacgtg agccacgaag accctgaggt caagttcaac tggtacgtgg    1020
acggcgtgga ggtgcataat gccaagacaa agccgcggga ggagcagtac aacagcacgt    1080
accgtgtggt cagcgtcctc accgtcctgc accaggactg gctgaatggc aaggagtaca    1140
agtgcaaggt ctccaacaaa gccctcccag cccccatcga gaaaaccatc tccaaagcca    1200
aagggcagcc ccgagaacca caggtgtaca ccctgccccc atcccgggag gagatgacca    1260
agaaccaggt cagcctgacc tgcctggtca aaggcttcta tcccagcgac atcgccgtgg    1320
agtgggagag caatgggcag ccggagaaca actacaagac cacgcctccc gtgctggact    1380
ccgacggctc cttcttcctc tacagcaagc tcaccgtgga caagagcagg tggcagcagg    1440
ggaacgtctt ctcatgctcc gtgatgcacg aggctctgca caaccactac acgcagaaga    1500
gcctctccct gtctccgggt aaatgagtgc tagctggcca gacatgataa gatacattga    1560
tgagtttgga caaaccacaa ctagaatgca gtgaaaaaaa tgctttattt gtgaaatttg    1620
tgatgctatt gctttatttg taaccattat aagctgcaat aaacaagtta acaacaacaa    1680
ttgcattcat tttatgtttc aggttcaggg ggaggtgtgg gaggttttt aaagcaagta    1740 aaacctctac aaatgtggta tggaattaat tctaaaatac agcatagcaa aactttaacc    1800
tccaaatcaa gcctctactt gaatcctttt ctgagggatg aataaggcat aggcatcagg    1860
ggctgttgcc aatgtgcatt agctgtttgc agcctcacct tctttcatgg agtttaagat    1920
```

```
atagtgtatt ttcccaaggt ttgaactagc tcttcatttc tttatgtttt aaatgcactg   1980
acctcccaca ttcccttttt agtaaaatat tcagaaataa tttaaataca tcattgcaat   2040
gaaaataaat gttttttatt aggcagaatc cagatgctca aggcccttca taatatcccc   2100
cagtttagta gttggactta gggaacaaag gaacctttaa tagaaattgg acagcaagaa   2160
agcgagcttc tagcttatcc tcagtcctgc tcctctgcca caaagtgcac gcagttgccg   2220
gccgggtcgc gcagggcgaa ctcccgcccc cacggctgct cgccgatctc ggtcatggcc   2280
ggcccggagg cgtcccggaa gttcgtggac acgacctccg accactcggc gtacagctcg   2340
tccaggccgc gcacccacac ccaggccagg gtgttgtccg gcaccacctg gtcctggacc   2400
gcgctgatga acagggtcac gtcgtcccgg accacaccgg cgaagtcgtc ctccacgaag   2460
tcccgggaga acccgagccg gtcggtccag aactcgaccg ctccggcgac gtcgcgcgcg   2520
gtgagcaccg gaacggcact ggtcaacttg gccatgatgg ctcctcctgt caggagagga   2580
aagagaagaa ggttagtaca attgctatag tgagttgtat tatactatgc agatatacta   2640
tgccaatgat taattgtcaa actagggctg cagggttcat agtgccactt ttcctgcact   2700
gccccatctc ctgcccaccc tttcccaggc atagacagtc agtgacttac caaactcaca   2760
ggagggagaa ggcagaagct tgagacagac ccgcgggacc gccgaactgc gagggacgt   2820
ggctagggcg gcttctttta tggtgcgccg gccctcggag gcagggcgct cggggaggcc   2880
tagcggccaa tctgcggtgg caggaggcgg ggccgaaggc cgtgcctgac caatccggag   2940
cacataggag tctcagcccc ccgccccaaa gcaaggggaa gtcacgcgcc tgtagcgcca   3000
gcgtgttgtg aaatggggc ttggggggt tgggcctg actagtcaaa caaactccc   3060
attgacgtca atggggtgga gacttggaaa tccccgtgag tcaaaccgct atccacgccc   3120
attgatgtac tgccaaaacc gcatcatcat ggtaatagcg atgactaata cgtagatgta   3180
ctgccaagta ggaaagtccc ataaggtcat gtactgggca taatgccagg cgggccattt   3240
accgtcattg acgtcaatag ggggcgtact tggcatatga tacacttgat gtactgccaa   3300
gtgggcagtt taccgtaaat actccaccca ttgacgtcaa tggaaagtcc ctattggcgt   3360
tactatggga acatacgtca ttattgacgt caatgggcgg gggtcgttgg gcggtcagcc   3420
aggcgggcca tttaccgtaa gttatgtaac gcctgcaggt taattaagaa catgtgagca   3480
aaaggccagc aaaaggccag gaaccgtaaa aaggccgcgt tgctggcgtt tttccatagg   3540
ctccgccccc ctgacgagca tcacaaaaat cgacgctcaa gtcagaggtg gcgaaacccg   3600
acaggactat aaagatacca ggcgtttccc cctggaagct ccctcgtgcg ctctcctgtt   3660
ccgaccctgc cgcttaccgg atacctgtcc gcctttctcc cttcgggaag cgtggcgctt   3720
tctcatagct cacgctgtag gtatctcagt tcggtgtagg tcgttcgctc caagctgggc   3780
tgtgtgcacg aaccccccgt tcagcccgac cgctgcgcct tatccggtaa ctatcgtctt   3840
gagtccaacc cggtaagaca cgacttatcg ccactggcag cagccactgg taacaggatt   3900
agcagagcga ggtatgtagg cggtgctaca gagttcttga agtggtggcc taactacggc   3960
tacactagaa gaacagtatt tggtatctgc gctctgctga agccagttac cttcggaaaa   4020
agagttggta gctcttgatc cggcaaacaa accaccgctg gtagcggtgg tttttttgtt   4080
tgcaagcagc agattacgcg cagaaaaaaa ggatctcaag aagatccttt gatcttttct   4140
acggggtctg acgctcagtg gaacgaaaac tcacgttaag ggattttggt catggctagt   4200
taattaacat ttaaatcagc ggccgcaata aaatatcttt attttcatta catctgtgtg   4260
ttggttttt gtgtgaatcg taactaacat acgctctcca tcaaaacaaa acgaaacaaa   4320
```

-continued

| | |
|---|---|
| acaaactagc aaaataggct gtccccagtg caagtgcagg tgccagaaca tttctctatc | 4380 |
| gaa | 4383 |

<210> SEQ ID NO 97
<211> LENGTH: 4383
<212> TYPE: DNA
<213> ORGANISM: Artificial Sequence
<220> FEATURE:
<223> OTHER INFORMATION: pCXCL11-IgG4Fc

<400> SEQUENCE: 97

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgttccccat gttcaaaaga ggacgctgtc | 660 |
| tttgcatagg ccctggggta aaagcagtga agtggcaga tattgagaaa gcctccataa | 720 |
| tgtacccaag taacaactgt gacaaaatag aagtgattat taccctgaaa gaaaataaag | 780 |
| gacaacgatg cctaaatccc aaatcgaagc aagcaaggct tataatcaaa aagttgaaa | 840 |
| gaaagaattt tccccatgc ccatcatgcc cagcacctga gttcctgggg ggaccatcag | 900 |
| tcttcctgtt cccccaaaa cccaaggaca ctctcatgat ctcccggacc cctgaggtca | 960 |
| cgtgcgtggt ggtggacgtg agccaggaag accccgaggt ccagttcaac tggtacgtgg | 1020 |
| atggcgtgga ggtgcataat gccaagacaa agccgcggga ggagcagttc aacagcacgt | 1080 |
| accgtgtggt cagcgtcctc accgtcctgc accaggactg gctgaacggc aaggagtaca | 1140 |
| agtgcaaggt ctccaacaaa ggcctcccgt cctccatcga aaaaccatc tccaaagcca | 1200 |
| aagggcagcc ccgagagcca caggtgtaca ccctgccccc atcccaggag gagatgacca | 1260 |
| agaaccaggt cagcctgacc tgcctggtca aaggcttcta ccccagcgac atcgccgtgg | 1320 |
| agtgggagag caatgggcag ccggagaaca actacaagac cacgcctccc gtgctggact | 1380 |
| ccgacggctc cttcttcctc tacagcaggc taaccgtgga caagagcagg tggcaggagg | 1440 |
| ggaatgtctt ctcatgctcc gtgatgcatg aggctctgca caaccactac acacagaaga | 1500 |
| gcctctccct gtctccgggt aaatgagtgc tagctggcca gacatgataa gatacattga | 1560 |
| tgagtttgga caaaccacaa ctagaatgca gtgaaaaaaa tgctttattt gtgaaatttg | 1620 |
| tgatgctatt gctttatttg taaccattat aagctgcaat aaacaagtta acaacaacaa | 1680 |
| ttgcattcat tttatgtttc aggttcaggg ggaggtgtgg gaggttttt aaagcaagta | 1740 |
| aaacctctac aaatgtggta tggaattaat tctaaaatac agcatagcaa aactttaacc | 1800 |
| tccaaatcaa gcctctactt gaatcctttt ccgaggcatg aataaggcat aggcatcagg | 1860 |
| ggctgttgcc aatgtgcatt agctgtttgc agcctcacct tctttcatgg agtttaagat | 1920 |

```
atagtgtatt ttcccaaggt ttgaactagc tcttcatttc tttatgtttt aaatgcactg      1980
acctcccaca ttcccttttt agtaaaatat tcagaaataa tttaaataca tcattgcaat      2040
gaaaataaat gttttttatt aggcagaatc cagatgctca aggcccttca taatatcccc     2100
cagtttagta gttggactta gggaacaaag gaacctttaa tagaaattgg acagcaagaa     2160
agcgagcttc tagcttatcc tcagtcctgc tcctctgcca caaagtgcac gcagttgccg     2220
gccgggtcgc gcagggcgaa ctcccgcccc cacggctgct cgccgatctc ggtcatggcc     2280
ggcccggagg cgtcccggaa gttcgtggac acgacctccg accactcggc gtacagctcg     2340
tccaggccgc gcacccacac ccaggccagg gtgttgtccg gcaccacctg gtcctggacc     2400
gcgctgatga acagggtcac gtcgtcccgg accacaccgg cgaagtcgtc ctccacgaag     2460
tcccgggaga cccgagccg gtcggtccag aactcgaccg ctccggcgac gtcgcgcgcg     2520
gtgagcaccg gaacggcact ggtcaacttg gccatgatgg ctcctcctgt caggagagga     2580
aagagaagaa ggttagtaca attgctatag tgagttgtat tatactatgc agatatacta     2640
tgccaatgat taattgtcaa actagggctg cagggttcat agtgccactt ttcctgcact     2700
gccccatctc ctgcccaccc tttcccaggc atagacagtc agtgacttac caaactcaca     2760
ggagggagaa ggcagaagct tgagacagac ccgcgggacc gccgaactgc gagggacgt      2820
ggctagggcg gcttctttta tggtgcgccg gccctcggag gcagggcgct cggggaggcc     2880
tagcggccaa tctgcggtgg caggaggcgg ggccgaaggc cgtgcctgac caatccggag     2940
cacataggag tctcagcccc ccgccccaaa gcaaggggaa gtcacgcgcc tgtagcgcca     3000
gcgtgttgtg aaatgggggc ttggggggt tggggccctg actagtcaaa caaactcccc      3060
attgacgtca atggggtgga gacttggaaa tccccgtgag tcaaaccgct atccacgccc     3120
attgatgtac tgccaaaacc gcatcatcat ggtaatagcg atgactaata cgtagatgta     3180
ctgccaagta ggaaagtccc ataaggtcat gtactgggca taatgccagg cgggccattt     3240
accgtcattg acgtcaatag ggggcgtact tggcatatga tacacttgat gtactgccaa     3300
gtgggcagtt taccgtaaat actccaccca ttgacgtcaa tggaaagtcc ctattggcgt     3360
tactatggga acatacgtca ttattgacgt caatgggcgg gggtcgttgg gcggtcagcc     3420
aggcgggcca tttaccgtaa gttatgtaac gcctgcaggt taattaagaa catgtgagca     3480
aaaggccagc aaaaggccag gaaccgtaaa aaggccgcgt tgctggcgtt tttccatagg     3540
ctccgccccc ctgacgagca tcacaaaaat cgacgctcaa gtcagaggtg gcgaaacccg     3600
acaggactat aaagatacca ggcgtttccc cctggaagct ccctcgtgcg ctctcctgtt     3660
ccgaccctgc cgcttaccgg atacctgtcc gcctttctcc cttcgggaag cgtggcgctt     3720
tctcatagct cacgctgtag gtatctcagt tcggtgtagg tcgttcgctc caagctgggc     3780
tgtgtgcacg aaccccccgt tcagcccgac cgctgcgcct tatccggtaa ctatcgtctt     3840
gagtccaacc cggtaagaca cgacttatcg ccactggcag cagccactgg taacaggatt     3900
agcagagcga ggtatgtagg cggtgctaca gagttcttga agtggtggcc taactacggc     3960
tacactagaa gaacagtatt tggtatctgc gctctgctga agccagttac cttcggaaaa     4020
agagttggta gctcttgatc cggcaaacaa accaccgctg gtagcggtgg tttttttgtt     4080
tgcaagcagc agattacgcg cagaaaaaaa ggatctcaag aagatccttt gatcttttct     4140
acggggtctg acgctcagtg gaacgaaaac tcacgttaag ggattttggt catggctagt     4200
taattaacat ttaaatcagc ggccgcaata aaatatcttt attttcatta catctgtgtg     4260
ttggttttt gtgtgaatcg taactaacat acgctctcca tcaaaacaaa acgaaacaaa     4320
```

```
acaaactagc aaaataggct gtccccagtg caagtgcagg tgccagaaca tttctctatc    4380
gaa                                                                  4383

<210> SEQ ID NO 98
<211> LENGTH: 4374
<212> TYPE: DNA
<213> ORGANISM: Artificial Sequence
<220> FEATURE:
<223> OTHER INFORMATION: pCXCL11(4-73)-IgG4Fc

<400> SEQUENCE: 98
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa    120
actgggaaag tgatgtcgtg tactggctcc gccttttttcc cgagggtggg ggagaaccgt   180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgttcaaaag aggacgctgt ctttgcatag    660
gccctggggt aaaagcagtg aaagtggcag atattgagaa agcctccata atgtacccaa    720
gtaacaactg tgacaaaata gaagtgatta ttaccctgaa agaaaataaa ggacaacgat    780
gcctaaatcc caaatcgaag caagcaaggc ttataatcaa aaaagttgaa agaaagaatt    840
ttcccccatg cccatcatgc ccagcacctg agttcctggg gggaccatca gtcttcctgt    900
tccccccaaa acccaaggac actctcatga tctcccggac ccctgaggtc acgtgcgtgg    960
tggtggacgt gagccaggaa gaccccgagg tccagttcaa ctggtacgtg gatggcgtgg   1020
aggtgcataa tgccaagaca aagccgcggg aggagcagtt caacagcacg taccgtgtgg   1080
tcagcgtcct caccgtcctg caccaggact ggctgaacgg caaggagtac aagtgcaagg   1140
tctccaacaa aggcctcccg tcctccatcg agaaaaccat ctccaaagcc aaagggcagc   1200
cccgagagcc acaggtgtac accctgcccc catcccagga ggagatgacc aagaaccagg   1260
tcagcctgac ctgcctggtc aaaggcttct accccagcga catcgccgtg gagtgggaga   1320
gcaatgggca gccggagaac aactacaaga ccacgcctcc cgtgctggac tccgacggct   1380
ccttcttcct ctacagcagg ctaaccgtgg acaagagcag gtggcaggag gggaatgtct   1440
tctcatgctc cgtgatgcat gaggctctgc acaaccacta cacacagaag agcctctccc   1500
tgtctccggg taaatgagtg ctagctggcc agacatgata agatacattg atgagtttgg   1560
acaaaccaca actagaatgc agtgaaaaaa atgctttatt tgtgaaattt gtgatgctat   1620
tgctttattt gtaaccatta taagctgcaa taaacaagtt aacaacaaca attgcattca    1680
ttttatgttt caggttcagg gggaggtgtg ggaggttttt taaagcaagt aaaacctcta   1740
caaatgtggt atggaattaa ttctaaaata cagcatagca aactttaac ctccaaatca    1800 agcctctact tgaatccttt tctgagggat gaataaggca taggcatcag gggctgttgc   1860
caatgtgcat tagctgtttg cagcctcacc ttctttcatg gagtttaaga tatagtgtat   1920
```

```
tttcccaagg tttgaactag ctcttcattt ctttatgttt taaatgcact gacctcccac    1980
attccctttt tagtaaaata ttcagaaata atttaaatac atcattgcaa tgaaaataaa    2040
tgttttttat taggcagaat ccagatgctc aaggcccttc ataatatccc ccagtttagt    2100
agttggactt agggaacaaa ggaacccttta atagaaattg gacagcaaga aagcgagctt    2160
ctagcttatc ctcagtcctg ctcctctgcc acaaagtgca cgcagttgcc ggccgggtcg    2220
cgcagggcga actcccgccc ccacggctgc tcgccgatct cggtcatggc cggcccggag    2280
gcgtcccgga agttcgtgga cacgacctcc gaccactcgg cgtacagctc gtccaggccg    2340
cgcacccaca cccaggccag ggtgttgtcc ggcaccacct ggtcctggac cgcgctgatg    2400
aacagggtca cgtcgtcccg gaccacaccg gcgaagtcgt cctccacgaa gtcccgggag    2460
aacccgagcc ggtcggtcca gaactcgacc gctccggcga cgtcgcgcgc ggtgagcacc    2520
ggaacggcac tggtcaactt ggccatgatg gctcctcctg tcaggagagg aaagagaaga    2580
aggttagtac aattgctata gtgagttgta ttatactatg cagatatact atgccaatga    2640
ttaattgtca aactagggct gcaggggttca tagtgccact tttcctgcac tgccccatct    2700
cctgcccacc ctttcccagg catagacagt cagtgactta ccaaactcac aggagggaga    2760
aggcagaagc ttgagacaga cccgcgggac cgccgaactg cgaggggacg tggctagggc    2820
ggcttctttt atggtgcgcc ggccctcgga ggcagggcgc tcggggaggc ctagcggcca    2880
atctgcggtg gcaggaggcg gggccgaagg ccgtgcctga ccaatccgga gcacatagga    2940
gtctcagccc cccgccccaa agcaaggggga agtcacgcgc ctgtagcgcc agcgtgttgt    3000
gaaatggggg cttgggggggg ttggggcccct gactagtcaa aacaaactcc cattgacgtc    3060
aatggggtgg agacttggaa atcccgtga gtcaaaccgc tatccacgcc cattgatgta    3120
ctgccaaaac cgcatcatca tggtaatagc gatgactaat acgtagatgt actgccaagt    3180
aggaaagtcc cataaggtca tgtactgggc ataatgccag gcgggccatt taccgtcatt    3240
gacgtcaata gggggcgtac ttggcatatg atacacttga tgtactgcca agtgggcagt    3300
ttaccgtaaa tactccaccc attgacgtca atggaaagtc cctattggcg ttactatggg    3360
aacatacgtc attattgacg tcaatgggcg gggtcgttg ggcggtcagc caggcgggcc    3420
atttaccgta agttatgtaa cgcctgcagg ttaattaaga acatgtgagc aaaaggccag    3480
caaaaggcca ggaaccgtaa aaaggccgcg ttgctggcgt ttttccatag gctccgcccc    3540
cctgacgagc atcacaaaaa tcgacgctca agtcagaggt ggcgaaaccc gacaggacta    3600
taaagatacc aggcgtttcc ccctggaagc tccctcgtgc gctctcctgt tccgaccctg    3660
ccgcttaccg gatacctgtc cgcctttctc ccttcgggaa gcgtggcgct ttctcatagc    3720
tcacgctgta ggtatctcag ttcggtgtag gtcgttcgct ccaagctggg ctgtgtgcac    3780
gaaccccccg ttcagcccga ccgctgcgcc ttatccggta actatcgtct tgagtccaac    3840
ccggtaagac acgacttatc gccactggca gcagccactg gtaacaggat tagcagagcg    3900
aggtatgtag gcggtgctac agagttcttg aagtggtggc ctaactacgg ctacactaga    3960
agaacagtat ttggtatctg cgctctgctg aagccagtta ccttcggaaa aagagttggt    4020
agctcttgat ccggcaaaca aaccaccgct ggtagcggtg gtttttttgt ttgcaagcag    4080
cagattacgc gcagaaaaaa aggatctcaa gaagatcctt tgatcttttc tacggggtct    4140
gacgctcagt ggaacgaaaa ctcacgttaa gggattttgg tcatgctag ttaattaaca    4200 tttaaatcag cggccgcaat aaaatatctt tattttcatt acatctgtgt gttggttttt    4260
tgtgtgaatc gtaactaaca tacgctctcc atcaaaacaa aacgaaacaa aacaaactag    4320
```

```
caaaataggc tgtccccagt gcaagtgcag gtgccagaac atttctctat cgaa        4374
```

<210> SEQ ID NO 99
<211> LENGTH: 4374
<212> TYPE: DNA
<213> ORGANISM: Artificial Sequence
<220> FEATURE:
<223> OTHER INFORMATION: pCXCL11(4-73K/H-A)-IgG4Fc

<400> SEQUENCE: 99

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc ttttcgcaa cgggtttgcc gccagaacac     240
agctgaagct tcgaggggct cgcatctctc cttcacgcgc ccgccgccct acctgaggcc    300
gccatccacg ccggttgagt cgcgttctgc cgcctcccgc tgtggtgcc tcctgaactg     360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgttcaaaag gacgctgt ctttgcatag      660
gccctggggt aaaagcagtg aaagtggcag atattgaggc cgcctccata atgtacccaa    720
gtaacaactg tgacaaaata gaagtgatta ttaccctggc agaaaatgcc ggacaagcat    780
gcctaaatcc cgcctcggca caagcagccc ttataatcgc agccgttgaa gcagccaatt    840
ttccccccatg cccatcatgc ccagcacctg agttcctggg ggaccatca gtcttcctgt     900
tccccccaaa acccaaggac actctcatga tctcccggac ccctgaggtc acgtgcgtgg    960
tggtggacgt gagccaggaa gaccccgagg tccagttcaa ctggtacgtg gatggcgtgg   1020
aggtgcataa tgccaagaca aagccgcggg aggagcagtt caacagcacg taccgtgtgg   1080
tcagcgtcct caccgtcctg caccaggact ggctgaacgg caaggagtac aagtgcaagg   1140
tctccaacaa aggcctcccg tcctccatcg agaaaaccat ctccaaagcc aaagggcagc   1200
cccgagagcc acaggtgtac accctgcccc catcccagga ggagatgacc aagaaccagg   1260
tcagcctgac ctgcctggtc aaaggcttct accccagcga catcgccgtg gagtgggaga   1320
gcaatgggca gccggagaac aactacaaga ccacgcctcc cgtgctggac tccgacggct   1380
ccttcttcct ctacagcagg ctaaccgtgg acaagagcag gtggcaggag gggaatgtct   1440
tctcatgctc cgtgatgcat gaggctctgc acaaccacta cacacagaag agcctctccc   1500
tgtctccggg taaatgagtg ctagctggcc agacatgata agatacattg atgagtttgg   1560
acaaaccaca actagaatgc agtgaaaaaa atgctttatt tgtgaaattt gtgatgctat   1620
tgctttattt gtaaccatta taagctgcaa taaacaagtt aacaacaaca attgcattca   1680
ttttatgttt caggttcagg gggaggtgtg ggaggttttt taaagcaagt aaaacctcta   1740
caaatgtggt atggaattaa ttctaaaata cagcatagca aaactttaac ctccaaatca   1800
agcctctact tgaatccttt tctgagggat gaataaggca taggcatcag gggctgttgc   1860
caatgtgcat tagctgtttg cagcctcacc tttctttcatg gagtttaaga tatagtgtat   1920
tttcccaagg tttgaactag ctcttcattt ctttatgttt taaatgcact gacctcccac   1980
```

```
attccctttt tagtaaaata ttcagaaata atttaaatac atcattgcaa tgaaaataaa    2040 tgtttttat taggcagaat ccagatgctc aaggcccttc ataatatccc ccagtttagt      2100
agttggactt agggaacaaa ggaaccttta atagaaattg acagcaaga aagcgagctt      2160 ctagcttatc ctcagtcctg ctcctctgcc acaaagtgca cgcagttgcc ggccgggtcg    2220
cgcagggcga actcccgccc ccacggctgc tcgccgatct cggtcatggc cggcccggag    2280
gcgtcccgga agtcgtgga cacgacctcc gaccactcgg cgtacagctc gtccaggccg     2340
cgcacccaca cccaggccag ggtgttgtcc ggcaccacct ggtcctggac cgcgctgatg    2400
aacagggtca cgtcgtcccg gaccacaccg gcgaagtcgt cctccacgaa gtcccgggag   2460
aacccgagcc ggtcggtcca gaactcgacc gctccggcga cgtcgcgcgc ggtgagcacc   2520
ggaacggcac tggtcaactt ggccatgatg gctcctcctg tcaggagagg aaagagaaga   2580
aggttagtac aattgctata gtgagttgta ttatactatg cagatatact atgccaatga    2640
ttaattgtca aactagggct gcaggggttca tagtgccact tttcctgcac tgccccatct   2700
cctgcccacc ctttcccagg catagacagt cagtgactta ccaaactcac aggagggaga   2760
aggcagaagc ttgagacaga cccgcgggac cgccgaactg cgaggggacg tggctagggc   2820
ggcttctttt atggtgcgcc ggccctcgga ggcagggcgc tcggggaggc ctagcggcca   2880
atctgcggtg gcaggaggcg gggccgaagg ccgtgcctga ccaatccgga gcacatagga   2940
gtctcagccc cccgccccaa agcaagggga agtcacgcgc ctgtagcgcc agcgtgttgt   3000
gaaatggggg cttggggggg ttggggccct gactagtcaa acaaactcc cattgacgtc    3060 aatggggtgg agacttggaa atccccgtga gtcaaaccgc tatccacgcc cattgatgta   3120
ctgccaaaac cgcatcatca tggtaatagc gatgactaat acgtagatgt actgccaagt   3180
aggaaagtcc cataaggtca tgtactgggc ataatgccag gcgggccatt taccgtcatt   3240
gacgtcaata gggggcgtac ttggcatatg atacacttga tgtactgcca agtgggcagt   3300
ttaccgtaaa tactccaccc attgacgtca atggaaagtc cctattggcg ttactatggg   3360
aacatacgtc attattgacg tcaatgggcg ggggtcgttg gcggtcagc caggcgggcc    3420 atttaccgta agttatgtaa cgcctgcagg ttaattaaga acatgtgagc aaaaggccag   3480
caaaaggcca ggaaccgtaa aaaggccgcg ttgctggcgt ttttccatag gctccgcccc   3540
cctgacgagc atcacaaaaa tcgacgctca agtcagaggt ggcgaaaccc gacaggacta   3600
taaagatacc aggcgtttcc ccctggaagc tccctcgtgc gctctcctgt tccgaccctg   3660
ccgcttaccg gatacctgtc cgcctttctc ccttcgggaa gcgtggcgct ttctcatagc   3720
tcacgctgta ggtatctcag ttcggtgtag gtcgttcgct ccaagctggg ctgtgtgcac   3780
gaaccccccg ttcagcccga ccgctgcgcc ttatccggta actatcgtct tgagtccaac   3840
ccggtaagac acgacttatc gccactggca gcagccactg gtaacaggat tagcagagcg   3900
aggtatgtag gcggtgctac agagttcttg aagtggtggc ctaactacgg ctacactaga   3960
agaacagtat ttggtatctg cgctctgctg aagccagtta ccttcggaaa aagagttggt   4020
agctcttgat ccggcaaaca aaccaccgct ggtagcggtg gtttttttgt ttgcaagcag   4080
cagattacgc gcagaaaaaa aggatctcaa gaagatcctt tgatcttttc tacgggtct   4140 gacgctcagt ggaacgaaaa ctcacgttaa gggattttgg tcatgctag ttaattaaca    4200 tttaaatcag cggccgcaat aaaatatctt tattttcatt acatctgtgt gttggttttt    4260
tgtgtgaatc gtaactaaca tacgctctcc atcaaaacaa aacgaaacaa aacaaactag    4320
caaaataggc tgtccccagt gcaagtgcag gtgccagaac atttctctat cgaa          4374
```

<210> SEQ ID NO 100
<211> LENGTH: 4434
<212> TYPE: DNA
<213> ORGANISM: Artificial Sequence
<220> FEATURE:
<223> OTHER INFORMATION: pCXCL13-IgG1Fc

<400> SEQUENCE: 100

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc ttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggttctgga ggtctattac acaagcttga     660
ggtgtagatg tgtccaagag agctcagtct ttatccctag acgcttcatt gatcgaattc     720
aaatcttgcc ccgtgggaat ggttgtccaa gaaagaaat catagtctgg aagaagaaca     780
agtcaattgt gtgtgtggac cctcaagctg aatggataca agaatgatg gaagtattga     840
gaaaagaag ttcttcaact ctaccagttc cagtgtttaa gagaaagatt cccgacaaaa     900
ctcacacatg cccaccgtgc ccagcacctg aactcctggg gggaccgtca gtcttcctct     960
tccccccaaa acccaaggac accctcatga tctcccggac ccctgaggtc acatgcgtgg    1020
tggtggacgt gagccacgaa gaccctgagg tcaagttcaa ctggtacgtg gacggcgtgg    1080
aggtgcataa tgccaagaca aagccgcggg aggagcagta caacagcacg taccgtgtgg    1140
tcagcgtcct caccgtcctg caccaggact ggctgaatgg caaggagtac aagtgcaagg    1200
tctccaacaa agcccctccca gcccccatcg agaaaaccat ctccaaagcc aaagggcagc    1260
cccgagaacc acaggtgtac accctgcccc catcccggga ggagatgacc aagaaccagg    1320
tcagcctgac ctgcctggtc aaaggcttct atcccagcga catcgccgtg gagtgggaga    1380
gcaatgggca gccggagaac aactacaaga ccacgcctcc cgtgctggac tccgacggct    1440
ccttcttcct ctacagcaag ctcaccgtgg acaagagcag gtggcagcag gggaacgtct    1500
tctcatgctc cgtgatgcac gaggctctgc acaaccacta cacgcagaag agcctctccc    1560
tgtctccggg taaatgagtg ctagctggcc agacatgata agatacattg atgagtttgg    1620
acaaaccaca actagaatgc agtgaaaaaa atgctttatt tgtgaaattt gtgatgctat    1680
tgctttattt gtaaccatta taagctgcaa taaacaagtt aacaacaaca attgcattca    1740
ttttatgttt caggttcagg gggaggtgtg ggaggttttt taaagcaagt aaaacctcta    1800
caaatgtggt atggaattaa ttctaaaata cagcatagca aactttaac ctccaaatca    1860
agcctctact tgaatccttt tctgagggat gaataaggca taggcatcag gggctgttgc    1920
caatgtgcat tagctgtttg cagcctcacc ttctttcatg gagtttaaga tatagtgtat    1980
tttcccaagg tttgaactag ctcttcattt ctttatgttt taaatgcact gacctcccac    2040
```

-continued

```
attcccttt tagtaaaata ttcagaaata atttaaatac atcattgcaa tgaaaataaa   2100
tgttttttat taggcagaat ccagatgctc aaggcccttc ataatatccc ccagtttagt   2160
agttggactt agggaacaaa ggaaccttta atagaaattg gacagcaaga aagcgagctt   2220
ctagcttatc ctcagtcctg ctcctctgcc acaaagtgca cgcagttgcc ggccgggtcg   2280
cgcagggcga actcccgccc ccacggctgc tcgccgatct cggtcatggc cggcccggag   2340
gcgtcccgga agttcgtgga cacgacctcc gaccactcgg cgtacagctc gtccaggccg   2400
cgcacccaca cccaggccag ggtgttgtcc ggcaccacct ggtcctggac cgcgctgatg   2460
aacagggtca cgtcgtcccg gaccacaccg gcgaagtcgt cctccacgaa gtcccgggag   2520
aacccgagcc ggtcggtcca gaactcgacc gctccggcga cgtcgcgcgc ggtgagcacc   2580
ggaacggcac tggtcaactt ggccatgatg gctcctcctg tcaggagagg aaagagaaga   2640
aggttagtac aattgctata gtgagttgta ttatactatg cagatatact atgccaatga   2700
ttaattgtca aactagggct gcagggttca tagtgccact tttcctgcac tgccccatct   2760
cctgcccacc ctttcccagg catagacagt cagtgactta ccaaactcac aggagggaga   2820
aggcagaagc ttgagacaga cccgcgggac cgccgaactg cgaggggacg tggctagggc   2880
ggcttctttt atggtgcgcc ggccctcgga ggcagggcgc tcggggaggc ctagcggcca   2940
atctgcggtg gcaggaggcg gggccgaagg ccgtgcctga ccaatccgga gcacatagga   3000
gtctcagccc cccgccccaa agcaagggga agtcacgcgc ctgtagcgcc agcgtgttgt   3060
gaaatggggg cttggggggg ttggggccct gactagtcaa aacaaactcc cattgacgtc   3120
aatggggtgg agacttggaa atccccgtga gtcaaaccgc tatccacgcc cattgatgta   3180
ctgccaaaac cgcatcatca tggtaatagc gatgactaat acgtagatgt actgccaagt   3240
aggaaagtcc cataaggtca tgtactgggc ataatgccag gcgggccatt taccgtcatt   3300
gacgtcaata gggggcgtac ttggcatatg atacacttga tgtactgcca agtgggcagt   3360
ttaccgtaaa tactccaccc attgacgtca atggaaagtc cctattggcg ttactatggg   3420
aacatacgtc attattgacg tcaatgggcg ggggtcgttg ggcggtcagc caggcgggcc   3480
atttaccgta agttatgtaa cgcctgcagg ttaattaaga acatgtgagc aaaaggccag   3540
caaaaggcca ggaaccgtaa aaaggccgcg ttgctggcgt ttttccatag gctccgcccc   3600
cctgacgagc atcacaaaaa tcgacgctca agtcagaggt ggcgaaaccc gacaggacta   3660
taaagatacc aggcgtttcc ccctggaagc tccctcgtgc gctctcctgt tccgaccctg   3720
ccgcttaccg gatacctgtc cgcctttctc ccttcgggaa gcgtggcgct ttctcatagc   3780
tcacgctgta ggtatctcag ttcggtgtag gtcgttcgct ccaagctggg ctgtgtgcac   3840
gaaccccccg ttcagcccga ccgctgcgcc ttatccggta actatcgtct tgagtccaac   3900
ccggtaagac acgacttatc gccactggca gcagccactg gtaacaggat tagcagagcg   3960
aggtatgtag gcggtgctac agagttcttg aagtggtggc ctaactacgg ctacactaga   4020
agaacagtat ttggtatctg cgctctgctg aagccagtta ccttcggaaa aagagttggt   4080
agctcttgat ccggcaaaca aaccaccgct ggtagcggtg gtttttttgt ttgcaagcag   4140
cagattacgc gcagaaaaaa aggatctcaa gaagatcctt tgatcttttc tacggggtct   4200
gacgctcagt ggaacgaaaa ctcacgttaa gggattttgg tcatggctag ttaattaaca   4260
tttaaatcag cggccgcaat aaaatatctt tattttcatt acatctgtgt gttggttttt   4320
tgtgtgaatc gtaactaaca tacgctctcc atcaaaacaa aacgaaacaa aacaaactag   4380
caaaataggc tgtccccagt gcaagtgcag gtgccagaac atttctctat cgaa         4434
```

<210> SEQ ID NO 101
<211> LENGTH: 4428
<212> TYPE: DNA
<213> ORGANISM: Artificial Sequence
<220> FEATURE:
<223> OTHER INFORMATION: pCXCL13(3-87)-IgG1Fc

<400> SEQUENCE: 101

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc tgtggtgcc  tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggaggtcta ttacaagc ttgaggtgta       660
gatgtgtcca agagagctca gtctttatcc ctagacgctt cattgatcga attcaaatct     720
tgccccgtgg gaatggttgt ccaagaaaag aaatcatagt ctggaagaag aacaagtcaa     780
ttgtgtgtgt ggaccctcaa gctgaatgga tacaaagaat gatggaagta ttgagaaaaa     840
gaagttcttc aactctacca gttccagtgt ttaagagaaa gattcccgac aaaactcaca     900
catgcccacc gtgcccagca cctgaactcc tggggggacc gtcagtcttc ctcttccccc     960
caaaacccaa ggacaccctc atgatctccc ggacccctga ggtcacatgc gtggtggtgg    1020
acgtgagcca cgaagaccct gaggtcaagt tcaactggta cgtggacggc gtggaggtgc    1080
ataatgccaa gacaaagccg cgggaggagc agtacaacag cacgtaccgt gtggtcagcg    1140
tcctcaccgt cctgcaccag gactggctga atggcaagga gtacaagtgc aaggtctcca    1200
acaaagccct cccagccccc atcgagaaaa ccatctccaa agccaaaggg cagccccgag    1260
aaccacaggt gtacaccctg cccccatccc gggaggagat gaccaagaac caggtcagcc    1320
tgacctgcct ggtcaaaggc ttctatccca gcgacatcgc cgtggagtgg gagagcaatg    1380
ggcagccgga gaacaactac aagaccacgc ctcccgtgct ggactccgac ggctccttct    1440
tcctctacag caagctcacc gtggacaaga gcaggtggca gcagggaaac gtcttctcat    1500
gctccgtgat gcacgaggct ctgcacaacc actacacgca gaagagcctc tccctgtctc    1560
cgggtaaatg agtgctagct ggccagacat gataagatac attgatgagt ttggacaaac    1620
cacaactaga atgcagtgaa aaaaatgctt tatttgtgaa atttgtgatg ctattgcttt    1680
atttgtaacc attataagct gcaataaaca agttaacaac aacaattgca ttcattttat    1740
gtttcaggtt caggggggagg tgtgggaggt ttttta aagc aagtaaaacc tctacaaatg    1800
tggtatggaa ttaattctaa aatacagcat agcaaaactt taacctccaa atcaagcctc    1860
tacttgaatc cttttctgag ggatgaataa ggcataggca tcagggctg ttgccaatgt     1920
gcattagctg tttgcagcct caccttcttt catggagttt aagatatagt gtattttccc    1980
aaggtttgaa ctagctcttc atttctttat gttttaaatg cactgacctc ccacattccc    2040
```

```
tttttagtaa aatattcaga aataatttaa atacatcatt gcaatgaaaa taaatgtttt    2100
ttattaggca gaatccagat gctcaaggcc cttcataata tcccccagtt tagtagttgg    2160
acttagggaa caaaggaacc tttaatagaa attggacagc aagaaagcga gcttctagct    2220
tatcctcagt cctgctcctc tgccacaaag tgcacgcagt tgccggccgg gtcgcgcagg    2280
gcgaactccc gcccccacgg ctgctcgccg atctcggtca tggccggccc ggaggcgtcc    2340
cggaagttcg tggacacgac ctccgaccac tcggcgtaca gctcgtccag gccgcgcacc    2400
cacacccagg ccagggtgtt gtccggcacc acctggtcct ggaccgcgct gatgaacagg    2460
gtcacgtcgt cccggaccac accggcgaag tcgtcctcca cgaagtcccg ggagaacccg    2520
agccggtcgg tccagaactc gaccgctccg gcgacgtcgc gcgcggtgag caccggaacg    2580
gcactggtca acttggccat gatggctcct cctgtcagga gaggaaagag aagaaggtta    2640
gtacaattgc tatagtgagt tgtattatac tatgcagata tactatgcca atgattaatt    2700
gtcaaactag gctgcagggt tcatagtgcc cactttttcct gcactgcccc atctcctgcc    2760
caccctttcc caggcataga cagtcagtga cttaccaaac tcacaggagg gagaaggcag    2820
aagcttgaga cagacccgcg ggaccgccga actgcgaggg gacgtggcta gggcggcttc    2880
ttttatggtg cgccggccct cggaggcagg gcgctcgggg aggcctagcg gccaatctgc    2940
ggtggcagga ggcggggccg aaggccgtgc ctgaccaatc cggagcacat aggagtctca    3000
gccccccgcc ccaaagcaag gggaagtcac gcgcctgtag cgccagcgtg ttgtgaaatg    3060
ggggcttggg ggggttgggg ccctgactag tcaaaacaaa ctcccattga cgtcaatggg    3120
gtggagactt ggaaatcccc gtgagtcaaa ccgctatcca cgcccattga tgtactgcca    3180
aaaccgcatc atcatggtaa tagcgatgac taatacgtag atgtactgcc aagtaggaaa    3240
gtcccataag gtcatgtact gggcataatg ccaggcgggc catttaccgt cattgacgtc    3300 aataggggc gtacttggca tatgatacac ttgatgtact gccaagtggg cagtttaccg    3360
taaatactcc acccattgac gtcaatggaa agtccctatt ggcgttacta tgggaacata    3420
cgtcattatt gacgtcaatg ggcggggggtc gttgggcggt cagccaggcg ggccatttac    3480
cgtaagttat gtaacgcctg caggttaatt aagaacatgt gagcaaaagg ccagcaaaag    3540
gccaggaacc gtaaaaaggc cgcgttgctg gcgttttttcc ataggctccg ccccccctgac    3600 gagcatcaca aaaatcgacg ctcaagtcag aggtggcgaa acccgacagg actataaaga    3660
taccaggcgt ttccccctgg aagctccctc gtgcgctctc ctgttccgac cctgccgctt    3720
accggatacc tgtccgcctt tctcccttcg ggaagcgtgg cgctttctca tagctcacgc    3780
tgtaggtatc tcagttcggt gtaggtcgtt cgctccaagc tgggctgtgt gcacgaaccc    3840
cccgttcagc ccgaccgctg cgccttatcc ggtaactatc gtcttgagtc aacccggta    3900 agacacgact tatcgccact ggcagcagcc actggtaaca ggattagcag agcgaggtat    3960
gtaggcggtg ctacagagtt cttgaagtgg tggcctaact acggctacac tagaagaaca    4020
gtatttggta tctgcgctct gctgaagcca gttaccttcg gaaaaagagt tggtagctct    4080
tgatccggca acaaaccac cgctggtagc ggtggttttt tgtttgcaa gcagcagatt    4140 acgcgcagaa aaaaggatc tcaagaagat cctttgatct tttctacggg gtctgacgct    4200
cagtggaacg aaaactcacg ttaagggatt ttggtcatga ctagttaatt aacatttaaa    4260
tcagcggccg caataaaata tctttatttt cattacatct gtgtgttggt tttttgtgtg    4320
aatcgtaact aacatacgct ctccatcaaa acaaaacgaa acaaaacaaa ctagcaaaat    4380
aggctgtccc cagtgcaagt gcaggtgcca gaacatttct ctatcgaa               4428
```

<210> SEQ ID NO 102
<211> LENGTH: 4428
<212> TYPE: DNA
<213> ORGANISM: Artificial Sequence
<220> FEATURE:
<223> OTHER INFORMATION: pCXCL13(3-87K/H-A)-IgG1Fc

<400> SEQUENCE: 102

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc tgtggtgcc tcctgaactg     360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggaggtcta ttacaagc ttgaggtgta       660
gatgtgtcca agagagctca gtctttatcc ctagacgctt cattgatgcc attcaaatct    720
tgccccgtgg gaatggttgt ccaagaaaag aaatcatagt ctgggctgcg aacgcttcaa    780
ttgtgtgtgt ggaccctcaa gctgaatgga tacaagccat gatggaagta ttggctgcgg    840
ctagttcttc aactctacca gttccagtgt ttgccgctgc gattcccgac aaaactcaca    900
catgcccacc gtgcccagca cctgaactcc tggggggacc gtcagtcttc ctcttccccc    960
caaaacccaa ggacaccctc atgatctccc ggacccctga ggtcacatgc gtggtggtgg   1020
acgtgagcca cgaagaccct gaggtcaagt tcaactggta cgtggacggc gtggaggtgc   1080
ataatgccaa gacaaagccg cgggaggagc agtacaacag cacgtaccgt gtggtcagcg   1140
tcctcaccgt cctgcaccag gactggctga atggcaagga gtacaagtgc aaggtctcca   1200
acaaagccct cccagccccc atcgagaaaa ccatctccaa agccaaaggg cagccccgag   1260
aaccacaggt gtacaccctg cccccatccc gggaggagat gaccaagaac caggtcagcc   1320
tgacctgcct ggtcaaaggc ttctatccca gcgacatcgc cgtggagtgg gagagcaatg   1380
ggcagccgga gaacaactac aagaccacgc ctcccgtgct ggactccgac ggctccttct   1440
tcctctacag caagctcacc gtggacaaga gcaggtggca gcagggaac gtcttctcat   1500
gctccgtgat gcacgaggct ctgcacaacc actacacgca gaagagcctc tccctgtctc   1560
cgggtaaatg agtgctagct ggccagacat gataagatac attgatgagt ttggacaaac   1620
cacaactaga atgcagtgaa aaaaatgctt tatttgtgaa atttgtgatg ctattgcttt   1680
atttgtaacc attataagct gcaataaaca agttaacaac aacaattgca ttcattttat   1740
gtttcaggtt caggggagg tgtgggaggt tttttaaagc aagtaaaacc tctacaaatg   1800
tggtatggaa ttaattctaa aatacagcat agcaaaactt taacctccaa atcaagcctc   1860
tacttgaatc cttttctgag ggatgaataa ggcataggca tcaggggctg ttgccaatgt   1920
gcattagctg tttgcagcct caccttcttt catggagttt aagatatagt gtattttccc   1980
aaggtttgaa ctagctcttc atttctttat gttttaaatg cactgacctc ccacattccc   2040
```

|     |     |     |     |     |      |
| --- | --- | --- | --- | --- | ---- |
| tttttagtaa | aatattcaga | aataatttaa | atacatcatt | gcaatgaaaa | taaatgtttt | 2100 |
| ttattaggca | gaatccagat | gctcaaggcc | cttcataata | tcccccagtt | tagtagttgg | 2160 |
| acttagggaa | caaaggaacc | tttaatagaa | attggacagc | aagaaagcga | gcttctagct | 2220 |
| tatcctcagt | cctgctcctc | tgccacaaag | tgcacgcagt | tgccggccgg | gtcgcgcagg | 2280 |
| gcgaactccc | gccccacgg | ctgctcgccg | atctcggtca | tggccggccc | ggaggcgtcc | 2340 |
| cggaagttcg | tggacacgac | ctccgaccac | tcggcgtaca | gctcgtccag | gccgcgcacc | 2400 |
| cacacccagg | ccagggtgtt | gtccggcacc | acctggtcct | ggaccgcgct | gatgaacagg | 2460 |
| gtcacgtcgt | cccggaccac | accggcgaag | tcgtcctcca | cgaagtcccg | ggagaacccg | 2520 |
| agccggtcgg | tccagaactc | gaccgctccg | gcgacgtcgc | gcgcggtgag | caccggaacg | 2580 |
| gcactggtca | acttggccat | gatggctcct | cctgtcagga | gaggaaagag | aagaaggtta | 2640 |
| gtacaattgc | tatagtgagt | tgtattatac | tatgcagata | tactatgcca | atgattaatt | 2700 |
| gtcaaactag | ggctgcaggg | ttcatagtgc | cacttttcct | gcactgcccc | atctcctgcc | 2760 |
| cacccttcc | caggcataga | cagtcagtga | cttaccaaac | tcacaggagg | gagaaggcag | 2820 |
| aagcttgaga | cagacccgcg | ggaccgccga | actgcgaggg | gacgtggcta | gggcggcttc | 2880 |
| ttttatggtg | cgccggccct | cggaggcagg | gcgctcgggg | aggcctagcg | gccaatctgc | 2940 |
| ggtggcagga | ggcggggccg | aaggccgtgc | ctgaccaatc | cggagcacat | aggagtctca | 3000 |
| gcccccgcc | ccaaagcaag | gggaagtcac | gcgcctgtag | cgccagcgtg | ttgtgaaatg | 3060 |
| ggggcttggg | ggggttgggg | ccctgactag | tcaaaacaaa | ctcccattga | cgtcaatggg | 3120 |
| gtggagactt | ggaaatcccc | gtgagtcaaa | ccgctatcca | cgcccattga | tgtactgcca | 3180 |
| aaaccgcatc | atcatggtaa | tagcgatgac | taatacgtag | atgtactgcc | aagtaggaaa | 3240 |
| gtcccataag | gtcatgtact | gggcataatg | ccaggcgggc | catttaccgt | cattgacgtc | 3300 |
| aatagggggc | gtacttggca | tatgatacac | ttgatgtact | gccaagtggg | cagtttaccg | 3360 |
| taaatactcc | acccattgac | gtcaatggaa | agtccctatt | ggcgttacta | tgggaacata | 3420 |
| cgtcattatt | gacgtcaatg | ggcggggtc | gttgggcggt | cagccaggcg | ggccatttac | 3480 |
| cgtaagttat | gtaacgcctg | caggttaatt | aagaacatgt | gagcaaaagg | ccagcaaaag | 3540 |
| gccaggaacc | gtaaaaaggc | cgcgttgctg | gcgtttttcc | ataggctccg | cccccctgac | 3600 |
| gagcatcaca | aaaatcgacg | ctcaagtcag | aggtggcgaa | acccgacagg | actataaaga | 3660 |
| taccaggcgt | ttccccctgg | aagctccctc | gtgcgctctc | ctgttccgac | cctgccgctt | 3720 |
| accggatacc | tgtccgcctt | tctcccttcg | ggaagcgtgg | cgctttctca | tagctcacgc | 3780 |
| tgtaggtatc | tcagttcggt | gtaggtcgtt | cgctccaagc | tgggctgtgt | gcacgaaccc | 3840 |
| cccgttcagc | ccgaccgctg | cgccttatcc | ggtaactatc | gtcttgagtc | caacccggta | 3900 |
| agacacgact | tatcgccact | ggcagcagcc | actggtaaca | ggattagcag | agcgaggtat | 3960 |
| gtaggcggtg | ctacagagtt | cttgaagtgg | tggcctaact | acggctacac | tagaagaaca | 4020 |
| gtatttggta | tctgcgctct | gctgaagcca | gttaccttcg | gaaaaagagt | tggtagctct | 4080 |
| tgatccggca | aacaaaccac | cgctggtagc | ggtggttttt | ttgtttgcaa | gcagcagatt | 4140 |
| acgcgcagaa | aaaaggatc | tcaagaagat | cctttgatct | tttctacggg | gtctgacgct | 4200 |
| cagtggaacg | aaaactcacg | ttaagggatt | ttggtcatga | ctagttaatt | aacatttaaa | 4260 |
| tcagcggccg | caataaaata | tctttatttt | cattacatct | gtgtgttggt | tttttgtgtg | 4320 |
| aatcgtaact | aacatacgct | ctccatcaaa | acaaaacgaa | acaaaacaaa | ctagcaaaat | 4380 |
| aggctgtccc | cagtgcaagt | gcaggtgcca | gaacatttct | ctatcgaa |      | 4428 |

<210> SEQ ID NO 103
<211> LENGTH: 4425
<212> TYPE: DNA
<213> ORGANISM: Artificial Sequence
<220> FEATURE:
<223> OTHER INFORMATION: pCXCL13-IgG4Fc

<400> SEQUENCE: 103

```
ggatctgcga tcgctccggt gcccgtcagt gggcagagcg cacatcgccc acagtccccg      60
agaagttggg gggagggtc ggcaattgaa cgggtgccta gagaaggtgg cgcggggtaa     120
actgggaaag tgatgtcgtg tactggctcc gccttttcc cgagggtggg ggagaaccgt     180
atataagtgc agtagtcgcc gtgaacgttc ttttcgcaa cgggtttgcc gccagaacac     240
agctgaagct cgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggttctgga ggtctattac acaagcttga     660
ggtgtagatg tgtccaagag agctcagtct ttatccctag acgcttcatt gatcgaattc     720
aaatcttgcc ccgtgggaat ggttgtccaa gaaagaaat catagtctgg aagaagaaca     780
agtcaattgt gtgtgtggac cctcaagctg aatggataca agaatgatg gaagtattga     840
gaaaagaag ttcttcaact ctaccagttc cagtgtttaa gagaaagatt ccccccccat     900
gcccatcatg cccagcacct gagttcctgg ggggaccatc agtcttcctg ttcccccca     960
aacccaagga cactctcatg atctcccgga cccctgaggt cacgtgcgtg gtggtggacg    1020
tgagccagga agaccccgag gtccagttca actggtacgt ggatggcgtg gaggtgcata    1080
atgccaagac aaagccgcgg gaggagcagt tcaacagcac gtaccgtgtg gtcagcgtcc    1140
tcaccgtcct gcaccaggac tggctgaacg gcaaggagta caagtgcaag gtctccaaca    1200
aaggcctccc gtcctccatc gagaaaacca tctccaaagc caaagggcag ccccgagagc    1260
cacaggtgta caccctgccc ccatcccagg aggagatgac caagaaccag gtcagcctga    1320
cctgcctggt caaaggcttc taccccagcg acatcgccgt ggagtgggag agcaatgggc    1380
agccggagaa caactacaag accacgcctc ccgtgctgga ctccgacggc tccttcttcc    1440
tctacagcag gctaaccgtg gacaagagca ggtggcagga ggggaatgtc ttctcatgct    1500
ccgtgatgca tgaggctctg cacaaccact acacacagaa gagcctctcc ctgtctccgg    1560
gtaaatgagt gctagctggc cagacatgat aagatacatt gatgagtttg gacaaaccac    1620
aactagaatg cagtgaaaaa aatgctttat ttgtgaaatt tgtgatgcta ttgctttatt    1680
tgtaaccatt ataagctgca ataaacaagt taacaacaac aattgcattc atttatgtt    1740
tcaggttcag ggggaggtgt gggaggtttt ttaaagcaag taaaacctct acaaatgtgg    1800
tatggaatta attctaaaat acagcatagc aaaactttaa cctccaaatc aagcctctac    1860
ttgaatcctt ttctgaggga tgaataaggc ataggcatca gggctgttg ccaatgtgca    1920
ttagctgttt gcagcctcac cttctttcat ggagtttaag atatagtgta ttttcccaag    1980
gtttgaacta gctcttcatt tctttatgtt ttaaatgcac tgacctccca cattccttt    2040
```

| | |
|---|---|
| ttagtaaaat attcagaaat aatttaaata catcattgca atgaaaataa atgtttttta | 2100 |
| ttaggcagaa tccagatgct caaggcccct cataatatcc cccagtttag tagttggact | 2160 |
| tagggaacaa aggaaccttt aatagaaatt ggacagcaag aaagcgagct tctagcttat | 2220 |
| cctcagtcct gctcctctgc cacaaagtgc acgcagttgc cggccgggtc gcgcagggcg | 2280 |
| aactcccgcc cccacggctg ctcgccgatc tcggtcatgg ccggcccgga ggcgtcccgg | 2340 |
| aagttcgtgg acacgacctc cgaccactcg gcgtacagct cgtccaggcc gcgcacccac | 2400 |
| acccaggcca gggtgttgtc cggcaccacc tggtcctgga ccgcgctgat gaacagggtc | 2460 |
| acgtcgtccc ggaccacacc ggcgaagtcg tcctccacga agtcccggga gaacccgagc | 2520 |
| cggtcggtcc agaactcgac cgctccggcg acgtcgcgcg cggtgagcac cggaacggca | 2580 |
| ctggtcaact tggccatgat ggctcctcct gtcaggagag gaaagagaag aaggttagta | 2640 |
| caattgctat agtgagttgt attatactat gcagatatac tatgccaatg attaattgtc | 2700 |
| aaactagggc tgcaggggtt catagtgcca cttttcctgca ctgccccatc tcctgcccac | 2760 |
| cctttcccag gcatagacag tcagtgactt accaaactca caggagggag aaggcagaag | 2820 |
| cttgagacag acccgcggga ccgccgaact gcgagggggac gtggctaggg cggcttcttt | 2880 |
| tatggtgcgc cggccctcgg aggcagggcg ctcggggagg cctagcggcc aatctgcggt | 2940 |
| ggcaggaggc ggggccgaag gccgtgcctg accaatccgg agcacatagg agtctcagcc | 3000 |
| ccccgcccca aagcaagggg aagtcacgcg cctgtagcgc cagcgtgttg tgaaatgggg | 3060 |
| gcttgggggg gttggggccc tgactagtca aaacaaactc ccattgacgt caatggggtg | 3120 |
| gagacttgga aatccccgtg agtcaaaccg ctatccacgc ccattgatgt actgccaaaa | 3180 |
| ccgcatcatc atggtaatag cgatgactaa tacgtagatg tactgccaag taggaaagtc | 3240 |
| ccataaggtc atgtactggg cataatgcca ggcgggccat ttaccgtcat tgacgtcaat | 3300 |
| aggggggcgta cttggcatat gatacacttg atgtactgcc aagtgggcag tttaccgtaa | 3360 |
| atactccacc cattgacgtc aatggaaagt ccctattggc gttactatgg gaacatacgt | 3420 |
| cattattgac gtcaatgggc ggggtcgtt gggcggtcag ccaggcgggc catttaccgt | 3480 |
| aagttatgta acgcctgcag gttaattaag aacatgtgag caaaaggcca gcaaaaggcc | 3540 |
| aggaaccgta aaaaggccgc gttgctggcg ttttccata ggctccgccc ccctgacgag | 3600 |
| catcacaaaa atcgacgctc aagtcagagg tggcgaaacc cgacaggact ataaagatac | 3660 |
| caggcgtttc cccctggaag ctccctcgtg cgctctcctg ttccgaccct gccgcttacc | 3720 |
| ggatacctgt ccgcctttct cccttcggga agcgtggcgc tttctcatag ctcacgctgt | 3780 |
| aggtatctca gttcggtgta ggtcgttcgc tccaagctgg gctgtgtgca cgaaccccc | 3840 |
| gttcagcccg accgctgcgc cttatccggt aactatcgtc ttgagtccaa cccggtaaga | 3900 |
| cacgacttat cgccactggc agcagccact ggtaacagga ttagcagagc gaggtatgta | 3960 |
| ggcggtgcta cagagttctt gaagtggtgg cctaactacg gctacactag aagaacagta | 4020 |
| tttggtatct gcgctctgct gaagccagtt accttcggaa aaagagttgg tagctcttga | 4080 |
| tccggcaaac aaaccaccgc tggtagcggt ggtttttttg tttgcaagca gcagattacg | 4140 |
| cgcagaaaaa aaggatctca agaagatcct ttgatctttt ctacgggtc tgacgctcag | 4200 |
| tggaacgaaa actcacgtta agggattttg gtcatggcta gttaattaac atttaaatca | 4260 |
| gcggccgcaa taaatatct ttattttcat tacatctgtg tgttggtttt ttgtgtgaat | 4320 |
| cgtaactaac atacgctctc catcaaaaca aaacgaaaca aaacaaacta gcaaaatagg | 4380 |
| ctgtccccag tgcaagtgca ggtgccagaa catttctcta tcgaa | 4425 |

<210> SEQ ID NO 104
<211> LENGTH: 4419
<212> TYPE: DNA
<213> ORGANISM: Artificial Sequence
<220> FEATURE:
<223> OTHER INFORMATION: pCXCL13(3-87)-IgG4Fc

<400> SEQUENCE: 104

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct cgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg taccggcgc     540
ctacctgaga tcaccggcga aggagggcca ccatgtacag gatgcaactc ctgtcttgca     600
ttgcactaag tcttgcactt gtcacgaatt cggaggtcta ttacaaagc ttgaggtgta     660
gatgtgtcca agagagctca gtctttatcc ctagacgctt cattgatcga attcaaatct     720
tgccccgtgg gaatggttgt ccaagaaaag aaatcatagt ctggaagaag aacaagtcaa     780
ttgtgtgtgt ggaccctcaa gctgaatgga tacaaagaat gatggaagta ttgagaaaaa     840
gaagttcttc aactctacca gttccagtgt ttaagagaaa gattcccccc ccatgcccat     900
catgcccagc acctgagttc ctggggggac catcagtctt cctgttcccc ccaaaaccca     960
aggacactct catgatctcc cggacccctg aggtcacgtg cgtggtggtg gacgtgagcc    1020
aggaagaccc cgaggtccag ttcaactggt acgtggatgg cgtggaggtg cataatgcca    1080
agacaaagcc gcgggaggag cagttcaaca gcacgtaccg tgtggtcagc gtcctcaccg    1140
tcctgcacca ggactggctg aacggcaagg agtacaagtg caaggtctcc aacaaaggcc    1200
tcccgtcctc catcgagaaa accatctcca aagccaaagg gcagccccga gagccacagg    1260
tgtacaccct gcccccatcc caggaggaga tgaccaagaa ccaggtcagc ctgacctgcc    1320
tggtcaaagg cttctacccc agcgacatcg ccgtggagtg ggagagcaat gggcagccgg    1380
agaacaacta caagaccacg cctcccgtgc tggactccga cggctccttc ttcctctaca    1440
gcaggctaac cgtggacaag agcaggtggc aggaggggaa tgtcttctca tgctccgtga    1500
tgcatgagge tctgcacaac cactacacac agaagagcct ctccctgtct ccgggtaaat    1560
gagtgctagc tggccagaca tgataagata cattgatgag tttggacaaa ccacaactag    1620
aatgcagtga aaaaaatgct ttatttgtga atttgtgat gctattgctt tatttgtaac    1680
cattataagc tgcaataaac aagttaacaa caacaattgc attcatttta tgtttcaggt    1740
tcagggggag gtgtgggagg ttttttaaag caagtaaaac ctctacaaat gtggtatgga    1800
attaattcta aaatacagca tagcaaaact ttaacctcca aatcaagcct ctacttgaat    1860
ccttttctga gggatgaata aggcataggc atcagggct gttgccaatg tgcattagct    1920
gtttgcagcc tcaccttctt tcatggagtt aagatatag tgtattttcc caaggtttga    1980
actagctctt catttcttta tgtttaaat gcactgacct cccacattcc cttttagta    2040
```

```
aaatattcag aaataattta aatacatcat tgcaatgaaa ataaatgttt tttattaggc    2100
agaatccaga tgctcaaggc ccttcataat atcccccagt ttagtagttg gacttaggga    2160
acaaaggaac ctttaataga aattggacag caagaaagcg agcttctagc ttatcctcag    2220
tcctgctcct ctgccacaaa gtgcacgcag ttgccggccg ggtcgcgcag ggcgaactcc    2280
cgcccccacg gctgctcgcc gatctcggtc atggccggcc cggaggcgtc ccggaagttc    2340
gtggacacga cctccgacca ctcggcgtac agctcgtcca ggccgcgcac ccacacccag    2400
gccagggtgt tgtccggcac cacctggtcc tggaccgcgc tgatgaacag ggtcacgtcg    2460
tcccggacca caccggcgaa gtcgtcctcc acgaagtccc gggagaaccc gagccggtcg    2520
gtccagaact cgaccgctcc ggcgacgtcg cgcgcggtga gcaccggaac ggcactggtc    2580
aacttggcca tgatggctcc tcctgtcagg agaggaaaga gaagaaggtt agtacaattg    2640
ctatagtgag ttgtattata ctatgcagat atactatgcc aatgattaat tgtcaaacta    2700
gggctgcagg gttcatagtg ccactttttcc tgcactgccc catctcctgc ccaccctttc    2760
ccaggcatag acagtcagtg acttaccaaa ctcacaggag ggagaaggca gaagcttgag    2820
acagacccgc gggaccgccg aactgcgagg ggacgtggct agggcggctt cttttatggt    2880
gcgccggccc tcgaggcag ggcgctcggg gaggcctagc ggccaatctg cggtggcagg    2940
aggcggggcc gaaggccgtg cctgaccaat ccggagcaca taggagtctc agccccccgc    3000
cccaaagcaa ggggaagtca cgcgcctgta gcgccagcgt gttgtgaaat gggggcttgg    3060
gggggttggg gccctgacta gtcaaaacaa actcccattg acgtcaatgg ggtggagact    3120
tggaaatccc cgtgagtcaa accgctatcc acgcccattg atgtactgcc aaaaccgcat    3180
catcatggta atagcgatga ctaatacgta gatgtactgc caagtaggaa agtcccataa    3240
ggtcatgtac tgggcataat gccaggcggg ccatttaccg tcattgacgt caataggggg    3300
cgtacttggc atatgataca cttgatgtac tgccaagtgg gcagtttacc gtaaatactc    3360
cacccattga cgtcaatgga aagtccctat tggcgttact atgggaacat acgtcattat    3420
tgacgtcaat gggcgggggt cgttgggcgg tcagccaggc gggccattta ccgtaagtta    3480
tgtaacgcct gcaggttaat taagaacatg tgagcaaaag gccagcaaaa ggccaggaac    3540
cgtaaaaagg ccgcgttgct ggcgtttttc cataggctcc gccccccctga cgagcatcac    3600 aaaaatcgac gctcaagtca gaggtggcga aacccgacag gactataaag ataccaggcg    3660
tttccccctg gaagctccct cgtgcgctct cctgttccga ccctgccgct taccggatac    3720
ctgtccgcct ttctcccttc gggaagcgtg gcgctttctc atagctcacg ctgtaggtat    3780
ctcagttcgg tgtaggtcgt tcgctccaag ctgggctgtg tgcacgaacc ccccgttcag    3840
cccgaccgct gcgccttatc cggtaactat cgtcttgagt ccaacccggt aagacacgac    3900
ttatcgccac tggcagcagc cactggtaac aggattagca gagcgaggta tgtaggcggt    3960
gctacagagt tcttgaagtg gtggcctaac tacggctaca ctagaagaac agtatttggt    4020
atctgcgctc tgctgaagcc agttaccttc ggaaaaagag ttggtagctc ttgatccggc    4080
aaacaaacca ccgctggtag cggtggtttt tttgtttgca agcagcagat tacgcgcaga    4140
aaaaaaggat ctcaagaaga tcctttgatc ttttctacgg ggtctgacgc tcagtggaac    4200
gaaaactcac gttaagggat tttggtcatg gctagttaat taacatttaa atcagcggcc    4260
gcaataaaat atctttatt tcattacatc tgtgtgttgg ttttttgtgt gaatcgtaac    4320
taacatacgc tctccatcaa aacaaaacga aacaaaacaa actagcaaaa taggctgtcc    4380
ccagtgcaag tgcaggtgcc agaacatttc tctatcgaa                          4419
```

<210> SEQ ID NO 105
<211> LENGTH: 4419
<212> TYPE: DNA
<213> ORGANISM: Artificial Sequence
<220> FEATURE:
<223> OTHER INFORMATION: pCXCL13(3-87K/H-A)-IgG4Fc

<400> SEQUENCE: 105

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac     240
agctgaagct cgaggggct cgcatctctc cttcacgcgc ccgccgccct acctgaggcc      300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggaggtcta ttacaagc ttgaggtgta       660
gatgtgtcca agagagctca gtctttatcc ctagacgctt cattgatgcc attcaaatct     720
tgccccgtgg gaatggttgt ccaagaaaag aaatcatagt ctgggctgcg aacgcttcaa     780
ttgtgtgtgt ggaccctcaa gctgaatgga tacaagccat gatggaagta ttggctgcgg     840
ctagttcttc aactctacca gttccagtgt tgccgctgc gattcccccc ccatgcccat     900
catgcccagc acctgagttc ctgggggac catcagtctt cctgttcccc ccaaaaccca      960
aggacactct catgatctcc cggacccctg aggtcacgtg cgtggtggtg gacgtgagcc    1020
aggaagaccc cgaggtccag ttcaactggt acgtggatgg cgtggaggtg cataatgcca    1080
agacaaagcc gcgggaggag cagttcaaca gcacgtaccg tgtggtcagc gtcctcaccg    1140
tcctgcacca ggactggctg aacggcaagg agtacaagtg caaggtctcc aacaaaggcc    1200
tcccgtcctc catcgagaaa accatctcca aagccaaagg gcagccccga gagccacagg    1260
tgtacaccct gcccccatcc caggaggaga tgaccaagaa ccaggtcagc ctgacctgcc    1320
tggtcaaagg cttctacccc agcgacatcg ccgtggagtg ggagagcaat gggcagccgg    1380
agaacaacta caagaccacg cctcccgtgc tggactccga cggctccttc ttcctctaca    1440
gcaggctaac cgtggacaag agcaggtggc aggaggggaa tgtcttctca tgctccgtga    1500
tgcatgagc tctgcacaac cactacacac agaagagcct ctccctgtct ccgggtaaat     1560
gagtgctagc tggccagaca tgataagata cattgatgag tttggacaaa ccacaactag    1620
aatgcagtga aaaaaatgct ttatttgtga aatttgtgat gctattgctt tatttgtaac    1680
cattataagc tgcaataaac aagttaacaa caacaattgc attcatttta tgtttcaggt    1740
tcagggggag gtgtgggagg ttttttaaag caagtaaaac ctctacaaat gtggtatgga    1800
attaattcta aaatacagca tagcaaaact ttaacctcca aatcaagcct ctacttgaat    1860
ccttttctga gggatgaata aggcataggc atcaggggct gttgccaatg tgcattagct    1920
gtttgcagcc tcaccttctt tcatggagtt taagatatag tgtattttcc caaggtttga    1980
actagctctt catttcttta tgttttaaat gcactgacct cccacattcc cttttttagta   2040
```

```
aaatattcag aaataattta aatacatcat tgcaatgaaa ataaatgttt tttattaggc    2100
agaatccaga tgctcaaggc ccttcataat atcccccagt ttagtagttg gacttaggga    2160
acaaaggaac ctttaataga aattggacag caagaaagcg agcttctagc ttatcctcag    2220
tcctgctcct ctgccacaaa gtgcacgcag ttgccggccg ggtcgcgcag ggcgaactcc    2280
cgcccccacg gctgctcgcc gatctcggtc atggccggcc cggaggcgtc ccggaagttc    2340
gtggacacga cctccgacca ctcggcgtac agctcgtcca ggccgcgcac ccacacccag    2400
gccagggtgt tgtccggcac cacctggtcc tggaccgcgc tgatgaacag ggtcacgtcg    2460
tcccggacca caccggcgaa gtcgtcctcc acgaagtccc gggagaaccc gagccggtcg    2520
gtccagaact cgaccgctcc ggcgacgtcg cgcgcggtga gcaccggaac ggcactggtc    2580
aacttggcca tgatggctcc tcctgtcagg agaggaaaga gaagaaggtt agtacaattg    2640
ctatagtgag ttgtattata ctatgcagat atactatgcc aatgattaat tgtcaaacta    2700
gggctgcagg gttcatagtg ccactttttcc tgcactgccc catctcctgc ccacccttc     2760 ccaggcatag acagtcagtg acttaccaaa ctcacaggag ggagaaggca gaagcttgag    2820
acagacccgc gggaccgccg aactgcgagg ggacgtggct agggcggctt ctttttatggt   2880 gcgccggccc tcggaggcag ggcgctcggg gaggcctagc ggccaatctg cggtggcagg    2940
aggcggggcc gaaggccgtg cctgaccaat ccggagcaca taggagtctc agcccccgc     3000 cccaaagcaa ggggaagtca cgcgcctgta gcgccagcgt gttgtgaaat gggggcttgg    3060
gggggttggg gccctgacta gtcaaaacaa actcccattg acgtcaatgg ggtggagact    3120
tggaaatccc cgtgagtcaa accgctatcc acgcccattg atgtactgcc aaaaccgcat    3180
catcatggta atagcgatga ctaatacgta gatgtactgc caagtaggaa agtcccataa    3240
ggtcatgtac tgggcataat gccaggcggg ccatttaccg tcattgacgt caataggggg    3300
cgtacttggc atatgataca cttgatgtac tgccaagtgg gcagtttacc gtaaatactc    3360
cacccattga cgtcaatgga aagtccctat tggcgttact atgggaacat acgtcattat    3420
tgacgtcaat gggcggggt cgttgggcgg tcagccaggc gggccattta ccgtaagtta    3480
tgtaacgcct gcaggttaat taagaacatg tgagcaaaag gccagcaaaa ggccaggaac    3540
cgtaaaaagg ccgcgttgct ggcgtttttc cataggctcc gcccccctga cgagcatcac    3600
aaaaatcgac gctcaagtca gaggtggcga acccgacag gactataaag ataccaggcg    3660
tttccccctg gaagctccct cgtgcgctct cctgttccga ccctgccgct taccggatac    3720
ctgtccgcct ttctcccttc gggaagcgtg gcgctttctc atagctcacg ctgtaggtat    3780
ctcagttcgg tgtaggtcgt tcgctccaag ctgggctgtg tgcacgaacc ccccgttcag    3840
cccgaccgct gcgccttatc cggtaactat cgtcttgagt ccaacccggt aagacacgac    3900
ttatcgccac tggcagcagc cactggtaac aggattagca gagcgaggta tgtaggcggt    3960
gctacagagt tcttgaagtg gtggcctaac tacggctaca ctagaagaac agtatttggt    4020
atctgcgctc tgctgaagcc agttaccttc ggaaaaagag ttggtagctc ttgatccggc    4080
aaacaaacca ccgctggtag cggtggtttt tttgtttgca agcagcagat tacgcgcaga    4140
aaaaaaggat ctcaagaaga tcctttgatc ttttctacgg ggtctgacgc tcagtggaac    4200
gaaaactcac gttaagggat tttggtcatg ctagttaat taacatttaa atcagcggcc    4260
gcaataaaat atcttatttt tcattacatc tgtgtgttgg ttttttgtgt gaatcgtaac    4320
taacatacgc tctccatcaa aacaaaacga aacaaaacaa actagcaaaa taggctgtcc    4380
ccagtgcaag tgcaggtgcc agaacatttc tctatcgaa                           4419
```

```
<210> SEQ ID NO 106
<211> LENGTH: 20
<212> TYPE: PRT
<213> ORGANISM: Artificial Sequence
<220> FEATURE:
<223> OTHER INFORMATION: IL-2 Secretion Signal

<400> SEQUENCE: 106

Met Tyr Arg Met Gln Leu Leu Ser Cys Ile Ala Leu Ser Leu Ala Leu
1               5                   10                  15

Val Thr Asn Ser
            20
```

CHEMOKINE-IMMUNOGLOBULIN FUSION POLYPEPTIDES, COMPOSITIONS, METHOD OF MAKING AND USE THEREOF

This application is a continuation-in-part application of U.S. patent application Ser. No. 13/480,526, filed May 25, 2012, which claims priority of U.S. Provisional Patent Application No. 61/492,260, filed on Jun. 1, 2011. The entirety of the aforementioned applications is incorporated herein by reference.

FIELD

The present application generally relates to compositions that can be used for treating chemokine receptor-mediated disorders and modulating inflammation, inflammatory cell motility, cancer cell motility, or cancer cell survival.

BACKGROUND

Chemokines are chemotactic cytokines, of molecular weight 6-15 kDa, that are released by a wide variety of cells to attract and activate, among other cell types, macrophages, T and B lymphocytes, eosinophils, basophils and neutrophils. There are four classes of chemokines, CXC, CC, C, and CX3C, depending on whether the first two cysteines in the amino acid sequence are separated by a single amino acid (CXC) or are adjacent (CC). Unlike other chemokines, C chemokines have only two cysteines; one N-terminal and one downstream cysteine. The only CX3C chemokine, CX3CL1, has three amino acids between two N-terminal cysteines. The CXC chemokines, such as interleukin-8 (IL-8/CXCL8), neutrophil-activating protein-2 (NAP-2/CXCL7) and melanoma growth stimulatory activity protein (MGSA/CXCL1) are chemotactic primarily for neutrophils and T lymphocytes, whereas the CC chemokines, such as RANTES/CCL5, MIP-1α/CCL3, MIP-1β/CCL4, the monocyte chemotactic proteins (MCP-1/CCL2, MCP-2/CCL8, MCP-3/CCL7, MCP-4/CCL13, and MCP-5/CCL12) and the eotaxins (-1/CCL11 and -2/CCL24) are chemotactic for, among other cell types, macrophages, T lymphocytes, eosinophils, dendritic cells, and basophils. There also exist the chemokines lymphotactin-1/XCL1, lymphotactin-2/XCL2 (both C chemokines), and fractalkine/CX3CL1 (a CX3C chemokine) that do not fall into either of the major chemokine subfamilies, CXC and CC.

Chemokines bind to specific cell-surface receptors belonging to the family of G-protein-coupled seven-transmembrane-domain proteins, which are termed "chemokine receptors." On binding to their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration.

Chemokine receptors have been implicated as being important mediators of inflammatory, infectious, and immunoregulatory disorders and diseases, including cancer, asthma and allergic diseases, as well as autoimmune pathologies such as rheumatoid arthritis and atherosclerosis. For example, the chemokine receptor CCR3 plays a pivotal role in attracting eosinophils to sites of allergic inflammation and in subsequently activating these cells. The chemokine ligands for CCR3 induce a rapid increase in intracellular calcium concentration, increased expression of cellular adhesion molecules, cellular degranulation, and the promotion of eosinophil migration. Another chemokine receptor, CCR2, contributes to cancer progression and can induce tumor cell proliferation or chemotaxis. Accordingly, agents which modulate chemokine receptors would be useful in such disorders and diseases.

Chemokines have also been implicated in the pathogenesis of cell proliferative disorders, including for example induction of tumor angiogenesis and growth. Many tumor cells have also been shown to express chemokine receptors, such as CXCR1, CXCR2, CXCR3, CXCR4, CXCR5, CXCR6, CXCR7, CX3CL1, CCR2, CCR5, and CCR9, and thus tumor cells may also stimulate their own growth, migration, and/or invasion when responding to secreted chemokines Chemokines are critical for leukocyte recruitment to injured tissues and play an important role in the wound healing process. Impaired wound healing in diabetic patients is accompanied by decreased early inflammatory cell infiltration, but persistence of neutrophils and macrophages leading to chronic, nonhealing wounds. Chemokines may have both direct and inflammatory-mediated effects on many different aspects of diabetic wound healing, including: impairments in growth factor expression, angiogenesis, extracellular matrix formation, and reepithelialization. Certain chemokine receptor expression in wounds may accelerate healing, and be beneficial in the context of surgery, chronic ulcers, and other conditions.

Chemokine receptors therefore represent promising targets for the development of novel anti-inflammatory and anti-tumor as well as angiostatic, angiogenic, and wound healing agents. Thus, there remains a need for compositions that are capable of modulating activity of chemokine receptors.

SUMMARY

One aspect of the present application relates to an isolated chemokine-immunoglobulin fusion polypeptide having a chemokine moiety and an immunoglobulin moiety. In some embodiments, the chemokine moiety comprises a chemokine selected from the group consisting of human CCL1, CCL2, CCL3, CCL4, CCL4L1, CCL5, CCL7, CCL8, CCL11, CCL13, CCL14-1, CCL14-2, CCL15, CCL16, CCL17, CCL18, CCL19, CCL20-1, CCL20-2, CCL21, CCL22, CCL23-1, CCL23-1, CCL24, CCL25-1, CCL25-2, CCL25-3, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and the immunoglobulin moiety comprises a peptide selected from the group consisting of the constant region of human Ig G1, the constant region of human Ig G2, the constant region of human Ig G3, the constant region of human Ig G4, and functional variants thereof. In one embodiment, the isolated chemokine-immunoglobulin fusion polypeptide is a pegylated chemokine-immunoglobulin fusion polypeptide.

In one particular embodiment, the chemokine-immunoglobulin fusion polypeptide is selected from the group consisting of CCL2-IgG1Fc, CCL2(5-76)-IgG1Fc, CCL2(5-76K/H→A)-IgG1Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H/R→A)-IgG1Fc, CCL8-IgG4Fc, CCL8(5-76)-IgG4Fc, CCL8(5-76K/H/R→A)-IgG4Fc, CCL13-IgG1Fc, CCL13(5-75)-IgG1Fc, CCL13(5-75K/H→A)-IgG1Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H/R→A)-IgG1Fc, CCL25-IgG4Fc, CCL25(4-127)-IgG4Fc, CCL25(4-127K/H/R→A)-IgG4Fc, CXCL11-IgG1Fc, CXCL11(4-73)-IgG1Fc, CXCL11(4-73K/R→A)-IgG1Fc, CXCL11(4-73)-IgG4Fc, CXCL11(4-73K/R→A)-IgG4Fc, CXCL12α-IgG1Fc, CXCL12α(3-67)-IgG1Fc, CXCL12α(3-67K/R→A)-IgG1Fc, CXCL12α-IgG4Fc, CXCL12α(3-67)-IgG4Fc, CXCL12α(3-67K/R→A)-IgG4Fc, CXCL13-IgG1Fc, CXCL13(3-87)-IgG1Fc, CXCL13(3-87K/R→A)-IgG1Fc, CXCL13-IgG4Fc, CXCL13(3-87)-IgG4Fc, and CXCL13(3-87K/R→A)-IgG4Fc.

Another aspect of the present application is directed to an isolated polynuecleotide encoding a chemokine-immunoglobulin fusion polypeptide having a chemokine moiety and an immunoglobulin moiety, wherein the chemokine moiety comprises a chemokine selected from the group consisting of human CCL1, CCL2, CCL3, CCL4, CCL5, CCL7, CCL8, CCL11, CCL13, CCL14, CCL15, CCL16, CCL17, CCL19, CCL21, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, XCL1, XCL2, CX3CL1 and functional variants thereof and wherein the immunoglobulin moiety comprises a peptide selected from the group consisting of the constant regions of human IgG1 (hIgG1Fc), the constant regions of human IgG2 (hIgG2Fc), the constant regions of human IgG3 (hIgG3Fc), the constant regions of human IgG4 (hIgG4Fc), and functional variants thereof.

In a particular embodiment, the isolated polynuecleotide encoding a cchemokine-immunoglobulin fusion polypeptide is selected from the group consisting of CCL2-IgG1Fc, CCL2 (5-76)-IgG1Fc, CCL2(5-76K/H→A)-IgG1Fc, CCL2-IgG2Fc, CCL2(5-76)-IgG2Fc, CCL2(5-76K/H→A)-IgG2Fc, CCL2-IgG3Fc, CCL2(5-76)-IgG3Fc, CCL2(5-76K/H→A)-IgG3Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG2Fc, CCL7(5-76)-IgG2Fc, CCL7(5-76K/H→A)-IgG2Fc, CCL7-IgG3Fc, CCL7(5-76)-IgG3Fc, CCL7(5-76K/H→A)-IgG3Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H/R→A)-IgG1Fc, CCL8-IgG1Fc, CCL8(5-76)-IgG1Fc, CCL8(5-76K/H/R→A)-IgG1Fc, CCL8-IgG2Fc, CCL8(5-76)-IgG2Fc, CCL8(5-76K/H/R→A)-IgG2Fc, CCL8(5-76)-IgG2Fc, CCL8(5-76K/H/R→A)-IgG2Fc, CCL8-IgG3Fc, CCL8(5-76)-IgG3Fc, CCL8(5-76K/H/R→A)-IgG3Fc, CCL8-IgG4Fc, CCL8(5-76)-IgG4Fc, CCL8(5-76K/H/R→A)-IgG4Fc, CCL13-IgG1Fc, CCL13(5-75)-IgG1Fc, CCL13(5-75K/H→A)-IgG1Fc, CCL13-IgG2Fc, CCL13(5-75)-IgG2Fc, CCL13(5-75K/H→A)-IgG2Fc, CCL13-IgG3Fc, CCL13(5-75)-IgG3Fc, CCL13(5-75K/H→A)-IgG3Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H/R→A)-IgG1Fc, CCL25-IgG2Fc, CCL25(4-127)-IgG2Fc, CCL25(4-127K/H/R→A)-IgG2Fc, CCL25-IgG3Fc, CCL25(4-127)-IgG3Fc, CCL25(4-127K/H/R→A)-IgG3Fc, CCL25-IgG4Fc, CCL25(4-127)-IgG4Fc, CCL25(4-127K/H/R→A)-IgG4Fc, CXCL11-IgG1Fc, CXCL11(4-73)-IgG1Fc, CXCL11(4-73K/R→A)-IgG1Fc, CXCL11-IgG2Fc, CXCL11(4-73)-IgG2Fc, CXCL11(4-73K/R→A)-IgG2Fc, CXCL11-IgG3Fc, CXCL11(4-73)-IgG3Fc, CXCL11(4-73K/R→A)-IgG3Fc, CXCL11-IgG4Fc, CXCL11(4-73)-IgG4Fc, CXCL11(4-73K/R→A)-IgG4Fc, CXCL12α-IgG1Fc, CXCL12α(3-67)-IgG1Fc, CXCL12α(3-67K/R→A)-IgG1Fc, CXCL12α(3-67)-IgG2Fc, CXCL12α(3-67)-IgG2Fc, CXCL12α(3-67K/R→A)-IgG2Fc, CXCL12α-IgG3Fc, CXCL12α(3-67)-IgG3Fc, CXCL12α(3-67K/R→A)-IgG3Fc, CXCL12α-IgG4Fc, CXCL12α(3-67)-IgG4Fc, CXCL12α(3-67K/R→A)-IgG4Fc, CXCL13-IgG1Fc, CXCL13(3-87)-IgG1Fc, CXCL13(3-87K/R→A)-IgG1Fc, CXCL13-IgG2Fc, CXCL13(3-87)-IgG2Fc, CXCL13(3-87K/R→A)-IgG2Fc, CXCL13-IgG3Fc, CXCL13(3-87)-IgG3Fc, CXCL13(3-87K/R→A)-IgG3Fc, CXCL13-IgG4Fc, CXCL13(3-87)-IgG4Fc, and CXCL13(3-87K/R→A)-IgG4Fc.

A further aspect of the present application is directed to a pharmaceutical composition comprising (1) a chemokine-immunoglobulin fusion polypeptide of the present applicaiton or an expression vector encoding a chemokine-immunoglobulin fusion polypeptide of the present application, and (2) a pharmaceutically acceptable carrier.

A further aspect of the present application is directed to a method for treating a chemokine receptor-mediated disorder in a subject, comprising administering to said subject an effective amount of the pharmaceuical composition of the present application.

Another aspect of the present application relates to a method for modulating inflammation in a subject, comprising comprising administering to said subject an effective amount of the pharmaceuical composition of the present application.

Another aspect of the present application relates to a method for treating a chemokine receptor-mediated disorder in a subject, comprising administering to said subject an effective amount of a pegylated chemokine, wherein the chemokine is selected from the group consisting of human CCL1, CCL2, CCL3, CCL4, CCL5, CCL7, CCL8, CCL11, CCL13, CCL14, CCL15, CCL16, CCL17, CCL19, CCL21, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, XCL1, XCL2, CX3CL1 and functional variants thereof.

In a further embodiment, the pegylated chemokine is selected from the group consisting of CCL2-PEG, var-CCL2-PEG, CCL7-PEG, var-CCL7-PEG, CCL8-PEG, var-CCL8-PEG, CCL13-PEG, var-CCL13-PEG, CCL25-PEG, var-CCL25-PEG, CXCL11-PEG, var-CXCL11-PEG, CXCL13-PEG, var-CXCL13-PEG, CXCL16-PEG, and var-CXCL16-PEG.

BRIEF DESCRIPTION OF THE DRAWINGS

FIG. 1A depicts the expression vector pCCL2.hIgG1Fc. The Fc region comprises the CH2 and CH3 domains of the IgG heavy chain and the hinge region. The hinge serves as a flexible spacer between the two parts of the Fc-fusion protein, allowing each part of the molecule to function independently. hEF1-HTLV prom is a composite promoter comprising the Elongation Factor-1α (EF-1α) core promoter 1 and the R segment and part of the U5 sequence (R-U5') of the Human T-Cell Leukemia Virus (HTLV) Type 1 Long Terminal Repeat2. The EF-1α promoter exhibits a strong activity and yields long lasting expression of a transgene in vivo. The R-U5' has been coupled to the EF-1α core promoter to enhance stability of RNA. MCS: The multiple cloning site. SV40 pAn: the Simian Virus 40 late polyadenylation signal. ori: a minimal *E. coli* origin of replication. CMV enh/hFerL prom: This composite promoter combines the human cytomegalovirus immediate-early gene 1 enhancer and the core promoter of the human ferritin light chain gene. This ubiquitous promoter drives the expression of the Zeocin™-resistance gene in mammalian cells. EM2KC is a bacterial promoter that enables the constitutive expression of the antibiotic resistance gene in *E. coli*. EM2KC is located within an intron and is spliced out in mammalian cells. Zeo: Resistance to Zeocin™ is conferred by the Sh ble gene from *Streptoal-*

*loteichus hindustanus* The same resistance gene confers selection in both mammalian cells and *E. coli*βGlo pAn: The human beta-globin 3'UTR and polyadenylation sequence allows efficient arrest of the transgene transcription4

FIG. 1B depicts the expression vector pCCL2(5-76).hIgG1Fc.

FIG. 1C shows the nuceotide sequence of the expression vector pCCL2.hIgG1Fc.

FIG. 1D shows the nuceotide sequence of the expression vector pCCL2(5-76).hIgG1Fc.

FIG. 1E shows the nuceotide sequence of the expression vector pCCL2(5-76).hIgG1Fc with alanine substitutions for removal of GAG binding sites—lys and his.

Figure 2A:
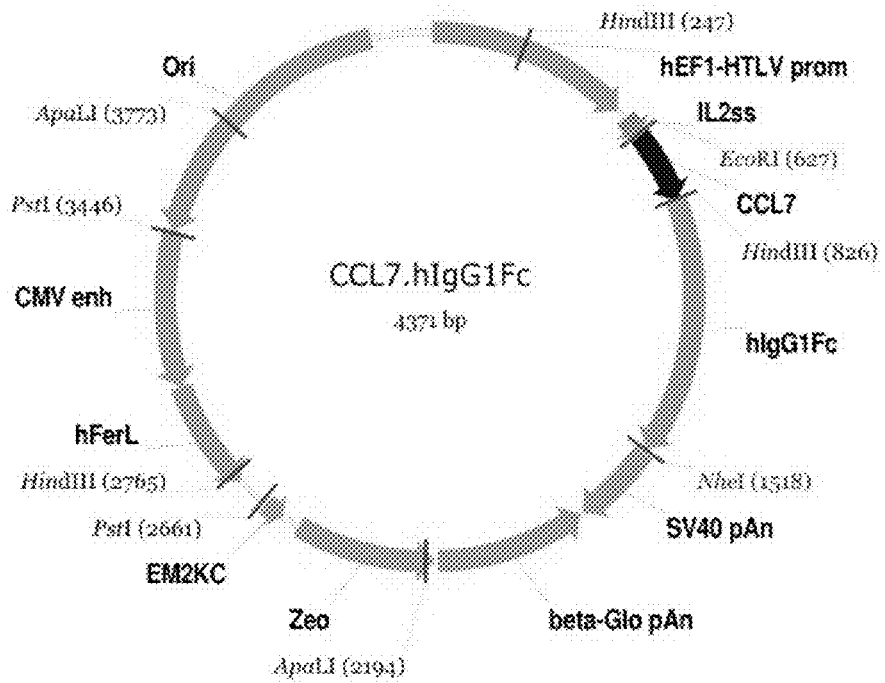

FIG. 2A depicts the expression vector pCCL7.hIgG1Fc.

Figure 2B:
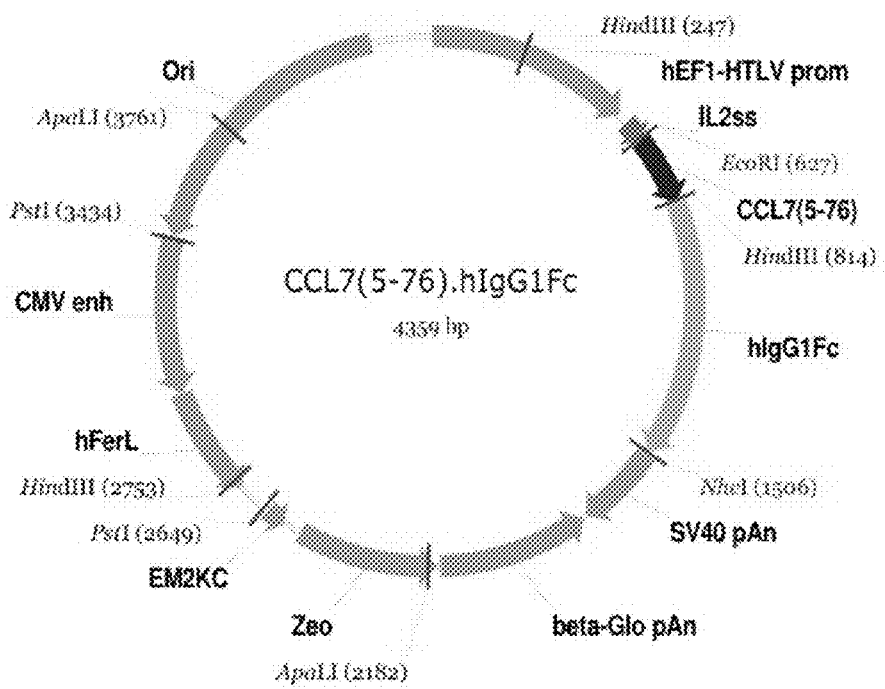

FIG. 2B depicts the expression vector pCCL7(5-76).hIgG1Fc.

FIG. 2C shows the nuceotide sequence of the expression vector pCCL7.hIgG1Fc.

FIG. 2D shows the nuceotide sequence of the expression vector pCCL7(5-76).hIgG1Fc.

FIG. 2E shows the nuceotide sequence of the expression vector pCCL7(5-76).hIgG1Fc with alanine substitutions for removal of GAG binding sites—lys and his.

Figure 3A:
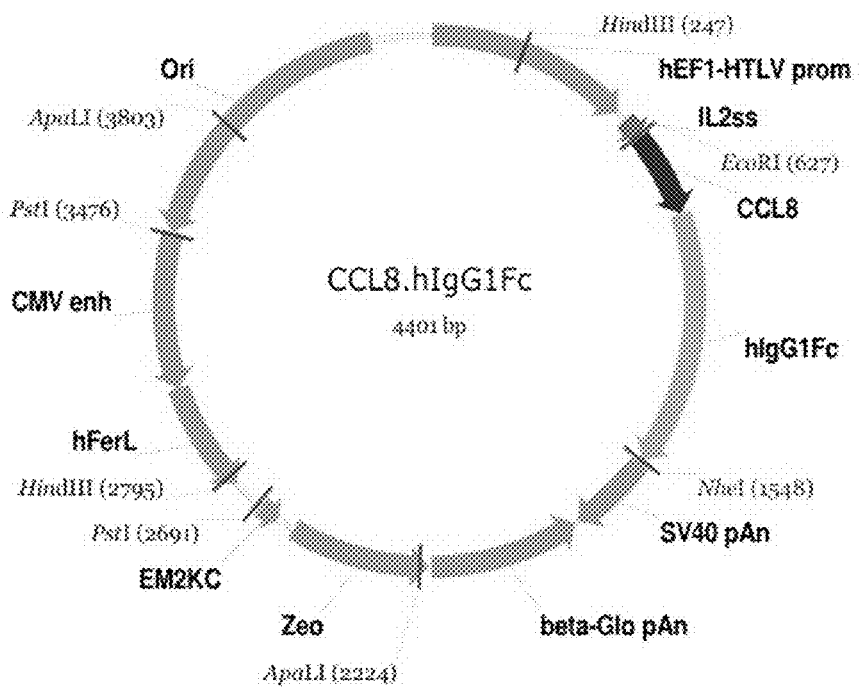

FIG. 3A depicts the expression vector pCCL8.hIgG1Fc.

Figure 3B:
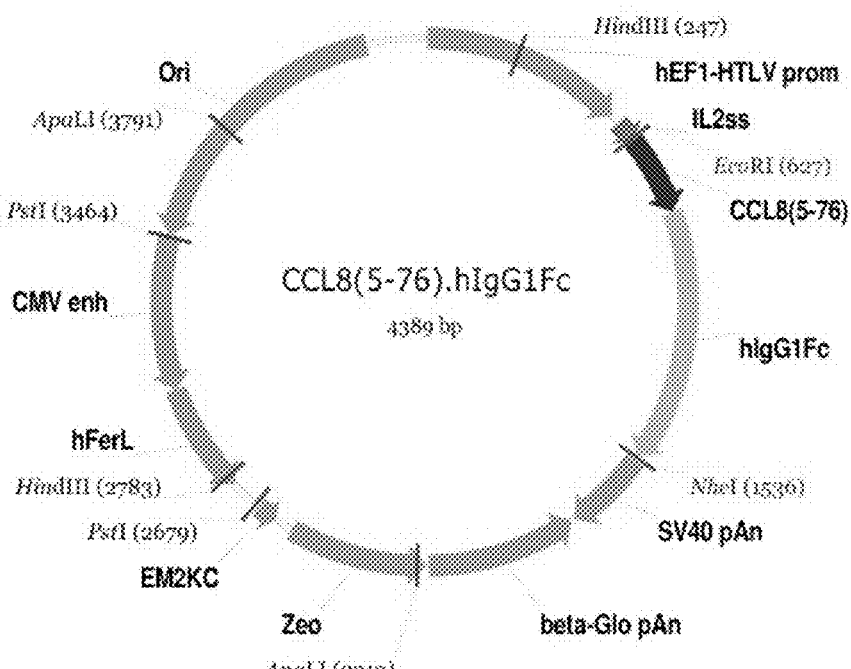

FIG. 3B depicts the expression vector pCCL8(5-76).hIgG1Fc.

FIG. 3C shows the nuceotide sequence of the expression vector pCCL8.hIgG1Fc.

FIG. 3D shows the nuceotide sequence of the expression vector pCCL8(5-76).hIgG1Fc.

Figure 4A:
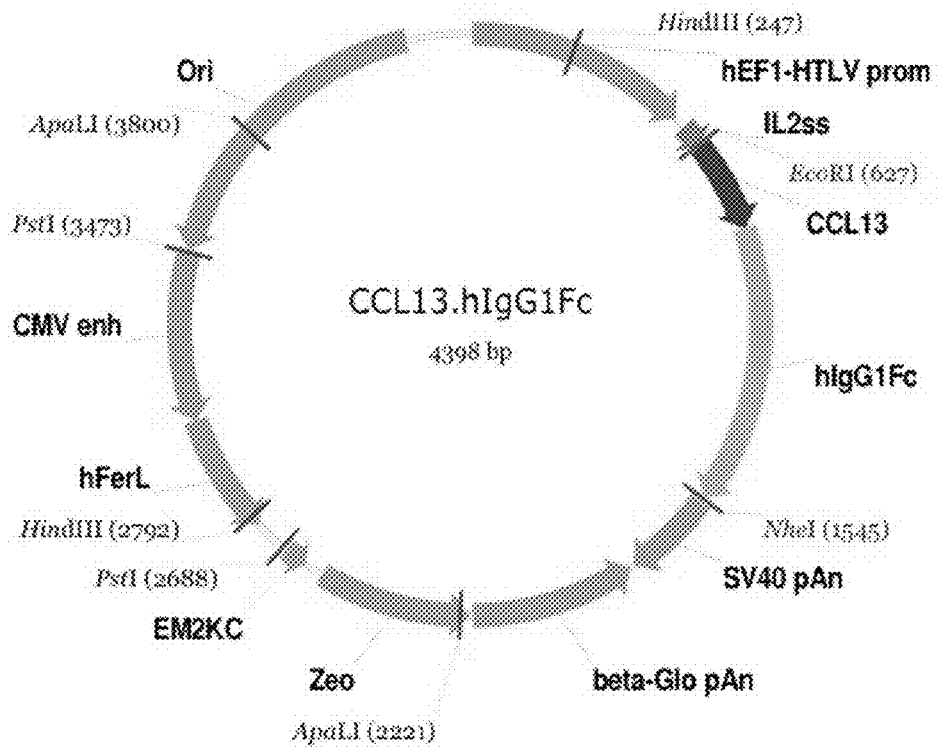

FIG. 3E shows the nuceotide sequence of the expression vector pCCL8(5-76).hIgG1Fc with alanine substitutio FIG. 4A depicts the expression vector pCCL13.hIgG1Fc.

Figure 4B:
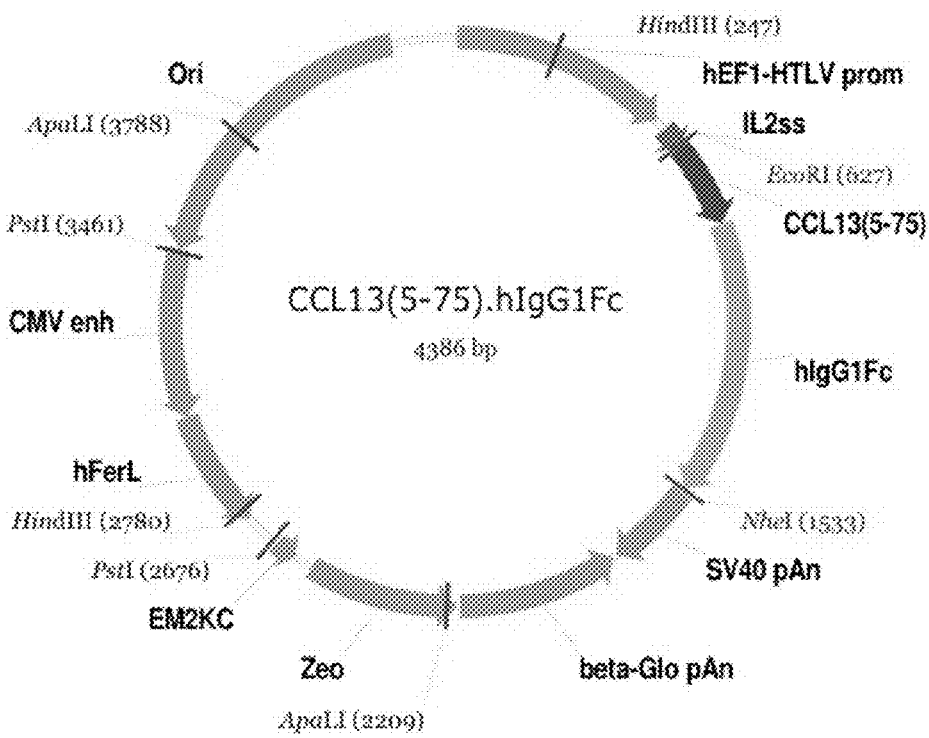

FIG. 4B depicts the expression vector pCCL13(5-75).hIgG1Fc.

FIG. 4C shows the nuceotide sequence of the expression vector pCCL13.hIgG1Fc.

FIG. 4D shows the nuceotide sequence of the expression vector pCCL13(5-75).hIgG1Fc.

FIG. 4E shows the nuceotide sequence of the expression vector pCCL13(5-76).hIgG1Fc with alanine substitutios for removal of GAG binding sites—lys and his.

Figure 5A:
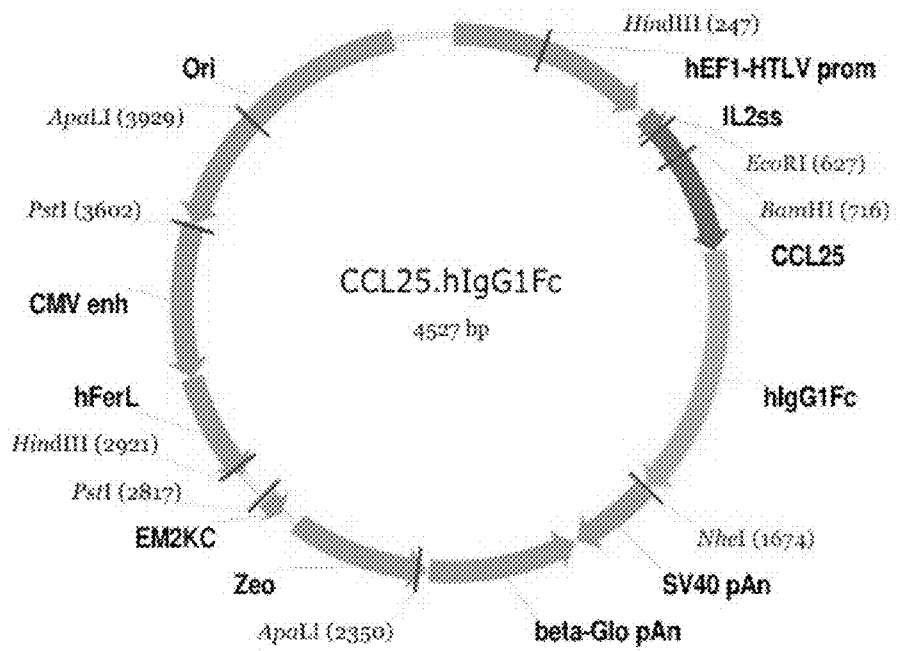

FIG. 5A depicts the expression vector pCCL25.hIgG1Fc.

Figure 5B:
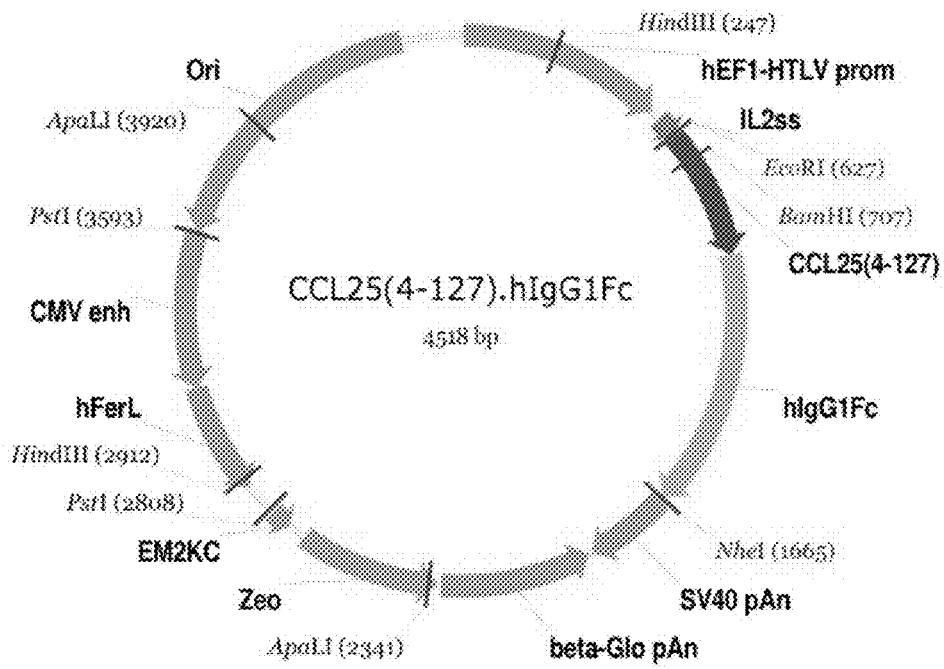

FIG. 5B depicts the expression vector pCCL25(4-127).hIgG1Fc.

Figure 5C:
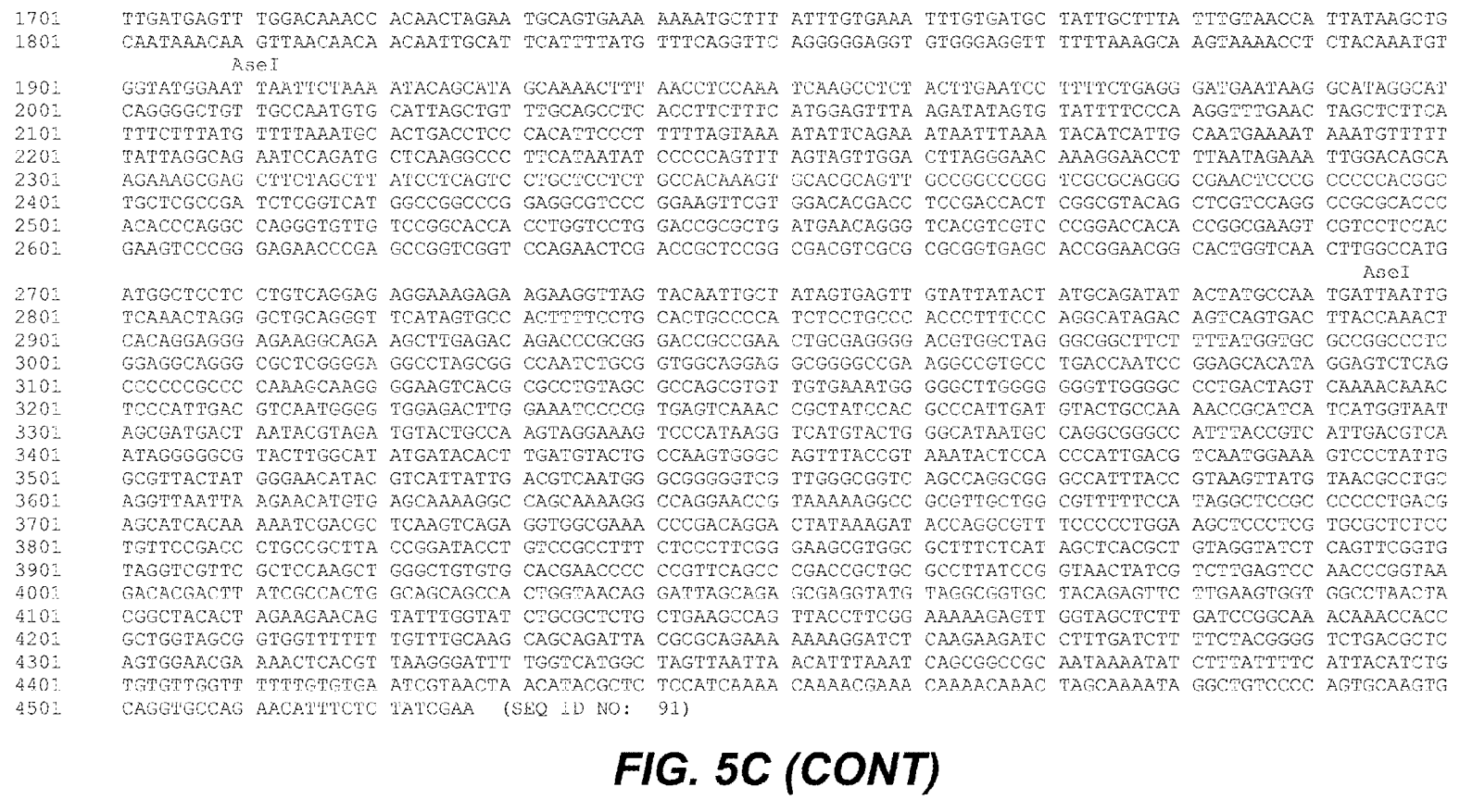

FIG. 5C shows the nuceotide sequence of the expression vector pCCL25.hIgG1Fc.

FIG. 5D shows the nuceotide sequence of the expression vector pCCL25(4-127).hIgG1Fc.

FIG. 5E shows the nuceotide sequence of the expression vector pCCL25(4-127).hIgG1Fc with alanine substitutios for removal of GAG binding sites—lys and his.

Figure 6A:
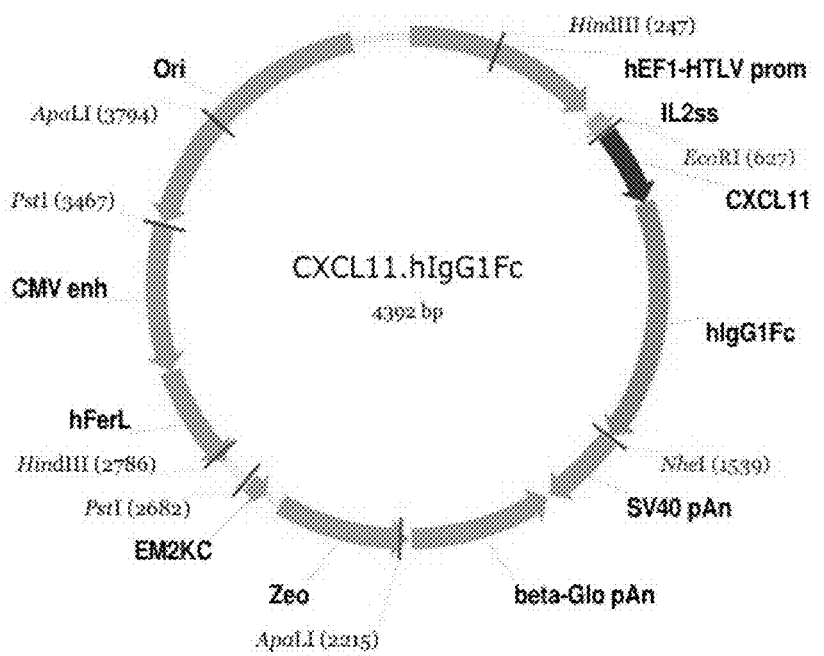

FIG. 6A depicts the expression vector pCXCL11.hIgG1Fc.

Figure 6B:
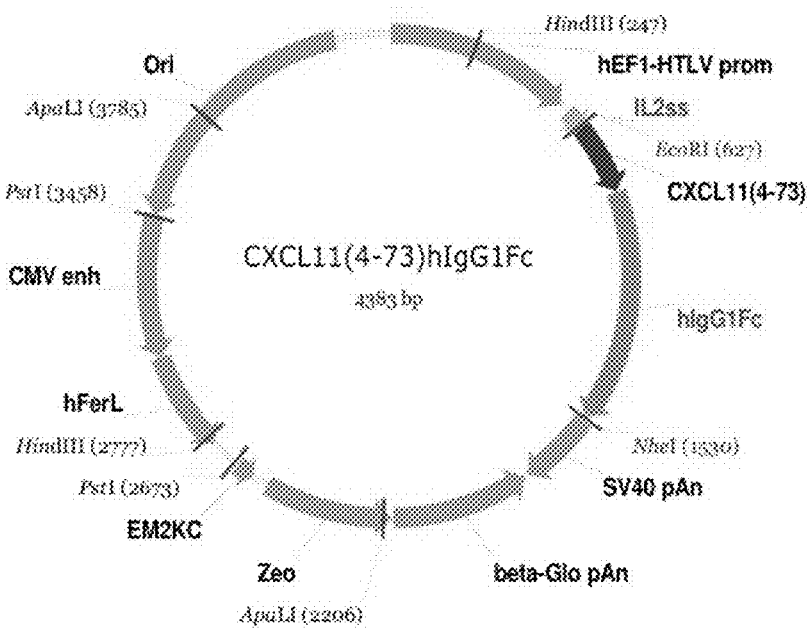

FIG. 6B depicts the expression vector pCXCL11(4-73).hIgG1Fc.

FIG. 6C shows the nuceotide sequence of the expression vector pCXCL11.hIgG1Fc.

Figure 6D:
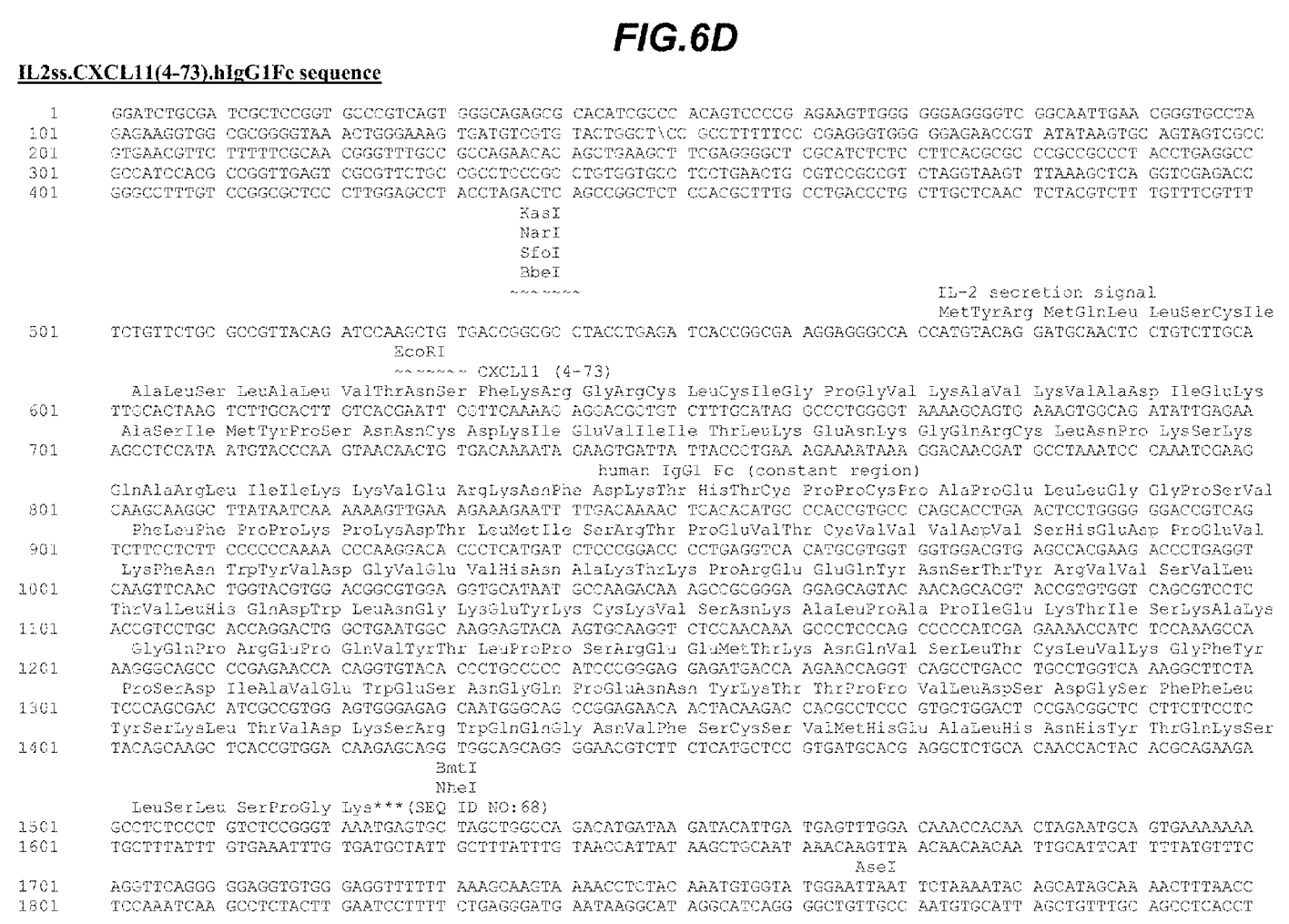

FIG. 6D shows the nuceotide sequence of the expression vector pCXCL11(4-73).hIgG1Fc.

FIG. 6E shows the nuceotide sequence of the expression vector pCXCL11(4-127).hIgG1Fc with alanine substitutios for removal of GAG binding sites—lys and his.

Figure 7A:
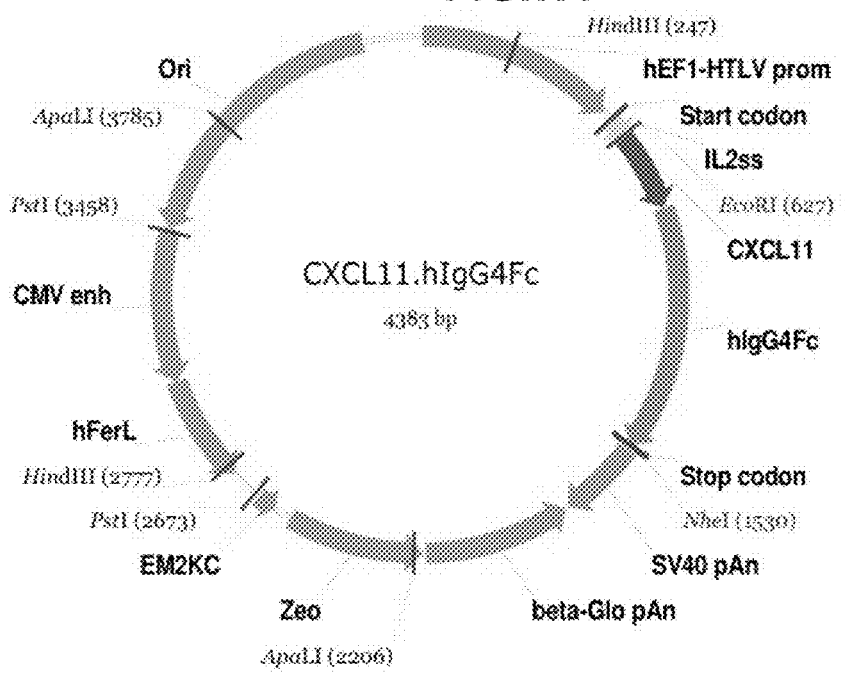

FIG. 7A depicts the expression vector pCXCL11.hIgG4Fc.

Figure 7B:
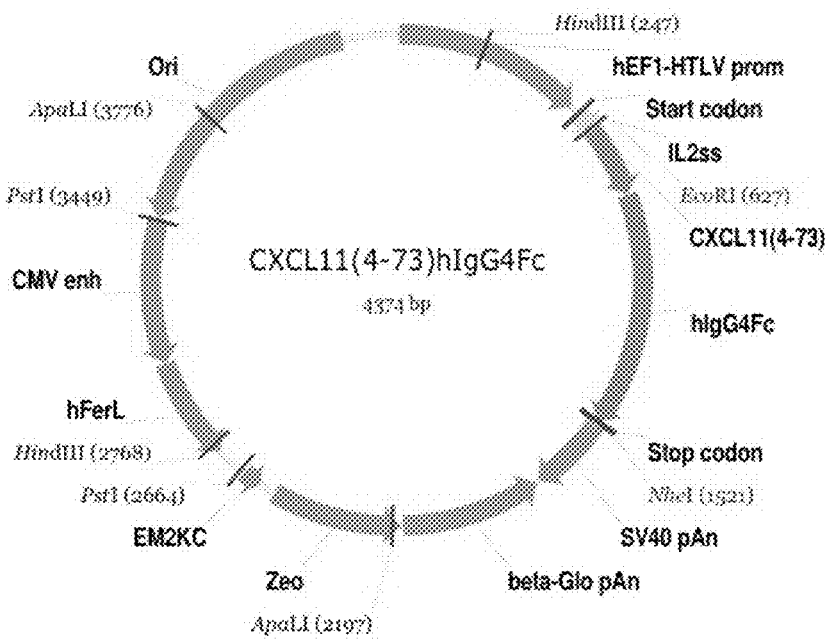

FIG. 7B depicts the expression vector pCXCL11(4-73).hIgG4Fc.

FIG. 7C shows the nuceotide sequence of the expression vector pCXCL11.hIgG4Fc.

FIG. 7D shows the nuceotide sequence of the expression vector pCXCL11(4-73).hIgG4Fc.

FIG. 7E shows the nuceotide sequence of the expression vector pCXCL11(4-127).hIgG4Fc with alanine substitutios for removal of GAG binding sites—lys and his.

FIG. 8A depicts the expression vector pCXCL13.hIgG1Fc.

FIG. 8B depicts the expression vector pCXCL13(3-87).hIgG1Fc.

FIG. 8C shows the nuceotide sequence of the expression vector pCXCL13.hIgG1Fc.

FIG. 8D shows the nuceotide sequence of the expression vector pCXCL13(4-73).hIgG1Fc.

FIG. 8E shows the nuceotide sequence of the expression vector pCXCL13(4-127).hIgG1Fc with alanine substitutios for removal of GAG binding sites—lys and his.

Figure 9A:
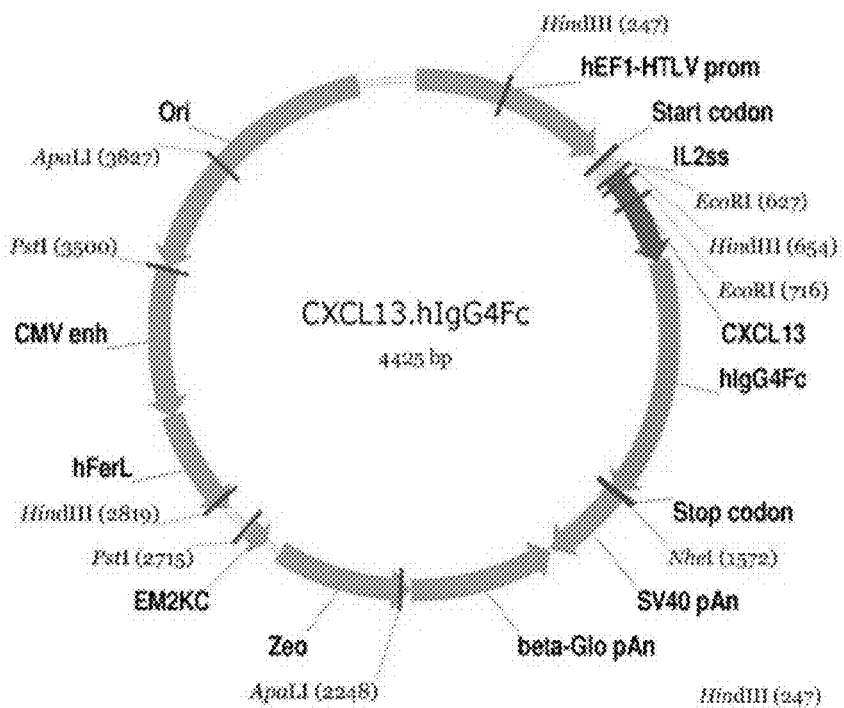

FIG. 9A depicts the expression vector pCXCL13.hIgG4Fc.

Figure 9B:
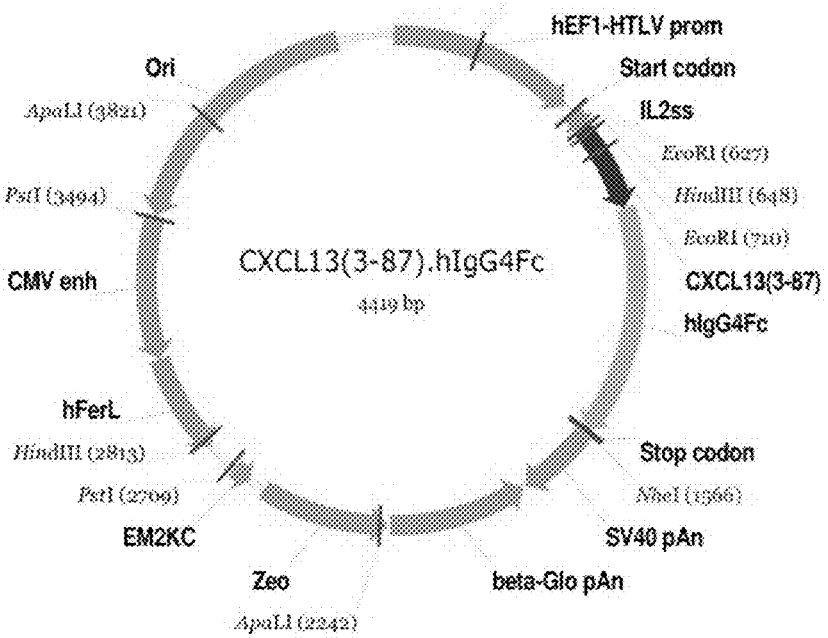

FIG. 9B depicts the expression vector pCXCL13(3-87).hIgG4Fc.

FIG. 9C shows the nuceotide sequence of the expression vector pCXCL13.hIgG4Fc.

FIG. 9D shows the nuceotide sequence of the expression vector pCXCL13(3-87).hIgG4Fc.

FIG. 9E shows the nuceotide sequence of the expression vector pCXCL11(4-127).hIgG4Fc with alanine substitutios for removal of GAG binding sites—lys and his.

Figure 10A:
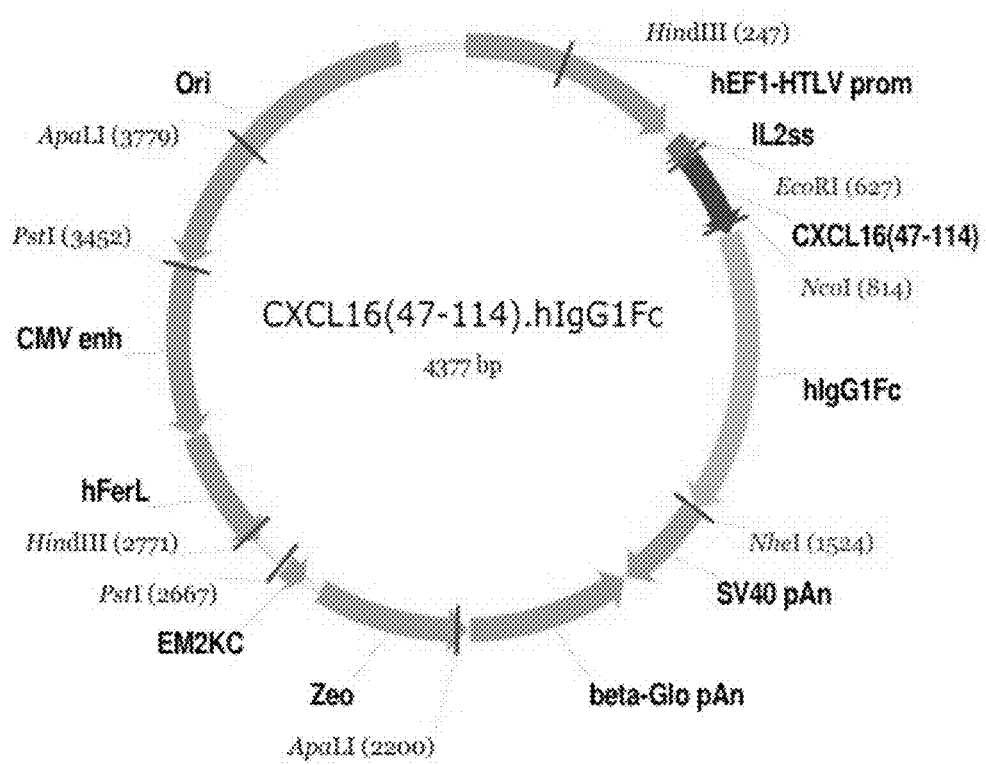

FIG. 10A depicts the expression vector pCXCL16(47-114).hIgG1Fc.

Figure 11:
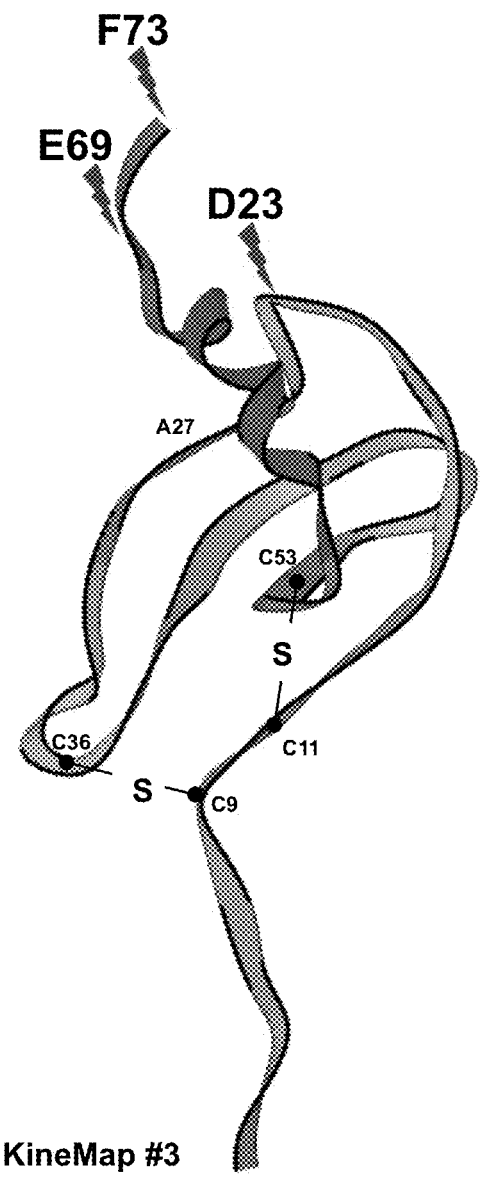

FIG. 11 depicts a cartoon of the structure of CXCL11 indication potential pegylation sites.

FIG. 12 shows the amino acid sequences of the chemokines and human IgG Fc fragments listed in Table 1.

DETAILED DESCRIPTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Unless otherwise defined, scientific and technical terms used in connection with the present invention shall have the meanings that are commonly understood by those of ordinary skill in the art. Although any methods, devices, and materials similar or equivalent to those described herein can be used in the practice or testing of the presently disclosed subject matter, representative methods, devices, and materials are now described. Further, unless otherwise required by context, singular terms shall include pluralities and plural terms shall include the singular.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

The present application generally relates to compositions and methods for treating chemokine receptor-mediated disorders and modulating inflammation. Particularly, the present application relates to chemokine-immunoglobulin fusion polypeptides, chemokine-polymer conjugates, and uses thereof to modulate immunity, cancer progression, and inflammation as well as treat chemokine receptor-mediated disorders, including tissue regeneration, wound repair, stem cell homeostasis, cell proliferative disorders, and inflammatory.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "treat," "treating" or "treatment" as used herein, refers to a method of alleviating or abrogating a disorder and/or its attendant symptoms. The terms "prevent", "preventing" or "prevention," as used herein, refer to a method of barring a subject from acquiring a disorder and/or its attendant symptoms. In certain embodiments, the terms "prevent," "preventing" or "prevention" refer to a method of reducing the risk of acquiring a disorder and/or its attendant symptoms.

In a pharmacological sense, in the context of the present invention, an "effective amount" of a composition efers to an amount effective in the prevention or treatment of a disorder for the treatment of which the composition is effective. A "disorder" is any condition that would benefit from treatment with the composition.

"Mammal" for purposes of treatment refers to any animal classified as a mammal, including humans, non-human primates, domestic and farm animals, and zoo, sports, or pet animals, such as dogs, horses, cats, cows, etc. Preferably, the mammal is human.

The term "inhibits" is a relative term, an agent inhibits a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, a composition that reduces or prevents an infection or a response, such as a pathological response, can, but does not necessarily completely eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

Chemokine-Immunoglobulin Fusion Polypeptides

Chemokines have been demonstrated to mediate a number of cellular functions involving motility, invasion, adherence, proliferation, and survival. At the appropriate levels and expression, these chemotactic cytokines promote proper wound healing, neovascularization or immunity. If inappropriately expressed, these factors can dictate chronic diseases like keloid formation, angiogenesis, metastasis/drug resistance of cancer cells, autoimmunity, graft rejection, inflammation (e.g., arthritis, ulcerative colitis, Crohn's disease, multiple sclerosis, COPD, etc.), diabetes. Both beneficial and deleterious functions are mediated by binding and activation of chemokine receptors, which are class A, G protein coupled receptors.

A number of small molecule antagonists have been constructed to block the action of these receptors. Remarkably, many of these compounds have high affinities (5-50 nM) and specificities for their target. However, these inhibitors have two major limitations: (i) hydrophobicity and possible liver retention/toxicity and (ii) relative short serum-half life or bioavailability (<6 hours).

The present application provides isolated chemokine-immunoglobulin fusion polypeptides for clinical use. The fusion polypeptides comprise a wild-type human chemokine or a variant thereof fused to the constant region (i.e., CH2 and CH3) of a human immunoglobulin (Ig) G or a variant thereof. The chemokine-immunoglobulin fusion polypeptide can bind with specificity to one or more particular chemokine receptors and thereby modulate one or more biological activities (e.g., receptor activation) of the receptor(s).

One aspect of the present invention relates to an isolated chemokine-immunoglobulin fusion polypeptide having a chemokine moiety and an immunoglobulin moiety. In some embodiments, the chemokine moiety comprises a chemokine selected from the group consisting of human CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof. In some embodiments, the chemokine moiety comprises CCL2 and functional variants thereof. In other embodiments, the chemokine moiety comprises CCL25 and functional variants thereof. In other embodiments, the chemokine moiety comprises CXCL12 and functional variants thereof. In other embodiments, the chemokine moiety comprises CXCL13 and functional variants thereof. In other embodiments, the chemokine moiety comprises CXCL16 and functional variants thereof. As used herein, each chemokine noted above refers to all isoforms of the chemokine The immunoglobulin moiety comprises a human immunoglobulin fragment, such as a constant region of a human immunoglobulin, a Fc fragment of a human immunoglobulin, or a functional variant thereof. In certain embodiments, human immunoglobulin fragment is selected from the group consisting of the constant region (Fc) of human IgG1 (IgG1Fc), the constant region of human IgG2 (IgG2Fc), the constant region of human IgG3 (IgG3Fc), the constant region of human IgG4 (IgG4Fc), and functional variants thereof. The complete amino acid sequences of the above-described chemokines and the Fc regions of human IgG1, IgG2, IgG3 and IgG4 are listed in Table 1 below and shown in FIG. 12.

TABLE 1

| Chemokine/Receptor | Protein Accession No. | SEQ ID NO: |
|---|---|---|
| CCL1 | NP_002972 | 1 |
| CCL2 | NP_002973 | 2 |
| CCL3 | NP_002974 | 3 |
| CCL4 | NP_002975 | 4 |
| CCL4L1 | NP_001001435 | 5 |
| CCL5 | NP_002976 | 6 |
| CCL7 | NP_006264 | 7 |
| CCL8 | NP_005614 | 8 |
| CCL11 | CAG33702 | 9 |

TABLE 1-continued

| Chemokine/Receptor | Protein Accession No. | SEQ ID NO: |
|---|---|---|
| CCL13 | NP_005399 | 10 |
| CCL14-1 | NP_116739 | 11 |
| CCL14-2 | NP_116738 | 12 |
| CCL15 | NP_116741 | 13 |
| CCL16 | NP_004581 | 14 |
| CCL17 | NP_002978 | 15 |
| CCL18 | NP_002979 | 16 |
| CCL19 | NP_006265 | 17 |
| CCL20-1 | NP_004582 | 18 |
| CCL20-2 | NP_001123518 | 19 |
| CCL21 | NP_002980 | 20 |
| CCL22 | NP_002981 | 21 |
| CCL23-1 | NP_665905 | 22 |
| CCL23-2 | NP_005055 | 23 |
| CCL24 | NP_002982 | 24 |
| CCL25-1 | NP_005615 | 25 |
| CCL25-2 | NP_683686 | 26 |
| CCL25-3 | EAW68951 | 27 |
| CCL26 | NP_006063 | 28 |
| CCL27 | NP_006655 | 29 |
| CCL28 | NP_683513 | 30 |
| CXCL1 | NP_001502 | 31 |
| CXCL2 | NP_002080 | 32 |
| CXCL3 | NP_002081 | 33 |
| CXCL4 | NP_002610 | 34 |
| CXCL5 | NP_002985 | 35 |
| CXCL6 | NP_002984 | 36 |
| CXCL7 | NP_002695 | 37 |
| CXCL8 | NP_000575 | 38 |
| CXCL9 | NP_002407 | 39 |
| CXCL10 | NP_001556 | 40 |
| CXCL11 | NP_005400 | 41 |
| CXCL12 | NP_000600 | 42 |
| CXCL13 | NP_006410 | 43 |
| CXCL16 | NP_071342 | 44 |
| XCL1 | AAH69817 | 45 |
| XCL2 | NP_003166 | 46 |
| CX3CL1 | NP_002987 | 47 |
| IgG1Fc | CBX54381.1 | 48 |
| IgG2Fc | CBX54382.1 | 49 |
| IgG3Fc | CBX54383.1 | 50 |
| IgG4Fc | CBX54384.1 | 51 |

Without wishing to be bound by any particular theory of operation, the immunoglobulin region can increase serum-half life or bioavailability of the fusion polypeptide and the precise polypeptide sequences of the Fc portion can be selected to maximize serum-half life and/or bioavailability. In addition, Fc regions from different IgG subclasses (e.g., IgG1, IgG2, IgG3, and IgG4) exhibit different immunological activities, and therefore the IgG Fc region can be selected based on a desired immunological activity. For example, the Fc region of IgG1 can activate complement, while the Fc region of IgG4 has reduced complement activity.

Thus, a particular Fc region can be selected for a particular application based on the desired immunological activities manifested by each region. In some particular embodiments, the Fc region can be the Fc region of human IgG1, IgG2, IgG3 or IgG4. As such, the chemokine-immunoglobulin fusion polypeptide find utility in enhancing immunity, suppressing autoimmunity, suppressing inflammation, and/or inhibiting growth/metastasis of proliferative disorder cells. The present application further provides isolated polynucleotide which encode the chemokine-immunoglobulin fusion polypeptide disclosed herein and expression vectors capable of expressing the chemokine-immunoglobulin fusion polypeptide in vivo.

The term "isolated", when applied to a protein or polynucleotide, denotes that the protein or polynucleotide is essentially free of other cellular components with which it is associated in the natural state. It can be in a homogeneous state although it can be in either a dry or aqueous solution. Homogeneity and whether a molecule is isolated can be determined using analytical chemistry techniques such as poly-acrylamide gel electrophoresis or high performance liquid chromatography. A protein that is the predominant species present in a preparation is substantially isolated. The term "isolated" denotes that a protein or polynucleotide gives rise to essentially one band in an electrophoretic gel. Particularly, it means that the protein or polynucleotide is in some embodiments at least about 50% pure, in some embodiments at least about 85% pure, and in some embodiments at least about 99% pure.

The term "polynucleotide" refers to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues. The term "polynucleotide" or "polynucleotide sequence" can also be used interchangeably with gene, open reading frame (ORF), cDNA, and mRNA encoded by a gene.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The chemokine portion of the chemokine-immunoglobulin fusion polypeptide can be selected based on the chemokine receptor or receptors to which it exhibits binding specificity. This provides for the selective targeting of the chemokine-immunoglobulin fusion polypeptide to one or more specific chemokine receptors to thereby modulate activation and subsequent biological activities of the receptor(s). Table 1 (adapted from Allen et al. (2007) Annu Rev. Immunol. 25:787-820) provides an exemplary list of receptors that can be targeted by one or more chemokines, which can be incorporated into the chemokine-immunoglobulin fusion polypeptide of the presently-disclosed subject matter.

As disclosed in Table 2, certain chemokines can specifically bind more than one chemokine receptor. For example, CXCL11 can bind with specificity to chemokine receptors CXCR3-A, CXCR3-B, CXCR7, and DARC/Duffy. As such, if it is desirable to target more than one chemokine receptor, a particular chemokine, such as CXC11, can be selected for incorporation into the chemokine-immunoglobulin fusion polypeptide of the presently-disclosed subject matter. In some embodiments of the presently disclosed subject matter, the chemokine-immunoglobulin fusion polypeptide can comprise of a chemokine portion selected from the group consisting of CCL2, CCL7, CCL8, CCL13, CCL25, CXCL11, CXCL13, and mutations thereof. "Mutations" of the polypeptides include variants and fragments of the reference polypeptides.

TABLE 2

Chemokine receptors and their ligands

| Receptor | Ligands |
|---|---|
| CCR1 | CCL3, CCL5, CCL7, CCL13, CCL14, CCL15, CCL16, CCL23 |
| CCR2 | CCL2, CCL7, CCL8, CCL13, CCL16 |
| CCR3 | CCL5, CCL7, CCL8, CCL11, CCL13, CCL15, CCL16, CCL24, CCL26, CCL28 |
| CCR4 | CCL17, CCL22 |
| CCR5 | CCL3, CCL4, CCL5, CCL8, CCL11, CCL14, CCL16 |
| CCR6 | CCL20 |
| CCR7 | CCL19, CCL21 |
| CCR8 | CCL1 |
| CCR9 | CCL25 |
| CCR10 | CCL27, CCL28 |
| CXCR1 | CXCL6, CXCL7, CXCL8 |
| CXCR2 | CXCL1, CXCL2, CXCL3, CXCL5, CXCL6, CXCL7, CXCL8 |
| CXCR3-A | CXCL9, CXCL10, CXCL11, CCL11 |
| CXCR3-B | CXCL4, CXCL9, CXCL10, CXCL11, CCL11 |
| CXCR4 | CXCL12 |
| CXCR5 | CXCL13 |
| CXCR6 | CXCL16 |
| CXCR7 | CXCL12, CXCL11 |
| XCR1 | XCL1, XCL2 |
| $CX_3CR1$ | $CX_3CL1$ |
| CCX-CKR | CCL19, CCL21, CCL25 |
| D6 | CCL2, CCL3L1, CCL4, CCL5, CCL7, CCL8, CCL11, CCL13, CCL14, CCL17, CCL22 |
| DARC/Duffy | CCL2, CCL7, CCL8, CCL11, CCL13, CCL14, CCL16, CCL17, CXCL1, CXCL5, CXCL6, CXCL7, CXCL8, CXCL9, CXCL11, CXCL13 |

The term "functional variant" refers to protein or polypeptide that is different from the reference protein or polypeptide by one or more amino acids, e.g., one or more amino acid substitutions, but substaintially maintains the biological function of the reference protein or polypeptide. As used herein, a functional variant of a chemokine is a variant that maintains the receptor binding function of the original chemokine and a functional variant of the Fc region of IgG is a variant that maintains the immunologivla activities of the original Fc region.

A functional variant of a polypeptide may be a fragment of the original polypeptide. The term "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 3, 5, 6, 8 or 10 amino acids long, at least 14 amino acids long, at least 20, 30, 40 or 50 amino acids long, at least 75 amino acids long, or at least 100, 150, 200, or more amino acids long.

The term "functional variant" further includes conservatively substituted variants. The term "conservatively substituted variant" refers to a peptide comprising an amino acid residue sequence that differs from a reference peptide by one or more conservative amino acid substitution, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another, such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically derivatized residue, provided that the resulting peptide maintains some or all of the activity of the reference peptide as described herein. In some embodiments, the functional variant of a peptide shares a sequence identity of 70%, 75%, 80%, 85%, 90%, 91%, 92%, 93%, 94%, 95%, 96%, 97%, 98% or 99% with the reference peptide. For example, a functional variant of a chemokine may shares a sequence identity of 70%, 75%, 80%, 85%, 90%, 91%, 92%, 93%, 94%, 95%, 96%, 97%, 98% and 99% with the reference chemokine; a functional variant of an immunoglobin Fc fragment may shares a sequence identity of 70%, 75%, 80%, 85%, 90%, 91%, 92%, 93%, 94%, 95%, 96%, 97%, 98% and 99% with the reference immunoglobin Fc fragment; and a functional variant of a chemokine-immunoglobin fusion protein may shares a sequence identity of 70%, 75%, 80%, 85%, 90%, 91%, 92%, 93%, 94%, 95%, 96%, 97%, 98% and 99% with the reference chemokine-immunoglobin fusion protein.

The term "sequence identity," as used herein, means that two peptide sequences are identical (i.e., on an amino acid-by-amino acid basis) over the window of comparison. The term "percentage of sequence identity" is calculated by comparing two optimally aligned sequences over the window of comparison, determining the number of positions at which the identical amino acid residue occurs in both sequences to yield the number of matched positions, dividing the number of matched positions by the total number of positions in the window of comparison (i.e., the window size), and multiplying the result by 100 to yield the percentage of sequence identity. The reference sequence may be a subset of a larger sequence, for example, as a segment of the full-length sequences of the compositions claimed in the present invention.

In some particular embodiments, the chemokine-immunoglobulin fusion polypeptides disclosed herein include functional variants to the chemokine portion that introduce amino acid substitutions to eliminate glycosaminoglycan (e.g., heparin, laminin, GAG)-binding, which can thereby increase the serum half-life of the polypeptide. For example, in some embodiments one or more alanines can be substituted for lysines, arginines and/or histidines within GAG binding sites of the chemokine portions.

Specific chemokine-immunoglobulin fusion polypeptides disclosed herein that include a chemokine variant having one or more mutations in the chemokine sequence are named accordingly to indicate the particular mutation. For example "var-" before the chemokine name (e.g., var-CCL2) is indicative of a functional variant having an engineered mutation to the chemokine portion that results in a polypeptide sequence that differs from the reference chemokine sequence (e.g., CCL2). A fragment mutation resulting from a truncation is notated be the sequence remaining after truncation. For example, a truncation of the N-terminal 4 amino acids of the 76 amino acid CCL2 chemokine would be notated as "var-CCL2" or "CCL2(5-76)". A variant mutation resulting from one or more amino acid substitutions would be notated as a parenthetical after the chemokine name in the form "X#Y" or "X→Y", wherein the amino acid X (in standard one letter amino acid code, as is known in the art) in the reference polypeptide is substituted with the amino acid Y either at a particular residue (#) or throughout the polypeptide, or a particular region of the polypeptide (X→Y), such as for example a GAG-binding region of the chemokine polypeptide. In some embodiments, a mutation can include both a variant and a fragment of the reference chemokine polypeptide. These mutants are indicated in the named polypeptide in succession in a parenthetical following the chemokine name. For example, "CCL2(5-76K/H→A)" indicates a chemokine-immunoglobulin fusion polypeptide including in the chemokine portion a mutant CCL2 polypeptide that has been truncated at the N-terminus to remove residues 1-4 and also mutated to substitute alanines (A) for lysines (K) and histidines (H) within the sequence. In some embodiments, a chemokine variant (e.g., var-CXCL13) shares a sequence identity of 70%, 75%, 80%, 85%, 90%, 91%, 92%, 93%, 94%, 95%, 96%, 97%, 98% and 99% with the reference chemokine (i.e., CXCL13). Finally, in reference to nomenclature, the chemokine-immunoglobulin fusion polypeptides disclosed herein are named according to the chemokine portion (A) and the immunoglobulin portion (B) fused together (i.e. A-B). Thus, for example, CCL2-IgG1Fc refers to a chemokine-immunoglobulin fusion polypeptide comprising a wild-type CCL2 chemokine portion fused with an Fc constant region of an IgG class 1 immunoglobulin.

In some embodiments, the present application provides a human chemokine polypeptide fused to a human immunoglobulin polypeptide. In some embodiments, the present application provides the following novel isolated chemokine-immunoglobulin fusion polypeptides: CCL2-IgG1Fc, var-CCL2-IgG1Fc, CCL2-IgG2Fc, var-CCL2-IgG2Fc, CCL2-IgG3Fc, var-CCL2-IgG3Fc, CCL2-IgG4Fc, var-CCL2-IgG4Fc, CCL7-IgG1Fc, var-CCL7-IgG1Fc, CCL7-IgG2Fc, var-CCL7-IgG2Fc, CCL7-IgG3Fc, var-CCL7-IgG3Fc, CCL7-IgG4Fc, var-CCL7-IgG4Fc, CCL8-IgG1Fc, var-CCL8-IgG1Fc, CCL8-IgG2Fc, var-CCL8-IgG2Fc, CCL8-IgG3Fc, var-CCL8-IgG3Fc, CCL8-IgG4Fc, var-CCL8-IgG4Fc, CCL13-IgG1Fc, var-CCL13-IgG1Fc, CCL13-IgG2Fc, var-CCL13-IgG2Fc, CCL13-IgG3Fc, var-CCL13-IgG3Fc, CCL13-IgG4Fc, var-CCL13-IgG4Fc, CCL25-IgG1Fc, var-CCL25-IgG1Fc, CCL25-IgG2Fc, var-CCL25-IgG2Fc, CCL25-IgG3Fc, var-CCL25-IgG3Fc, CCL25-IgG4Fc, var-CCL25-IgG4Fc, CXCL11-IgG1Fc, var-CXCL11-IgG1Fc, CXCL11-IgG2Fc, var-CXCL11-IgG2Fc, CXCL11-IgG3Fc, var-CXCL11-IgG3Fc, CXCL11-IgG4Fc, var-CXCL11-IgG4Fc, CXCL13-IgG1Fc, var-CXCL13-IgG1Fc, CXCL13-IgG2Fc, var-CXCL13-IgG2Fc, CXCL13-IgG3Fc, var-CXCL13-IgG3Fc, CXCL13-IgG4Fc, and var-CXCL13-IgG4Fc.

In particular embodiments, the present application provides the following novel isolated chemokine-immunoglobulin fusion polypeptides: CCL2-IgG1Fc (SEQ ID NO:52), CCL2(5-76)-IgG1Fc (SEQ ID NO:53), CCL2(5-76K/H→A)-IgG1Fc (SEQ ID NO:54), CCL7-IgG1Fc (SEQ ID NO:55), CCL7(5-76)-IgG1Fc (SEQ ID NO:56), CCL7(5-76K/H→A)-IgG1Fc (SEQ ID NO:57), CCL8-IgG1Fc (SEQ ID NO:58), CCL8(5-76)-IgG1Fc (SEQ ID NO:59), CCL8(5-76K/H→A)-IgG1Fc (SEQ ID NO:60), CCL13-IgG1Fc (SEQ ID NO:61), CCL13(5-75)-IgG1Fc (SEQ ID NO:62), CCL13(5-75K/H→A)-IgG1Fc (SEQ ID NO:63), CCL25-IgG1Fc (SEQ ID NO:64), CCL25(4-127)-IgG1Fc (SEQ ID NO:65), CCL25(4-127K/H→A)-IgG1Fc (SEQ ID NO:66), CXCL11-IgG1Fc (SEQ ID NO:67), CXCL11(4-73)-IgG1Fc (SEQ ID NO:68), CXCL11(4-73K/H→A)-IgG1Fc (SEQ ID NO:69), CXCL11-IgG4Fc (SEQ ID NO:70), CXCL11(4-73)-IgG4Fc (SEQ ID NO:71), CXCL11(4-73K/H→A)-IgG4Fc (SEQ ID NO:72), CXCL13-IgG1Fc (SEQ ID NO:73), CXCL13(3-87)-IgG1Fc (SEQ ID NO:74), CXCL13(3-87K/H→A)-IgG1Fc (SEQ ID NO:75), CXCL13-IgG4Fc (SEQ ID NO:76), CXCL13(3-87)-IgG4Fc (SEQ ID NO:77), and CXCL13(3-87K/H→A)-IgG4Fc (SEQ ID NO:78).

The novel chemokine-immunoglobulin fusion polypeptides disclosed herein can be produced using any of a variety of peptide production techniques generally known in the art. For example, recombinant genetic techniques can be utilized to produce the fusion polypeptides disclosed herein. As such, in some embodiments, an isolated nucleic acid molecule which encodes a chemokine-immunoglobulin fusion polypeptide selected from the group consisting of CCL2-IgG1Fc, var-CCL2-IgG1Fc, CCL2-IgG2Fc, var-CCL2-IgG2Fc, CCL2-IgG3Fc, var-CCL2-IgG3Fc, CCL2-IgG4Fc, var-CCL2-IgG4Fc, CCL7-IgG1Fc, var-CCL7-IgG1Fc, CCL7-IgG2Fc, var-CCL7-IgG2Fc, CCL7-IgG3Fc, var-CCL7-IgG3Fc, CCL7-IgG4Fc, var-CCL7-IgG4Fc, CCL8-IgG1Fc, var-CCL8-IgG1Fc, CCL8-IgG2Fc, var-CCL8-IgG2Fc, CCL8-IgG3Fc, var-CCL8-IgG3Fc, CCL8-IgG4Fc, var-CCL8-IgG4Fc, CCL13-IgG1Fc, var-CCL13-IgG1Fc, CCL13-IgG2Fc, var-CCL13-IgG2Fc, CCL13-IgG3Fc, var-CCL13-IgG3Fc, CCL13-IgG4Fc, var-CCL13-IgG4Fc, CCL25-IgG1Fc, var-CCL25-IgG1Fc, CCL25-IgG2Fc, var-CCL25-IgG2Fc, CCL25-IgG3Fc, var-CCL25-IgG3Fc, CCL25-IgG4Fc, var-CCL25-IgG4Fc, CXCL11-IgG1Fc, var-CXCL11-IgG1Fc, CXCL11-IgG2Fc, var-CXCL11-IgG2Fc, CXCL11-IgG3Fc, var-CXCL11-IgG3Fc, CXCL11-IgG4Fc, var-CXCL11-IgG4Fc, CXCL13-IgG1Fc, var-CXCL13-IgG1Fc, CXCL13-IgG2Fc, var-CXCL13-IgG2Fc, CXCL13-IgG3Fc, var-CXCL13-IgG3Fc, CXCL13-IgG4Fc, and var-CXCL13-IgG4Fcis provided.

In particular embodiments, the isolated nucleic acid molecule encodes a chemokine-immunoglobulin fusion polypeptide selected from the group consisting of CCL2-IgG1Fc, CCL2(5-76)-IgG1Fc, CCL2(5-76K/H→A)-IgG1Fc, CCL2-IgG2Fc, CCL2(5-76)-IgG2Fc, CCL2(5-76K/H→A)-IgG2Fc, CCL2-IgG3Fc, CCL2(5-76)-IgG3Fc, CCL2(5-76K/H→A)-IgG3Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG2Fc, CCL7(5-76)-IgG2Fc, CCL7(5-76K/H→A)-IgG2Fc, CCL7-IgG3Fc, CCL7(5-76)-IgG3Fc, CCL7(5-76K/H→A)-IgG3Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H→A)-IgG1Fc, CCL8-IgG2Fc, CCL8(5-76)-IgG2Fc, CCL8(5-76K/H→A)-IgG2Fc, CCL8-IgG3Fc, CCL8(5-76)-IgG3Fc, CCL8(5-76K/H→A)-IgG3Fc, CCL8-IgG4Fc, CCL8(5-76)-IgG4Fc, CCL8(5-76K/H→A)-IgG4Fc, CCL13-IgG1Fc, CCL13(5-75)-IgG1Fc, CCL13(5-75K/H→A)-IgG1Fc, CCL13-IgG2Fc, CCL13(5-75)-IgG2Fc, CCL13(5-75K/H→A)-IgG2Fc, CCL13-IgG3Fc, CCL13(5-75)-IgG3Fc, CCL13(5-75K/H→A)-IgG3Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H→A)-IgG1Fc, CCL25-IgG2Fc, CCL25(4-127)-IgG2Fc, CCL25(4-127K/H→A)-IgG2Fc, CCL25-IgG3Fc, CCL25(4-127)-IgG3Fc, CCL25(4-127K/H→A)-IgG3Fc, CCL25-IgG4Fc, CCL25(4-127)-IgG4Fc, CCL25(4-127K/H→A)-IgG4Fc, CXCL11-IgG1Fc, CXCL11(4-73)-IgG1Fc, CXCL11(4-73K/H→A)-IgG1Fc, CXCL11-IgG2Fc, CXCL11(4-73)-IgG2Fc, CXCL11(4-73K/H→A)-IgG2Fc, CXCL11-IgG3Fc, CXCL11(4-73)-IgG3Fc, CXCL11(4-73K/H→A)-IgG3Fc, CXCL11-IgG4Fc, CXCL11(4-73)-IgG4Fc, CXCL11(4-73K/H→A)-IgG4Fc, CXCL13-IgG1Fc, CXCL13(3-87)-IgG1Fc, CXCL13(3-87K/H→A)-IgG1Fc, CXCL13-IgG2Fc, CXCL13(3-87)-IgG2Fc, CXCL13(3-87K/H→A)-IgG2Fc, CXCL13-IgG3Fc, CXCL13(3-87)-IgG3Fc, CXCL13(3-87K/H→A)-IgG3Fc, CXCL13-IgG4Fc, CXCL13(3-87)-IgG4Fc, and CXCL13(3-87K/H→A)-IgG4Fc. Recombinant cloning techniques may also be used to construct the heterologous gene sequences that encode for the fusion polypeptide gene product, as is known in the art.

Expression Vectors

Recombinant exprtession vectors comprising nucleic acid molecules which encode the polypeptides disclosed herein are also provided. Particularly useful vectors are contemplated to be those vectors in which the coding portion of the DNA segment is positioned under the control of a promoter. The promoter may be in the form of the promoter which is naturally associated with the chemokine or immunoglobulin gene, e.g., in mammalian tissues, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a chemokine or immunoglobulin gene in its natural environment. Such promoters may include promoters isolated from plant, insect, bacterial, viral, eukaryotic, fish, avian or mammalian cells. Naturally, it will be important to employ a promoter that effectively directs the expression of the DNA segment in the cell type chosen for expression. The use of promoter and cell type combinations for protein expression is generally known to those of skill in the art of molecular biology. The promoters employed may be constitutive, or inducible, and can be used under the appropriate conditions to direct high level expression of the introduced DNA segment, such as is advantageous in the large-scale production of recombinant proteins or peptides.

Expression vectors generally contain sequences for transcriptional termination, and may additionally contain one or more elements positively affecting mRNA stability. An expression vector may further include an internal ribosome entry site (IRES) between adjacent protein coding regions to facilitate expression two or more proteins from a common mRNA in an infected or transfected cell. Additionally, the expression vectors may further include nucleic acid sequence encoding a marker product. This marker product may be used to determine if the gene has been delivered to the cell and is being expressed. Preferred marker genes are the *E. coli* lacZ gene, which encodes β-galactosidase, and green fluorescent protein (GFP).

In some embodiments, the expression vectors of the present application are plasmid expression vectors that are capable of expressing the chemokine-immunoglobulin fusion polypeptides of the present application in an in vitro setting. The expressed fusion polypeptide is then isolated and purified using methods well known to a person skilled in the art.

In other embodiments, the expression vectors of the present application are plasmid expression vectors that are capable of expressing the chemokine-immunoglobulin fusion polypeptides of the present application in an in vivo setting. These expression vectors may be introduced into a subject using delivery systems such as liposomes, including cationic liposomes (e.g., DOTMA, DOPE, DC-cholesterol) and anionic liposomes, microcapsules, nanoparticles and electroporation. In some embodiments, the expression vectors are targeted to a particular cell type via antibodies, receptors, or receptor ligands. Vehicles such as "stealth" and other antibody conjugated liposomes (including lipid mediated drug targeting to cells of interest), receptor mediated targeting of DNA through cell specific ligands or viral vectors targeting e.g., lymphoid, epithelial or endothelial cells. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor level regulation. Many receptors follow more than one intracellular pathway, depending on the cell type, receptor concentration, type of ligand, ligand valency, and ligand concentration.

In yet other embodiments, the expression vectors of the present application are virus-based expression vectors that are capable of expressing the chemokine-immunoglobulin fusion polypeptides of the present application in an in vivo setting. Exemplary viral vectors may include or be derived from adenovirus, adeno-associated virus, herpesvirus, vaccinia virus, poliovirus, poxvirus, HIV virus, lentivirus, retrovirus, Sindbis and other RNA viruses, and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers, and can be delivered in aerosol formulation, and can transfect non-dividing cells. Poxyiral vectors are large and have several sites for inserting genes, they are thermostable and can be stored at room temperature. Viral delivery systems typically utilize viral vectors having one or more genes removed and with and an exogenous gene and/or gene/promotor cassette being inserted into the viral genome in place of the removed viral DNA. The necessary functions of the removed gene(s) may be supplied by cell lines which have been engineered to express the gene products of the early genes in trans.

In other embodiments, the expression vectors are phage DNA, yeast plasmids or baculovirus.

Exemplary expression vector constructs comprising polynucleotides which encode chemokine-immunoglobulin fusion polypeptides disclosed herein are shown in FIGS. 1-10. These expression vectors include pCCL2-IgG1Fc (SEQ ID NO:79), pCCL2(5-76)-IgG1Fc (SEQ ID NO:80), pCCL2(5-76K/H→A)-IgG1Fc (SEQ ID NO:81), pCCL7-IgG1Fc (SEQ ID NO:82), pCCL7(5-76)-IgG1Fc (SEQ ID NO:83), pCCL7(5-76K/H→A)-IgG1Fc (SEQ ID NO:84), pCCL8-IgG1Fc (SEQ ID NO:85), pCCL8(5-76)-IgG1Fc (SEQ ID NO:86), pCCL8(5-76K/H→A)-IgG1Fc (SEQ ID NO:87), pCCL13-IgG1Fc (SEQ ID NO:88), pCCL13(5-75)-IgG1Fc (SEQ ID NO:89), pCCL13(5-75K/H→A)-IgG1Fc (SEQ ID NO:90), pCCL25-IgG1Fc (SEQ ID NO:91), pCCL25(4-127)-IgG1Fc (SEQ ID NO:92), pCCL25(4-127K/H→A)-IgG1Fc (SEQ ID NO:93), pCXCL11-IgG1Fc (SEQ ID NO:94), pCXCL11(4-73)-IgG1Fc (SEQ ID NO:95), pCXCL11(4-73K/H→A)-IgG1Fc (SEQ ID NO:96), pCXCL11-IgG4Fc (SEQ ID NO:97), pCXCL11(4-73)-IgG4Fc (SEQ ID NO:98), pCXCL11(4-73K/H→A)-IgG4Fc (SEQ ID NO:99), pCXCL13-IgG1Fc (SEQ ID NO:100), pCXCL13(3-87)-IgG1Fc (SEQ ID NO:101), pCXCL13(3-87K/H→A)-IgG1Fc (SEQ ID NO:102), pCXCL13-IgG4Fc (SEQ ID NO:103), pCXCL13(3-87)-IgG4Fc (SEQ ID NO:104), and CXCL13(3-87K/H→A)-IgG4Fc (SEQ ID NO:105). It is understood that additional combinations of vectors and genes than those specifically disclosed above are contemplated by the presently-disclosed subject matter, as would be understood by one of ordinary skill in the art.

Protein Conjugates

In some embodiments, the chemokine-immunglobulin fusion polypeptides of the present application, as well as certain chemokines and variants thereof, are conjugated to a non-protein polymer to form protein-polymer conjugates. Unless specifically indicated to the contrary, the term "non-protein polymer" is defined as a molecule formed by covalent linkage of two or more monomers, wherein none of the monomers is contained in the group consisting of alanine (Ala), cysteine (Cys), aspartic acid (Asp), glutamic acid (Glu), phenylalanine (Phe), glycine (Gly), histidine (H is), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), and tyrosine (Tyr) residues. Serum soluble non-protein polymers, such as polyethylene glycol, and tissue or fat soluble polymers, such as polycaprolactone, can be used for delivery, release, and/or retention of polypeptides. In some embodiments, the protein-polymer conjugate is a pegylated chemokine-immunglobulin fusion polypeptide, chemokine or a variant thereof.

In one aspect, the present application encompass a conjugate having any molar ratio of polymer to chemokine or fragment thereof that endows the conjugate with an apparent size in the desired range as taught herein. The apparent size of the conjugate will depend in part upon the size and shape of the polymer used, the size and shape of the chemokine or fragment thereof used, the number of polymer molecules attached to the chemokine or fragment thereof, and the location of such attachment site(s) on the chemokine or fragment thereof. These parameters can easily be identified and maximized to obtain the conjugate with the desired apparent size for any type of chemokine or fragment thereof, polymer and linkage system.

In some embodiments, the protein-polymer conjugate of the present application has an effective size of at least about 500,000 D, or at least about 800,000 D, or at least about 900,000 D, or at least about 1,000,000 D, or at least about 1,200,000 D, or at least about 1,400,000 D, or at least about 1,500,000 D, or at least about 1,800,000 D, or at least about 2,000,000 D, or at least about 2,500,000 D. In one embodiment, the polymer is PEG.

In other embodiments, the protein-polymer conjugate of the present application has an effective size of at or about 500,000 D to at or about 10,000,000 D, or an effective size of at or about 500,000 D to at or about 8,000,000 D, or an effective size of at or about 500,000 D to at or about 5,000,000 D, or an effective size of at or about 500,000 D to at or about 4,000,000 D, or an effective size of at or about 500,000 D to at or about 3,000,000 D, or an effective size of at or about 500,000 D to at or about 2,500,000 D, or an effective size of at or about 500,000 D to at or about 2,000,000 D, or an effective size of at or about 500,000 D to at or about 1,800,000 D, or an effective size of at or about 500,000 D to at or about 1,600,000 D, or an effective size of at or about 500,000 D to at or about 1,500,000 D, or an effective size of at or about 500,000 D to at or about 1,000,000 D. In one embodiment, the polymer is PEG.

In a further embodiment, the protein-polymer conjugate has an effective size that is at least about 8 fold greater, or at least about 10 fold greater, or at least about 12 fold greater, or at least about 15 fold greater, or at least about 18 fold greater, or at least about 20 fold greater, or at least about 25 fold greater, or at least about 28 fold greater, or at least about 30 fold greater, or at least about 40 fold greater, than the effective size of the unconjugated chemokine-immunglobulin fusion polypeptide, chemokine or variant thereof. In one embodiment, the polymer is PEG.

In another embodiment, the protein-polymer conjugate has an effective size that is about 8 fold to about 100 fold greater, or is about 8 fold to about 80 fold greater, or is about 8 fold to about 50 fold greater, or is about 8 fold to about 40 fold greater, or is about 8 fold to about 30 fold greater, or is about 8 fold to about 28 fold greater, or is about 8 fold to about 25 fold greater, or is about 8 fold to about 20 fold greater, or is about 8 fold to about 18 fold greater, or is about 8 fold to about 15 fold greater, than the effective size of the unconjugated chemokine-immunglobulin fusion polypeptide, chemokine or variant thereof. In one embodiment, the polymer is PEG.

In another embodiment, the protein-polymer conjugate has an effective size that is about 25 fold to about 100 fold greater, or is about 25 fold to about 80 fold greater, or is about 25 fold to about 50 fold greater, or is about 25 fold to about 40 fold greater, or is about 25 fold to about 30 fold greater, or is about 25 fold to about 28 fold greater, than the effective size of the unconjugated chemokine-immunglobulin fusion polypeptide, chemokine or variant thereof. In one embodiment, the polymer is PEG.

In another embodiment, the protein-polymer conjugate has a polymer-to-protein molar ratio of no more than about 10:1, or no more than about 5:1, or no more than about 4:1, or no more than about 3:1, or no more than about 2:1, or no more than 1:1. In one embodiment, the polymer is PEG.

In still another embodiment, the protein-polymer conjugate is a chemokine-immunglobulin fusion polypeptide, chemokine or variant thereof covalently attached to at least one polymer having an actual MW of at least about 20,000 D. In one embodiment, the polymer is PEG.

In a further embodiment, the conjugate is a chemokine-immunglobulin fusion polypeptide, chemokine or variant thereof covalently attached to at least one polymer having an actual MW of at least about 30,000 D. In one embodiment, the polymer is PEG.

In yet another embodiment, the conjugate is a chemokine-immunglobulin fusion polypeptide, chemokine or variant thereof covalently attached to at least one polymer having an actual MW of at least about 40,000 D. In one embodiment, the polymer is PEG.

In another embodiment, the conjugate is a chemokine-immunglobulin fusion polypeptide, chemokine or variant thereof covalently attached to at least one polymer having an actual MW that is at or about 20,000 D to at or about 300,000 D, or is at or about 30,000 D to at or about 300,000 D, or is at or about 40,000 D to at or about 300,000 D. In one embodiment, the polymer is PEG.

The conjugates of the present application can be made using any suitable technique now known or hereafter developed for derivatizing chemokines or fragments thereof with polymers. It will be appreciated that the invention is not limited to conjugates utilizing any particular type of linkage between a chemokine or fragment thereof and a polymer.

The conjugates of the present application include species wherein a polymer is covalently attached to a non-specific site or non-specific sites on a chemokine-immunoglobulin fusion polypeptide, a chemokine or a variant thereof (i.e. the polymer attachment is not targeted to a particular region or a particular amino acid residue in the unconjugated chemokine or fragment thereof). In such embodiments, the coupling chemistry can, for example, utilize the free epsilon amino groups of lysine residues in the unconjugated antibody as attachment sites for the polymer, wherein such lysine residue amino groups are randomly derivatized with polymer.

In addition, the conjugates of the invention include species wherein a polymer is covalently attached to a specific site or specific sites on the unconjugated chemokine or fragment thereof (i.e. a polymer attachment is targeted to a particular region or a particular amino acid residue or residues in the unconjugated chemokine or fragment thereof). FIG. 11 depicts a cartoon of the structure of CXCL11 indication potential pegylation sites. In such embodiments, the coupling chemistry can, for example, utilize the free sulfhydryl group of a cysteine residue not in a disulfide bridge in the unconjugated chemokine or fragment thereof. In one embodiment, one or more cysteine residue(s) is (are) engineered into a selected site or sites in the unconjugated chemokine or fragment thereof for the purpose of providing a specific attachment site or sites for polymer. The polymer can be activated with any functional group that is capable of reacting specifically with the free sulfhydryl or thiol group(s) on the unconjugated antibody, such as maleimide, sulfhydryl, thiol, triflate, tesylate, aziridine, exirane, and 5-pyridyl functional groups. The polymer can be coupled to the unconjugated chemokine or fragment thereof using any protocol suitable for the chemistry of the coupling system selected.

In another embodiment, polymer attachment is targeted to the receptor binding site of the unconjugated chemokine or fragment thereof. In another embodiment, polymer attachment is targeted to a site on the chemokine or fragment thereof away from the receptor binding site of the unconjugated chemokine or fragment thereof.

In certain embodiments, the protein portion of the protein-polymer conjugate is selected from the group consisting of human CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and the polymer portion of the protein-polymer conjugate is PEG. FIG. 11 depicts a cartoon of the structure of CXCL11 indication potential pegylation sites.

In other embodiments, the protein portion of the protein-polymer conjugate is a chemokine-immunoglobulin fusion polypeptide wherein the chemokine moiety is selected from the group consisting of a human CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and the immunoglobulin moiety is selected from the group consisting of the Fc region of human IgG1, the Fc region of human IgG2, the Fc region of human IgG3, the Fc region of human IgG4 and variants thereof.

In some embodiments, the protein-polymer conjugate is a serum labile polypeptide selected from the group consisting of CCL2-PEG, var-CCL2-PEG, CCL7-PEG, var-CCL7-PEG, CCL8-PEG, var-CCL8-PEG, CCL13-PEG, var-CCL13-PEG, CCL25-PEG, var-CCL25-PEG, CXCL11-PEG, var-CXCL11-PEG, CXCL13-PEG, var-CXCL13-PEG, CXCL16-PEG, and var-CXCL16-PEG.

In particular embodiments, the protein-polymer conjugate is a serum labile polypeptide selected from the group consisting of CCL2-PEG, CCL2(5-76)-PEG, CCL2(5-76K/H→A)-PEG, CCL7-PEG, CCL7(5-76)-PEG, CCL7(5-76K/H→A)-PEG, CCL8-PEG, CCL8(5-76)-PEG, CCL8(5-76K/H→A)-PEG, CCL13-PEG, CCL13(5-75)-PEG, CCL13(5-75K/H→A)-PEG, CCL25-PEG, CCL25(4-127)-PEG, CCL25(4-127K/H→A)-PEG, CXCL11-PEG, CXCL11(4-73)-PEG, CXCL11(4-73K/H→A)-PEG, CXCL11-IgG4Fc, CXCL11(4-73)-IgG4Fc, CXCL11(4-73K/H→A)-IgG4Fc, CXCL13-PEG, CXCL13(3-87)-PEG, CXCL13(3-87K/H→A)-PEG, CXCL16-PEG, CXCL16(3-87)-PEG, and CXCL16(3-87K/H→A)-PEG.

It is believed that the serum half-life, MRT and/or serum clearance rate of any chemokine or fragment thereof can be greatly improved by derivatizing the chemokine or fragment thereof with polymer as taught herein. In a preferred embodiment, the conjugate contains a chemokine or fragment thereof selected from the group consisting of CCL2, CCL7, CCL8, CCL13, CCL25, CXCL11, CXCL12α, CXCL13, and mutations, variants and fragments thereof.

Methods of Producing Chemokine-Immunoglobulin Fusion Polypeptides

The chemokine-immunglobulin fusion polypeptides or variants thereof may be produced using methods well known in the art. In certain embodiments, the chemokine-immunglobulin fusion polypeptide or variants thereof are produced by chemical synthesis. Briefly, a chemokine-immunglobulin fusion polypeptide may be synthesized by coupling the carboxyl group or C-terminus of one amino acid to the amino group or N-terminus of another. Due to the possibility of unintended reactions, protecting groups are usually necessary. Chemical peptide synthesis starts at the C-terminal end of the peptide and ends at the N-terminus. This is the opposite of protein biosynthesis, which starts at the N-terminal end.

In some embodiments, the chemokine-immunglobulin fusion polypeptide may be synthesized using traditional liquid- or solid-phase synthesis. Fmoc and t-Boc solid phase peptide synthesis (SPPS) can be employed to grow the peptides from carboxy to amino-terminus. In certain embodiments, the last "amino acid" added to the reaction is pegylated. This last amino acid is often referred to as a carboxyl-PEG-amine, carboxyl-PEO-amine, or amine-PEG-acid, whereby the amine is blocked to protect against reaction and the acid is free to react with the amine group from the previously added amino acid in the reaction.

In other embodiments, the chemokine-immunglobulin fusion polypeptides or variants thereof are produced using recombinant DNA technologies. Procedures for the expression and purification of recombinant proteins are well established.

In certain embodiments, the chemokine-immunglobulin fusion polypeptides are expressed using the expression vectors such as bacterial plasmids; phage DNA; baculovirus; yeast plasmids; vectors derived from combinations of plasmids and phage DNA, and viral vectors ushc as vaccinia, adenovirus, fowl pox virus, pseudorabies, adenovirus, adeno-associated virus, retroviruses and many others viruses.

Expression vectors carrying the chemokine-immunglobulin fusion polypeptides can be introduced into host cells by any of a variety of well-known procedures, such as electroporation, liposome mediated transfection, calcium phosphate precipitation, infection, transfection and the like, depending on the selection of vectors and host cells.

Host cells that contain expression vectors of chemokine-immunglobulin fusion polypeptides are, thus, also a feature of this disclosure. Favorable host cells include prokaryotic (i.e., bacterial) host cells, such as *E. coli*, as well as numerous eukaryotic host cells, including fungal (e.g., yeast, such as *Saccharomyces cerevisiae* and *Picchia pastoris*) cells, insect cells, plant cells, and mammalian cells (such as CHO cells). Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art and in the references cited herein. The chemokine-immunglobulin fusion polypeptides can also be produced in non-animal cells such as plants, yeast, fungi, bacteria and the like. In bacterial systems, a number of expression vectors can be selected depending upon the use intended for the expressed product. For example, when large quantities of a polypeptide or fragments thereof are needed for the production of antibodies, vectors which direct high level expression of fusion polypeptides that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described above, can be ligated into the vector in-frame with sequences for the amino-terminal translation initiating Methionine and the subsequent 7 residues of beta-galactosidase producing a catalytically active beta galactosidase fusion polypeptide; pIN vectors (Van Heeke & Schuster (1989) J Biol Chem 264:5503-5509); pET vectors (Novagen, Madison Wis.), in which the amino-terminal methionine is ligated in frame with a histidine tag; and the like.

Similarly, in yeast, such as *Saccharomyces cerevisiae*, a number of vectors containing constitutive or inducible promoters such as alpha factor, alcohol oxidase and PGH can be used for production of the desired expression products. In mammalian host cells, a number expression systems, including both plasmids and viral-based systems, can be utilized.

For long-term, high-yield production of the chemokine-immunglobulin fusion polypeptides, stable expression systems are typically used. For example, polynucleotides encoding a the chemokine-immunglobulin fusion polypeptide are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells, which successfully express the introduced sequences. For example, resistant groups or colonies of stably transformed cells can be proliferated using tissue culture techniques appropriate to the cell type. Host cells transformed with a nucleic acid encoding a c the chemokine-immunglobulin fusion polypeptide are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

Expressed the chemokine-immunglobulin fusion polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art.

In another example, a polynucleotide sequence that encodes the chemokine-immunglobulin fusion polypeptide is introduced into insect cells using a Baculovirus Expression Vector System (BEVS). Recombinant baculovirus capable of infecting insect cells can be generated using commercially available vectors, kits and/or systems, such as the BD BaculoGold system from BD BioScience. Briefly, the polynucleotide sequence encoding the chemokine-immunglobulin fusion polypeptide is inserted into the pAcSG2 transfer vector. Then, host cells SF9 (*Spodoptera frugiperda*) are co-transfected by pAcSG2-chimer plasmid and BD BaculoGold, containing the linearized genomic DNA of the baculovirus *Autographa californica* nuclear polyhedrosis virus (AcNPV). Following transfection, homologous recombination occurs between the pACSG2 plasmid and the Baculovirus genome to generate the recombinant virus. In one example, the chemokine-immunglobulin fusion polypeptide is expressed under the regulatory control of the polyhedrin promoter (pH). Similar transfer vectors can be produced using other promoters, such as the basic (Ba) and p10 promoters. Similarly, alternative insect cells can be employed, such as SF21, which is closely related to the Sf9, and the High Five (Hi5) cell line derived from a cabbage looper, *Trichoplusia ni*. Following transfection and induction of expression (according to the selected promoter and/or enhancers or other regulatory elements), the expressed the chemokine-immunglobulin fusion polypeptides are recovered (e.g., purified or enriched) and renatured to ensure folding into a biologically active conformation.

In yet other embodiments, the chemokine-immunglobulin fusion polypeptides are expressed in vivo by a plasmid vector or a viral vector.

Treatment Methods

The present application further provides methods of using the chemokine-immunoglobulin fusion polypeptides disclosed herein to modulate inflammation and/or treat chemokine receptor-mediated disorders. In some embodiments, a method for treating a chemokine receptor-mediated disorder in a subject is provided. In some embodiments, the method comprises administering an effective amount of a chemokine-immunoglobulin fusion polypeptide disclosed herein to a subject in need thereof.

As used herein, the terms "treatment" or "treating" relate to any treatment of a chemokine receptor-mediated disorder, including but not limited to prophylactic treatment and therapeutic treatment. As such, the terms "treatment" or "treating" include, but are not limited to: preventing a chemokine receptor-mediated disorder or the development of a chemokine receptor-mediated disorder; inhibiting the progression of a chemokine receptor-mediated disorder; arresting or preventing the development of a chemokine receptor-mediated disorder; reducing the severity of a chemokine receptor-mediated disorder; ameliorating or relieving symptoms associated with a chemokine receptor-mediated disorder; and causing a regression of the chemokine receptor-mediated disorder or one or more of the symptoms associated with the chemokine receptor-mediated disorder.

The embodiments of the therapeutic compounds exhibit activity in the treatment of chemokine receptor-mediated disorders and inflammation, when administered in effective amounts. An effective amount of a composition disclosed herein is a nontoxic, but sufficient amount of the composition, such that the desired prophylactic or therapeutic effect is produced. The exact amount of the composition that is required will vary from subject to subject, depending on the species, age, condition of the animal, severity of the inflammation or chemokine receptor-mediated disorder in the animal, the particular carrier or adjuvant being used, its mode of administration, and the like. Accordingly, the effective amount of any particular therapeutic composition disclosed herein will vary based on the particular circumstances, and an appropriate effective amount can be determined in each case of application by one of ordinary skill in the art using only routine experimentation. The compositions disclosed herein can be administered in amounts ranging from about 0.1 μg to about 100 mg per kilogram of body weight. For example, the dosage regimen could be from about 1 μg to about 10 mg per kilogram of body weight, and such dosage units could be employed so that a total of from about 7 μg to about 700 mg of the composition is administered to a subject of about 70 kg of body weight.

A dosage regimen can be adjusted to provide an optimum therapeutic response and can be administered daily, biweekly, weekly, bimonthly, monthly, or at other appropriate time intervals. For example, compositions disclosed herein can be administered from once a day to once a week in dosages of about 5-250 mg per administration. For another example, several divided doses can be administered daily or the dose can be proportionally reduced as indicated by the exigencies of the therapeutic situation. One practical advantage is that the compound can be administered in a convenient manner such as intravenously, intratumorally, subcutaneously, transdermally, intraperitoneally or orally.

In some embodiments, the active composition is administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The form should be sterile and fluid to the extent that easy syringability exists. It should be stable under the conditions of manufacture and storage and should be preserved against the contaminating action of microorganisms, such as bacteria and fungi. The pharmaceutical carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, the inclusion of isotonic agents can be desirable, for example, sugars or sodium chloride. Prolonged absorption of the injectable compositions can be brought about by the use in the compositions of agents, delaying absorption, for example, aluminum monostearate and gelatin.

Sterile injectable solutions can be prepared by incorporating the composition in the required amount in the appropriate solvent with various of the other ingredients enumerated above, followed by filtered sterilization. Generally, dispersions can be prepared by incorporating the various sterilized active ingredient into a sterile vehicle containing the basic dispersion medium and the required other ingredients from those enumerated above. In the case of sterile powders for the preparation of sterile injectable solutions, methods of preparation include vacuum drying and freeze drying techniques, which yield a powder of the active ingredient plus any additional desired ingredient from previously sterile filtered solution thereof.

As used herein, "pharmaceutically acceptable carrier" and "pharmaceutical carrier" are used interchangeably and include solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Parenteral compositions may be formulated in dosage-unit form for ease of administration and uniformity of dosage. Dosage-unit form, as used herein, refers to physically discrete units suited as unitary dosages for the subjects to be treated, each unit containing a predetermined quantity of active material calculated to produce the desired therapeutic effect in association with the required pharmaceutical carrier. The specification for the dosage-unit forms of the present application can be chosen based upon: (a) the unique characteristics of the active material and the particular therapeutic effect to be achieved, and (b) the limitations inherent in the art of compounding such an active material for the treatment of conditions in living subjects having a condition in which bodily health is impaired as described herein.

The active ingredient can be compounded for convenient and effective administration in effective amounts with a suitable pharmaceutically acceptable carrier in dosage unit form as described herein. A unit dosage form can, for example, contain the principle active compound in amounts ranging from, for example, about 0.1 to about 1000 mg or, for another example, from about 5 to about 500 mg. Expressed in proportions, the compound is generally present in from about 1 to about 100 mg/ml of carrier. In the case of compositions containing supplementary active ingredients, the dosages can be determined by reference to the usual dose and manner of administration of the ingredients.

Further, with respect to the therapeutic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently application provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments of the presently-disclosed subject matter, the chemokine receptor-mediated disorder treated is a cell proliferative disorder, such as tumor or cancer. The present application provides chemokine-immunoglobulin fusion polypeptides that can target specific chemokine receptors expressed on cells of proliferative disorders disclosed herein. Cancer cells express functionally active chemokine receptors that may support adhesion, invasion, and cell survival. Chemokine receptor signaling and aggregation following binding of chemokines is coupled to integrin clustering, which enhances cell survival and firm cell adhesion. Without wishing to be bound by theory, the novel chemokine-immunoglobulin fusion polypeptides disclosed herein can bind chemokine receptors on these diseased cells and inhibit cellular events, including cell survival, migration, invasion, adhesion, or combinations thereof, and thereby treat the cell proliferative disorder. Table 3 lists various cancers and associations of the listed cancers with particular chemokines and chemokine receptors.

TABLE 3

Chemokine, Chemokine Receptor and Cancer Association (dependent of stage of disease)

| Cancer | Chemokine | Chemokine Receptor |
|---|---|---|
| Carcinoma | CCL1, CCL4, CCL17, CCL19, CCL21, CCL22, CCL25, CXCL1, CXCL2, CXCL5, CXCL8, CXCL11, CXCL12, CXCL13, CXCL16 | CCR7, CCR8, CCR9, CXCR1, CXCR2, CXCR3, CXCR4, CXCR5, CXCR6, CXCR7, CX3CR1 |
| Leukemia | CCL1, CCL4, CCL17, CCL19, CCL21, CCL22, CCL25, CXCL12 | CCR7, CCR8, CCR9, CXCR4 |
| Lymphoma | CXCL12, CXCL13 | CXCR4, CXCR5 |
| Melanoma | CCL25, CCL27, CXCL1, CXCL2, CXCL3, CXCL5, CXCL6, CXCL7, CXCL8, CXCL12, CXCL13, CXCL16 CX3CL1 | CCR9, CCR10, CXCR1, CXCR2, CXCR4, CXCR5, CXCR6, CX3CR1 |

TABLE 3-continued

Chemokine, Chemokine Receptor and Cancer Association (dependent of stage of disease)

| Cancer | Chemokine | Chemokine Receptor |
|---|---|---|
| Sarcoma | CCL1, CCL3, CCL4, CCL5, CCL7, CCL8, CCL11, CCL13, CCL17, CCL19, CCL22, CCL24, CXCL12, CX3CL1 | CCR3, CCR5, CCR8, CXCR4 CX3CR1, CCXCKR |

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. "Cancer" refers to any of various malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Examples of cancers are cancer of the brain, bladder, breast, cervix, colon, head and neck, kidney, lung, non-small cell lung, mesothelioma, ovary, prostate, stomach and uterus, leukemia, and medulloblastoma.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

In some embodiments, a chemokine-immunoglobulin fusion polypeptide of the present application is used for the treatment of cancer. The chemokine-immunoglobulin fusion polypeptide comprises a chemokine moiety selected from the group consisting of CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and an immunoglobulin moiety selected from the group consisting of the constant region of human IgG1 and functional variants thereof.

In other embodiments, the chemokine receptor-mediated disorder treated is an inflammatory disorder. Without wishing to be bound by theory, the novel chemokine-immunoglobulin fusion polypeptides disclosed herein can bind chemokine receptors on these cells and inhibit cellular events that can result in inflammation and inflammatory disorders. Table 4 lists various exemplary inflammatory disorders and associations of the listed disorders with particular chemokines and chemokine receptors. Targeting of the listed chemokine receptors with chemokine-immunoglobulin fusion polypeptides disclosed herein that act as specific ligands of the receptors can be useful for treating the listed inflammatory disorders.

In some embodiments, a chemokine-immunoglobulin fusion polypeptide of the present application is used for the treatment of an inflammatory disorder. The chemokine-immunoglobulin fusion polypeptide comprises a chemokine moiety selected from the group consisting of CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and an immunoglobulin moiety selected from the group consisting of the constant region of human IgG4 and functional variants thereof.

TABLE 4

Chemokine, Chemokine Receptor and Inflammatory Disorder Association (dependent of stage of disease)

| Inflammatory Disorder | Chemokine | Chemokine Receptor |
|---|---|---|
| Allergies (Skin, Food & Respiratory) | CCL1, CCL2, CCL5, CCL7, CCL8, CCL11, CCL13, CCL17, CCL22, CCL24, CCL25, CCL26 | CCR3, CCR4, CCR8, CCR9 |
| Asthma | CCL3, CCL4, CCL5, CCL7, CCL8, CCL11, CCL15, CCL17, CCL22, CCL24, CCL26 | CCR3, CCR4, CCR5 |
| Septic Shock, Anaphylaxis | CXCL1, CXCL2, CXCL3, CXCL5, CXCL6, CXCL7, CXCL8, CXCL9, CXCL10, CXCL11, CCL5 | CXCR1, CXCR2, CXCR3 |
| Arthritis (septic, rheumatoid, psoriatic) | CXCL9, CXCL10, CXCL11, CXCL12, CXCL13 | CXCR3, CXCR4, CXCR5 |
| | CCL20 | CCR6 |
| | XCL1 | XCR1 |
| | CX3CL1 | CX3CR1 |

TABLE 4-continued

Chemokine, Chemokine Receptor and Inflammatory Disorder Association (dependent of stage of disease)

| Inflammatory Disorder | Chemokine | Chemokine Receptor |
|---|---|---|
| Osteoarthritis | CXCL1, CXCL2, CXCL3, CXCL5, CXCL6, CXCL7, CXCL8, CXCL12, CXCL13 | CXCR1, CXCR2 |
| | CCL2, CCL3, CCL4, CCL7, CCL8, CCL13, CCL5, CCL18 | CCR2, CCR5 |
| Atherosclerosis | CXCL1, CXCL2, CXCL3, CXCL4, CXCL5, CXCL8 | CXCR1, CXCR2 |
| | CCL2, CCL3, CCL4, CCL8, CCL12, CCL13, CCL17, CCL22 | CCR2, CCR8 |
| | CX3CL1 | CX3CR1 |
| Dermatitis & Delayed-Typed Hypersensitivity | CXCL9, CXCL10, CXCL11 | CXCR3 |
| | CCL2, CCL3, CCL4, CCL5, CCL17, CCL20, CCL22, CCL27 | CCR4, CCR5, CCR6, CCR10 |
| Diabetes | CXCL9, CXCL10, CXCL11 | CXCR3 |
| | CCL2, CCL9 | CCR2, CCR4 |
| | CX3CL1 | CX3CR1 |
| Graft rejection | CXCL9, CXCL10, CXCL11 | CXCR3 |
| | CCL3, CCL4, CCL5 | CCR5 |
| | XCL1, XCL2 | XCR1 |
| Inflammatory Bowel Disorders | CXCL9, CXCL10, CXCL11 | CXCR3 |
| | CCL3, CCL4, CCL5, CCL25 | CCR5 |
| Interstitial Cystitis | CXCL9, CXCL10, CXCL11 | CXCR3 |
| | CCL3, CCL4, CCL5 | CCR5 |
| Multiple Sclerosis | CXCL9, CXCL10, CXCL11 | CXCR3 |
| | CCL3, CCL4, CCL5, CCL7, CCL14, CCL15, CCL23 | CCR1, CCR5 |
| Myasthemia gravis, Grave's disease, & Hashimoto thyroiditis | CXCL9, CXCL10, CXCL11 | CXCR3 |
| | CCL3, CCL4, CCL5 | CCR5 |
| | XCL1, XCL2 | XCR1 |
| Nephritis & Systemic Lupus Erthematosus | CXCL9, CXCL10, CXCL11, CXCL13 | CXCR3, CXCR5 |
| | CCL2, CCL3, CCL4, CCL5, CCL8, CCL12, CCL13 | CCR2, CCR4 |
| | CX3CL1 | CX3CR1 |
| Pneumonitis, Chronic Obstructive Pulmonary Disease, & Chronic Bronchitis | CXCL1, CXCL2, CXCL3, CXCL5, CXCL7, CXCL8 | CXCR2, CXCR3 |
| | CCL3, CCL5, CCL7, CCL8, CCL11, CCL13, CCL24, CCL26 | CCR3 |

As used herein, the term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cell proliferative disorders, or other agents Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include, but are not limited to, inflammatory disorders of the central or peripheral nervous system (e.g., abscess, AIDS related infections, Alzheimer's disease, chronic fatigue syndrome, congenital infections, encephalitis, ischemia, meningitis, multiple sclerosis, traumatic brain injury, etc.); inflammatory disorders of the urogenital system (e.g., endometriosis, glomerulosclerosis, infections of the vagina and cervix, intra-amniotic infection, pelvic inflammatory disease, renal inflammation/nephritis, sexually transmitted diseases, urethritis, urinary tract infections, yeast infection, etc.); inflammatory disorders of the digestive system (e.g., colon cancer, hepatitis, inflammatory bowel disease, interstitial cystitis, irritable bowel syndrome, ulcers, etc.); inflammatory disorders of the respiratory system (e.g., chronic lung disease, asthma, tuberculosis, pneumonia, etc.); inflammatory disorders of the skin, integument and musculoskeletal system (e.g., Behcet's disease, Crohn's disease, dermatitis, gingivitis, gout, myalgias, osteoarthritis, periodontitis, psoriasis, rheumatoid arthritis, spondyloarthropathies, skin sunburn, etc.); inflammatory disorders of the cardiovascular system (e.g., atherosclerosis, pericarditis, endocarditis, Kawasaki's disease, myocarditis, rheumatic fever, vasculitis); autoimmune disorders; cat scratch disease; infections of the eye; Lyme disease; lymphadenopathy; lymphatic inflammation; radiation-induced inflammation; sarcoidosis; Sjogren's syndrome; systemic lupus erythematosus and related disorders; and inflammatory disorders resulting from infections by microorganisms and inflammatory molecules. As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism. As noted, an inflammatory disorder is often caused, at least in part, or exacerbated by, inflammation, which may be characterized by symptoms and/or manifestations of the inflammatory disorder which may include, but are not limited to, increased blood flow, edema, activation of immune cells (e.g., proliferation, cytokine production, or enhanced phagocytosis), heat, redness, swelling, pain and loss of function in the affected tissue and organ. As such, the present application further provides methods of modulating inflammation. The term "modulating inflammation" refers to either inducement of inflammation or alleviating inflammation where inflammation is pathological, as occurs in inflammatory disorders. The term "alleviating" as used herein refers to preventing the symptoms and/or manifestations of inflammation or the development of the symptoms and/or manifestations of inflammation; inhibiting the progression of the symptoms and/or manifestations of inflammation; arresting or preventing the development of the symptoms and/or manifestations of inflammation; reducing the severity of symptoms and/or manifestations inflammation; ameliorating or relieving the symptoms and/or manifestations associated with inflammation; and/or causing a regression of the symptoms and/or manifestations of inflammation. The present invention is further illustrated by the following examples that should not be construed as limiting. The following examples may include compilations of data that are representative of data gathered at various times during the course of development and experimentation related to the present subject matter.

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

EXAMPLE 1

Generation of plasmid expression vectors

Expression vectors capable of expressing a chemokine-immunoglobulin fusion polypeptide are generated from pFUSE-hIgG1-Fc1, pFUSE-hIgG2-Fc1, pFUSE-hIgG3-Fc1 and pFUSE-hIgG4-Fc1 vectors from InvivoGen (San Diego, Calif.) using standard molecular biology procedures. Examples of the expression vectors are shown in FIGS. 1-10.

EXAMPLE 2

Expression of Chemokine Receptors in Breast Cancer Cell Lines

Expereiments are conducted to compare expression levels of CXCR7 and CXCR3 in breast cancer tissue of various stages, in non-neoplstic breast tissue. Non-neoplastic breast tissue does not express detectable levels of CXCR7. CXCR7 expression is significantly higher in tissues with advanced breast cancer, comparing to non-neoplastic breast tissue. CXCR7 and CXCR3 mRNAs are also elevated in breast cancer cell lines (MDA-MB-231), compared to normal breast cells (MCF-10A).

EXAMPLE 3 var-CXCL11-IgG Fusion Polypeptide Inhibits CXCR7 and CXCR3 Activation in Breast Cancer Cells Using Amnis ImageStream analysis, we found that CXCL11 stimulates CXCR3 and CXCR7 aggregation and rapid desensitization, that CXCL12 modulates modest CXCR7 clustering, and that adrenomedullin (AM) stimulates CXCR3 and CXCR7 clustering. CXCL11-IgG fusion polypeptide abrogates CXCR3 and CXCR7, but not CXCR4, clustering and desensitization by CXCL11, CXCL12 and AM.

The above description is for the purpose of teaching the person of ordinary skill in the art how to practice the present invention, and is not intended to detail all those obvious modifications and variations of it that will become apparent to the skilled worker upon reading the description. It is intended, however, that all such obvious modifications and variations be included within the scope of the present invention, which is defined by the following embodiments. The embodiments are intended to cover the components and steps in any sequence that is effective to meet the objectives there intended, unless the context specifically indicates the contrary. All the references cited in the specification are herein incorporated by reference in their entirely.

What is claimed is:

1. An isolated chemokine-immunoglobulin fusion polypeptide, comprising:
a CCL2 moiety and an immunoglobulin moiety comprising a constant region of a human immunoglobulin wherein when the chemokine-immunoglobulin fusion polypeptide comprises an amino acid sequence selected from the group consisting of SEQ ID NO:52, SEQ ID NO:53 and SEQ ID NO:54.

2. The isolated chemokine-immunoglobulin fusion polypeptide of claim 1, wherein said fusion polypeptide is a pegylated fusion polypeptide.

3. The isolated chemokine-immunoglobulin fusion polypeptide of claim 2, wherein said pegylated fusion polypeptide comprising PEG molecules, wherein said PEG molecules have a molecular weight of at least about 20,000 Dalton.

4. The isolated chemokine-immunoglobulin fusion polypeptide of claim 2, wherein said pegylated fusion polypeptide has a molecular weight of at least 500,000 Daltons.

5. The isolated chemokine-immunoglobulin fusion polypeptide of claim 2, wherein said pegylated fusion polypeptide has a PEG-to-fusion polypeptide molar ratio of no more than about 10:1.

6. The isolated chemokine-immunoglobulin fusion polypeptide of claim 2, wherein said pegylated fusion polypeptide has a PEG-to-fusion polypeptide molar ratio of no more than about 2:1.

* * * * *